US011731944B2

(12) United States Patent
Ding et al.

(10) Patent No.: US 11,731,944 B2
(45) Date of Patent: Aug. 22, 2023

(54) SARS-COV-2 INHIBITORS FOR TREATING CORONAVIRUS INFECTIONS

(71) Applicant: Insilico Medicine IP Limited, Hong Kong (HK)

(72) Inventors: Xiao Ding, Shanghai (CN); Jingjing Peng, Shanghai (CN); Feng Ren, Shanghai (CN); Xiaoyu Ding, Shanghai (CN); Bogdan Zagribelnyy, Moscow (RU); Yan A. Ivanenkov, Moscow (RU)

(73) Assignee: Insilico Medicine IP Limited, Hong Kong (HK)

( * ) Notice: Subject to any disclaimer, the term of this patent is extended or adjusted under 35 U.S.C. 154(b) by 0 days.

(21) Appl. No.: 18/107,127

(22) Filed: Feb. 8, 2023

(65) Prior Publication Data
US 2023/0192624 A1    Jun. 22, 2023

Related U.S. Application Data

(63) Continuation of application No. PCT/CN2022/128916, filed on Nov. 1, 2022.

(30) Foreign Application Priority Data

Nov. 2, 2021   (WO) ............... PCT/CN2021/128243
Sep. 5, 2022   (WO) ............... PCT/CN2022/117034

(51) Int. Cl.
*C07D 233/96*   (2006.01)
*A61P 31/14*    (2006.01)

(52) U.S. Cl.
CPC ............ *C07D 233/96* (2013.01); *A61P 31/14* (2018.01)

(58) Field of Classification Search
CPC .............................. C07D 233/96; A61P 31/14
See application file for complete search history.

(56) References Cited

U.S. PATENT DOCUMENTS

| 9,975,885 | B2 * | 5/2018 | St. John ............... C07D 401/12 |
| 11,124,497 | B1 | 9/2021 | Arnold et al. |
| 11,174,231 | B1 | 11/2021 | Arnold et al. |
| 11,312,704 | B2 | 4/2022 | Arnold et al. |
| 2011/0269834 | A1 | 11/2011 | Ghosh et al. |
| 2017/0313685 | A1 | 11/2017 | St. John et al. |
| 2022/0162194 | A1 | 5/2022 | Arnold et al. |
| 2022/0411401 | A1 | 12/2022 | Ghosh et al. |

FOREIGN PATENT DOCUMENTS

| CN | 113845440 A | 12/2021 |
| WO | WO-2007062314 A2 | 5/2007 |
| WO | WO-2009150248 A1 | 12/2009 |
| WO | WO-2010022355 A1 | 2/2010 |
| WO | WO-2010151799 A2 | 12/2010 |
| WO | WO-2012009678 A1 | 1/2012 |
| WO | WO-2021183702 A1 | 9/2021 |
| WO | WO-2021201201 A1 | 10/2021 |
| WO | WO-2021211620 A1 | 10/2021 |
| WO | WO-2021212039 A1 | 10/2021 |
| WO | WO-2021219089 A1 | 11/2021 |
| WO | WO-2021252644 A1 | 12/2021 |
| WO | WO-2022023960 A1 | 2/2022 |
| WO | WO-2022119756 A1 | 6/2022 |
| WO | WO-2022119854 A1 | 6/2022 |
| WO | WO-2022221686 A1 | 10/2022 |
| WO | WO-2023078231 A1 | 5/2023 |
| WO | WO-2023078238 A1 | 5/2023 |

OTHER PUBLICATIONS

Abuhammad, et al. Computational modeling of the bat HKU4 coronavirus 3CLpro inhibitors as a tool for the development of antivirals against the emerging Middle East respiratory syndrome (MERS) coronavirus. J Mol Recognit. Nov. 2017;30(11):e2644. doi: 10.1002/jmr.2644. Epub Jun. 13, 2017.

Chuck, et al. Design, synthesis and crystallographic analysis of nitrile-based broad-spectrum peptidomimetic inhibitors for coronavirus 3C-like proteases. Eur J Med Chem. Jan. 2013;59:1-6. doi: 10.1016/j.ejmech.2012.10.053. Epub Nov. 7, 2012.

Co-pending U.S. Appl. No. 18/049,757, inventors Zavoronkovs; Aleksandrs et al., filed Oct. 26, 2022.

Eaton, et al. Structure-activity relationships of GPX4 inhibitor warheads. Bioorg Med Chem Lett. Dec. 1, 2020;30(23):127538. doi: 10.1016/j.bmcl.2020.127538. Epub Sep. 11, 2020.

Gul, et al. In silico identification of widely used and well-tolerated drugs as potential SARS-CoV-2 3C-like protease and viral RNA-dependent RNA polymerase inhibitors for direct use in clinical trials. J Biomol Struct Dyn. Oct. 2021;39(17):6772-6791. doi: 10.1080/07391102.2020.1802346. Epub Aug. 5, 2020.

International search report with written opinion dated Jan. 18, 2023 for PCT/CN2022/128916.

Jacobs, et al. Discovery, synthesis, and structure-based optimization of a series of N-(tert-butyl)-2-(N-arylamido)-2-(pyridin-3-yl)acetamides (ML188) as potent noncovalent small molecule inhibitors of the severe acute respiratory syndrome coronavirus (SARS-CoV) 3CL protease. J Med Chem. Jan. 24, 2013;56(2):534-546. doi: 10.1021/jm301580n. Epub Jan. 3, 2013.

Jacobs, et al. Discovery, synthesis, and structure-based optimization of a series of N-(tert-butyl)-2-(N-arylamido)-2-(pyridin-3-yl)acetamides (ML188) as potent noncovalent small molecule inhibitors of the severe acute respiratory syndrome coronavirus (SARS-CoV) 3CL protease. J Med Chem. Jan. 24, 2013;56(2):534-546. doi: 10.1021/jm301580n. Epub Jan. 3, 2013. Supporting Information.

St. John, et al. Targeting zoonotic viruses: Structure-based inhibition of the 3C-like protease from bat coronavirus HKU4—The likely reservoir host to the human coronavirus that causes Middle East Respiratory Syndrome (MERS). Bioorg Med Chem. Sep. 1, 2015;23(17):6036-6048. doi: 10.1016/j.bmc.2015.06.039. Epub Jun. 19, 2015.

(Continued)

*Primary Examiner* — D Margaret M Seaman
(74) *Attorney, Agent, or Firm* — Wilson Sonsini Goodrich & Rosati

(57) ABSTRACT

Provided herein are compounds, pharmaceutical compositions, and methods for treating a SARS-CoV-2 infection.

27 Claims, No Drawings

(56) References Cited

OTHER PUBLICATIONS

St. John, et al. X-Ray Structure and Inhibition of 3C-like Protease from Porcine Epidemic Diarrhea Virus. Sci Rep. May 13, 2016;6:25961. doi: 10.1038/srep25961.

Stille, et al. Design, synthesis and biological evaluation of novel SARS-CoV-2 3CLpro covalent inhibitors. ChemRxiv. https://chemrxiv.org/engage/chemrxiv/article-details/60c7572d9abda2033ff8e651 Apr. 1, 2021 (Apr. 1, 2021) Version 2.

Turlington, et al. Discovery of N-(benzo[1,2,3]triazol-1-yl)-N-(benzyl)acetamido)phenyl) carboxamides as severe acute respiratory syndrome coronavirus (SARS-CoV) 3CLpro inhibitors: identification of ML300 and noncovalent nanomolar inhibitors with an induced-fit binding. Bioorg Med Chem Lett. Nov. 15, 2013;23(22):6172-6177. doi: 10.1016/j.bmcl.2013.08.112. Epub Sep. 7, 2013.

Wang, et al. Recent progress in the discovery of inhibitors targeting coronavirus proteases. Virol Sin. Feb. 2016;31(1):24-30. doi: 10.1007/s12250-015-3711-3. Epub Feb. 19, 2016.

Wu, et al. Novel synthesis of pseudopeptides bearing a difluoromethyl group by Ugi reaction and desulfanylation. Beilstein J Org Chem. 2011;7:1070-1074. doi: 10.3762/bjoc.7.123. Epub Aug. 8, 2011.

Yamane, et al. Selective covalent targeting of SARS-CoV-2 main protease by enantiopure chlorofluoroacetamide. ChemRxiv. https://chemrxiv.org/engage/chemrxiv/article-details/6152f9b3aade361750c52ada, Sep. 28, 2021 (Sep. 28, 2021) Version 1.

* cited by examiner

SARS-COV-2 INHIBITORS FOR TREATING CORONAVIRUS INFECTIONS

CROSS-REFERENCE

This application is a continuation of International Application No. PCT/CN2022/128916, filed Nov. 1, 2022, which claims the benefit of International Application No. PCT/CN2021/128243, filed Nov. 2, 2021 and International Application No. PCT/CN2022/117034, filed Sep. 5, 2022; which are incorporated herein by reference in their entirety.

BACKGROUND

SARS-CoV-2 (also known as 2019-nCoV or COVID-19) first appeared in 2019. Symptoms linked with the disease include fever, myalgia, cough, dyspnea, and fatigue (Huang et al., 2020). Currently, there is no treatment available for SARS-CoV-2. Nevertheless, treatments with well-known drugs such as chloroquine or investigational drugs such as remdesivir are suggested for this disease (Colson et al., 2020; Wang et al., 2020). A cocktail of human immunodeficiency virus (HIV) drugs, lopinavir/ritonavir is also being investigated as a therapy for SARS-CoV-2 as they exhibited anti-coronavirus effect in vitro (Que et al., 2003; Chu et al., 2004; Chan et al., 2015; Li and De Clercq, 2020).

SARS-CoV-2 is a beta-coronavirus and is member of the family Coronaviridae, which comprises the largest positive-sense, single-stranded RNA viruses. (Cui et al., 2019). The virus contains four non-structural proteins: papain-like (PL$^{pro}$) and 3-chymotrypsin-like (3CL$^{pro}$) proteases, RNA polymerase and helicase (Zumla et al., 2016). Both proteases (PL$^{P}$r$^{o}$ and 3CL$^{pro}$) are involved with transcription and replication of the virus. Amongst the four types, the 3CL$^{pro}$ is considered to be mainly involved in the replication of the virus (de Wit et al., 2016). 3CLpro hydrolyses the viral polyproteins ppla and pplab to produce functional proteins during coronavirus replication. A study reported that the cysteine protease 3CL$^{pro}$ of SARS-CoV-2 showed 96% sequence similarity with that of SARS-CoV (Xu et al., 2020). Because of its highly conserved sequence and essential functional properties, 3CL$^{pro}$ has been validated as a potential target for the development of drugs to treat SARS-CoV-2.

Because viable treatments remain elusive, there is a need for a compound and/or method for inhibiting SARS-CoV-2 and for a treatment for a subject infected with the SARS-CoV-2.

SUMMARY

Disclosed herein is a compound of Formula (I), or a pharmaceutically acceptable salt, solvate, or stereoisomer thereof:

Formula (I)

wherein:

$R^1$ is halogen;

$R^2$ is halogen;

Ring A is cycloalkyl, heterocycloalkyl, aryl, or heteroaryl;

each $R^3$ is independently halogen, —CN, —$NO_2$, —OH, —OR$^a$, —OC(═O)R$^a$, —OC(═O)OR$^b$, —OC(═O)NR$^c$R$^d$, —SH, —SR$^a$, —$SF_5$, —S(═O)R$^a$, —S(═O)$_2$R$^a$, —S(═O)$_2$NR$^c$R$^d$, —NR$^c$R$^d$, —NR$^b$C(═O)NR$^c$R$^d$, —NR$^b$C(═O)R$^a$, —NR$^b$C(═O)OR$^b$, —NR$^b$S(═O)$_2$R$^a$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{3a}$;

or two $R^3$ on the same atom are taken together to form an oxo;

each $R^{3a}$ is independently halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)$_2$R$^a$, —S(═O)$_2$NR$^c$R$^d$, —NR$^c$R$^d$, —NR$^b$C(═O)NR$^c$R$^d$, —NR$^b$C(═O)R$^a$, —NR$^b$C(═O)OR$^b$, —NR$^b$S(═O)$_2$R$^a$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{3a}$ on the same atom are taken together to form an oxo;

n is 0-4;

L is —$(CR^4R^4)_p$—;

each $R^4$ is independently hydrogen, halogen, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;

or two $R^4$ on the same carbon are taken together to form a cycloalkyl or heterocycloalkyl, each optionally substituted with one or more $R^{4a}$;

each $R^{4a}$ is independently halogen, —CN, —$NO_2$, —OH, —OR$^a$, —NR$^c$R$^d$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;

p is 0-4;

$R^5$ is deuterium, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl;

Ring B is cycloalkyl, heterocycloalkyl, aryl, or heteroaryl;

each $R^6$ is independently halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)$_2$R$^a$, —S(═O)$_2$NR$^c$R$^d$, —NR$^c$R$^d$, —NR$^b$C(═O)NR$^c$R$^d$, —NR$^b$C(═O)R$^a$, —NR$^b$C(═O)OR$^b$, —NR$^b$S(═O)$_2$R$^a$, —C(═O)R$^a$, —C(═O)OR$^b$, —C(═O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{6a}$;

or two $R^6$ on the same atom are taken together to form an oxo;

each $R^{6a}$ is independently halogen, —CN, —$NO_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)$_2$R$^a$, —S(═O)$_2$NR$^c$R$^d$, —NR$^c$R$^d$, —NR$^b$C(═O)NR$^c$R$^d$, —NR$^b$C(═O)R$^a$, —NR$^b$C(═O)OR$^b$, —NR$^b$S(═O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two R$^{6a}$ on the same atom are taken together to form an oxo;

m is 0-4;

R$^7$ is hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl;

R$^8$ is C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkenyl, alkynyl, cycloalkyl, heterocycloalkyl, aryl, and heteroaryl is optionally and independently substituted with one or more R$^{8a}$;

each R$^{8a}$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two R$^{8a}$ on the same atom are taken together to form an oxo;

or R$^7$ and R$^8$ are taken together to form a heterocycloalkyl optionally and independently substituted with one or more R$^{7a}$;

each R$^{7a}$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two R$^{7a}$ on the same atom are taken together to form an oxo;

each R$^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkylene, alkenyl, alkynyl, cycloalkyl, heterocycloalkyl, aryl, and heteroaryl is independently optionally substituted with one or more R;

each R$^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkylene, alkenyl, alkynyl, cycloalkyl, heterocycloalkyl, aryl, and heteroaryl is independently optionally substituted with one or more R;

each R$^c$ and R$^d$ are independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkylene, alkenyl, alkynyl, cycloalkyl, heterocycloalkyl, aryl, and heteroaryl is independently optionally substituted with one or more R;

or R$^c$ and R$^d$ are taken together with the atom to which they are attached to form a heterocycloalkyl optionally substituted with one or more R; and each R is independently halogen, —CN, —OH, —OC$_1$-C$_6$alkyl, —S(=O)C$_1$-C$_6$alkyl, —S(=O)$_2$C$_1$-C$_6$alkyl, —S(=O)$_2$NH$_2$, —S(=O)$_2$NHC$_1$-C$_6$alkyl, —S(=O)$_2$N(C$_1$-C$_6$alkyl)$_2$, —NH$_2$, —NHC$_1$-C$_6$alkyl, —N(C$_1$-C$_6$alkyl)$_2$, —NHC(=O)OC$_1$-C$_6$alkyl, —C(=O)C$_1$-C$_6$alkyl, —C(=O)OH, —C(=O)OC$_1$-C$_6$alkyl, —C(=O)NH$_2$, —C(=O)N(C$_1$-C$_6$alkyl)$_2$, —C(=O)NHC$_1$-C$_6$alkyl, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;

or two R on the same atom are taken together to form an oxo.

Also disclosed herein is a pharmaceutical composition comprising a therapeutically effective amount of a compound disclosed herein, or a pharmaceutically acceptable salt, solvate, or stereoisomer thereof, and a pharmaceutically acceptable excipient.

Also disclosed herein is a method of treating or preventing a coronavirus infection in a patient in need thereof, comprising administering to the patient a compound disclosed herein or a pharmaceutically acceptable salt, solvate, or stereoisomer thereof, or the pharmaceutical composition disclosed herein.

Also disclosed herein is a method of treating or preventing a SARS-CoV-2 infection in a patient in need thereof, comprising administering to the patient a compound disclosed herein or a pharmaceutically acceptable salt, solvate, or stereoisomer thereof, or the pharmaceutical composition disclosed herein.

In some embodiments, the compound or the pharmaceutical composition is administered to the patient until the infection is reduced or eliminated. In some embodiments, the method comprises treating one or more symptoms of SARS-CoV-2 in the patient in need thereof.

Also disclosed herein is an in vivo method of inhibiting a protease of SARS-CoV-2, comprising contacting the protease with a compound disclosed herein, or a pharmaceutically acceptable salt, solvate, or stereoisomer thereof.

In some embodiments, the compound binds to a cysteine residue of the protease. In some embodiments, the compound binds reversibly or irreversibly to the cysteine residue. In some embodiments, the compound binds irreversibly to the cysteine residue. In some embodiments, the compound covalently binds to the cysteine residue. In some embodiments, the protease is 3CL-protease. In some embodiments, the cysteine is cysteine 145 of 3CL-protease. In some embodiments, the protease is SARS-CoV-2 MPRO.

Also disclosed herein is a modified SARS-CoV-2 MPRO protein, comprising a SARS-CoV-2 MPRO protein and a compound disclosed herein covalently binds to the SARS-CoV-2 MPRO protein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Definitions

In the following description, certain specific details are set forth in order to provide a thorough understanding of various embodiments. However, one skilled in the art will understand that the disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

Reference throughout this specification to "some embodiments" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.

"Carboxyl" refers to —COOH.

"Cyano" refers to —CN.

"Alkyl" refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —NH$_2$, or —NO$_2$. In some embodiments, the alkyl is optionally substituted with halogen, —CN, —OH, or —OMe. In some embodiments, the alkyl is optionally substituted with halogen.

"Alkenyl" refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited, to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —NH$_2$, or —NO$_2$. In some embodiments, the alkenyl is optionally substituted with halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —NH$_2$, or —NO$_2$. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —NH$_2$, or —NO$_2$. In some embodiments, the alkylene is optionally substituted with halogen, —CN, —OH, or —OMe. In some embodiments, the alkylene is optionally substituted with halogen.

"Alkoxy" refers to a radical of the formula —OR$^a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —NH$_2$, or —NO$_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —CF$_3$, —OH, —OMe, —NH$_2$, or —NO$_2$. In some embodiments, the aryl is optionally substituted with halogen, methyl, ethyl, —CN, —CF$_3$, —OH, or —OMe. In some embodiments, the aryl is optionally substituted with halogen.

"Cycloalkyl" refers to a partially or fully saturated, monocyclic, or polycyclic carbocyclic ring, which may include fused (when fused with an aryl or a heteroaryl ring, the cycloalkyl is bonded through a non-aromatic ring atom), spiro, or bridged ring systems. In some embodiments, the cycloalkyl is fully saturated. Representative cycloalkyls include, but are not limited to, cycloalkyls having from three to fifteen carbon atoms (C$_3$-C$_{15}$ fully saturated cycloalkyl or C$_3$-C$_{15}$ cycloalkenyl), from three to ten carbon atoms (C$_3$-C$_{10}$ fully saturated cycloalkyl or C$_3$-C$_{10}$ cycloalkenyl), from three to eight carbon atoms (C$_3$-C$_5$ fully saturated cycloalkyl or C$_3$-C$_5$ cycloalkenyl), from three to six carbon atoms (C$_3$-C$_6$ fully saturated cycloalkyl or C$_3$-C$_6$ cycloalkenyl), from three to five carbon atoms (C$_3$-C$_5$ fully saturated cycloalkyl or C$_3$-C$_5$ cycloalkenyl), or three to four carbon atoms (C$_3$-C$_4$ fully saturated cycloalkyl or C$_3$-C$_4$ cycloalkenyl). In some embodiments, the cycloalkyl is a 3- to 10-membered fully saturated cycloalkyl or a 3- to 10-membered cycloalkenyl. In some embodiments, the cycloalkyl is a 3- to 6-membered fully saturated cycloalkyl or a 3- to 6-membered cycloalkenyl. In some embodiments, the cycloalkyl is a 5- to 6-membered fully saturated cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a C$_1$-C$_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, —CH$_2$CH$_2$NHCH$_3$, or —CH$_2$CH$_2$N(CH$_3$)$_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous, silicon, and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through a non-aromatic ring atom), spiro, or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ fully saturated heterocycloalkyl or $C_2$-$C_{15}$ heterocycloalkenyl), from two to ten carbon atoms ($C_2$-$C_{10}$ fully saturated heterocycloalkyl or $C_2$-$C_{10}$ heterocycloalkenyl), from two to eight carbon atoms ($C_2$-$C_8$ fully saturated heterocycloalkyl or $C_2$-$C_8$ heterocycloalkenyl), from two to seven carbon atoms ($C_2$-$C_7$ fully saturated heterocycloalkyl or $C_2$-$C_7$ heterocycloalkenyl), from two to six carbon atoms ($C_2$-$C_6$ fully saturated heterocycloalkyl or $C_2$-$C_6$ heterocycloalkenyl), from two to five carbon atoms ($C_2$-$C_5$ fully saturated heterocycloalkyl or $C_2$-$C_8$ heterocycloalkenyl), or two to four carbon atoms ($C_2$-$C_4$ fully saturated heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocloalkyl also includes all ring forms of the carbohydrates, including but not limited to the monosaccharides, the disaccharides, and the oligosaccharides. In some embodiments, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —CF$_3$, —OH, —OMe, —NH$_2$, or —NO$_2$. In some embodiments, the heterocycloalkyl is optionally substituted with halogen, methyl, ethyl, —CN, —CF$_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —CF$_3$, —OH, —OMe, —NH$_2$, or —NO$_2$. In some embodiments, the heteroaryl is optionally substituted with halogen, methyl, ethyl, —CN, —$CF_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —$CH_2CH_3$), fully substituted (e.g., —$CF_2CF_3$), mono-substituted (e.g., —$CH_2CH_2F$) or substituted at a level anywhere in-between fully substituted and mono-substituted (e.g., —$CH_2CHF_2$, —$CH_2CF_3$, —$CF_2CH_3$, —$CFHCHF_2$, etc.). It will be understood by those skilled in the art with respect to any group containing one or more substituents that such groups are not intended to introduce any substitution or substitution patterns that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition.

Compounds

The present disclosure includes compounds and/or materials for use as SARS-CoV-2 inhibitors and for treating a subject infected with SARS-CoV-2.

Disclosed herein is a compound of Formula (I), or a pharmaceutically acceptable salt, solvate, or stereoisomer thereof:

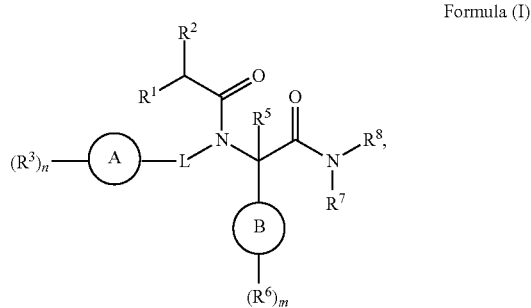

Formula (I)

wherein:

$R^1$ is halogen;

$R^2$ is halogen;

Ring A is cycloalkyl, heterocycloalkyl, aryl, or heteroaryl;

each $R^3$ is independently halogen, —CN, —$NO_2$, —OH, —$OR^a$, —OC(═O)$R^a$, —OC(═O)$OR^b$, —OC(═O)$NR^cR^d$, —SH, —$SR^a$, —$SF_5$, —S(═O)$R^a$, —S(═O)$_2R^a$, —S(═O)$_2NR^cR^d$, —$NR^cR^d$, —$NR^b$C(═O)$NR^cR^d$, —$NR^b$C(═O)$R^a$, —$NR^b$C(═O)$OR^b$, —$NR^b$S(═O)$_2R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{3a}$;

or two $R^3$ on the same atom are taken together to form an oxo;

each $R^{3a}$ is independently halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$_2R^a$, —S(═O)$_2NR^cR^d$, —$NR^cR^d$, —$NR^b$C(═O)$NR^cR^d$, —$NR^b$C(═O)$R^a$, —$NR^b$C(═O)$OR^b$, —$NR^b$S(═O)$_2R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{3a}$ on the same atom are taken together to form an oxo;

n is 0-4;

L is —$(CR^4R^4)_p$—;

each $R^4$ is independently hydrogen, halogen, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;

or two $R^4$ on the same carbon are taken together to form a cycloalkyl or heterocycloalkyl, each optionally substituted with one or more $R^{4a}$;

each $R^{4a}$ is independently halogen, —CN, —$NO_2$, —OH, —$OR^a$, —$NR^cR^d$, —C(═O)$R^a$, —C(═O)$OR^b$, —C(═O)$NR^cR^d$, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;

p is 0-4;

$R^5$ is deuterium, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl;

Ring B is cycloalkyl, heterocycloalkyl, aryl, or heteroaryl;

each $R^6$ is independently halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$_2R^a$, —S(═O)$_2NR^cR^d$, —$NR^cR^d$, —$NR^b$C(═O)$NR^cR^d$, —$NR^b$C(═O)$R^a$, —$NR^b$C(═O)$OR^b$, —$NR^b$S(═O)$_2R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{6a}$;

or two $R^6$ on the same atom are taken together to form an oxo;

each $R^{6a}$ is independently halogen, —CN, —$NO_2$, —OH, —$OR^a$, —OC(═O)$R^a$, —OC(═O)$OR^b$, —OC(═O)$NR^cR^d$, —SH, —$SR^a$, —S(═O)$R^a$, —S(═O)$_2R^a$, —S(═O)$_2NR^cR^d$, —$NR^cR^d$, —$NR^b$C(═O)$NR^cR^d$, —$NR^b$C(═O)$R^a$, —$NR^b$C(═O)$OR^b$, —$NR^b$S(═O)$_2R^a$, —C(═O)$R^a$, —C(═O)$OR^b$, —C(═O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two R$^{6a}$ on the same atom are taken together to form an oxo;

m is 0-4;

R$^7$ is hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, cycloalkyl, or heterocycloalkyl;

R$^8$ is C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkenyl, alkynyl, cycloalkyl, heterocycloalkyl, aryl, and heteroaryl is optionally and independently substituted with one or more R$^{8a}$;

each R$^{8a}$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two R$^{8a}$ on the same atom are taken together to form an oxo;

or R$^7$ and R$^8$ are taken together to form a heterocycloalkyl optionally and independently substituted with one or more R$^{7a}$;

each R$^{7a}$ is independently halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two R$^{7a}$ on the same atom are taken together to form an oxo;

each R$^a$ is independently C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkylene, alkenyl, alkynyl, cycloalkyl, heterocycloalkyl, aryl, and heteroaryl is independently optionally substituted with one or more R;

each R$^b$ is independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkylene, alkenyl, alkynyl, cycloalkyl, heterocycloalkyl, aryl, and heteroaryl is independently optionally substituted with one or more R;

each R$^c$ and R$^d$ are independently hydrogen, C$_1$-C$_6$alkyl, C$_1$-C$_6$haloalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkylene, alkenyl, alkynyl, cycloalkyl, heterocycloalkyl, aryl, and heteroaryl is independently optionally substituted with one or more R;

or R$^c$ and R$^d$ are taken together with the atom to which they are attached to form a heterocycloalkyl optionally substituted with one or more R; and each R is independently halogen, —CN, —OH, —OC$_1$-C$_6$alkyl, —S(=O)C$_1$-C$_6$alkyl, —S(=O)$_2$C$_1$-C$_6$alkyl, —S(=O)$_2$NH$_2$, —S(=O)$_2$NHC$_1$-C$_6$alkyl, —S(=O)$_2$N(C$_1$-C$_6$alkyl)$_2$, —NH$_2$, —NHC$_1$-C$_6$alkyl, —N(C$_1$-C$_6$alkyl)$_2$, —NHC(=O)OC$_1$-C$_6$alkyl, —C(=O)C$_1$-C$_6$alkyl, —C(=O)OH, —C(=O)OC$_1$-C$_6$alkyl, —C(=O)NH$_2$, —C(=O)N(C$_1$-C$_6$alkyl)$_2$, —C(=O)NHC$_1$-C$_6$alkyl, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;

or two R on the same atom are taken together to form an oxo.

In some embodiments, the compound of Formula (I), or a pharmaceutically acceptable salt, solvate, or stereoisomer thereof is:

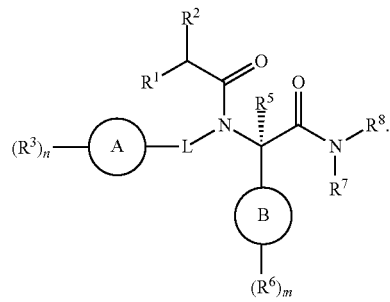

In some embodiments, the compound of Formula (I), or a pharmaceutically acceptable salt, solvate, or stereoisomer thereof is:

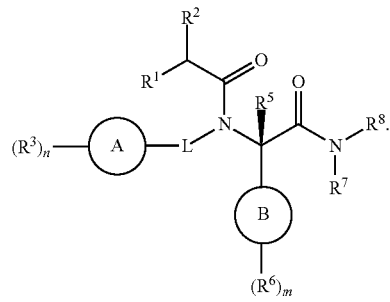

In some embodiments of a compound of Formula (I), R$^8$ is C$_1$-C$_6$haloalkyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkenyl, alkynyl, cycloalkyl, heterocycloalkyl, aryl, and heteroaryl is optionally and independently substituted with one or more R$^{8a}$. In some embodiments of a compound of Formula (I), R$^8$ is C$_1$-C$_6$alkylene(aryl); wherein the alkyl and aryl is optionally and independently substituted with one or more R$^{8a}$. In some embodiments of a compound of Formula (I), R$^8$ is cycloalkyl or heterocycloalkyl; wherein the cycloalkyl and heterocycloalkyl is optionally and independently substituted with one or more R$^{8a}$. In some embodiments of a compound of Formula (I), R$^8$ is cycloalkyl optionally and independently substituted with one or more $R^{8a}$. In some embodiments of a compound of Formula (I), $R^8$ is heterocycloalkyl optionally and independently substituted with one or more $R^{8a}$. In some embodiments of a compound of Formula (I), $R^8$ is heterocycloalkyl containing 1 to 2 heteroatoms selected from O and N. In some embodiments of a compound of Formula (I), $R^8$ is a bridged bicyclic ring. In some embodiments of a compound of Formula (I), $R^8$ is a fused bicyclic ring. In some embodiments of a compound of Formula (I), $R^8$ is a monocyclic 6-membered cycloalkyl or heterocycloalkyl, each of which is optionally substituted with one or more $R^{8a}$.

In some embodiments of a compound Formula (I), $R^8$ is

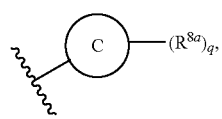

wherein Ring C is cycloalkyl, heterocycloalkyl, aryl, or heteroaryl; and q is 0-4.

In some embodiments of a compound of Formula (I), $R^8$ is

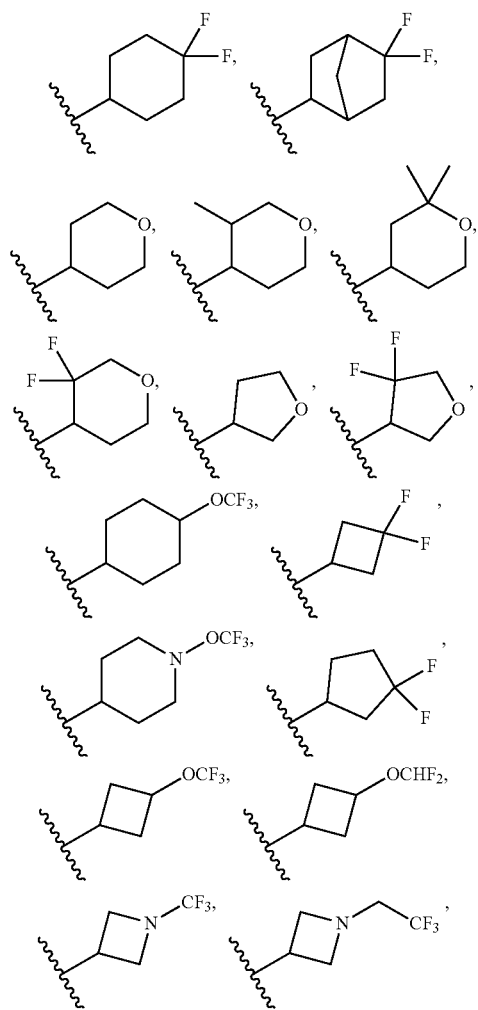

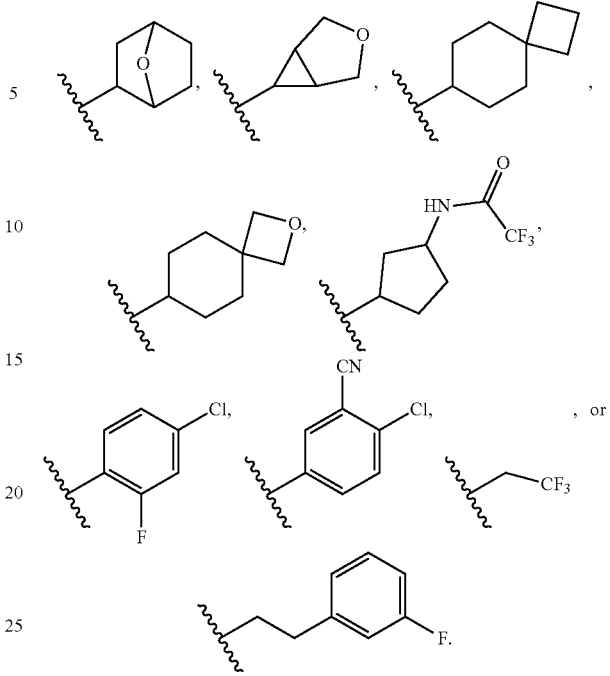

In some embodiments of a compound of Formula (I), $R^8$ is

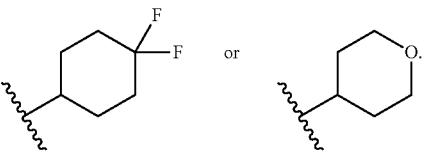 [SMILES: *C1CCC(F)(F)CC1 ; *C1CCOCC1]

In some embodiments of a compound of Formula (I), $R^8$ is

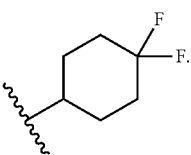 [SMILES: *C1CCC(F)(F)CC1]

In some embodiments of a compound of Formula (I), $R^8$ is

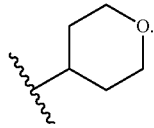 [SMILES: *C1CCOCC1]

In some embodiments of a compound of Formula (I), $R^7$ and $R^8$ are taken together to form a heterocycloalkyl optionally and independently substituted with one or more $R^{7a}$.

In some embodiments of a compound of Formula (I), each $R^{7a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I), each $R^{7a}$ is independently halogen, —CN, —OH, —OR$^a$, —NR$^c$R$^d$, $C_1$-$C_6$alkyl, or $C_1$-$C_6$haloalkyl.

In some embodiments of a compound of Formula (I), the compound is of Formula (Ia):

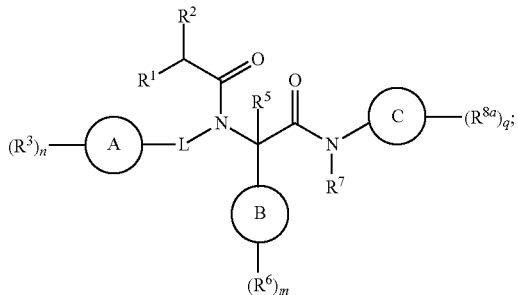

Formula (Ia)

wherein:
Ring C is cycloalkyl, heterocycloalkyl, aryl, or heteroaryl; and
q is 0-4.

In some embodiments, the compound of Formula (Ia), or a pharmaceutically acceptable salt, solvate, or stereoisomer thereof is:

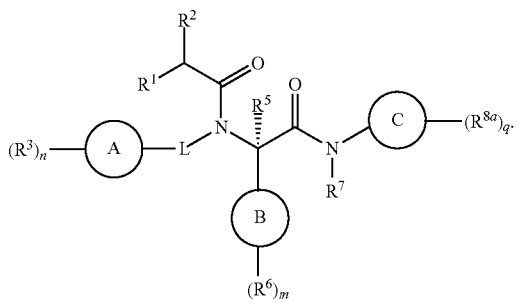

In some embodiments, the compound of Formula (Ia), or a pharmaceutically acceptable salt, solvate, or stereoisomer thereof is:

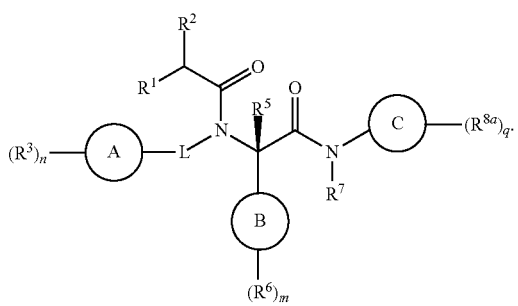

In some embodiments of a compound of Formula (I) or (Ia), Ring C is cycloalkyl or heterocycloalkyl. In some embodiments of a compound of Formula (I) or (Ia), Ring C is cycloalkyl. In some embodiments of a compound of Formula (I) or (Ia), Ring C is heterocycloalkyl. In some embodiments of a compound of Formula (I) or (Ia), Ring C is a 6-membered ring.

In some embodiments of a compound of Formula (I) or (Ia), q is 0-2. In some embodiments of a compound of Formula (I) or (Ia), q is 1-3. In some embodiments of a compound of Formula (I) or (Ia), q is 1 or 2. In some embodiments of a compound of Formula (I) or (Ia), q is 0 or 1. In some embodiments of a compound of Formula (I) or (Ia), q is 0. In some embodiments of a compound of Formula (I) or (Ia), q is 1. In some embodiments of a compound of Formula (I) or (Ia), q is 2. In some embodiments of a compound of Formula (I) or (Ia), q is 3. In some embodiments of a compound of Formula (I) or (Ia), q is 4.

In some embodiments of a compound of Formula (I) or (Ia), $R^1$ is fluoro or chloro. In some embodiments of a compound of Formula (I) or (Ia), $R^2$ is fluoro or chloro. In some embodiments of a compound of Formula (I) or (Ia), $R^1$ is fluoro and $R^2$ is chloro. In some embodiments of a compound of Formula (I) or (Ia), $R^1$ is chloro and $R^2$ is fluoro.

In some embodiments of a compound of Formula (I) or (Ia), Ring A is aryl or heteroaryl. In some embodiments of a compound of Formula (I) or (Ia), Ring A is phenyl. In some embodiments of a compound of Formula (I) or (Ia), Ring A is 6-membered heteroaryl. In some embodiments of a compound of Formula (I) or (Ia), Ring A is monocyclic ring. In some embodiments of a compound of Formula (I) or (Ia), Ring A is bicyclic ring. In some embodiments of a compound of Formula (I) or (Ia), Ring A is tricyclic ring.

In some embodiments of a compound of Formula (I) or (Ia), each $R^3$ is independently halogen, —CN, —OH, —OR$^a$, —SR$^a$, —SF$_5$, —S(=O)$_2$R$^a$, —S(=O)$_2$NR$^c$R$^d$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein the alkyl, cycloalkyl, heterocycloalkyl, aryl, and heteroaryl is optionally and independently substituted with one or more $R^{3a}$. In some embodiments of a compound of Formula (I) or (Ia), each $R^3$ is independently halogen, —CN, —OR$^a$, —SR$^a$, —SF$_5$, —S(=O)$_2$R$^a$, $C_1$-$C_6$alkyl, $C_1$-$C_6$haloalkyl, cycloalkyl, heterocycloalkyl, aryl, or heteroaryl; wherein the alkyl, cycloalkyl, heterocycloalkyl, aryl, and heteroaryl is optionally and independently substituted with one or more $R^{3a}$. In some embodiments of a compound of Formula (I) or (Ia), each $R^3$ is independently halogen, —CN, —OR$^a$, —SR$^a$, —SF$_5$, —S(=O)$_2$R$^a$, $C_1$-$C_6$alkyl, $C_1$-$C_6$haloalkyl, cycloalkyl, or heteroaryl; wherein the alkyl, cycloalkyl, and heteroaryl is optionally and independently substituted with one or more $R^{3a}$. In some embodiments of a compound of Formula (I) or (Ia), each $R^3$ is independently halogen, —OR$^a$, —SR$^a$, —SF$_5$, —S(=O)$_2$R$^a$, $C_1$-$C_6$haloalkyl, cycloalkyl, or heteroaryl. In some embodiments of a compound of Formula (I) or (Ia), each $R^3$ is independently —OR$^a$ or —SR$^a$. In some embodiments of a compound of Formula (I) or (Ia), each $R^3$ is independently —OR$^a$. In some embodiments of a compound of Formula (I) or (Ia), each $R^3$ is independently —SR$^a$. In some embodiments of a compound of Formula (I) or (Ia), each $R^3$ is independently heteroaryl.

In some embodiments of a compound of Formula (I) or (Ia), each $R^{3a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, cycloalkyl, or heterocycloalkyl. In some embodiments of a compound of Formula (I) or (Ia), each $R^{3a}$ is independently halogen, —CN, —OH, —OR$^a$, —NR$^c$R$^d$, $C_1$-$C_6$alkyl, or $C_1$-$C_6$haloalkyl. In some embodiments of a compound of Formula (I) or (Ia), each $R^{3a}$ is independently halogen, $C_1$-$C_6$alkyl, or $C_1$-$C_6$haloalkyl.

In some embodiments of a compound of Formula (I) or (Ia), n is 1 or 2. In some embodiments of a compound of Formula (I) or (Ia), n is 1-3. In some embodiments of a compound of Formula (I) or (Ia), n is 0-2. In some embodiments of a compound of Formula (I) or (Ia), n is 1. In some embodiments of a compound of Formula (I) or (Ia), n is 2. In some embodiments of a compound of Formula (I) or (Ia), n is 3. In some embodiments of a compound of Formula (I) or (Ia), n is 4.

In some embodiments of a compound of Formula (I) or (Ia), p is 0. In some embodiments of a compound of Formula (I) or (Ia), p is 1. In some embodiments of a compound of Formula (I) or (Ia), p is 2. In some embodiments of a compound of Formula (I) or (Ia), p is 3. In some embodiments of a compound of Formula (I) or (Ia), p is 1-3. In some embodiments of a compound of Formula (I) or (Ia), p is 0-2. In some embodiments of a compound of Formula (I) or (Ia), p is 0 or 1. In some embodiments of a compound of Formula (I) or (Ia), p is 1 or 2. In some embodiments of a compound of Formula (I) or (Ia), p is 0 (i.e., L is a bond).

In some embodiments of a compound of Formula (I) or (Ia),

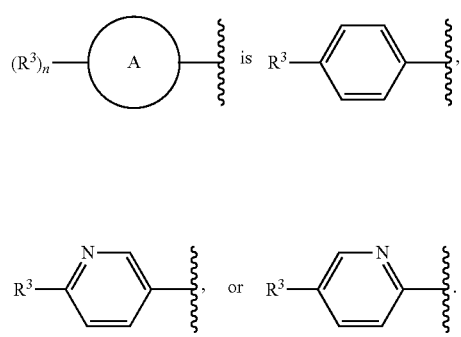

In some embodiments of a compound of Formula (I) or (Ia),

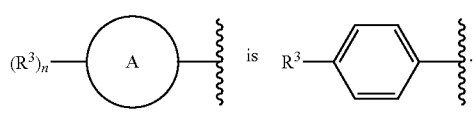

In some embodiments of a compound of Formula (I) or (Ia),

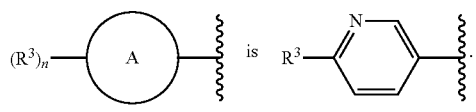

In some embodiments of a compound of Formula (I) or (Ia),

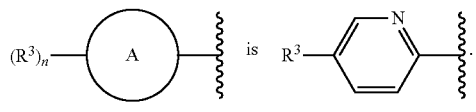

In some embodiments of a compound of Formula (I) or (Ia),

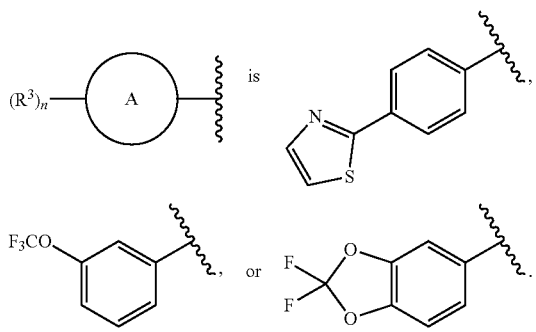

In some embodiments of a compound of Formula (I) or (Ia),

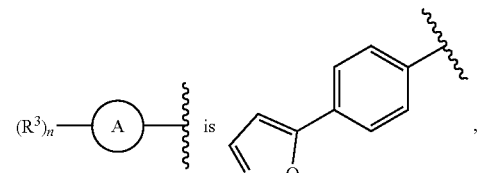

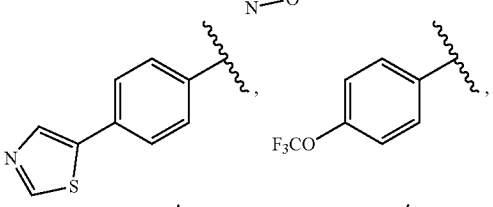

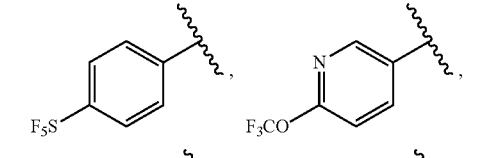

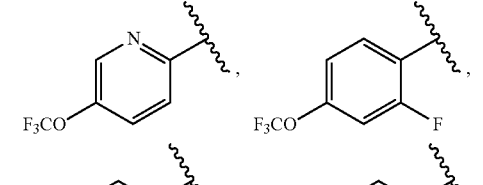

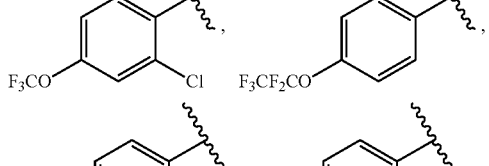

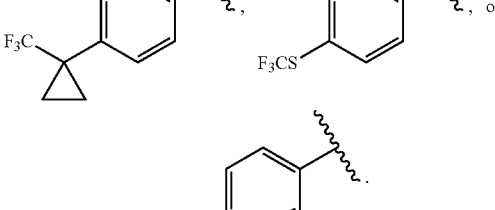

In some embodiments of a compound of Formula (I) or (Ia),

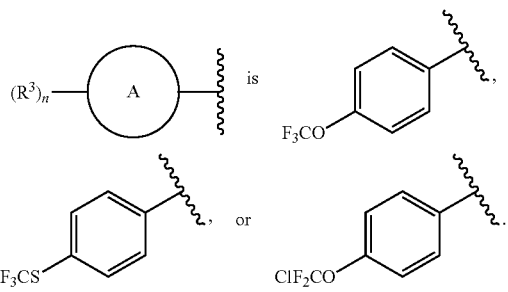 is

In some embodiments of a compound of Formula (I) or (Ia),

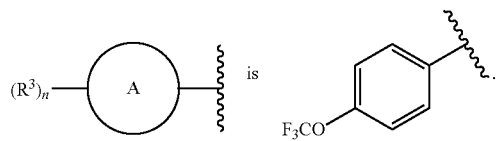

In some embodiments of a compound of Formula (I) or (Ia),

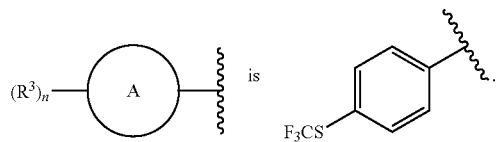

In some embodiments of a compound of Formula (I) or (Ia),

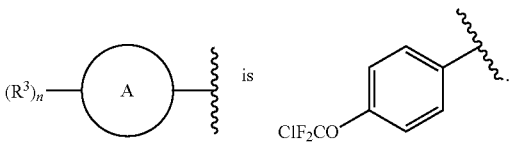

In some embodiments of a compound of Formula (I) or (Ia), each $R^4$ is independently hydrogen, halogen, or $C_1$-$C_6$alkyl. In some embodiments of a compound of Formula (I) or (Ia), each $R^4$ is independently hydrogen or $C_1$-$C_6$alkyl. In some embodiments of a compound of Formula (I) or (Ia), each $R^4$ is independently hydrogen or halogen. In some embodiments of a compound of Formula (I) or (Ia), each $R^4$ is hydrogen.

In some embodiments of a compound of Formula (I) or (Ia), two $R^4$ on the same carbon are taken together to form a cycloalkyl or heterocycloalkyl, each optionally substituted with one or more $R^{4a}$.

In some embodiments of a compound of Formula (I) or (Ia), each $R^{4a}$ is independently halogen, —CN, —OH, —$OR^a$, —$NR^cR^d$, $C_1$-$C_6$alkyl, or $C_1$-$C_6$haloalkyl. In some embodiments of a compound of Formula (I) or (Ia), each $R^{4a}$ is independently halogen, —OH, $C_1$-$C_6$alkyl, or $C_1$-$C_6$haloalkyl.

In some embodiments of a compound of Formula (I) or (Ia), each R is deuterium or $C_1$-$C_6$alkyl. In some embodiments of a compound of Formula (I) or (Ia), each R is deuterium, $C_1$-$C_6$alkyl, or $C_1$-$C_6$deuteroalkyl. In some embodiments of a compound of Formula (I) or (Ia), each R is $C_1$-$C_6$alkyl. In some embodiments of a compound of Formula (I) or (Ia), each $R^5$ is $C_1$-$C_3$alkyl. In some embodiments of a compound of Formula (I) or (Ia), each $R^5$ is methyl. In some embodiments of a compound of Formula (I) or (Ia), each R is $CD_3$. In some embodiments of a compound of Formula (I) or (Ia), each R is deuterium.

In some embodiments of a compound of Formula (I) or (Ia), Ring B is heterocycloalkyl or heteroaryl. In some embodiments of a compound of Formula (I) or (Ia), Ring B is heteroaryl. In some embodiments of a compound of Formula (I) or (Ia), Ring B is 5- or 6-membered heteroaryl. In some embodiments of a compound of Formula (I) or (Ia), Ring B is 6-membered heteroaryl. In some embodiments of a compound of Formula (I) or (Ia), Ring B is pyridinyl, pyrimidinyl, or pyrazinyl. In some embodiments of a compound of Formula (I) or (Ia), Ring B is pyridinyl or pyrimidinyl. In some embodiments of a compound of Formula (I) or (Ia), Ring B is pyridinyl. In some embodiments of a compound of Formula (I) or (Ia), Ring B is pyrimidinyl.

In some embodiments of a compound of Formula (I) or (Ia), each $R^6$ is independently halogen, —CN, —OH, —$OR^a$, —$NR^cR^d$, $C_1$-$C_6$alkyl, or $C_1$-$C_6$haloalkyl. In some embodiments of a compound of Formula (I) or (Ia), each $R^6$ is independently halogen or $C_1$-$C_6$alkyl. In some embodiments of a compound of Formula (I) or (Ia), each $R^6$ is independently halogen.

In some embodiments of a compound of Formula (I) or (Ia), each $R^{6a}$ is independently halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I) or (Ia), each $R^{6a}$ is independently halogen, —CN, —OH, —$OR^a$, —$NR^cR^d$, $C_1$-$C_6$alkyl, or $C_1$-$C_6$haloalkyl.

In some embodiments of a compound of Formula (I) or (Ia), m is 0-3. In some embodiments of a compound of Formula (I) or (Ia), m is 1-3. In some embodiments of a compound of Formula (I) or (Ia), m is 0-2. In some embodiments of a compound of Formula (I) or (Ia), m is 0 or 1. In some embodiments of a compound of Formula (I) or (Ia), m is 1 or 2. In some embodiments of a compound of Formula (I) or (Ia), m is 0. In some embodiments of a compound of Formula (I) or (Ia), m is 1. In some embodiments of a compound of Formula (I) or (Ia), m is 2. In some embodiments of a compound of Formula (I) or (Ia), m is 3.

In some embodiments of a compound of Formula (I) or (Ia),

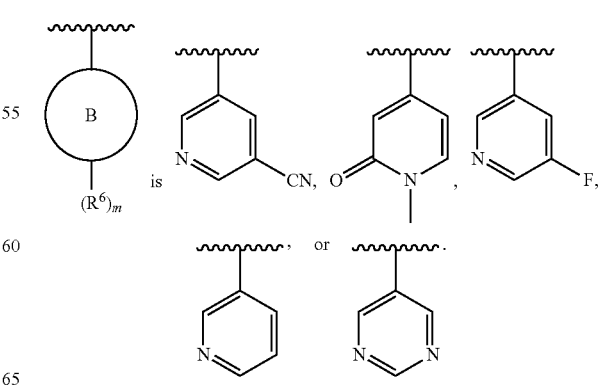

In some embodiments of a compound of Formula (I) or (Ia),

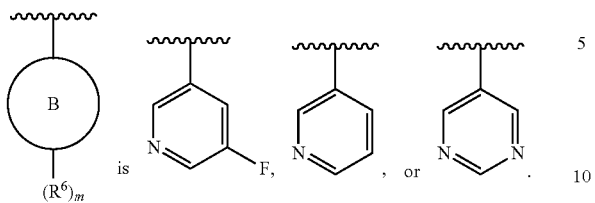 is

In some embodiments of a compound of Formula (Ia),

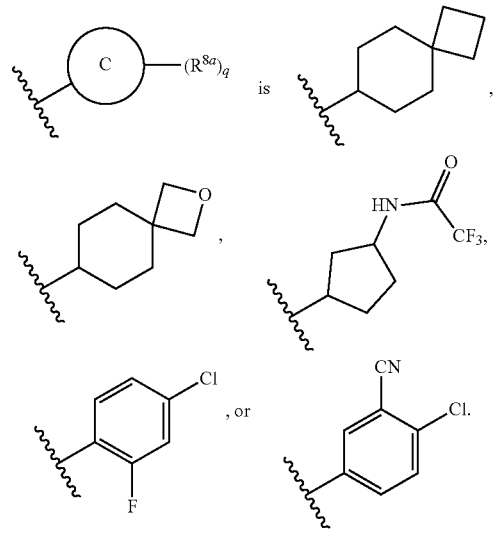

In some embodiments of a compound of Formula (I) or (Ia),

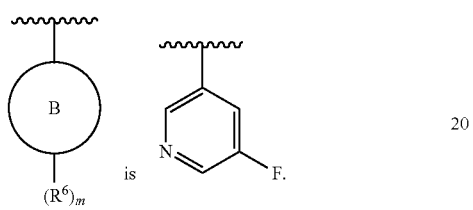

In some embodiments of a compound of Formula (I) or (Ia),

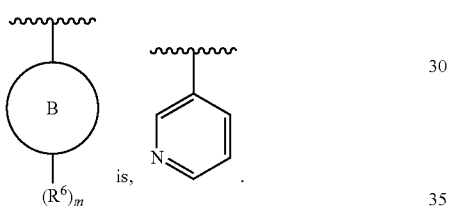

In some embodiments of a compound of Formula (Ia),

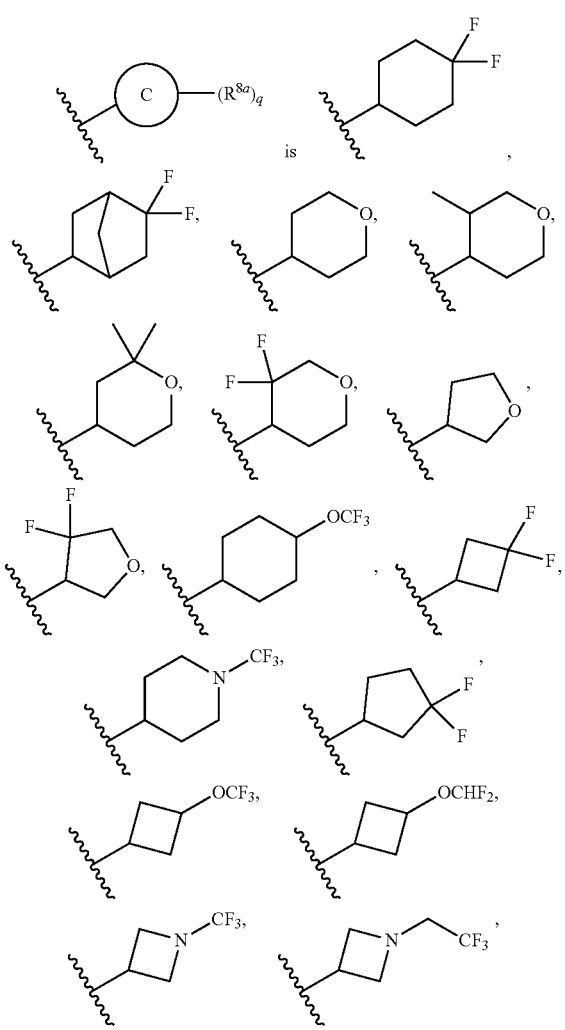

In some embodiments of a compound of Formula (I) or (Ia),

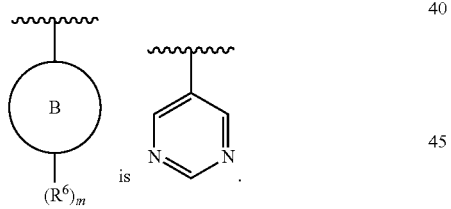

In some embodiments of a compound of Formula (I) or (Ia), $R^7$ is hydrogen or $C_1$-$C_6$alkyl. In some embodiments of a compound of Formula (I) or (Ia), $R^7$ is $C_1$-$C_6$alkyl. In some embodiments of a compound of Formula (I) or (Ia), $R^7$ is hydrogen.

In some embodiments of a compound of Formula (I) or (Ia), each $R^{8a}$ is independently halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I) or (Ia), each $R^{8a}$ is independently halogen, —CN, —OH, —OR$^a$, —NR$^c$R$^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I) or (Ia), each $R^{8a}$ is independently halogen, —OH, —OR$^a$, $C_1$-$C_6$alkyl, or $C_1$-$C_6$haloalkyl.

-continued

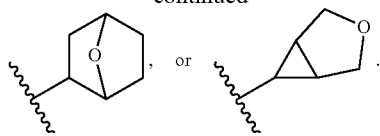

In some embodiments of a compound of Formula (Ia),

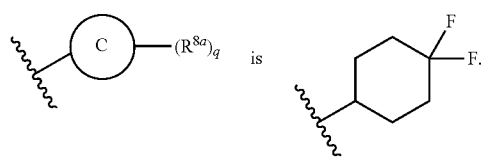

In some embodiments of a compound of Formula (Ia)

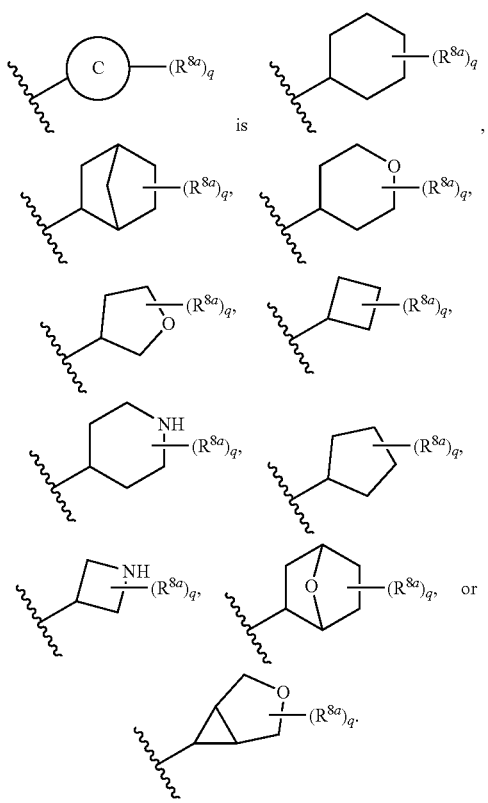

In some embodiments of a compound of Formula (Ia), $R^1$ is fluoro or chloro; $R^2$ is fluoro or chloro; R is $C_1$-$C_3$alkyl (e.g., methyl);

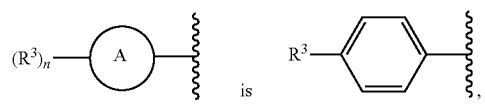

and $R^3$ is halogen, —CN, —OH, —$OR^a$, —$SR^a$, —$SF_5$, —S(=O)$_2R^a$, $C_1$-$C_6$alkyl, or $C_1$-$C_6$haloalkyl, wherein $R^a$ is $C_1$-$C_6$alkyl or $C_1$-$C_6$haloalkyl; L is —$(CR^4R^4)_p$— and p is 0 (i.e., L is a bond); Ring B is 6-membered heteroaryl, each $R^6$ is independently halogen or $C_1$-$C_6$alkyl and m is 0, 1, or 2; Ring C is 6-membered cycloalkyl or heterocycloalkyl; and each $R^{8a}$ is independently halogen, —OH, —$OR^a$, $C_1$-$C_6$alkyl, or $C_1$-$C_6$haloalkyl.

In some embodiments of a compound disclosed herein, each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, cycloalkyl, heterocycloalkyl, aryl, and heteroaryl is independently optionally substituted with one or more R. In some embodiments of a compound disclosed herein, each $R^a$ is independently $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound disclosed herein, each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound disclosed herein, each $R^a$ is independently $C_1$-$C_6$alkyl, $C_1$-$C_6$haloalkyl, or cycloalkyl, heterocycloalkyl. In some embodiments of a compound disclosed herein, each $R^a$ is independently $C_1$-$C_6$alkyl or $C_1$-$C_6$haloalkyl. In some embodiments of a compound disclosed herein, each $R^a$ is independently $C_1$-$C_6$alkyl. In some embodiments of a compound disclosed herein, each $R^a$ is independently $C_1$-$C_6$haloalkyl.

In some embodiments of a compound disclosed herein, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, cycloalkyl, heterocycloalkyl, aryl, and heteroaryl is independently optionally substituted with one or more R. In some embodiments of a compound disclosed herein, each $R^b$ is independently hydrogen, $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound disclosed herein, each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound disclosed herein, each $R^b$ is independently hydrogen, $C_1$-$C_6$alkyl, $C_1$-$C_6$haloalkyl, or cycloalkyl, heterocycloalkyl. In some embodiments of a compound disclosed herein, each $R^b$ is independently hydrogen, $C_1$-$C_6$alkyl or $C_1$-$C_6$haloalkyl. In some embodiments of a compound disclosed herein, each $R^b$ is independently hydrogen or $C_1$-$C_6$alkyl. In some embodiments of a compound disclosed herein, each $R^b$ is hydrogen. In some embodiments of a compound disclosed herein, each $R^b$ is independently $C_1$-$C_6$alkyl.

In some embodiments of a compound disclosed herein, each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkylene, cycloalkyl, heterocycloalkyl, aryl, and heteroaryl is independently optionally substituted with one or more R. In some embodiments of a compound disclosed herein, each $R^c$ and $R^d$ are independently hydrogen, $C_1$-$C_6$alkyl, $C_1$-$C_6$haloalkyl, or cycloalkyl, heterocycloalkyl; wherein each alkyl, cycloalkyl, and heterocycloalkyl is independently optionally substituted with one or more R. In some embodiments of a compound disclosed herein, each $R^c$ and $R^d$ are independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl). In some embodiments of a compound disclosed herein, each $R^c$ and $R^d$ are independently hydrogen, $C_1$-$C_6$alkyl, $C_1$-$C_6$haloalkyl, or cycloalkyl, heterocycloalkyl. In some embodiments of a compound disclosed herein, each $R^c$ and $R^d$ are independently hydrogen, $C_1$-$C_6$alkyl or $C_1$-$C_6$haloalkyl. In some embodiments of a compound disclosed herein, each $R^c$ and $R^d$ are independently hydrogen or $C_1$-$C_6$alkyl. In some embodiments of a compound disclosed herein, each $R^c$ and $R^d$ are hydrogen. In some embodiments of a compound disclosed herein, each $R^c$ and $R^d$ are independently $C_1$-$C_6$alkyl.

In some embodiments of a compound disclosed herein, $R^c$ and $R^d$ are taken together with the atom to which they are attached to form a heterocycloalkyl optionally substituted with one or more R.

In some embodiments of a compound disclosed herein, each R is independently halogen, —CN, —OH, —OC$_1$-C$_6$alkyl, —NH$_2$, —NHC$_1$-C$_6$alkyl, —N(C$_1$-C$_6$alkyl)$_2$, —NHC(═O)OC$_1$-C$_6$alkyl, —C(═O)C$_1$-C$_6$alkyl, —C(═O)OH, —C(═O)OC$_1$-C$_6$alkyl, —C(═O)NH$_2$, —C(═O)N(C$_1$-C$_6$alkyl)$_2$, —C(═O)NHC$_1$-C$_6$alkyl, C$_1$-C$_6$alkyl, or C$_1$-C$_6$haloalkyl. In some embodiments of a compound disclosed herein, each R is independently halogen, —CN, —OH, —OC$_1$-C$_6$alkyl, —NH$_2$, —C(═O)C$_1$-C$_6$alkyl, —C(═O)OH, —C(═O)OC$_1$-C$_6$alkyl, —C(═O)NH$_2$, C$_1$-C$_6$alkyl, or C$_1$-C$_6$haloalkyl. In some embodiments of a compound disclosed herein, each R is independently halogen, —CN, —OH, —OC$_1$-C$_6$alkyl, —NH$_2$, C$_1$-C$_6$alkyl, or C$_1$-C$_6$haloalkyl.

In some embodiments of a compound disclosed herein, each $R^3$, $R^6$, $R^8$, $R^a$, $R^b$, $R^c$, $R^d$, the ring formed when: two $R^4$ are taken together, $R^7$ and $R^8$ are taken together, and $R^c$ and $R^d$ are taken together, is optionally and independently substituted with one, two, three, or four substituents as defined herein. In some embodiments of a compound disclosed herein, each $R^3$, $R^6$, $R^8$, $R^a$, $R^b$, $R^c$, $R^d$, the ring formed when: two $R^4$ are taken together, $R^7$ and $R^8$ are taken together, and $R^c$ and $R^d$ are taken together, is optionally and independently substituted with one, two, or three substituents as defined herein. In some embodiments of a compound disclosed herein, each $R^3$, $R^6$, $R^8$, $R^a$, $R^b$, $R^c$, $R^d$, the ring formed when: two $R^4$ are taken together, $R^7$ and $R^8$ are taken together, and $R^c$ and $R^d$ are taken together, is optionally and independently substituted with one or two substituents as defined herein.

In some embodiments of a compound disclosed herein, one or more hydrogen on Ring A, Ring B, or Ring C is replaced with one or more deuteriums.

In some embodiments of a compound disclosed herein, one or more of R, $R^3$, $R^{3a}$, $R^4$, $R^{4a}$, $R^5$, $R^6$, $R^{6a}$, $R^7$, $R^{7a}$, $R^8$, $R^{8a}$, $R^9$, $R^{9a}$, $R^{10}$, $R^a$, $R^b$, $R^c$, and/or $R^d$ groups comprise deuterium at a percentage higher than the natural abundance of deuterium.

In some embodiments of a compound disclosed herein, one or more hydrogens are replaced with one or more deuteriums in one or more of the following groups R, $R^3$, $R^{3a}$, $R^4$, $R^{4a}$, $R^5$, $R^6$, $R^{6a}$, $R^7$, $R^{7a}$, $R^8$, $R^{8a}$, $R^9$, $R^{9a}$, $R^{10}$, $R^a$, $R^b$, $R^c$, and/or $R^d$.

In some embodiments of a compound disclosed herein, the abundance of deuterium in each of R, $R^3$, $R^{3a}$, $R^4$, $R^{4a}$, $R^5$, $R^6$, $R^{6a}$, $R^7$, $R^{7a}$, $R^8$, $R^{8a}$, $R^9$, $R^{9a}$, $R^{10}$, $R^a$, $R^b$, $R^c$, and/or $R^d$ is independently at least 100, at least 10%, at least 20%, at least 30%, at least 40%, at least 50%, at least 60%, at least 70%, at least 80%, at least 90%, or 10000 of a total number of hydrogen and deuterium.

Any combination of the groups described above for the various variables is contemplated herein. Throughout the specification, groups and substituents thereof are chosen by one skilled in the field to provide stable moieties and compounds.

In some embodiments the compound disclosed herein, or a pharmaceutically acceptable salt, solvate, or stereoisomer thereof, is one of the compounds in Table 1.

TABLE 1

| Ex.* | Structures |
|---|---|
| 1 (a and b) | 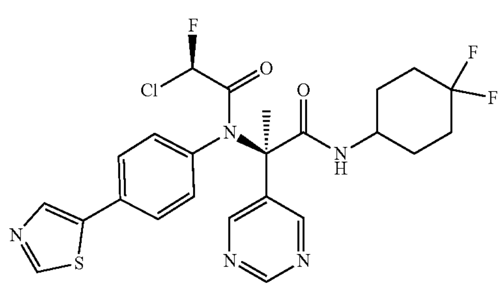 [SMILES: C[C@](C(=O)NC1CCC(F)(F)CC1)(c1cncnc1)N(C(=O)[C@H](F)Cl)c1ccc(-c2cncs2)cc1] |

TABLE 1-continued
| Ex.* | Structures |
|---|---|
| 2 (a and b) | 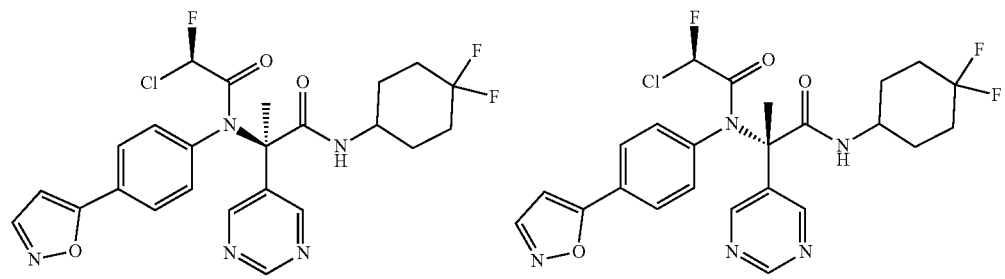 |
| 3 (a and b) | 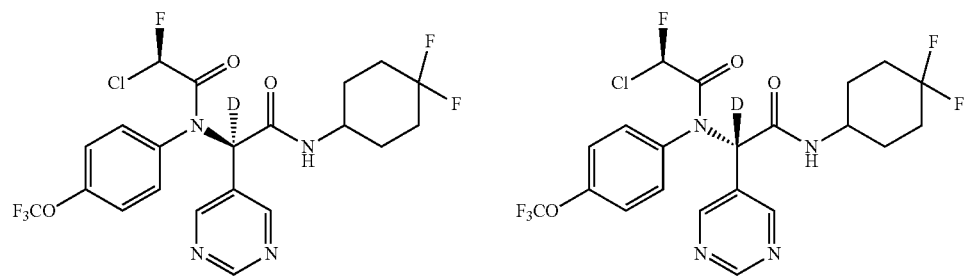 |
| 4 (a and b) | 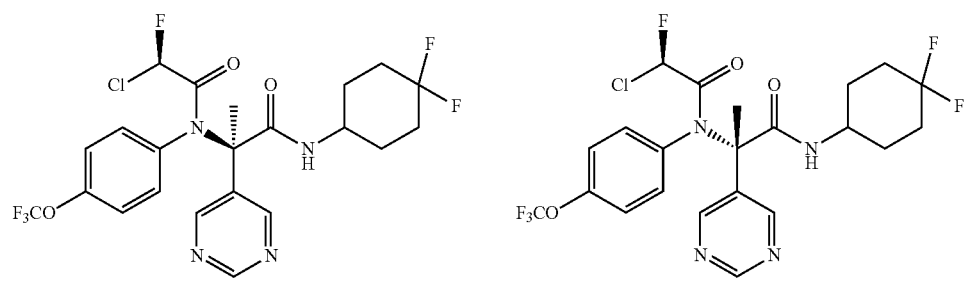 |
| 5 (a and b) | 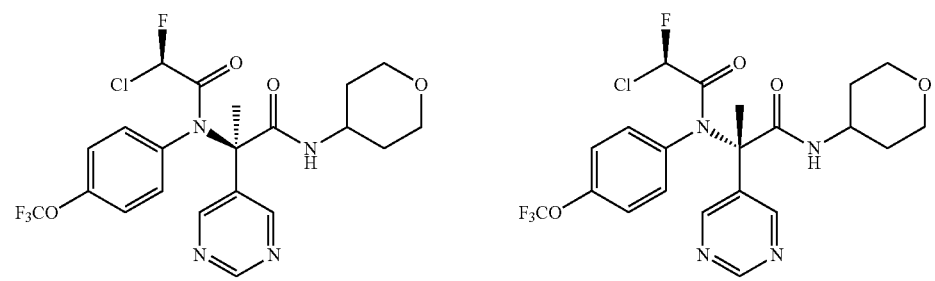 |
| 6 (a, b, c, and d) | 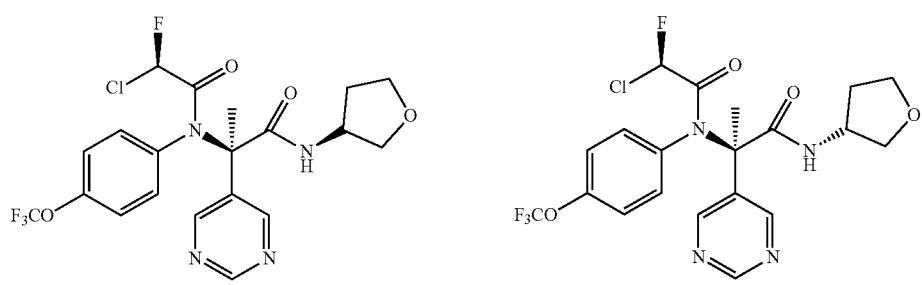 |

TABLE 1-continued
| Ex.* | Structures | |
|---|---|---|
| | 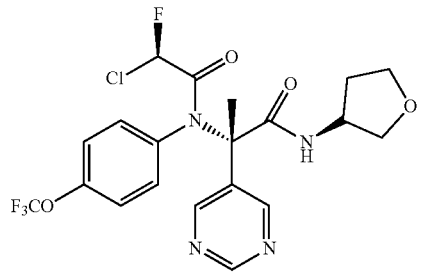 | 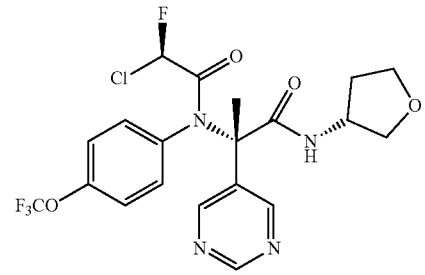 |
| 7 (a, b, c, and d) | 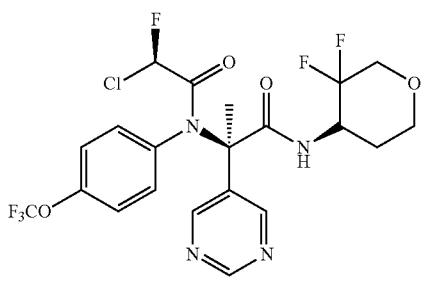 | 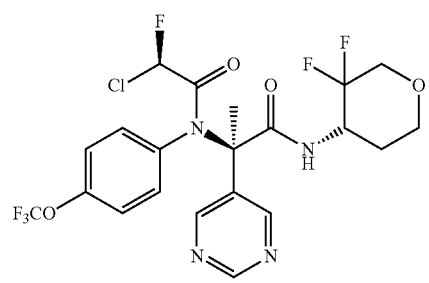 |
| | 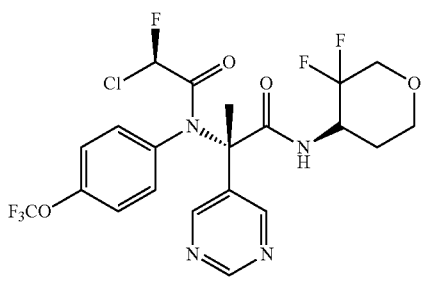 | 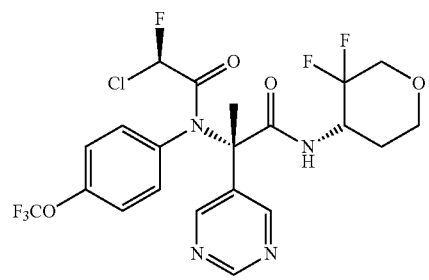 |
| 8 (a and b) | 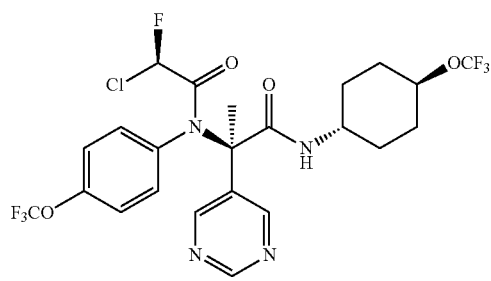 [SMILES: C[C@](C(=O)N[C@H]1CC[C@H](OC(F)(F)F)CC1)(c1cncnc1)N(C(=O)[C@H](F)Cl)c1ccc(OC(F)(F)F)cc1] | 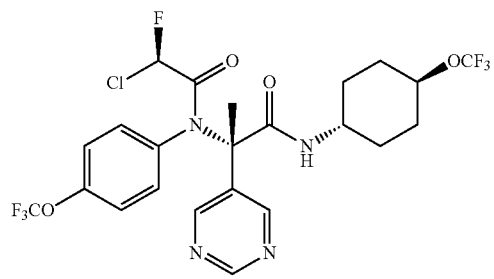 [SMILES: C[C@@](C(=O)N[C@H]1CC[C@H](OC(F)(F)F)CC1)(c1cncnc1)N(C(=O)[C@H](F)Cl)c1ccc(OC(F)(F)F)cc1] |
| 9 (a and b) | 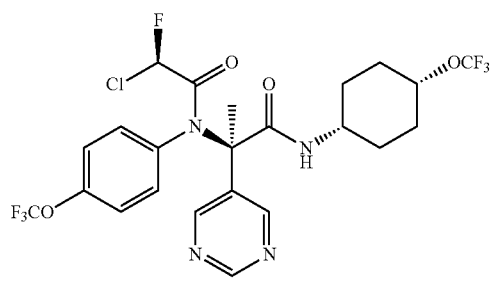 [SMILES: C[C@](C(=O)N[C@H]1CC[C@@H](OC(F)(F)F)CC1)(c1cncnc1)N(C(=O)[C@H](F)Cl)c1ccc(OC(F)(F)F)cc1] | 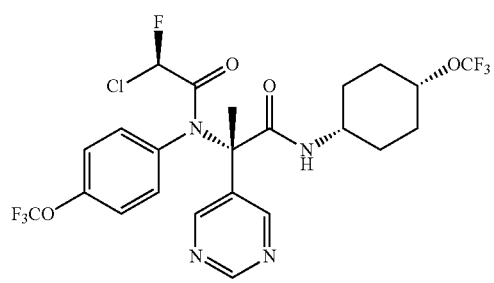 [SMILES: C[C@@](C(=O)N[C@H]1CC[C@@H](OC(F)(F)F)CC1)(c1cncnc1)N(C(=O)[C@H](F)Cl)c1ccc(OC(F)(F)F)cc1] |

TABLE 1-continued

| Ex.* | Structures |
|---|---|
| 10 (a and b) | 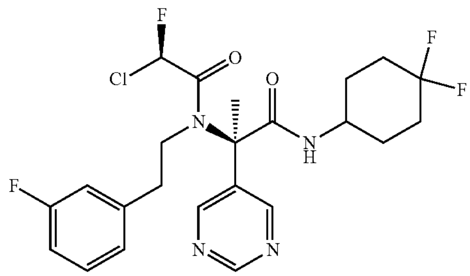 [SMILES: C[C@](C(=O)NC1CCC(F)(F)CC1)(c1cncnc1)N(CCc1cccc(F)c1)C(=O)[C@H](F)Cl] |
| 11 (a and b) | 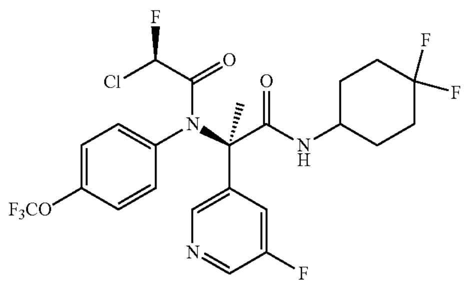 [SMILES: C[C@](C(=O)NC1CCC(F)(F)CC1)(c1cncc(F)c1)N(C(=O)[C@H](F)Cl)c1ccc(OC(F)(F)F)cc1] |
| 12 (a and b) | 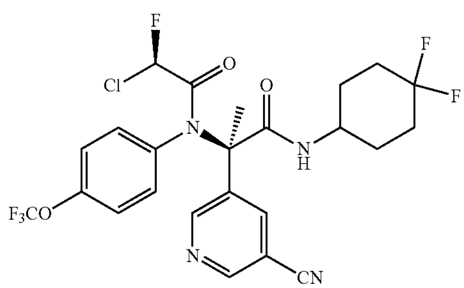 [SMILES: C[C@](C(=O)NC1CCC(F)(F)CC1)(c1cncc(C#N)c1)N(C(=O)[C@H](F)Cl)c1ccc(OC(F)(F)F)cc1] |
| 13 (a and b) | 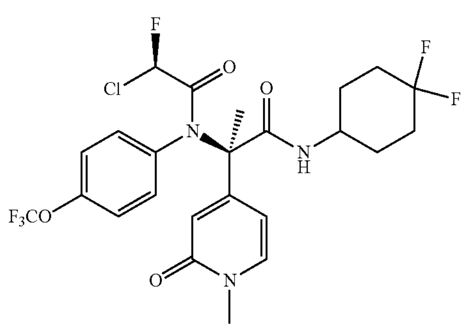 [SMILES: Cn1ccc([C@](C)(C(=O)NC2CCC(F)(F)CC2)N(C(=O)[C@H](F)Cl)c2ccc(OC(F)(F)F)cc2)cc1=O] |
| 14 (a and b) | 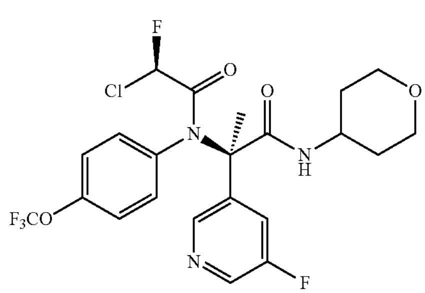 |

TABLE 1-continued

| Ex.* | Structures |
|---|---|
| 15 (a and b) | 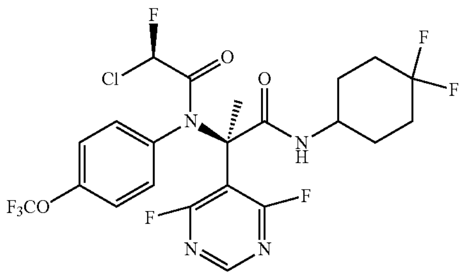 [SMILES: C[C@](C(=O)NC1CCC(F)(F)CC1)(c1c(F)ncnc1F)N(C(=O)[C@H](F)Cl)c1ccc(OC(F)(F)F)cc1] |
| 16 (a and b) | 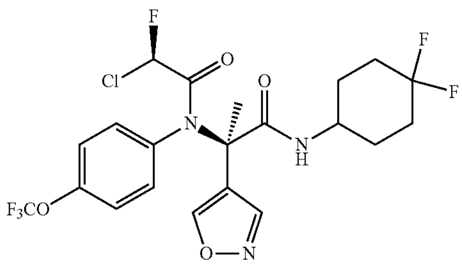 [SMILES: C[C@](C(=O)NC1CCC(F)(F)CC1)(c1cnoc1)N(C(=O)[C@H](F)Cl)c1ccc(OC(F)(F)F)cc1] |
| 17 (a and b) | 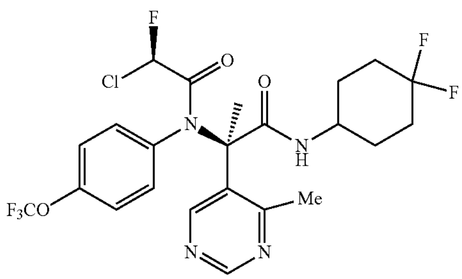 [SMILES: Cc1ncncc1[C@](C)(C(=O)NC1CCC(F)(F)CC1)N(C(=O)[C@H](F)Cl)c1ccc(OC(F)(F)F)cc1] |
| 18 (a and b) | 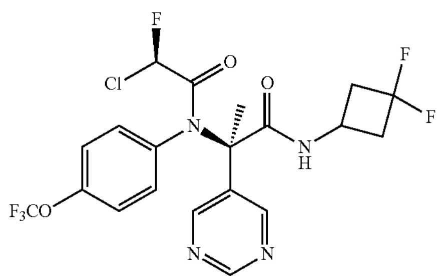 [SMILES: C[C@](C(=O)NC1CC(F)(F)C1)(c1cncnc1)N(C(=O)[C@H](F)Cl)c1ccc(OC(F)(F)F)cc1] |
| 19 (a and b) | 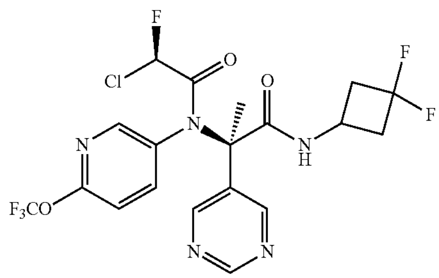 [SMILES: C[C@](C(=O)NC1CC(F)(F)C1)(c1cncnc1)N(C(=O)[C@H](F)Cl)c1ccc(OC(F)(F)F)nc1] |

TABLE 1-continued
| Ex.* | Structures |
|---|---|
| 20 (a and b) | 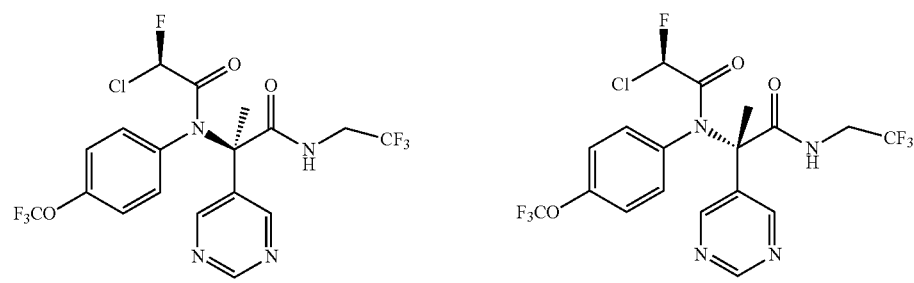 |
| 21 (a and b) | 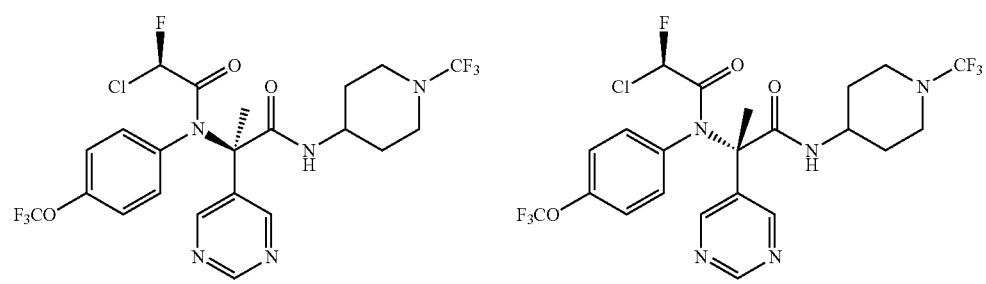 |
| 22 (a and b) | 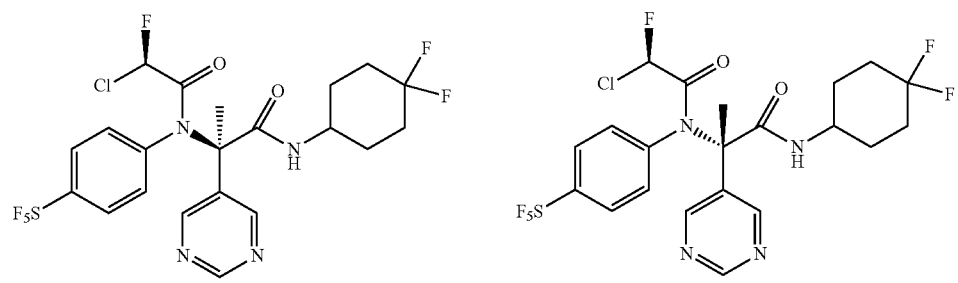 |
| 23 (a and b) | 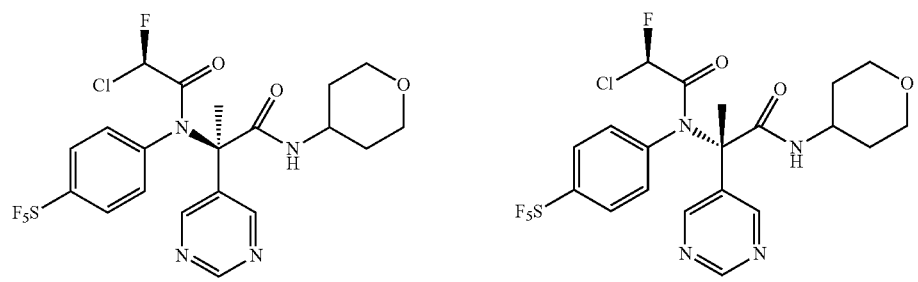 |
| 24 (a and b) | 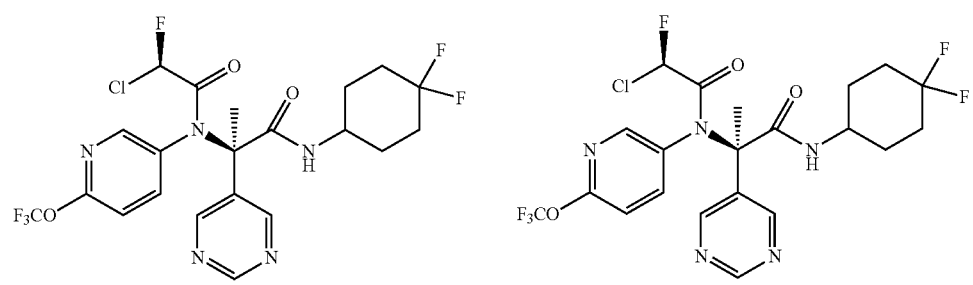 |

TABLE 1-continued
| Ex.* | Structures |
|---|---|
| 25 (a and b) | 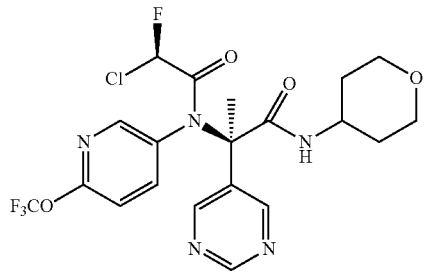 [SMILES: C[C@](C(=O)NC1CCOCC1)(c1cncnc1)N(C(=O)[C@H](F)Cl)c1ccc(OC(F)(F)F)nc1] 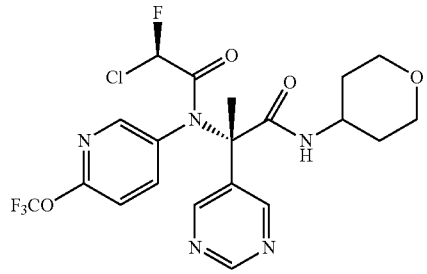 [SMILES: C[C@@](C(=O)NC1CCOCC1)(c1cncnc1)N(C(=O)[C@H](F)Cl)c1ccc(OC(F)(F)F)nc1] |
| 26 (a and b) | 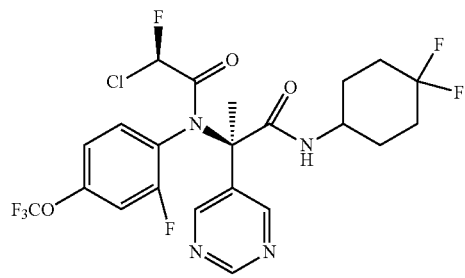 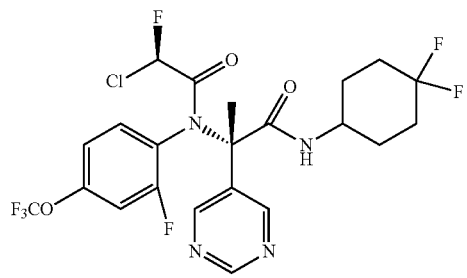 [SMILES: C[C@@](C(=O)NC1CCC(F)(F)CC1)(c1cncnc1)N(C(=O)[C@H](F)Cl)c1ccc(OC(F)(F)F)cc1F] |
| 27 (a and b) | 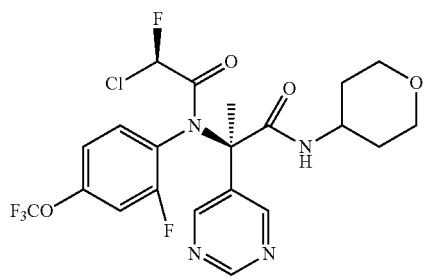 [SMILES: C[C@](C(=O)NC1CCOCC1)(c1cncnc1)N(C(=O)[C@H](F)Cl)c1ccc(OC(F)(F)F)cc1F] 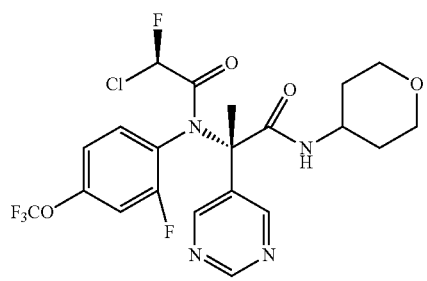 [SMILES: C[C@@](C(=O)NC1CCOCC1)(c1cncnc1)N(C(=O)[C@H](F)Cl)c1ccc(OC(F)(F)F)cc1F] |
| 28 (a and b) | 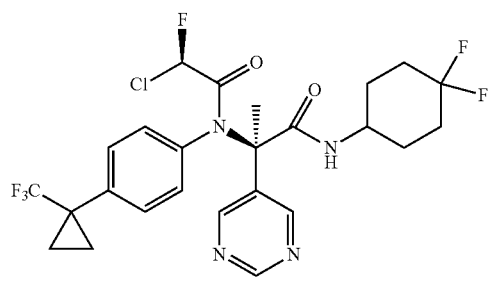 [SMILES: C[C@](C(=O)NC1CCC(F)(F)CC1)(c1cncnc1)N(C(=O)[C@H](F)Cl)c1ccc(C2(C(F)(F)F)CC2)cc1] 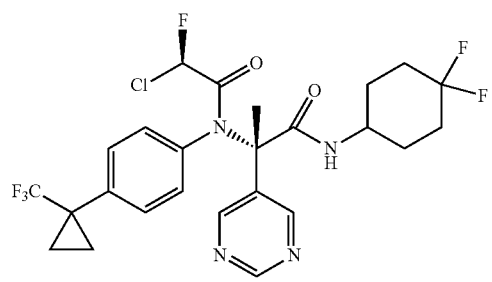 |
| 29 (a and b) | 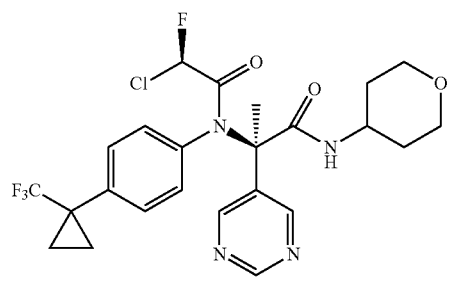 [SMILES: C[C@](C(=O)NC1CCOCC1)(c1cncnc1)N(C(=O)[C@H](F)Cl)c1ccc(C2(C(F)(F)F)CC2)cc1] 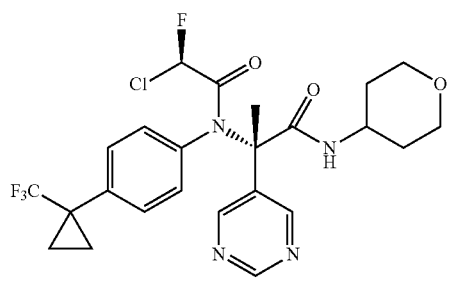 [SMILES: C[C@@](C(=O)NC1CCOCC1)(c1cncnc1)N(C(=O)[C@H](F)Cl)c1ccc(C2(C(F)(F)F)CC2)cc1] |

TABLE 1-continued
| Ex.* | Structures |
|---|---|
| 30 (a and b) | 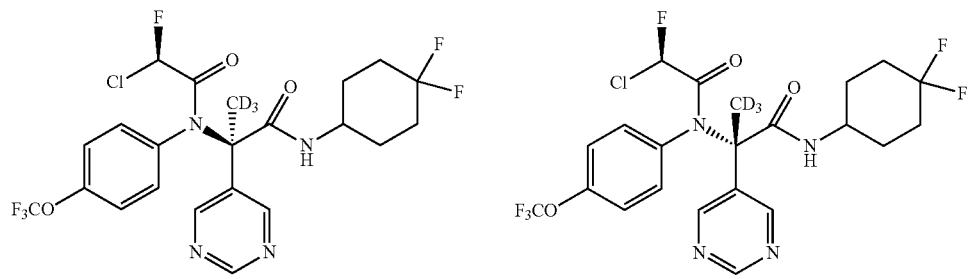 |
| 31 (a, b, c, and d) | 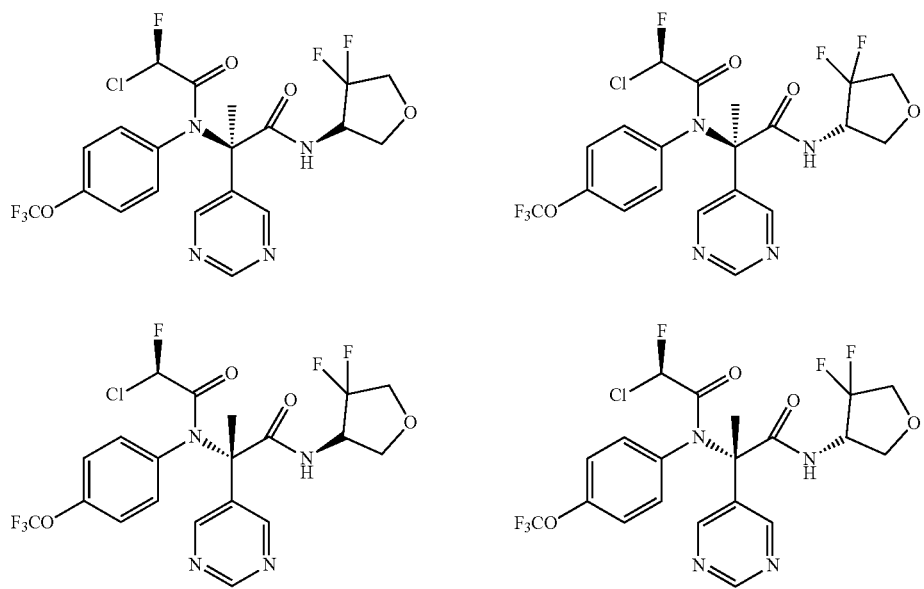 |
| 32 (a and b) | 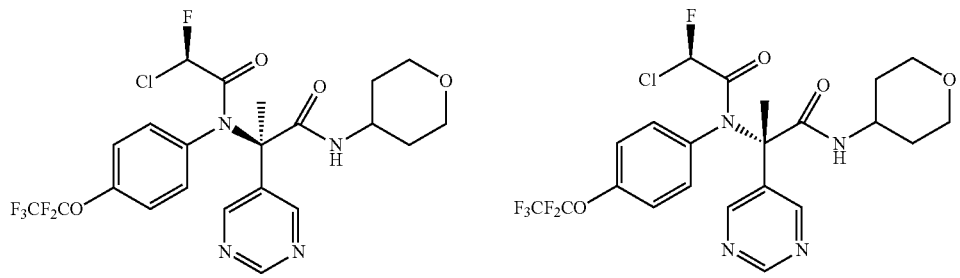 |
| 33 (a and b) | 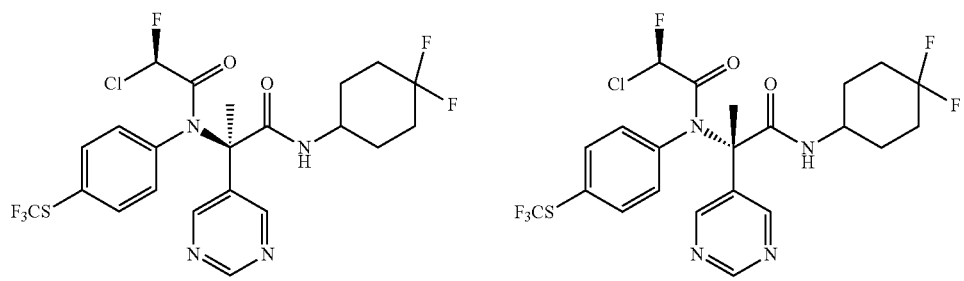 |

TABLE 1-continued
| Ex.* | Structures |
|---|---|
| 34 (a and b) | 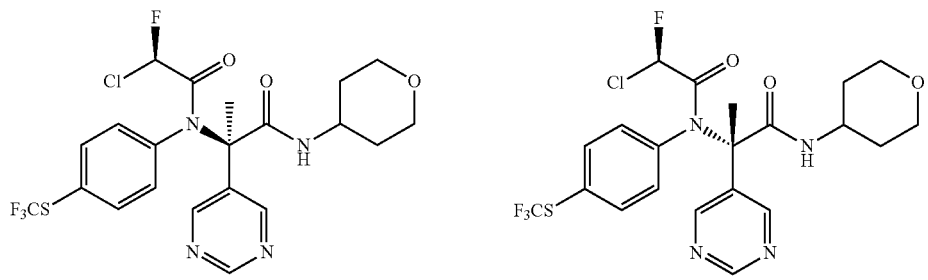 |
| 35 (a, b, c, and d) | 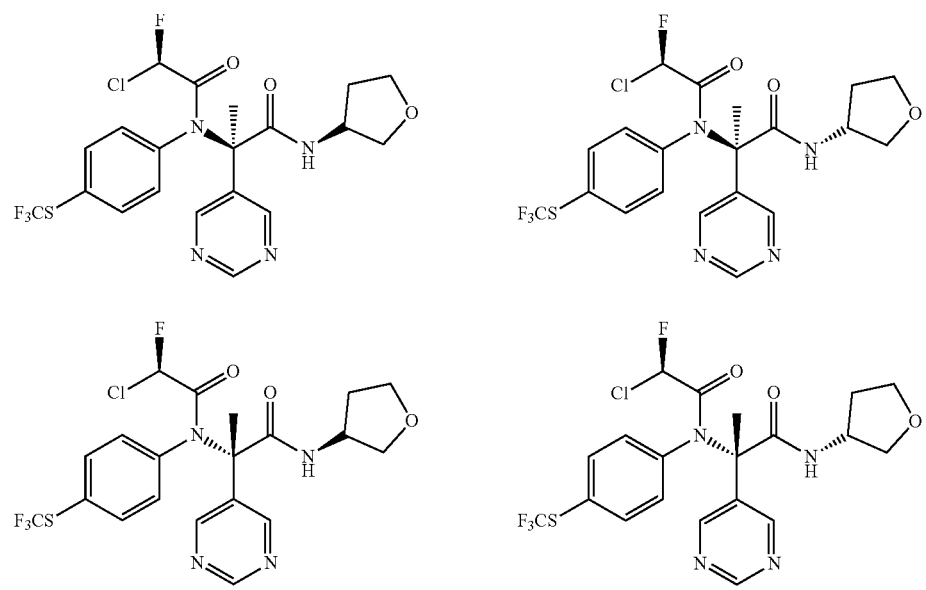 |
| 36 (a and b) | 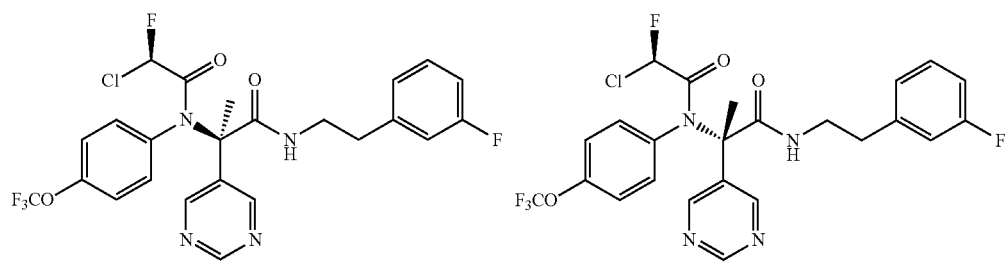 |
| 37 (a and b) | 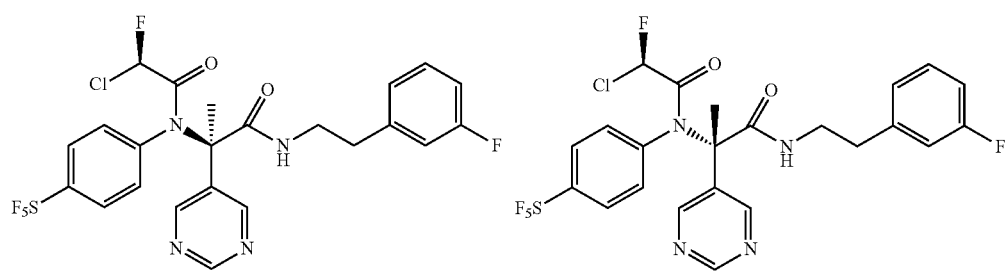 |

TABLE 1-continued
| Ex.* | Structures |
|---|---|
| 38 (a and b) | 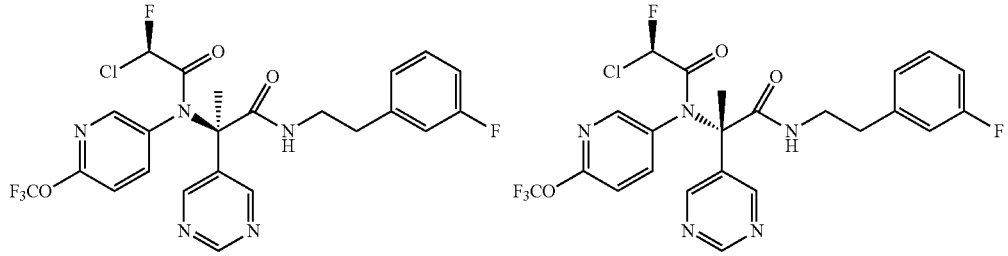 |
| 39 (a and b) | 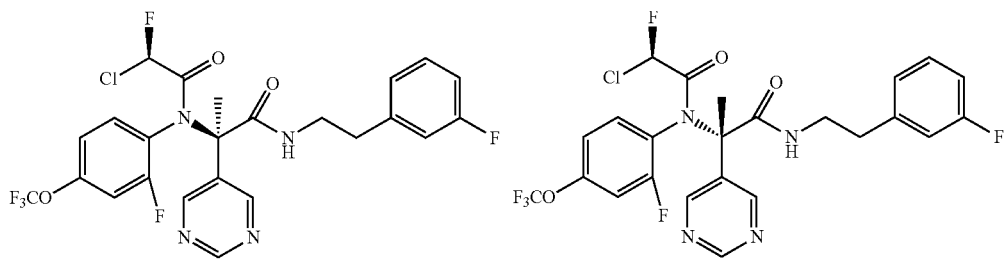 |
| 40 (a and b) | 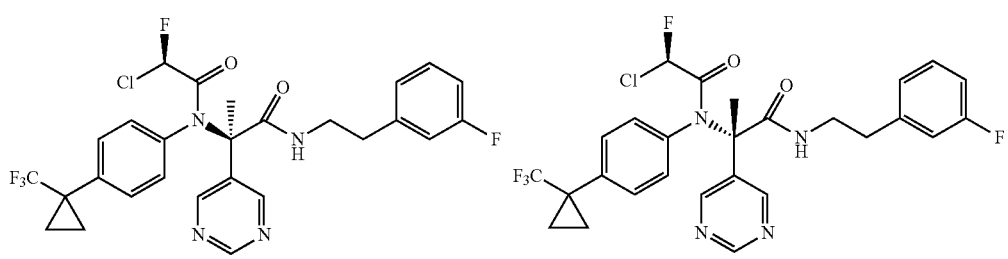 |
| 41 (a and b) | 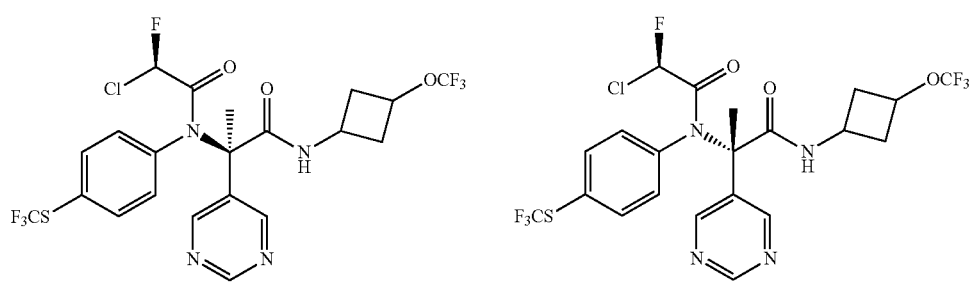 |
| 42 (a, b, c, and d) | 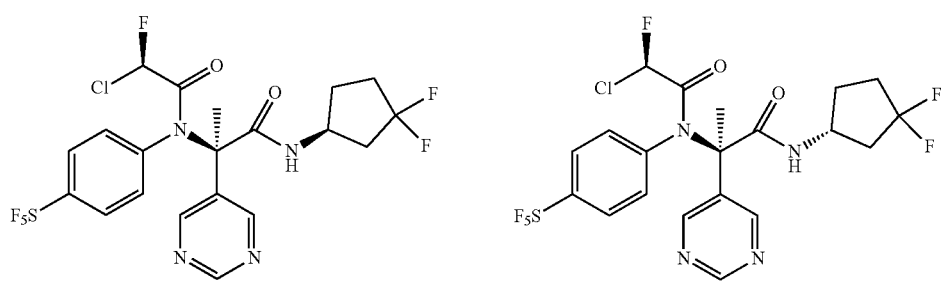 |

TABLE 1-continued
| Ex.* | Structures | |
|---|---|---|
| | 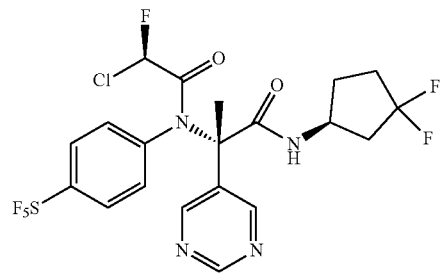 | 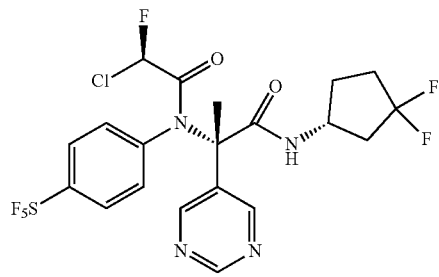 |
| 43 (a, b, c, and d) | 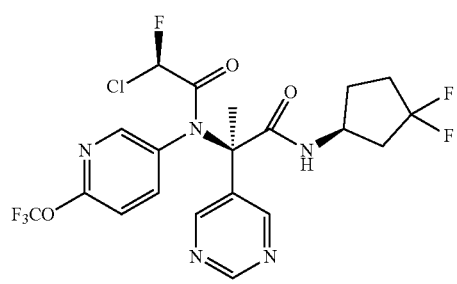 [SMILES: C[C@](C(=O)N[C@H]1CCC(F)(F)C1)(c1cncnc1)N(C(=O)[C@H](F)Cl)c1ccc(OC(F)(F)F)nc1] | 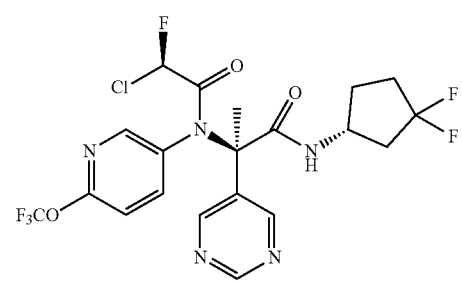 [SMILES: C[C@](C(=O)N[C@@H]1CCC(F)(F)C1)(c1cncnc1)N(C(=O)[C@H](F)Cl)c1ccc(OC(F)(F)F)nc1] |
| | 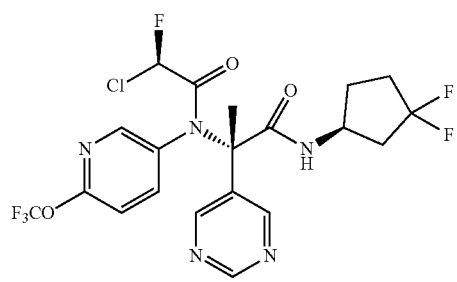 [SMILES: C[C@@](C(=O)N[C@H]1CCC(F)(F)C1)(c1cncnc1)N(C(=O)[C@H](F)Cl)c1ccc(OC(F)(F)F)nc1] | 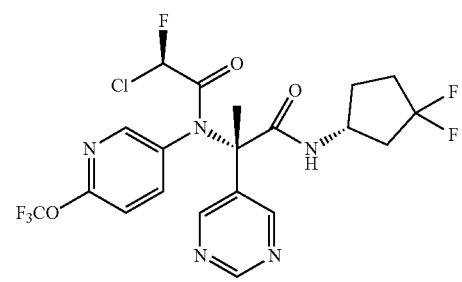 [SMILES: C[C@@](C(=O)N[C@@H]1CCC(F)(F)C1)(c1cncnc1)N(C(=O)[C@H](F)Cl)c1ccc(OC(F)(F)F)nc1] |
| 44 (a, b, c, and d) | 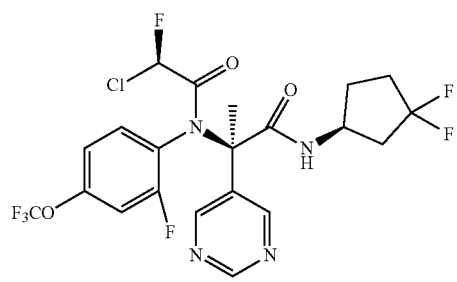 [SMILES: C[C@](C(=O)N[C@H]1CCC(F)(F)C1)(c1cncnc1)N(C(=O)[C@H](F)Cl)c1ccc(OC(F)(F)F)cc1F] | 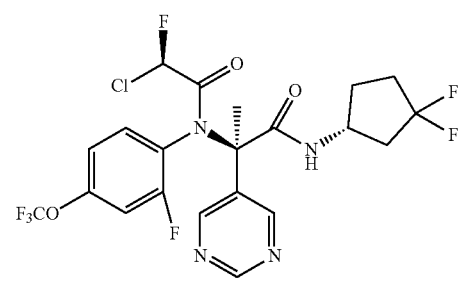 [SMILES: C[C@](C(=O)N[C@@H]1CCC(F)(F)C1)(c1cncnc1)N(C(=O)[C@H](F)Cl)c1ccc(OC(F)(F)F)cc1F] |
| | 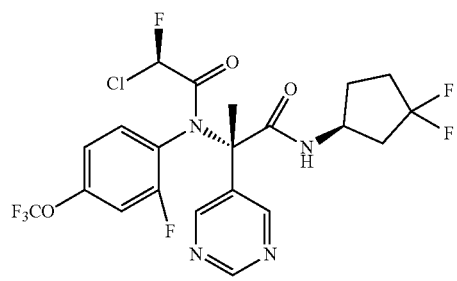 [SMILES: C[C@@](C(=O)N[C@H]1CCC(F)(F)C1)(c1cncnc1)N(C(=O)[C@H](F)Cl)c1ccc(OC(F)(F)F)cc1F] | 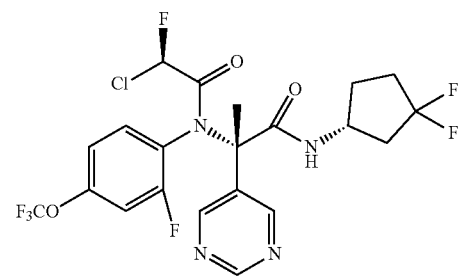 [SMILES: C[C@@](C(=O)N[C@@H]1CCC(F)(F)C1)(c1cncnc1)N(C(=O)[C@H](F)Cl)c1ccc(OC(F)(F)F)cc1F] |

TABLE 1-continued
| Ex.* | Structures |
|---|---|
| 45 (a, b, c, and d) | 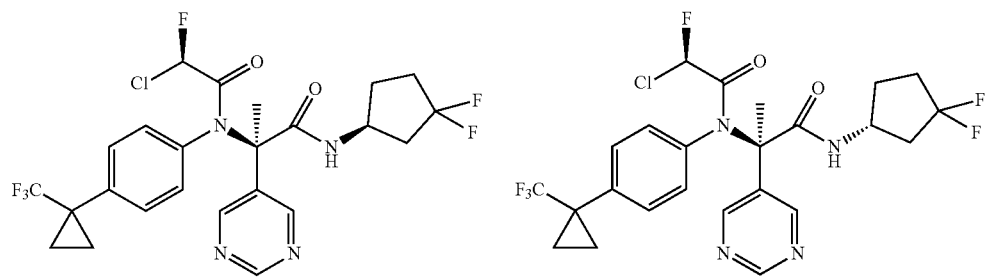 |
| 46 (a, b, c, and d) | 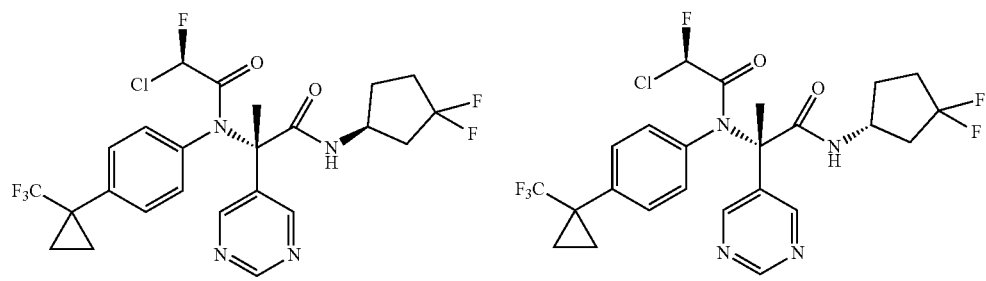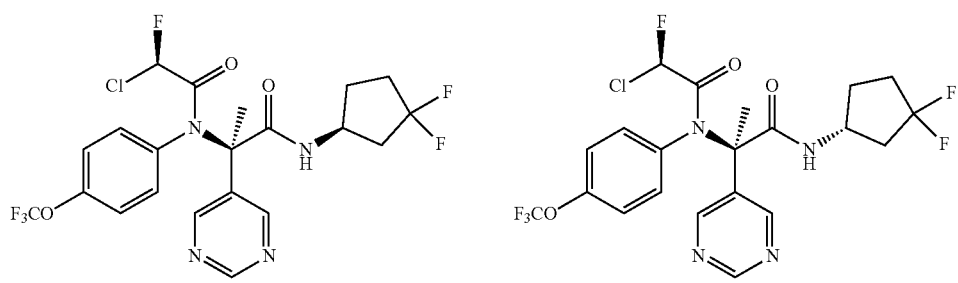 |
| 47 (a and b) | 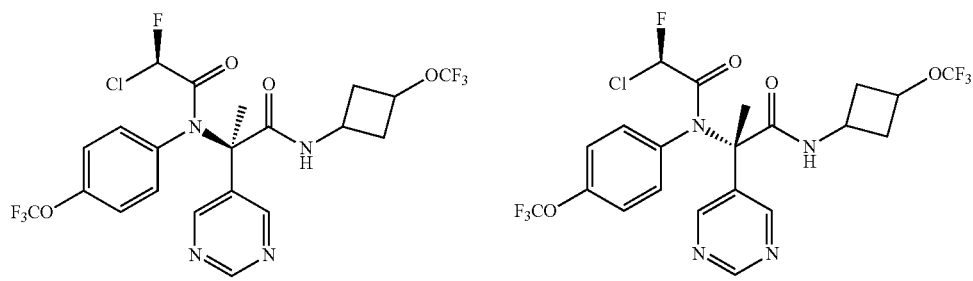 |

TABLE 1-continued

| Ex.* | Structures |
|---|---|
| 48 (a and b) | 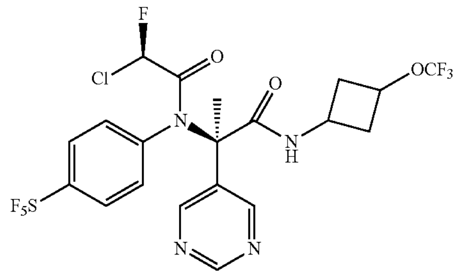 |
| 49 (a and b) | 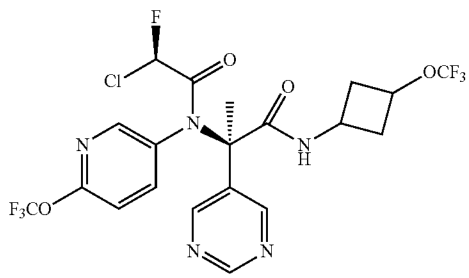 [SMILES: C[C@](C(=O)NC1CC(OC(F)(F)F)C1)(c1cncnc1)N(C(=O)[C@H](F)Cl)c1ccc(OC(F)(F)F)nc1] |
| 50 (a and b) | 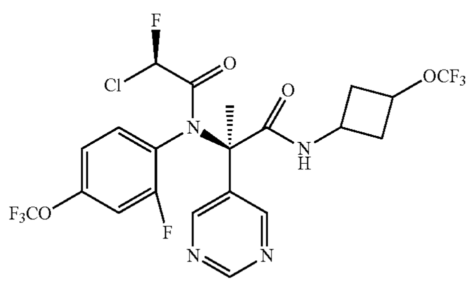 [SMILES: C[C@](C(=O)NC1CC(OC(F)(F)F)C1)(c1cncnc1)N(C(=O)[C@H](F)Cl)c1ccc(OC(F)(F)F)cc1F] |
| 51 (a and b) | 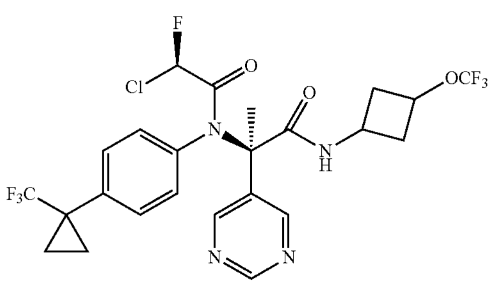 [SMILES: C[C@](C(=O)NC1CC(OC(F)(F)F)C1)(c1cncnc1)N(C(=O)[C@H](F)Cl)c1ccc(C2(C(F)(F)F)CC2)cc1] |
| 52 (a and b) | 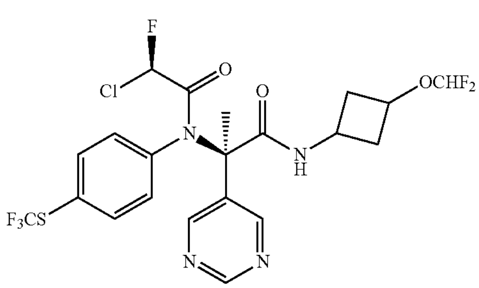 |

TABLE 1-continued
| Ex.* | Structures | |
|---|---|---|
| 53 (a and b) | 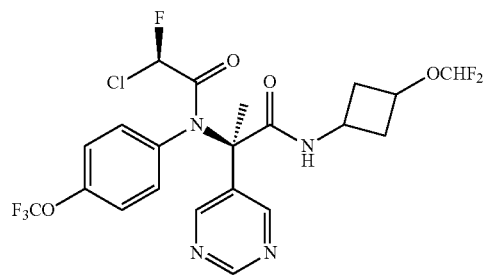 [SMILES: C[C@](C(=O)NC1CC(OC(F)F)C1)(c1cncnc1)N(C(=O)[C@H](F)Cl)c1ccc(OC(F)(F)F)cc1] | 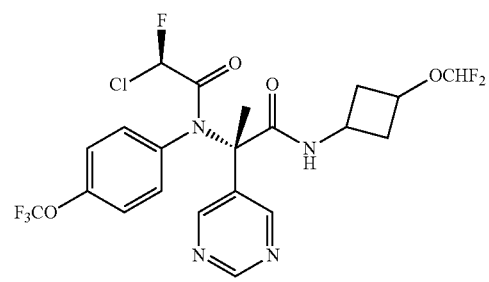 [SMILES: C[C@@](C(=O)NC1CC(OC(F)F)C1)(c1cncnc1)N(C(=O)[C@H](F)Cl)c1ccc(OC(F)(F)F)cc1] |
| 54 (a and b) | 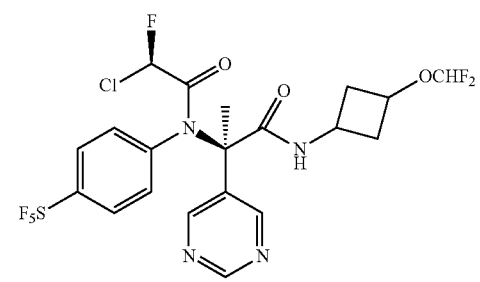 | 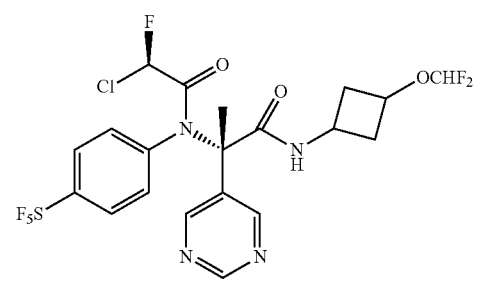 |
| 55 (a and b) | 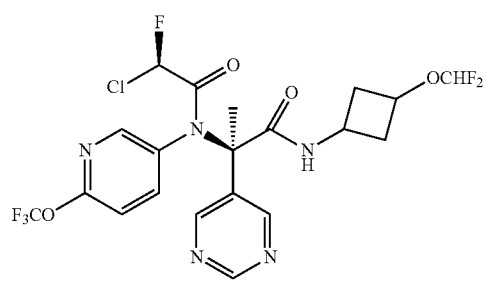 [SMILES: C[C@](C(=O)NC1CC(OC(F)F)C1)(c1cncnc1)N(C(=O)[C@H](F)Cl)c1ccc(OC(F)(F)F)nc1] | 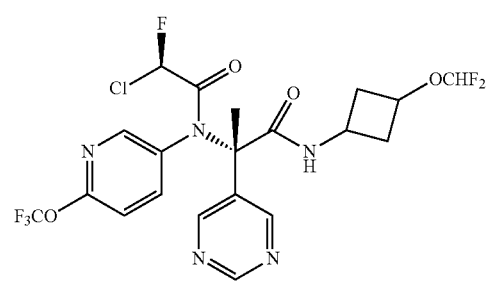 [SMILES: C[C@@](C(=O)NC1CC(OC(F)F)C1)(c1cncnc1)N(C(=O)[C@H](F)Cl)c1ccc(OC(F)(F)F)nc1] |
| 56 (a and b) | 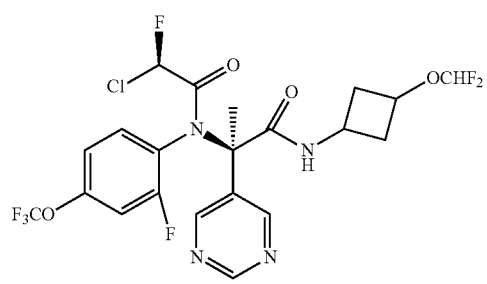 [SMILES: C[C@](C(=O)NC1CC(OC(F)F)C1)(c1cncnc1)N(C(=O)[C@H](F)Cl)c1ccc(OC(F)(F)F)cc1F] | 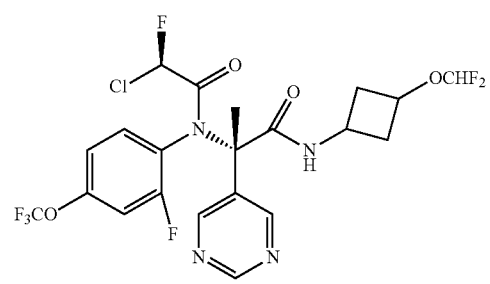 [SMILES: C[C@@](C(=O)NC1CC(OC(F)F)C1)(c1cncnc1)N(C(=O)[C@H](F)Cl)c1ccc(OC(F)(F)F)cc1F] |
| 57 (a and b) | 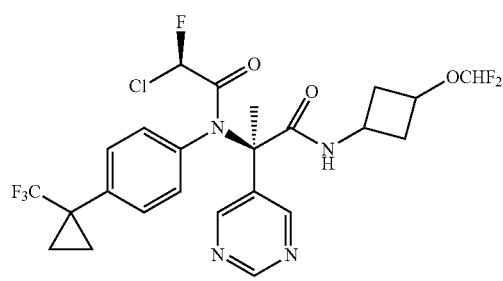 [SMILES: C[C@](C(=O)NC1CC(OC(F)F)C1)(c1cncnc1)N(C(=O)[C@H](F)Cl)c1ccc(C2(C(F)(F)F)CC2)cc1] | 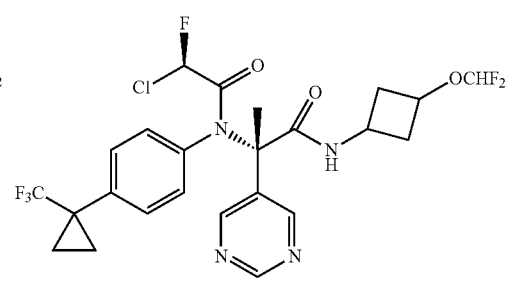 |

TABLE 1-continued
| Ex.* | Structures | |
|---|---|---|
| 58 (a, b, c, and d) | 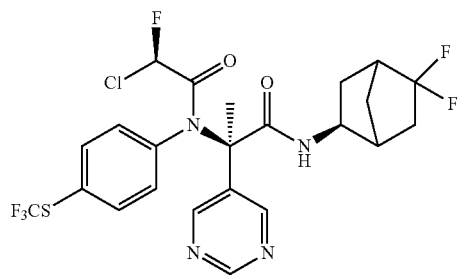 | 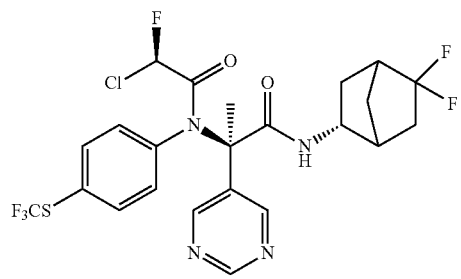 |
| | 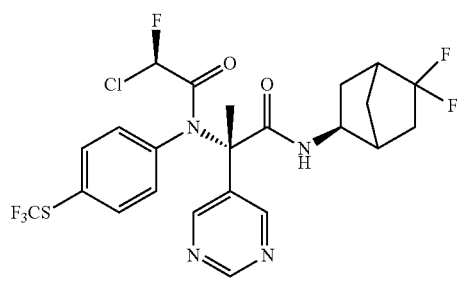 | 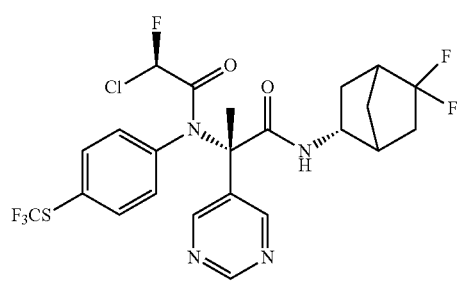 |
| 59 (a, b, c, and d) | 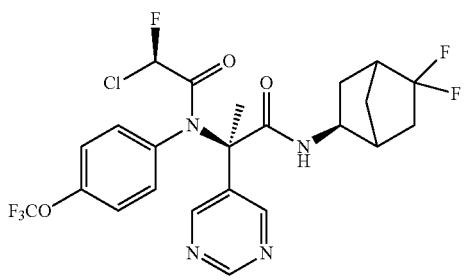 [SMILES: C[C@](C(=O)N[C@H]1CC2CC1CC2(F)F)(c1cncnc1)N(C(=O)[C@H](F)Cl)c1ccc(OC(F)(F)F)cc1] | 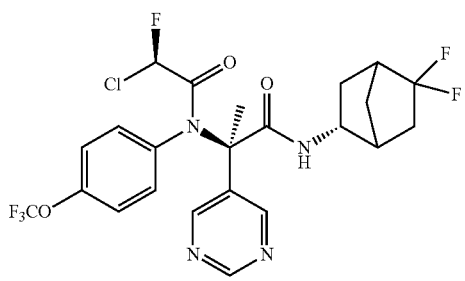 [SMILES: C[C@](C(=O)N[C@@H]1CC2CC1CC2(F)F)(c1cncnc1)N(C(=O)[C@H](F)Cl)c1ccc(OC(F)(F)F)cc1] |
| | 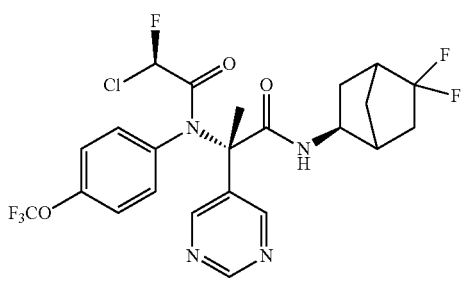 [SMILES: C[C@@](C(=O)N[C@H]1CC2CC1CC2(F)F)(c1cncnc1)N(C(=O)[C@H](F)Cl)c1ccc(OC(F)(F)F)cc1] | 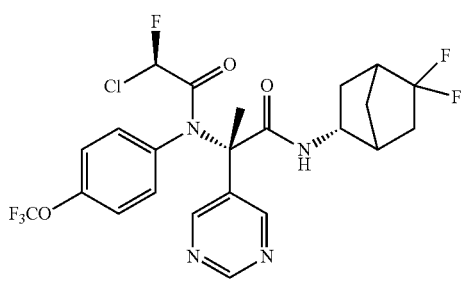 [SMILES: C[C@@](C(=O)N[C@@H]1CC2CC1CC2(F)F)(c1cncnc1)N(C(=O)[C@H](F)Cl)c1ccc(OC(F)(F)F)cc1] |
| 60 (a, b, c, and d) | 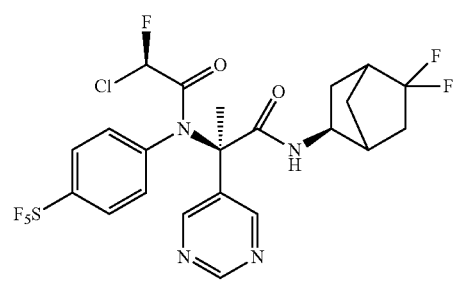 | 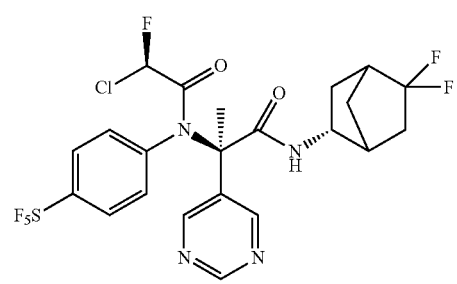 |

TABLE 1-continued
| Ex.* | Structures | |
|---|---|---|
| | 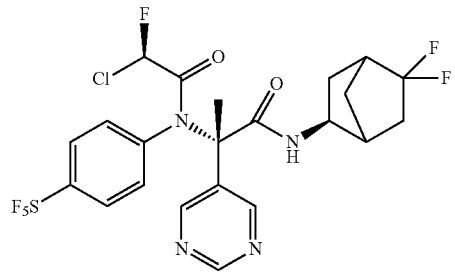 | 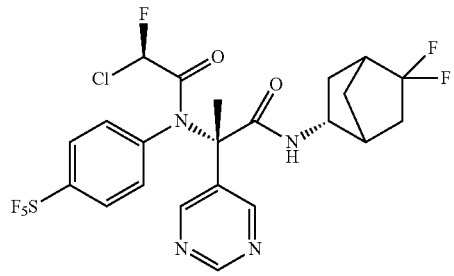 |
| 61 (a, b, c, and d) | 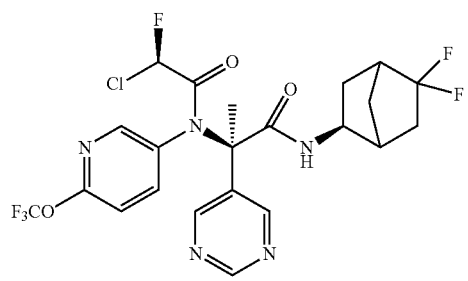 [SMILES: C[C@](C(=O)N[C@H]1CC2CC1CC2(F)F)(c1cncnc1)N(C(=O)[C@H](F)Cl)c1ccc(OC(F)(F)F)nc1] | 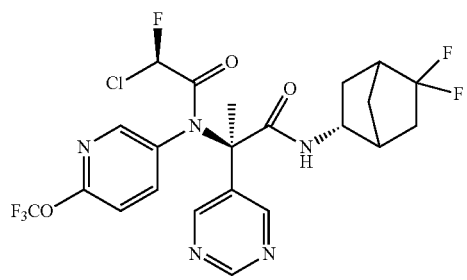 [SMILES: C[C@](C(=O)N[C@@H]1CC2CC1CC2(F)F)(c1cncnc1)N(C(=O)[C@H](F)Cl)c1ccc(OC(F)(F)F)nc1] |
| | 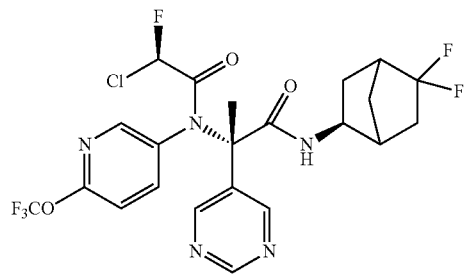 [SMILES: C[C@@](C(=O)N[C@H]1CC2CC1CC2(F)F)(c1cncnc1)N(C(=O)[C@H](F)Cl)c1ccc(OC(F)(F)F)nc1] | 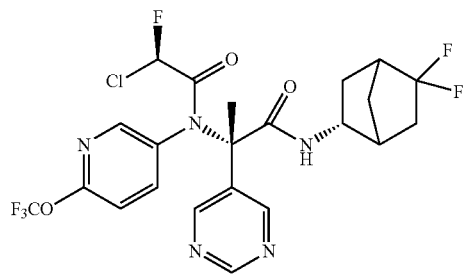 [SMILES: C[C@@](C(=O)N[C@@H]1CC2CC1CC2(F)F)(c1cncnc1)N(C(=O)[C@H](F)Cl)c1ccc(OC(F)(F)F)nc1] |
| 62 (a, b, c, and d) | 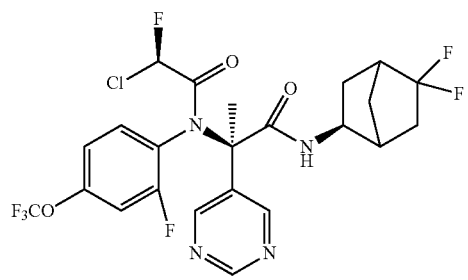 [SMILES: C[C@](C(=O)N[C@H]1CC2CC1CC2(F)F)(c1cncnc1)N(C(=O)[C@H](F)Cl)c1ccc(OC(F)(F)F)cc1F] | 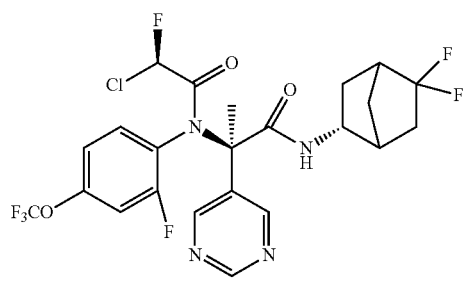 [SMILES: C[C@](C(=O)N[C@@H]1CC2CC1CC2(F)F)(c1cncnc1)N(C(=O)[C@H](F)Cl)c1ccc(OC(F)(F)F)cc1F] |
| | 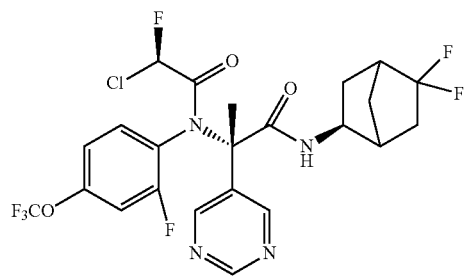 [SMILES: C[C@@](C(=O)N[C@H]1CC2CC1CC2(F)F)(c1cncnc1)N(C(=O)[C@H](F)Cl)c1ccc(OC(F)(F)F)cc1F] | 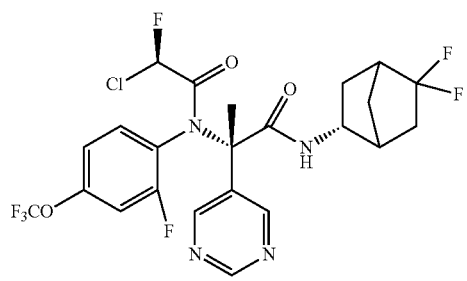 [SMILES: C[C@@](C(=O)N[C@@H]1CC2CC1CC2(F)F)(c1cncnc1)N(C(=O)[C@H](F)Cl)c1ccc(OC(F)(F)F)cc1F] |

TABLE 1-continued

| Ex.* | Structures |
|---|---|
| 63 (a, b, c, and d) | |
| 64 (a and b) | |
| 65 (a and b) | |
| 66 (a and b) | |

TABLE 1-continued
| Ex.* | Structures | |
|---|---|---|
| 67 (a and b) | 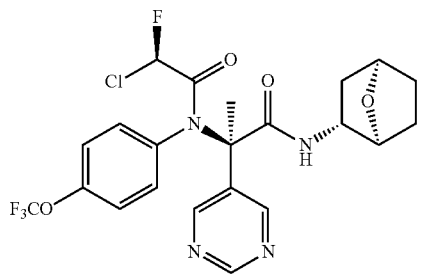 [SMILES: C[C@](C(=O)N[C@@H]1C[C@H]2CC[C@@H]1O2)(c1cncnc1)N(C(=O)[C@H](F)Cl)c1ccc(OC(F)(F)F)cc1] | 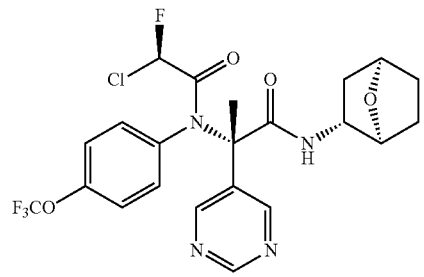 [SMILES: C[C@@](C(=O)N[C@@H]1C[C@H]2CC[C@@H]1O2)(c1cncnc1)N(C(=O)[C@H](F)Cl)c1ccc(OC(F)(F)F)cc1] |
| 68 (a and b) | 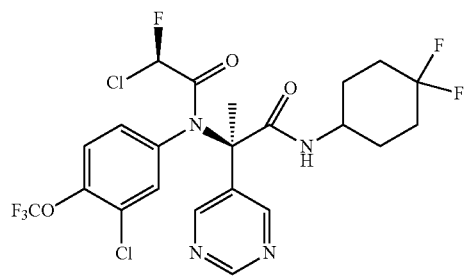 [SMILES: C[C@](C(=O)NC1CCC(F)(F)CC1)(c1cncnc1)N(C(=O)[C@H](F)Cl)c1ccc(OC(F)(F)F)c(Cl)c1] | 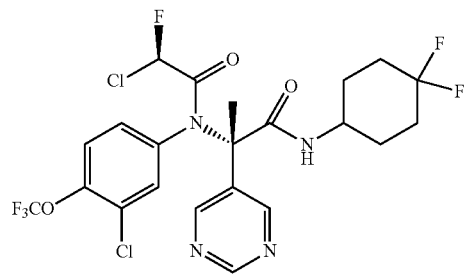 [SMILES: C[C@@](C(=O)NC1CCC(F)(F)CC1)(c1cncnc1)N(C(=O)[C@H](F)Cl)c1ccc(OC(F)(F)F)c(Cl)c1] |
| 69 (a and b) | 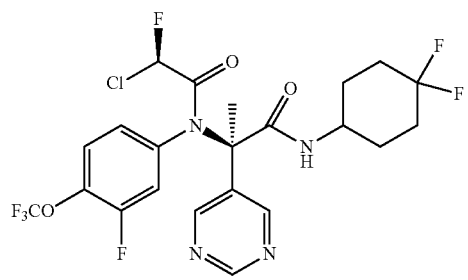 [SMILES: C[C@](C(=O)NC1CCC(F)(F)CC1)(c1cncnc1)N(C(=O)[C@H](F)Cl)c1ccc(OC(F)(F)F)c(F)c1] | 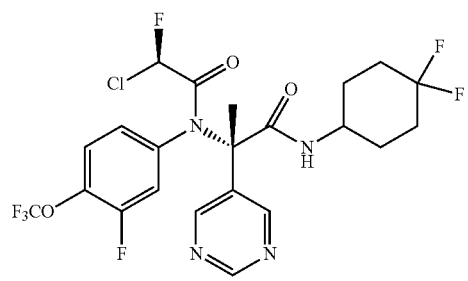 |
| 70 (a and b) | 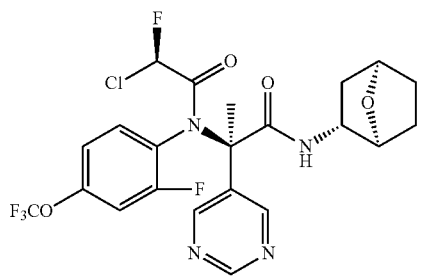 [SMILES: C[C@](C(=O)N[C@@H]1C[C@H]2CC[C@@H]1O2)(c1cncnc1)N(C(=O)[C@H](F)Cl)c1ccc(OC(F)(F)F)cc1F] | 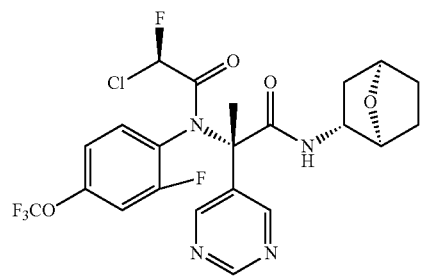 [SMILES: C[C@@](C(=O)N[C@@H]1C[C@H]2CC[C@@H]1O2)(c1cncnc1)N(C(=O)[C@H](F)Cl)c1ccc(OC(F)(F)F)cc1F] |
| 71 (a and b) | 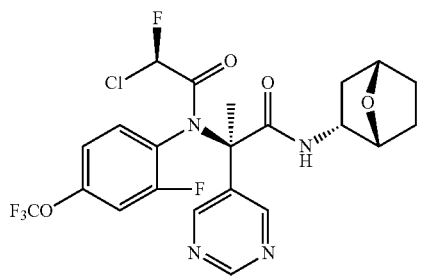 [SMILES: C[C@](C(=O)N[C@@H]1C[C@@H]2CC[C@H]1O2)(c1cncnc1)N(C(=O)[C@H](F)Cl)c1ccc(OC(F)(F)F)cc1F] | 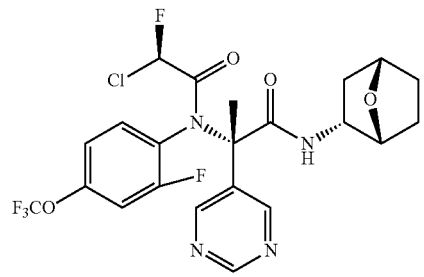 [SMILES: C[C@@](C(=O)N[C@@H]1C[C@@H]2CC[C@H]1O2)(c1cncnc1)N(C(=O)[C@H](F)Cl)c1ccc(OC(F)(F)F)cc1F] |

TABLE 1-continued
| Ex.* | Structures | |
|---|---|---|
| 72 (a and b) | 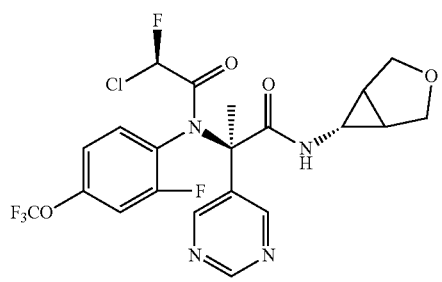 | 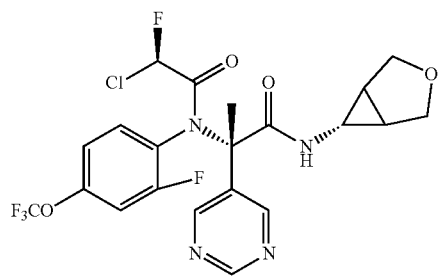 |
| 73 (a and b) | 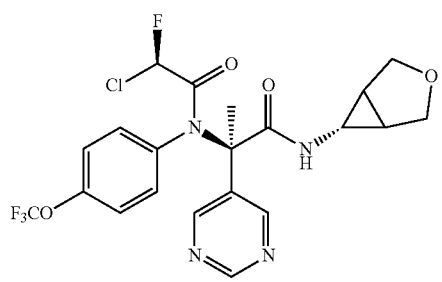 | 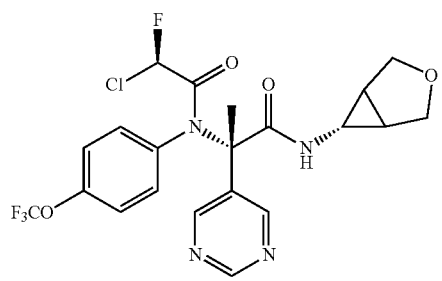 |
| 74 (a and b) | 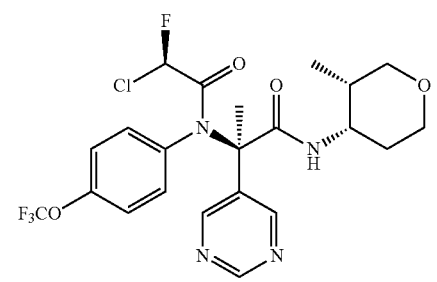 | 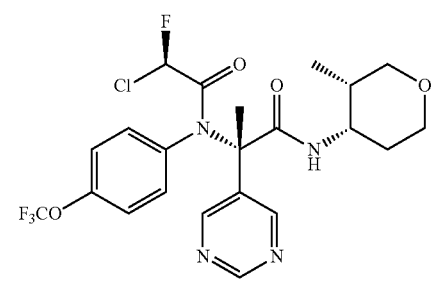 |
| 75 (a and b) | 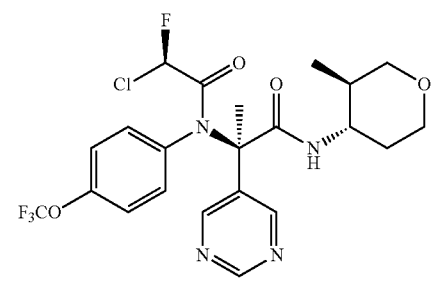 [SMILES: C[C@H]1COCC[C@@H]1NC(=O)[C@@](C)(c1cncnc1)N(C(=O)[C@H](F)Cl)c1ccc(OC(F)(F)F)cc1] | 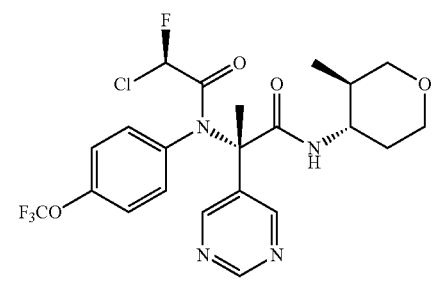 [SMILES: C[C@H]1COCC[C@@H]1NC(=O)[C@](C)(c1cncnc1)N(C(=O)[C@H](F)Cl)c1ccc(OC(F)(F)F)cc1] |
| 76 (a, b, c, and d) | 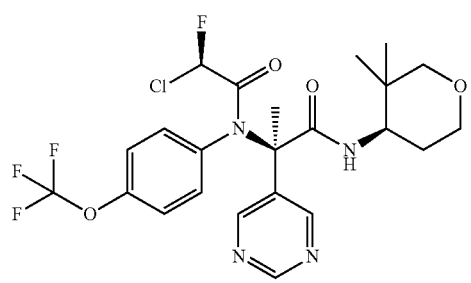 [SMILES: CC1(C)COCC[C@H]1NC(=O)[C@@](C)(c1cncnc1)N(C(=O)[C@H](F)Cl)c1ccc(OC(F)(F)F)cc1] | 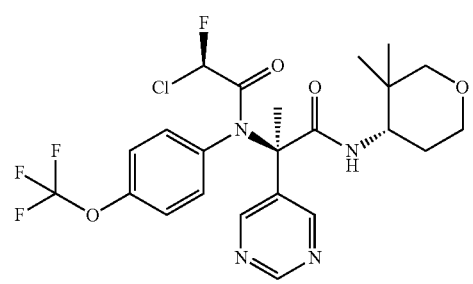 [SMILES: CC1(C)COCC[C@@H]1NC(=O)[C@@](C)(c1cncnc1)N(C(=O)[C@H](F)Cl)c1ccc(OC(F)(F)F)cc1] |

TABLE 1-continued
| Ex.* | Structures |
|---|---|
| | 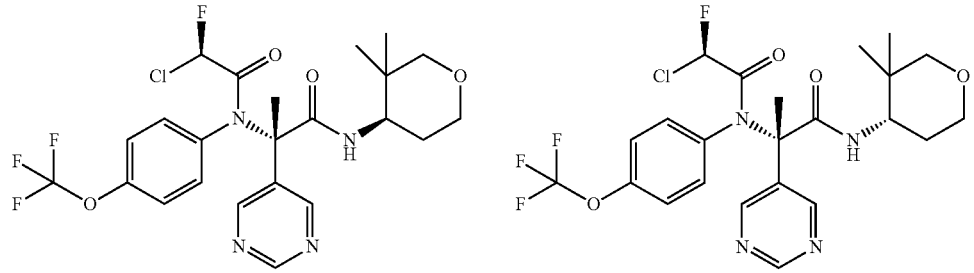 |
| 77 (a, b, c, and d) | 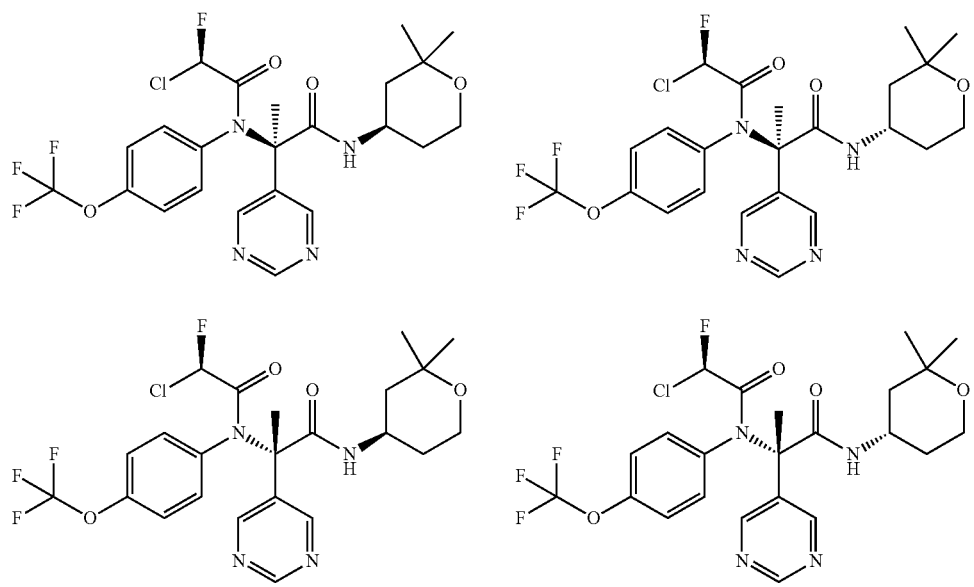 |
| 78 (a and b) | 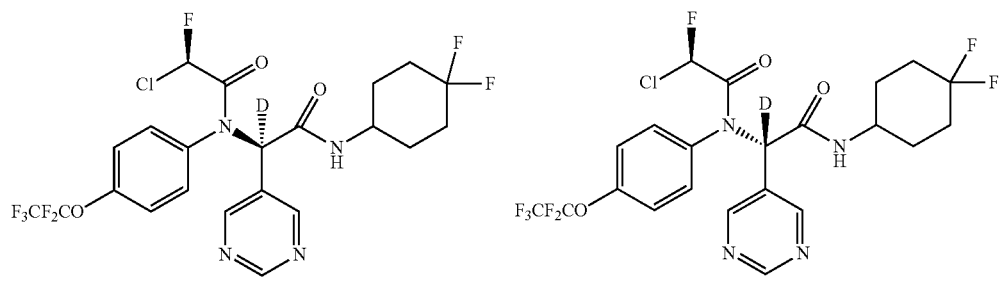 |
| 79 (a and b) | 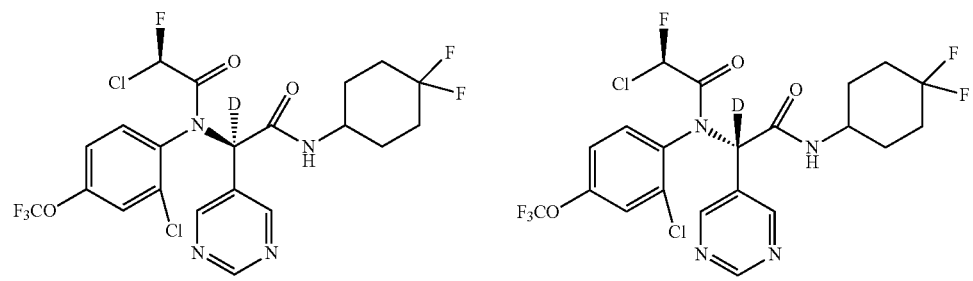 |

TABLE 1-continued
| Ex.* | Structures |
|---|---|
| 80 (a and b) | 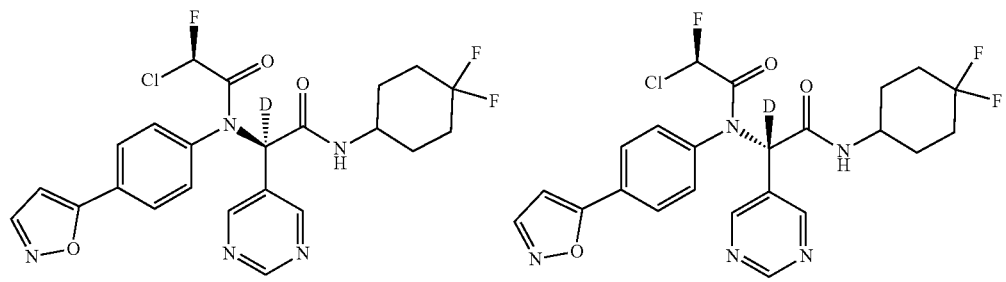 |
| 81 (a and b) | 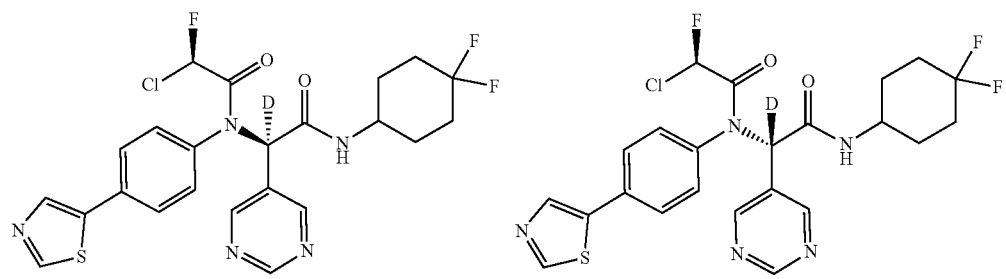 |
| 82 (a and b) | 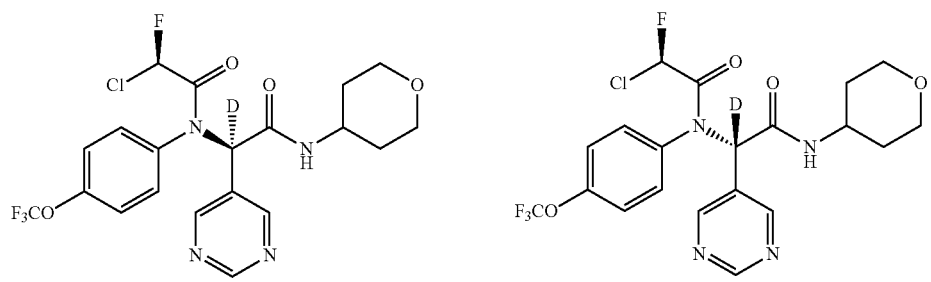 |
| 83 (a, b, c, and d) | 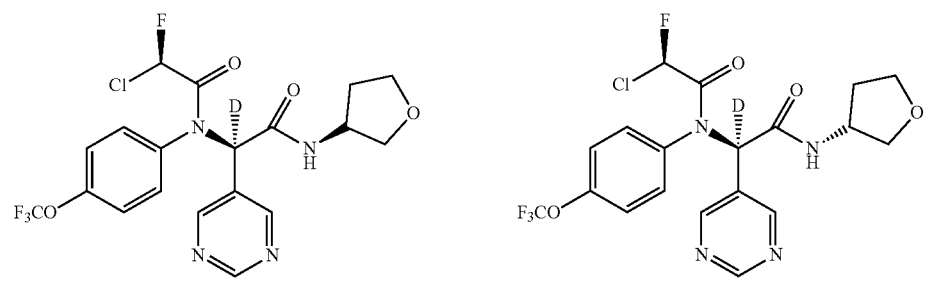 |
| | 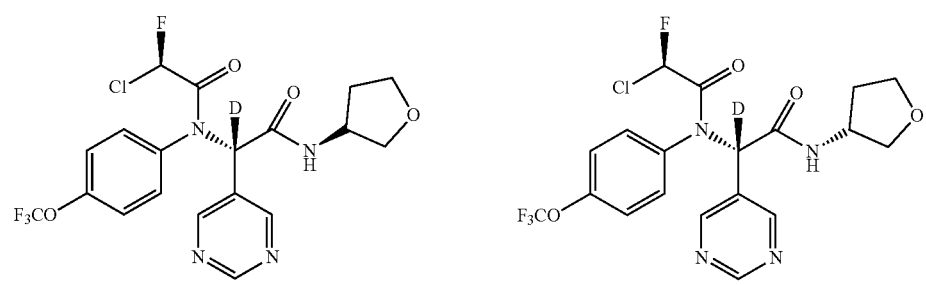 |

TABLE 1-continued

| Ex.* | Structures |
|---|---|
| 84 (a and b) | 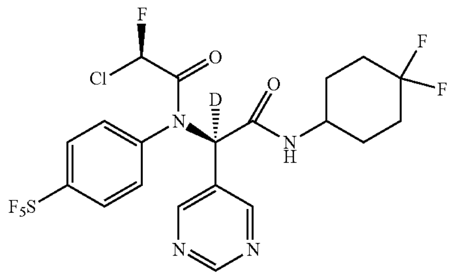 |
| 85 (a and b) | 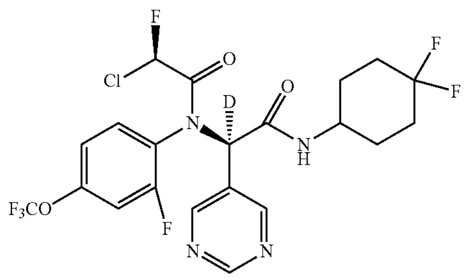 |
| 86 (a and b) | 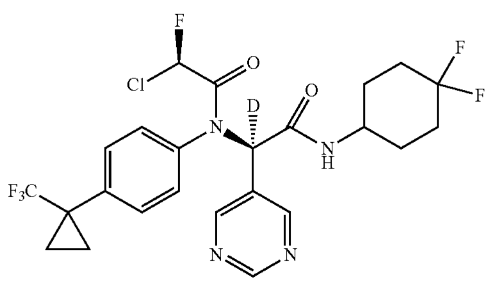 |
| 87 (a and b) | 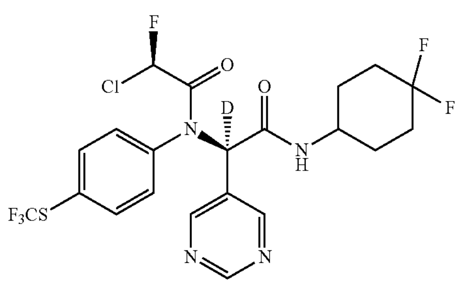 |
| 88 (a and b) | 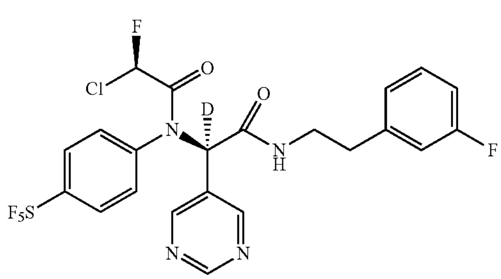 |

TABLE 1-continued

| Ex.* | Structures |
|---|---|
| 89 (a, b, c, and d) | |
| 90 (a and b) | |
| 91 (a and b) | |
| 92 (a and b) | |

TABLE 1-continued

| Ex.* | Structures |
|---|---|
| 93 (a and b) | |
| 94 (a and b) | |
| 95 (a and b) | |
| 96 (a and b) | |
| 97 (a and b) | |

TABLE 1-continued
| Ex.* | Structures |
|---|---|
| 98 (a and b) | 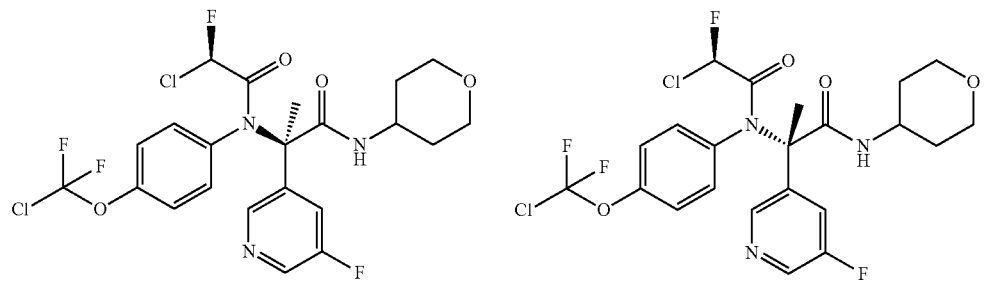 |
| 99 (a and b) | 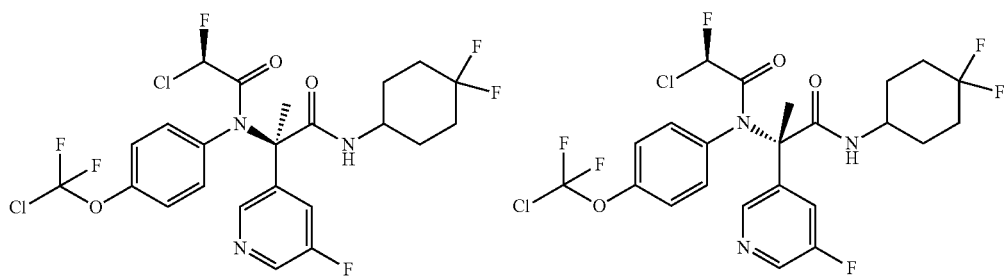 |
| 100 (a and b) | 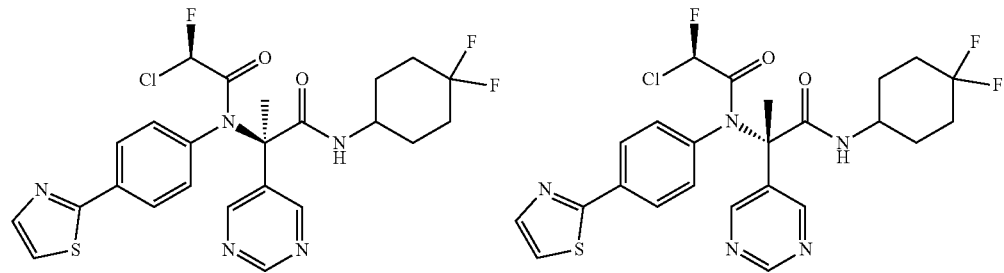 |
| 101 (a and b) | 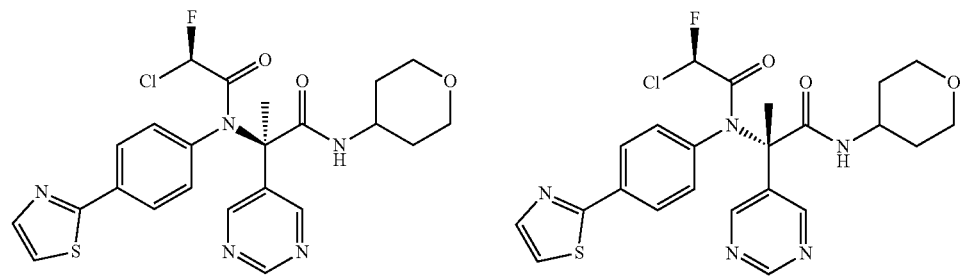 |
| 102 (a and b) | 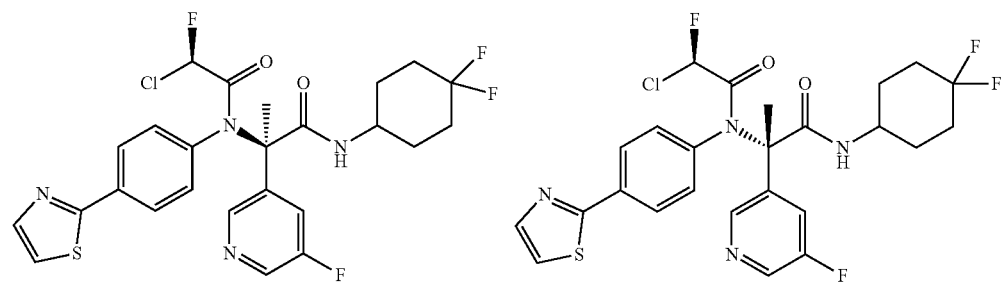 |

TABLE 1-continued

| Ex.* | Structures |
|---|---|
| 103 (a and b) | |
| 104 (a and b) | |
| 105 (a and b) | |
| 106 (a and b) | |
| 107 (a and b) | |

TABLE 1-continued
| Ex.* | Structures |
|---|---|
| 108 (a and b) | 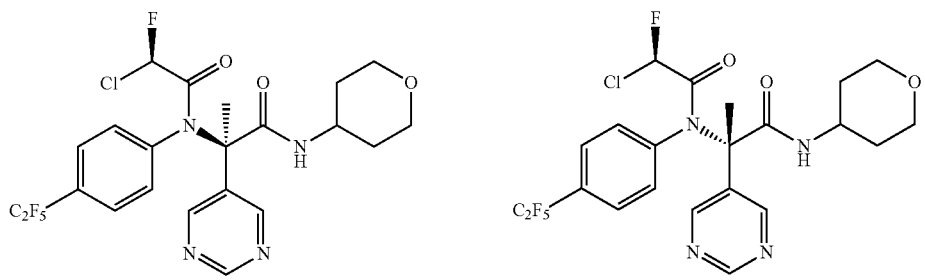 |
| 109 (a and b) | 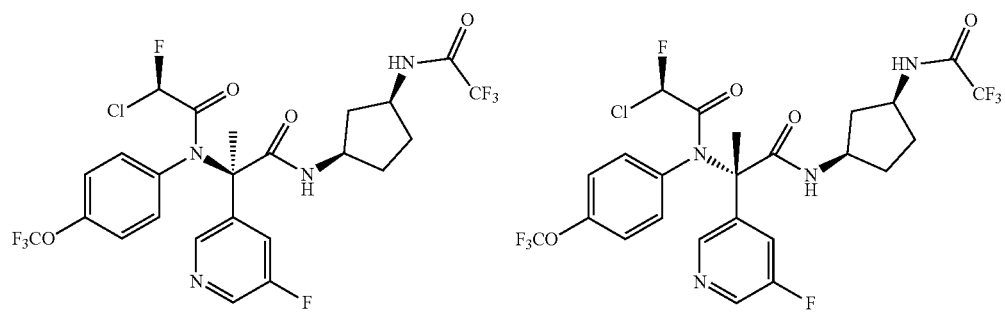 |
| 110 (a and b) | 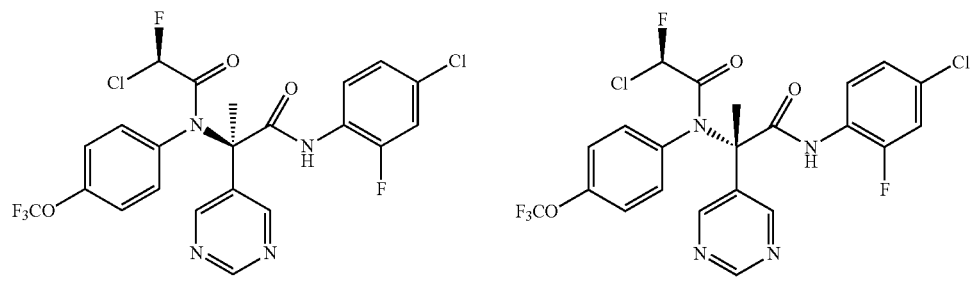 |
| 111 (a and b) | 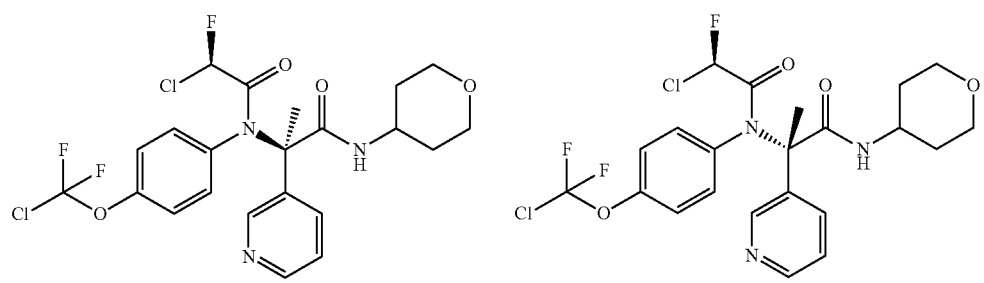 |
| 112 (a and b) | 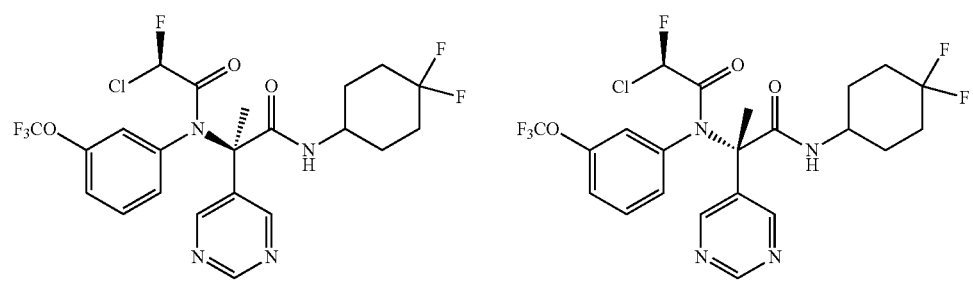 |

TABLE 1-continued

| Ex.* | Structures |
|---|---|
| 113(a and b) | 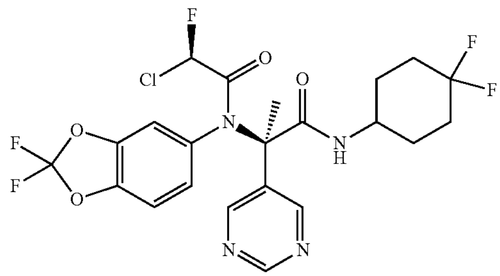 [SMILES: C[C@](C(=O)NC1CCC(F)(F)CC1)(c1cncnc1)N(C(=O)[C@H](F)Cl)c1ccc2c(c1)OC(F)(F)O2] |
| 114(a and b) | 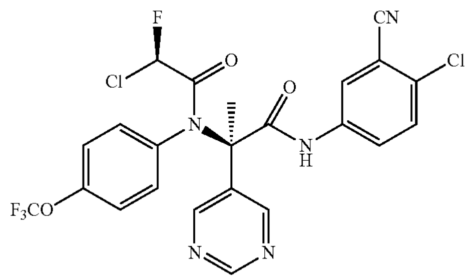 [SMILES: C[C@](C(=O)Nc1ccc(Cl)c(C#N)c1)(c1cncnc1)N(C(=O)[C@H](F)Cl)c1ccc(OC(F)(F)F)cc1] |
| 115(a and b) | 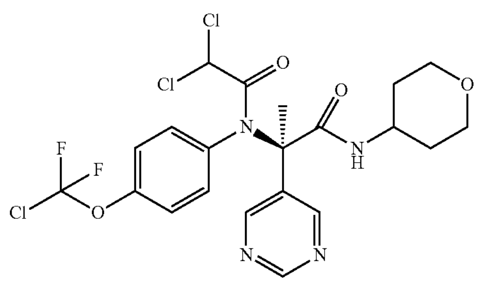 [SMILES: C[C@](C(=O)NC1CCOCC1)(c1cncnc1)N(C(=O)C(Cl)Cl)c1ccc(OC(F)(F)Cl)cc1] |

*Stereochemistry was arbitrarily assigned except for

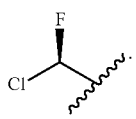 [SMILES: *[C@H](F)Cl]

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine, and chloride, such as $^2$H (D), $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the pharmaceutically acceptable salts, solvates, or stereoisomers thereof which contain the aforementioned isotopes and/or other isotopes of other atoms are within the scope of this disclosure. Certain isotopically-labeled compounds, for example those into which radioactive isotopes such as $^3$H and $^{14}$C are incorporated, are useful in drug and/or substrate tissue distribution assays. Tritiated, i.e., $^3$H and carbon-14, i.e., $^{14}$C, isotopes are particularly preferred for their ease of preparation and detectability.

In some embodiments, the abundance of deuterium in each of the substituents disclosed herein is independently at least 1%, at least 10%, at least 20%, at least 30%, at least 40%, at least 50%, at least 60%, at least 70%, at least 80%, at least 90%, or 100% of a total number of hydrogen and deuterium. In some embodiments, one or more of the substituents disclosed herein comprise deuterium at a percentage higher than the natural abundance of deuterium. In some embodiments, one or more hydrogens are replaced with one or more deuteriums in one or more of the substituents disclosed herein.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Disclosed herein is a method of treating or preventing a coronavirus infection in a patient in need thereof, comprising administering to the patient a compound or a pharmaceutical composition comprising a compound described herein, for example, a compound of Formula (I). In some embodiments, the coronavirus infection is caused by the SARS-CoV-2 virus. In some embodiments, the coronavirus infection is caused by the MERS-CoV virus. In some embodiments, the coronavirus infection is caused by the SARS-CoV virus. In some embodiments, the coronavirus infection is caused by the HCoV-229E virus. In some embodiments, the coronavirus infection is caused by the HCoV-OC43 virus. In some embodiments, the coronavirus infection is caused by the HCoV-NL63 virus. In some embodiments, the coronavirus infection is caused by the HCoV-HKU1 virus.

In another aspect, provided herein is a method of treating or preventing a SARS-CoV-2 infection in a patient in need thereof, comprising administering to the patient a compound or a pharmaceutical composition comprising a compound described herein, for example, a compound of Formula (I).

In some embodiments, the compound disclosed herein is administered to the subject prophylactically. In some embodiments, the subject is suspected of having a SARS-CoV-2 infection before the SARS-CoV-2 infection is diagnosed.

In some embodiments, the compounds of the present disclosure are administered to the subject until the infection is treated, inhibited, or reduced. In some embodiments, the compounds is administered to the subject until one or more symptoms of the SARS-CoV-2 infection is reduced.

In another aspect, provided herein is a method of inhibiting a viral infection, comprising providing a compound disclosed herein to the infection so as to inhibit the viral infection. In some embodiments, the viral infection is caused by SARS-CoV-2. In some embodiments, the viral infection is caused by MERS-CoV. In some embodiments, the viral infection is caused by SARS-CoV. In some embodiments the viral infection is caused by HCoV-229E. In some embodiments, the viral infection is caused by HCoV-OC43. In some embodiments, the viral infection is caused by HCoV-NL63. In some embodiments, the viral infection is caused by HCoV-HKU1.

In another aspect, provided herein is a method of inhibiting SARS-CoV-2 by binding with a protein thereof, comprising providing a compound disclosed herein to a SARS-CoV-2 so as to inhibit the SARS-CoV-2. In some embodiments, the SARS-CoV-2 binds to a protease on the SARS-CoV-2. In some embodiments, the compounds disclosed herein bind with a cysteine residue of the main protease, thereby inhibiting the SARS-CoV-2. In some embodiments, the cysteine residue is at position 145 of a main protease. In some embodiments, the protease is 3CL.

Dosing

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage, or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage, or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{10}$ and the $ED_{90}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the subject every 12 hours; (v) the compound is administered to the subject every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically. In yet other embodiments, the compound described herein is administered via inhalation. In some embodiments, the compounds disclosed herein are formulated for intranasal administration. Such formulations include nasal sprays, nasal mists, and the like.

Pharmaceutical Compositions/Formulations

The compounds described herein are administered to a subject in need thereof, either alone or in combination with pharmaceutically acceptable carriers, excipients, or diluents, in a pharmaceutical composition, according to standard pharmaceutical practice. In one embodiment, the compounds of this disclosure may be administered to animals. The compounds can be administered orally or parenterally, including the intravenous, intramuscular, intraperitoneal, subcutaneous, rectal, and topical routes of administration.

In another aspect, provided herein are pharmaceutical compositions comprising a compound described herein, or a pharmaceutically acceptable salt, solvate, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt, solvate, or stereoisomer thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt, solvate, or stereoisomer thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

Combination

Disclosed herein are methods of treating a disease or disorder associated with SARS-COV-2 using a compound disclosed herein, or a pharmaceutically acceptable salt, solvate, or stereoisomer thereof, in combination with an additional therapeutic agent.

In some embodiments, the additional therapeutic agent is administered at the same time as the compound disclosed herein. In some embodiments, the additional therapeutic agent and the compound disclosed herein are administered sequentially. In some embodiments, the additional therapeutic agent is administered less frequently than the compound disclosed herein. In some embodiments, the additional therapeutic agent is administered more frequently than the compound disclosed herein. In some embodiments, the additional therapeutic agent is administered prior than the administration of the compound disclosed herein. In some embodiments, the additional therapeutic agent is administered after the administration of the compound disclosed herein.

In some embodiments, the additional therapeutic agent is an interferon, such as interferon alpha, or a pegylated interferon, such as PEG-intron or Pegasus. In some embodiments, this combination provides a greater clinical benefit than dosing either the interferon, pegylated interferon or the compound disclosed herein alone. Examples of greater clinical benefits include a larger reduction in symptoms, a faster time to alleviation of symptoms, reduced lung pathology, a larger reduction in the amount of SARS coronavirus in the patient (viral load), and decreased mortality.

The SARS coronavirus infects cells which express p-glycoprotein. In some embodiments, the compounds disclosed herein are p-glycoprotein substrates. In some embodiments, compounds which inhibit the SARS coronavirus which are also p-glycoprotein substrates are dosed with a p-glycoprotein inhibitor. Examples of p-glycoprotein inhibitors include verapamil, vinblastine, ketoconazole, nelfinavir, ritonavir, and cyclosporine. The p-glycoprotein inhibitors act by inhibiting the efflux of the compounds disclosed herein out of the cell. The inhibition of the p-glycoprotein based efflux will prevent reduction of intracellular concentrations of the compound disclosed herein due to p-glycoprotein efflux. Inhibition of the p-glycoprotein efflux will result in larger intracellular concentrations of the compound disclosed herein. In some embodiments, dosing a SARS coronavirus infected patient with the compound disclosed herein and a p-glycoprotein inhibitor lower the amount of the compound disclosed herein required to achieve an efficacious dose by increasing the intracellular concentration of the compound disclosed herein.

Among the agents that may be used to increase the exposure of a mammal to a compound disclosed herein are those that can inhibit at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. In some embodiments, the compounds disclosed herein include compounds that are CYP3A4 substrates and are metabolized by CYP3A4. In some embodiments, dosing a SARS coronavirus infected patient with a compound that is a CYP3A4 substrate and a CYP3A4 inhibitor, such as ritonavir, nelfinavir or delavirdine, will reduce the metabolism of the compound by CYP3A4. This will result in reduced clearance of the compound and increased plasma concentrations. In some embodiments, the reduced clearance and higher plasma concentrations result in a lower efficacious dose of compound disclosed herein.

EXAMPLES

Examples 1a and 1b 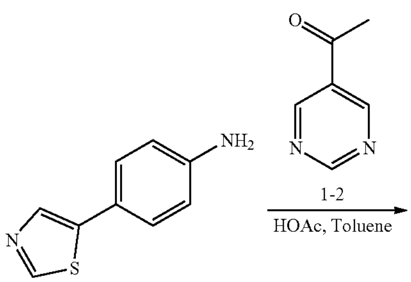 1-1

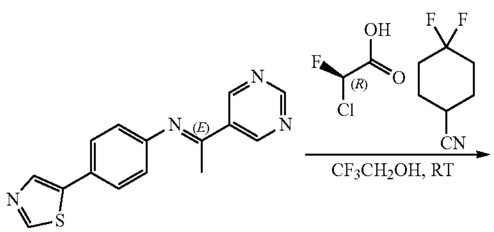

1-3

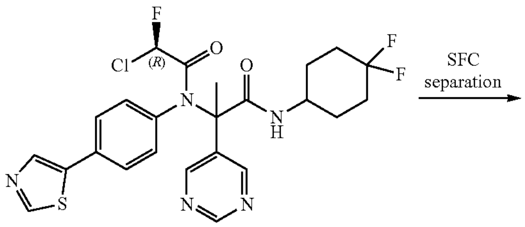

1-4

-continued

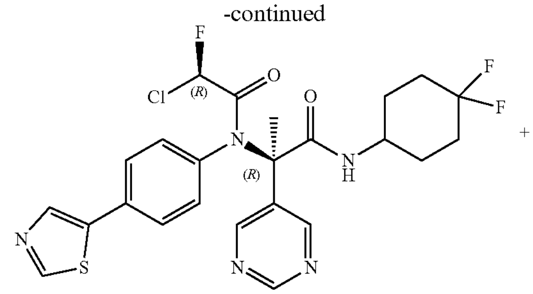

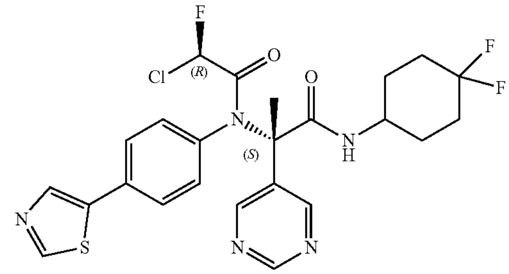

Example 1a and Example 1b
(Stereochemistry arbitrarily assigned at center betweeen two amides)

A mixture of compound 1-1 (1 g, 5.67 mmol), 1-(pyrimidin-5-yl)ethanone (compound 1-2, 831 mg, 6.80 mmol) and AcOH (2.10 g, 34.97 mmol, 2 mL) in toluene (20 mL) was degassed and purged with $N_2$ for 3 times, and then the mixture was heated at reflux for 16 hours with removal of water by Dean-Stark trap under $N_2$ atmosphere. The reaction mixture was concentrated under reduced pressure to give a residue. The residue was purified by flash silica gel chromatography (Eluent of 0~80% Ethyl acetate/Petroleum ether gradient) to give compound 1-3 (944 mg, 56.38% yield). $^1$H NMR (400 MHz, DMSO-$d_6$): δ 9.38-9.29 (m, 3H), 9.06 (s, 1H), 8.31 (s, 1H), 7.72 (d, J=8.4 Hz, 2H), 6.95 (d, J=8.4 Hz, 2H), 2.31 (s, 3H).

To a solution of compound 1-3 (944 mg, 3.37 mmol) in $CF_3CH_2OH$ (10 mL) was added (2R)-2-chloro-2-fluoroacetic acid (909 mg, 4.04 mmol, 50% purity) and 4,4-difluorocyclohexanecarbonitrile (489 mg, 3.37 mmol). The mixture was stirred at 25° C. for 18 hr. The reaction mixture was concentrated under reduced pressure to give a residue. The residue was purified by flash silica gel chromatography (Eluent of 0-100% Ethyl acetate/Petroleum ether gradient) and further purified by prep-HPLC (Welch Xtimate C18 150*30 mm*5 μm; Mobile phase: A: water (FA) B: ACN; Gradient condition: from 35% B to 65% B; Flow rate: 60 mL/min) to afford compound 1-4 (204 mg, 11.26% yield). LCMS: (M+H)=538.1. SFC: Retention time: 1.420 min & 2.366 min, AD-3_EtOH (DEA)_40_25ML_5MI. $^1$H NMR (400 MHz, DMSO-$d_6$): δ 9.16-9.11 (m, 1H), 9.09-9.01 (m, 1H), 8.90-8.82 (m, 2H), 8.44-8.38 (m, 1H), 7.88-7.69 (m, 3H), 7.68-7.59 (m, 1H), 7.42-7.15 (m, 1H), 6.47-6.21 (m, 1H), 3.88 (br s, 1H), 2.12-1.72 (m, 8H), 1.70-1.51 (m, 3H). $^{19}$F NMR (376 MHz, DMSO-$d_6$): δ −91.95 (br dd, J=90.2, 232.3 Hz, 1F), −98.51~−100.31 (m, 1F), −141.93 (br d, J=173.4 Hz, 1F).

Compound 1-4 (200 mg) was separated by SFC (DAICEL CHIRALPAK AD (250 mm*30 mm, 10 μm)); Mobile phase: A: Supercritical $CO_2$, B: Neu-ETOH; Isocratic: A:B=60:40; Flow rate: 80 mL/min) to afford two fractions.

Example 1a: (64 mg, 32.00% yield) was obtained. LCMS: (M+H)=538.2. SFC: Retention time: 1.424 min, AD-3_EtOH (DEA)_40_25ML_5MI.

$^1$H NMR (400 MHz, DMSO-d$_6$): δ 9.14 (s, 1H), 9.07 (s, 1H), 8.87 (s, 2H), 8.41 (s, 1H), 7.91-7.67 (m, 4H), 7.24 (d, J=8.4 Hz, 1H), 6.49-6.26 (m, 1H), 3.88 (d, J=8.4 Hz, 1H), 2.06-1.72 (m, 6H), 1.70-1.48 (m, 5H). $^{19}$F NMR (376 MHz, DMSO-d$_6$): δ -91.81 (br d, J=234.6 Hz, 1F), -99.36 (br d, J=234.6 Hz, 1F), -142.20 (s, 1F).

Example 1b: (79 mg, 38.25% yield) was obtained. LCMS: (M+H)=538.2. SFC: Retention time: 2.446 min, AD-3_EtOH (DEA)_40_25ML_5MI.

$^1$H NMR (400 MHz, DMSO-d$_6$): δ 9.13 (s, 1H), 9.03 (s, 1H), 8.85 (s, 2H), 8.40 (s, 1H), 7.81-7.69 (m, 2H), 7.68-7.60 (m, 2H), 7.44-7.30 (m, 1H), 6.43-6.21 (m, 1H), 3.88 (br s, 1H), 2.06-1.69 (m, 9H), 1.67-1.47 (m, 2H). $^{19}$F NMR (376 MHz, DMSO-d$_6$): δ -92.04 (br d, J=237.5 Hz, 1F), -99.15 (br d, J=240.3 Hz, 1F), -141.73 (br s, 1F).

Examples 2a and 2b

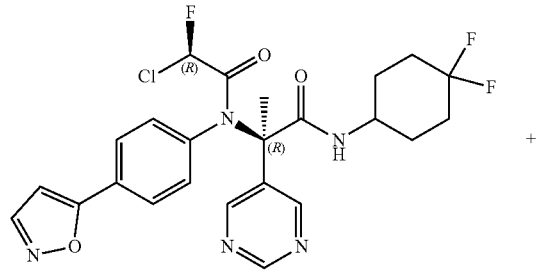

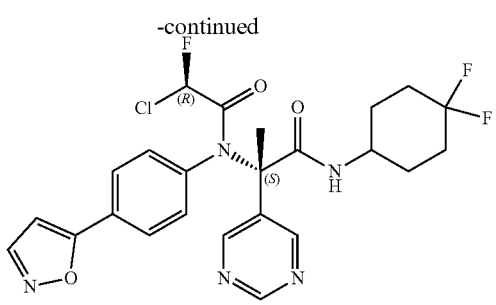

Example 2a and Example 2b
(Stereochemistry arbitrarily assigned at center between two amides)

The following compounds were prepared according to similar procedure as described for compounds Example 1a and 1b.

Example 2a: (12 mg) was obtained. LCMS: (M+H)=522.2. SFC: Retention time: 3.651 min, AD-3_EtOH (DEA)_5_40_25ML.

$^1$H NMR (400 MHz, DMSO-d$_6$): δ 9.07 (s, 1H), 8.87 (s, 2H), 8.71 (d, J=2.00 Hz, 1H), 8.01 (d, J=8.00 Hz, 1H), 7.83-7.94 (m, 2H), 7.75 (d, J=8.00 Hz, 1H), 7.35 (d, J=9.20 Hz, 1H), 7.15 (d, J=1.80 Hz, 1H), 6.26-6.50 (m, 1H), 3.81-4.02 (m, 1H), 1.95-2.06 (m, 2H), 1.74-1.93 (m, 4H), 1.68 (s, 3H), 1.49-1.65 (m, 2H). $^{19}$F NMR (376 MHz, DMSO-d$_6$): δ -142.25 (s, 1 F), -99.36 (br d, J=234.61 Hz, 1F), -91.83 (br d, J=234.61 Hz, 1 F).

Example 2b: (27.01 mg) was obtained. LCMS: (M+H)=522.1. SFC: Retention time: 4.920 min, AD-3_EtOH (DEA)_5_40_25ML.

$^1$H NMR (400 MHz, DMSO-d$_6$): δ 9.08-9.01 (m, 1H), 8.89-8.83 (m, 2H), 8.72-8.68 (m, 1H), 7.92 (br dd, J=8.3, 12.8 Hz, 2H), 7.80-7.64 (m, 2H), 7.54-7.33 (m, 1H), 7.18-7.10 (m, 1H), 6.48-6.24 (m, 1H), 3.88 (br d, J=7.3 Hz, 1H), 2.09-1.87 (m, 4H), 1.82 (s, 3H), 1.78-1.52 (m, 4H). $^{19}$F NMR (376 MHz, DMSO-d$_6$): δ -91.15--92.81 (m, 1F), -98.38--100.04 (m, 1F), -141.30--142.85 (m, 1F).

Examples 3a and 3b

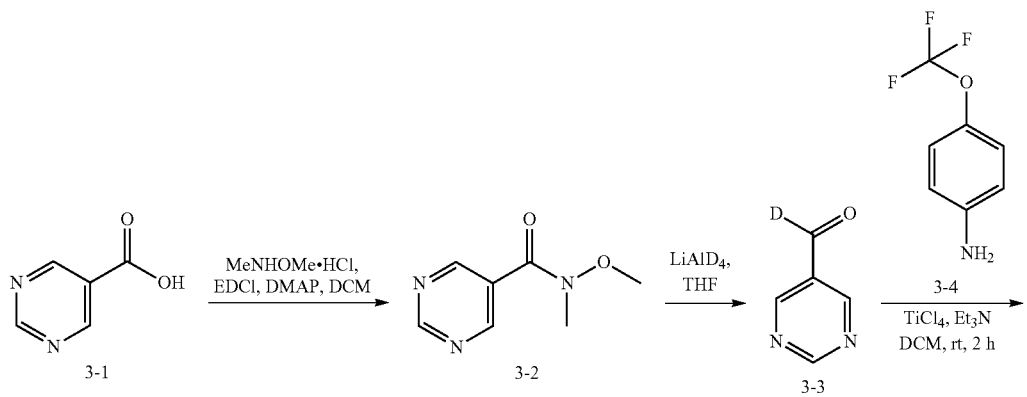

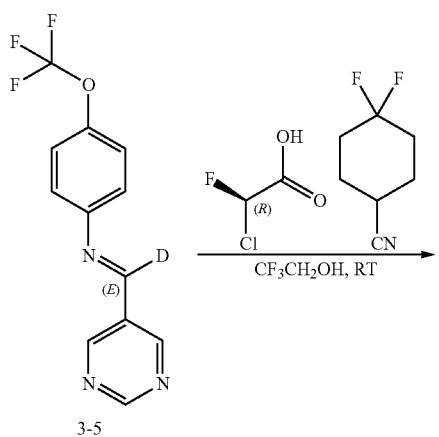
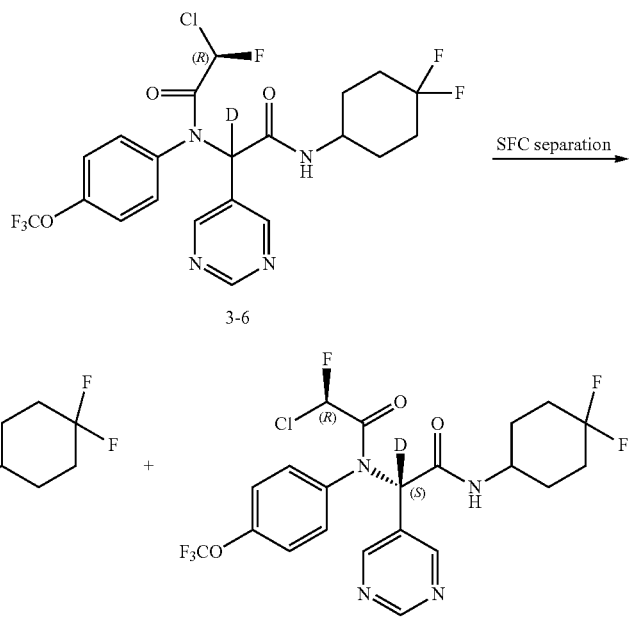

Example 3a and Example 3b
(Stereochemistry arbitrarily assigned at center between two amides)

To a solution of Compound 3-1 (2 g, 16.12 mmol) and N-methoxymethanamine (1.98 g, 20.31 mmol) in DCM (40 mL) was degassed and purged with $N_2$ for 3 times, and then EDCI (3.71 g, 19.34 mmol) and DMAP (2.95 g, 24.17 mmol) were added. The mixture was stirred at 25° C. for 18 hrs under $N_2$ atmosphere. The reaction mixture was diluted with $H_2O$ (50 mL) and extracted with DCM (3×50 mL). The combined organic layers were dried over $Na_2SO_4$, filtered, and concentrated under reduced pressure to give a residue. The reaction mixture was diluted with $H_2O$ (50 mL) and extracted with DCM (3×50 mL). The combined organic layers were dried over $Na_2SO_4$, filtered, and concentrated under reduced pressure to give compound 3-2 (1.78 g, 62.77% yield). $^1$H NMR (400 MHz, $CDCl_3$): δ 9.28 (s, 1H), 9.09 (s, 2H), 3.59 (s, 3H), 3.41 (s, 3H).

A mixture of $LiAlD_4$ (250 mg, 6.59 mmol) in THF (3 mL) was degassed and purged with $N_2$ for 3 times, and then a solution of compound 3-2 (500 mg, 2.99 mmol) in THF (2 mL) was added. The mixture was stirred at −78° C. for 2 hr under $N_2$ atmosphere. The reaction mixture was quenched by 1 N HCl (15 mL) at 0° C., and then diluted with $H_2O$ (10 mL) and extracted with EA (6×20 mL) and DCM (4×20 mL). The combined organic layers were dried over $Na_2SO_4$, filtered, and concentrated under reduced pressure to give compound 3-3 (176 mg, crude), which was used for next step without further purification. $^1$H NMR (400 MHz, DMSO-$d_6$): δ 9.43 (s, 1H), 8.81 (s, 2H).

To a solution of compound 3-4 (138 mg, 779.12 μmol) in DCM (2 mL) was added compound 3-3 (85 mg, 779.07 μmol). The mixture was degassed and purged with $N_2$ for 3 times, and then the mixture was added TEA (237 mg, 2.34 mmol) and $TiCl_4$ (74 mg, 390.13 μmol) at 0° C. The reaction mixture was stirred at 25° C. for 2 hr under $N_2$ atmosphere. The reaction mixture was diluted with ice cold water (15 mL) and extracted with DCM (3×20 mL). The organic layer were dried over $Na_2SO_4$, filtered, and concentrated under reduced pressure to give compound 3-5 (186 mg, crude), which was used for next step without further purification.

To a solution of Compound 3-5 (180 mg, 671.11 μmol) in $CF_3CH_2OH$ (3 mL) was added (2R)-2-chloro-2-fluoro-acetic acid (151 mg, 805.42 μmol, 60% purity) and 4,4-difluorocyclohexanecarbonitrile (98 mg, 675.17 μmol). The mixture was stirred at 25° C. for 16 hr. The reaction mixture was concentrated under reduced pressure to give a residue. The residue was purified by prep-HPLC. The pure fractions were collected and the volatile solvent was removed by evaporation. The aqueous residue was lyophilized to afford compound 3-6 (145 mg, 40.45% yield). LCMS: (M+H) =526.2.

Compound 3-6 (149 mg, 283.35 μmol) was separated by SFC (DAICEL CHIRALCEL OD-H (250 mm*30 mm, 5 μm)); Mobile phase: A: Supercritical $CO_2$, B: Neu-IPA; Isocratic: A:B=60:40; Flow rate: 80 mL/min) to afford two fractions.

Example 3a: (52 mg, 34.12% yield) was obtained. LCMS: (M+H)=526.2. SFC: Retention time: 2.957 min, OD_3_IPA_DEA_5_40_25ML.
$^1$H NMR (400 MHz, DMSO-$d_6$): δ 8.97 (s, 1H), 8.47 (s, 2H), 8.39 (d, J=7.6 Hz, 1H), 7.89-7.02 (m, 4H), 6.60-6.37 (m, 1H), 6.07 (s, 0.016H), 3.84 (br d, J=8.0 Hz, 1H), 2.09-1.67 (m, 6H), 1.58-1.44 (m, 1H), 1.39-1.25 (m, 1H).
$^{19}$F NMR (376 MHz, DMSO-$d_6$): δ −56.63--57.44 (m, 3F), −93.37 (br d, J=243.2 Hz, 1F), −97.75 (br d, J=191.7 Hz, 1F), −143.48 (s, 1F).

Example 3b: (56 mg, 37.35% yield) was obtained. LCMS: (M+H)=526.2. SFC: Retention time: 5.542 min, OD_3_IPA_DEA_5_40_25ML.

¹H NMR (400 MHz, DMSO-d₆): δ 8.99 (s, 1H), 8.50 (s, 2H), 8.37 (d, J=7.2 Hz, 1H), 7.31 (br s, 4H), 6.78-6.44 (m, 1H), 6.00 (s, 0.025H), 3.79 (br s, 1H), 2.09-1.66 (m, 6H), 1.57-1.41 (m, 1H), 1.40-1.25 (m, 1H). ¹⁹F NMR (376 MHz, DMSO-d₆): δ −56.98 (s, 3F), −93.33 (br d, J=243.2 Hz, 1F), −97.70 (br d, J=211.7 Hz, 1F), −142.72 (s, 1F).

Examples 4a and 4b

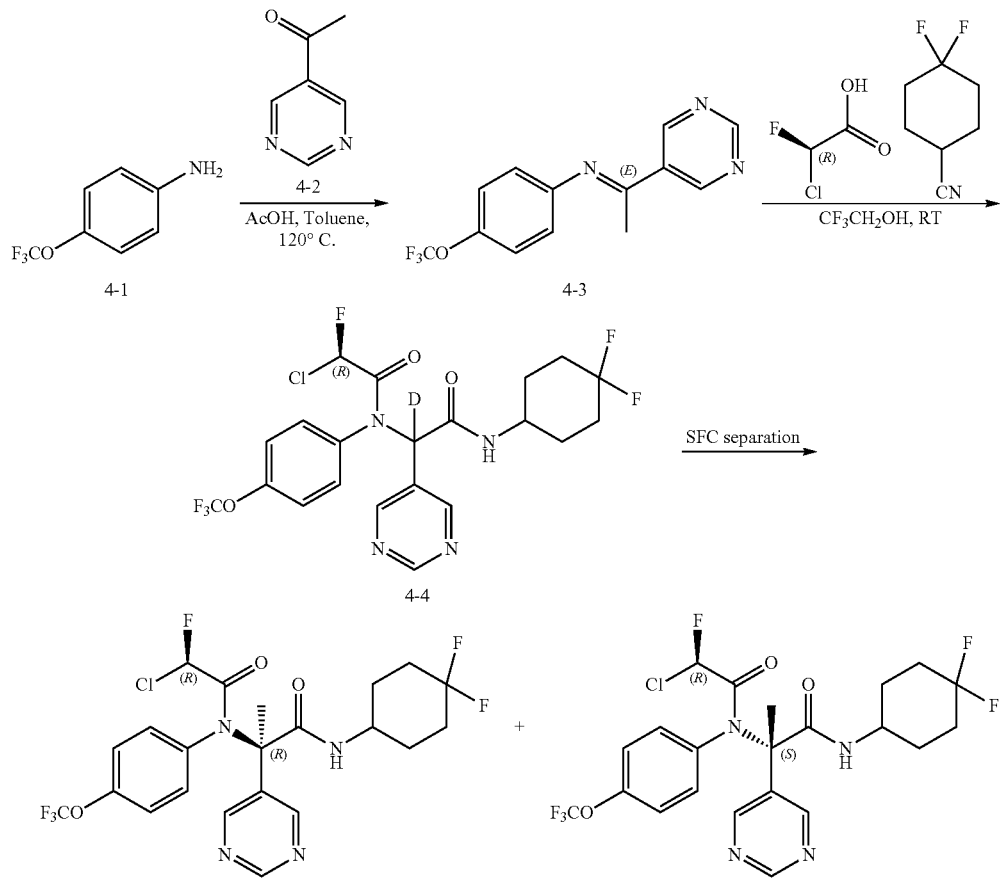

Example 4a and Example 4b
(Stereochemistry arbitrarily assigned at center between two amides)

A mixture of Compound 4-1 (2 g, 11.29 mmol), Compound 4-2 (1.66 g, 13.56 mmol), AcOH (4.20 g, 69.94 mmol, 4.00 mL) in toluene (30 mL) was degassed and purged with N₂ for 3 times, and then the mixture was heated to reflux (120° C.) for 48 hrs with removal of water by Dean-Stark trap under N₂ atmosphere. The reaction mixture was filtered and the filtrate was concentrated under reduced pressure to give compound 4-3 (2.16 g, crude), which was used for next step without further purification. ¹H NMR (400 MHz, DMSO-d₆): δ 9.34-9.24 (m, 3H), 7.39 (d, J=8.4 Hz, 2H), 6.96 (d, J=8.8 Hz, 2H), 2.38-2.17 (m, 3H).

To a solution of Compound 4-3 (1 g, 3.56 mmol) in CF₃CH₂OH (10 mL) was added (2R)-2-chloro-2-fluoro-acetic acid (667 mg, 3.56 mmol) and 4,4-difluorocyclo-hexanecarbonitrile (517 mg, 3.56 mmol). The mixture was stirred at 25° C. for 16 hr. The reaction mixture was concentrated under reduced pressure to give a residue. The residue was purified by flash silica gel chromatography (Eluent of 0~70% Ethyl acetate/Petroleum ether gradient) to get product. The product was purified by prep-HPLC. The pure fractions were collected and the volatile solvent was removed by evaporation. The aqueous residue was lyophilized to afford compound 4-4 (87 mg, 4.44% yield) was obtained. LCMS: (M+H)=539.1.

Compound 4-4 (87 mg, 161.45 μmol) was separated by SFC (DAICEL CHIRALPAK AD (250 mm*30 mm, 10 μm)); Mobile phase: A: Supercritical CO₂, B: Neu-MeOH; Isocratic: A:B=90:10; Flow rate: 50 mL/min) to afford two fractions.

Example 4a: (28 mg, 30.94% yield) was obtained. LCMS: (M+H)=539.1. SFC: Retention time: 1.816 min, AD-3_MeOH (DEA)_5_40_25ML.

¹H NMR (400 MHz, DMSO-d₆): δ 9.06 (s, 1H), 8.84 (s, 2H), 7.94-7.67 (m, 2H), 7.54-7.32 (m, 3H), 6.51-6.21 (m, 1H), 3.97-3.74 (m, 1H), 2.03-1.72 (m, 6H), 1.66 (s, 3H), 1.64-1.46 (m, 2H). ¹⁹F NMR (376 MHz, DMSO-d₆): δ −56.84 (br s, 3F), −91.85 (br d, J=234.6 Hz, 1F), −99.39 (br d, J=234.6 Hz, 1F), −142.32 (br s, 1F).

Example 4b: (34 mg, 61.78 μmol, 38.26% yield) was obtained. LCMS: (M+H)=539.1. SFC: Retention time: 2.406 min, AD-3_MeOH (DEA)_5_40_25ML. ¹H NMR (400 MHz, DMSO-d₆): δ 9.03 (s, 1H), 8.83 (s, 2H), 7.80-

7.61 (m, 2H), 7.56-7.33 (m, 3H), 6.47-6.18 (m, 1H), 3.93-3.74 (m, 1H), 2.09-1.81 (m, 5H), 1.79 (s, 3H), 1.75-1.65 (m, 1H), 1.62-1.47 (m, 2H). $^{19}$F NMR (376 MHz, DMSO-$d_6$): δ −56.89 (s, 3F), −92.02 (br d, J=234.6 Hz, 1F), −99.23 (br d, J=231.7 Hz, 1F), −141.94 (s, 1F).

Examples 5a and 5b

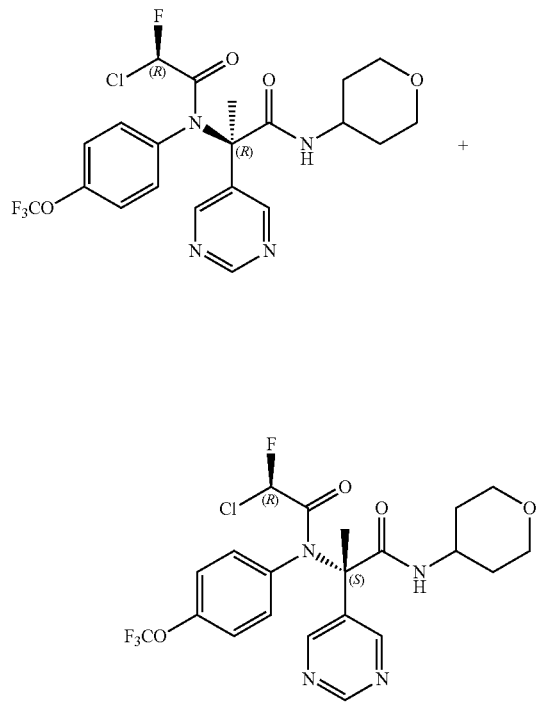

Example 5a and Example 5b
(Stereochemistry arbitrarily assigned at center between two amides)

The following compounds were prepared according to similar procedure as described for Example 4a and 4b.

Example 5a: (17 mg) was obtained. LCMS: (M+H)=505.2. SFC: Retention time: 2.558 min, AD_3_EtOH_DEA_5_40_25ML_7MIN.

$^1$H NMR (400 MHz, DMSO-$d_6$): δ 9.03 (s, 1H), 8.82 (s, 2H), 7.79 (d, J=8.0 Hz, 2H), 7.45 (d, J=8.4 Hz, 1H), 7.36 (s, 2H), 6.44-6.23 (m, 1H), 3.87-3.80 (m, 3H), 3.35-3.24 (m, 2H), 1.73-1.64 (m, 4H), 1.63-1.39 (m, 3H). $^{19}$F NMR (376 MHz, DMSO-$d_6$): δ −56.85 (s, 3F), −142.33 (s, 1F).

Example 5b: (20 mg) was obtained. LCMS: (M+H)=505.2. SFC: Retention time: 3.349 min, AD_3_EtOH_DEA_5_40_25ML_7MIN.

$^1$H NMR (400 MHz, DMSO-$d_6$): δ 9.00 (s, 1H), 8.80 (s, 2H), 7.76-7.63 (m, 2H), 7.52-7.46 (m, 1H), 7.43-7.32 (m, 2H), 6.38-6.19 (m, 1H), 3.86-3.79 (m, 3H), 3.35-3.27 (m, 2H), 1.81 (s, 3H), 1.71-1.61 (m, 1H), 1.59-1.38 (m, 3H). $^{19}$F NMR (376 MHz, DMSO-$d_6$): δ −56.90 (s, 3F), −142.06 (s, 1F).

Examples 6a, 6b, 6c, and 6d

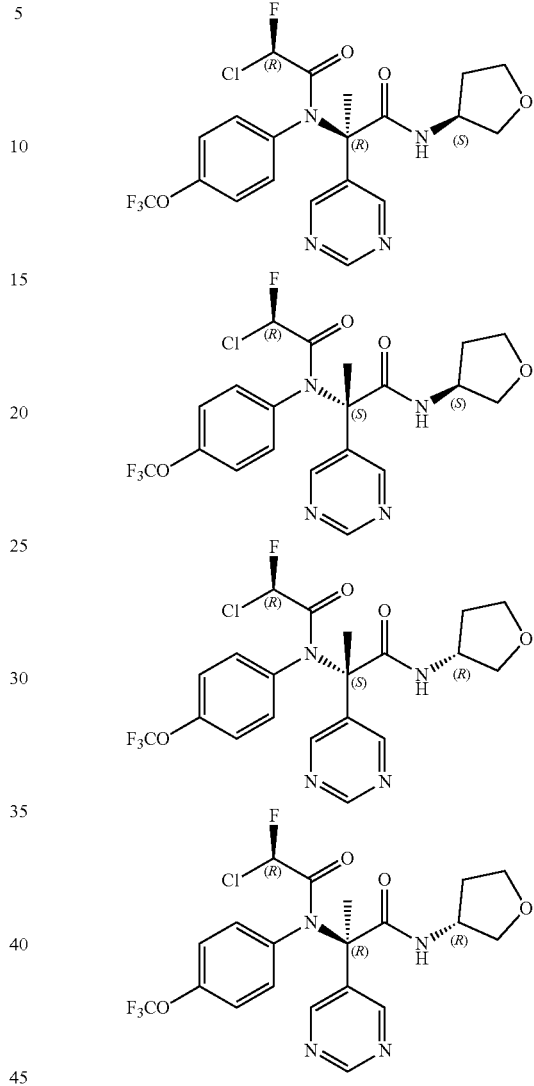

Example 6a, 6b, 6c, and 6d
(Sterochemistry arbitrarily assigned at center between two amides and heterocycloalkyl)

The following compounds were prepared according to similar procedure as described for Example 4a and 4b.

Example 6a: (6 mg) was obtained. LCMS: (M+H)=491.1. SFC: Retention time: 2.504 min, AD_3_EtOH_DEA_5_40_25ML_7MIN.

$^1$H NMR (400 MHz, DMSO-$d_6$): δ 9.06 (s, 1H), 8.84 (s, 2H), 8.04 (d, J=6.8 Hz, 1H), 7.86 (d, J=8.8 Hz, 1H), 7.49 (d, J=8.4 Hz, 1H), 7.43-7.30 (m, 2H), 6.49-6.24 (m, 1H), 4.44-4.29 (m, 1H), 3.85-3.74 (m, 2H), 3.70-3.62 (m, 1H), 3.51-3.47 (m, 1H), 2.20-2.05 (m, 1H), 1.91-1.78 (m, 1H), 1.67 (s, 3H). $^{19}$F NMR (376 MHz, DMSO-$d_6$): δ −142.27 (s, 3 F) −56.82 (s, 1 F).

Example 6b: (4 mg) was obtained. LCMS: (M+H)=491.1. SFC: Retention time: 2.773 min, AD_3_EtOH_DEA_5_40_25ML_7MIN. $^1$H NMR (400 MHz, DMSO-$d_6$): δ9.12-9.06 (m, 1H), 8.86-8.83 (m, 2H), 8.06 (d, J=6.4 Hz, 1H), 7.90 (dd, J=2.4, 8.8 Hz, 1H), 7.50 (d, J=8.4 Hz, 1H), 7.40 (d, J=8.8 Hz, 1H), 7.35-7.28 (m, 1H), 6.50-6.28 (m, 1H), 4.39-4.31 (m, 1H), 3.84-3.76 (m, 2H), 3.68 (m, 1H), 3.58 (dd, J=4.0, 9.0 Hz, 1H), 2.12-2.03 (m, 1H), 1.83-1.76 (m, 1H), 1.68-1.60 (m, 3H). $^{19}$F NMR (376 MHz, DMSO-$d_6$): δ −56.62~−56.97 (m, 3F), −141.95~−143.49 (m, 1F).

Example 6c: (7 mg) was obtained. LCMS: (M+H)=491.1. SFC: Retention time: 3.504 min, AD_3_EtOH_DEA_5_40_25ML_7MIN. $^1$H NMR (400 MHz, DMSO-$d_6$): δ 9.02 (s, 1H), 8.81 (s, 2H), 7.95 (d, J=6.8 Hz, 1H), 7.68 (dd, J=2.4, 8.8 Hz, 1H), 7.51 (dd, J=2.0, 8.8 Hz, 1H), 7.43-7.36 (m, 2H), 6.42-6.17 (m, 1H), 4.36-4.29 (m, 1H), 3.83-3.73 (m, 2H), 3.71-3.64 (m, 1H), 3.49-3.47 (m, 1H), 2.17-2.02 (m, 1H), 1.88-1.83 (m, 1H), 1.82 (s, 3H).

$^{19}$F NMR (376 MHz, DMSO-$d_6$): δ −54.84−−58.54 (m, 3F), −140.69−−146.03 (m, 1F).

Example 6d: (6 mg) was obtained. LCMS: (M+H)=491.1. SFC: Retention time: 4.030 min, AD_3_EtOH_DEA_5_40_25ML_7MIN.

$^1$H NMR (400 MHz, DMSO-$d_6$): δ 9.03 (s, 1H), 8.82 (s, 2H), 7.93 (d, J=6.40 Hz, 1H), 7.67-7.78 (m, 1H), 7.33-7.55 (m, 3H), 6.20-6.43 (m, 1H), 4.33 (br s, 1H), 3.73-3.83 (m, 2H), 3.62-3.70 (m, 1H), 3.52-3.59 (m, 1H), 2.01-2.11 (m, 1H), 1.79 (s, 3H), 1.72-1.78 (m, 1H). $^{19}$F NMR (376 MHz, DMSO-$d_6$): δ −141.85 (s, 3 F), −57.32−−56.43 (m, 1 F).

Example 8

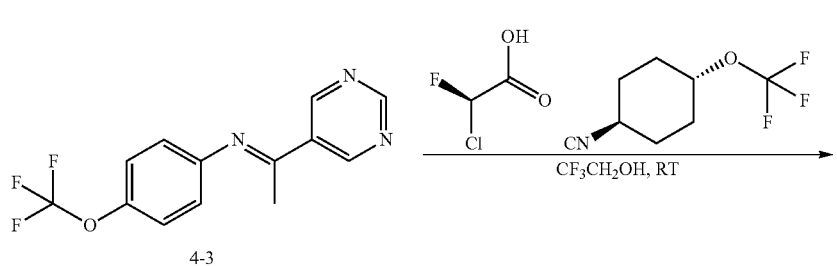

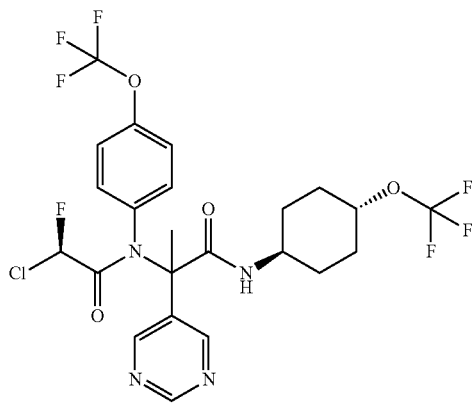

To a solution of Compound 4-3 (100 mg, 355.58 mol) in CF$_3$CH$_2$OH (1 mL) was added (2R)-2-chloro-2-fluoro-acetic acid (48.00 mg, 426.69 μmol) and (1R,4R)-1-isocyano-4-(trifluoromethoxy)cyclohexane (68.69 mg, 355.58 μmol). The mixture was stirred at 25° C. for 2 h. The mixture was concentrated under reduced pressure to give a residue. The residue was purified by prep-HPLC (column: Boston Green ODS 150*30 mm*5 m; mobile phase: [water (FA)-ACN]; B %: 55%-85%, 6 min) to give desired compound 8 (2.30 mg, 1.08% yield). LCMS: (M+H)=587.0. HPLC: Retention time: 5.290 min, 10-80AB_8 min. $^1$H NMR (400 MHz, CD$_3$OD): δ 9.04 (d, J=13.6 Hz, 1H), 8.92 (d, J=9.6 Hz, 2H), 7.76-7.65 (m, 1H), 7.47-7.28 (m, 3H), 6.30-6.11 (m, 1H), 4.29-4.18 (m, 1H), 3.89-3.75 (m, 1H), 2.17-2.07 (m, 2H), 2.05-1.95 (m, 2H), 1.92-1.75 (m, 3H), 1.70-1.58 (m, 2H), 1.52-1.40 (m, 2H). $^{19}$F NMR (376 MHz, CD$_3$OD): δ −145.470−−145.311 (m, 1F), −59.572−−59.277 (m, 6F).

Examples 11a and 11b

A mixture of Compound 4-1 (1.27 g, 7.19 mmol, 971.84 μL), Compound 11-1 (1 g, 7.19 mmol), AcOH (2.63 g, 43.71 mmol, 2.5 mL) and 4A molecular sieve (3 g, 7.19 mmol) in toluene (20 mL) was degassed and purged with N$_2$ for 3 times, and then the mixture was stirred at 125° C. for 18 hr under N$_2$ atmosphere. The reaction mixture was filtered and the filtrate was concentrated under reduced pressure to give a residue. The residue was purified by flash silica gel chromatography (Eluent of 0~100% Ethyl acetate/Petroleum ether gradient @ 35 mL/min). Compound 11-2 (1.3 g, 49.05% yield) was obtained. LCMS: Retention time: 4.398 min, (M+H)=299.1

To a solution of 11-2 (500 mg, 1.68 mmol) in CF$_3$CH$_2$OH (5 mL) was added (2R)-2-chloro-2-fluoro-acetic acid (405 mg, 2.02 mmol, 56% purity) and 1,1-difluoro-4-isocyano-cyclohexane (252 mg, 1.68 mmol, 97% purity). The mixture was stirred at 25° C. for 16 hr. The reaction mixture was concentrated under reduced pressure to give a residue. The residue was purified by prep-HPLC (Phenomenex Gemini-NX C18 75*30 mm*3 m; Mobile phase: A: water (FA) B: ACN; Gradient condition: from 37% B to 67% B; Flow rate: 25 mL/min). The pure fractions were collected and the volatile solvent was removed by evaporation. The aqueous residue was lyophilized to afford the title compound 11-3 (144 mg, 15.34% yield) was obtained. $^1$H NMR (400 MHz, DMSO-d$_6$): δ 8.51-8.40 (m, 2H), 7.81-7.54 (m, 3H), 7.52-7.40 (m, 1H), 7.39-7.27 (m, 2H), 6.47-6.21 (m, 1H), 3.86 (br s, 1H), 1.99 (br s, 3H), 1.93-1.68 (m, 6H), 1.66-1.43 (m, 2H). $^{19}$F NMR (376 MHz, DMSO-d$_6$): δ −56.93 (br d, J=20.0 Hz, 3F), −91.93 (br dd, J=55.8, 233.2 Hz, 1F), −99.31 (br dd, J=42.9, 228.9 Hz, 1F), −128.08 (br d, J=14.3 Hz, 1F), −141.88 (br d, J=14.3 Hz, 1F).

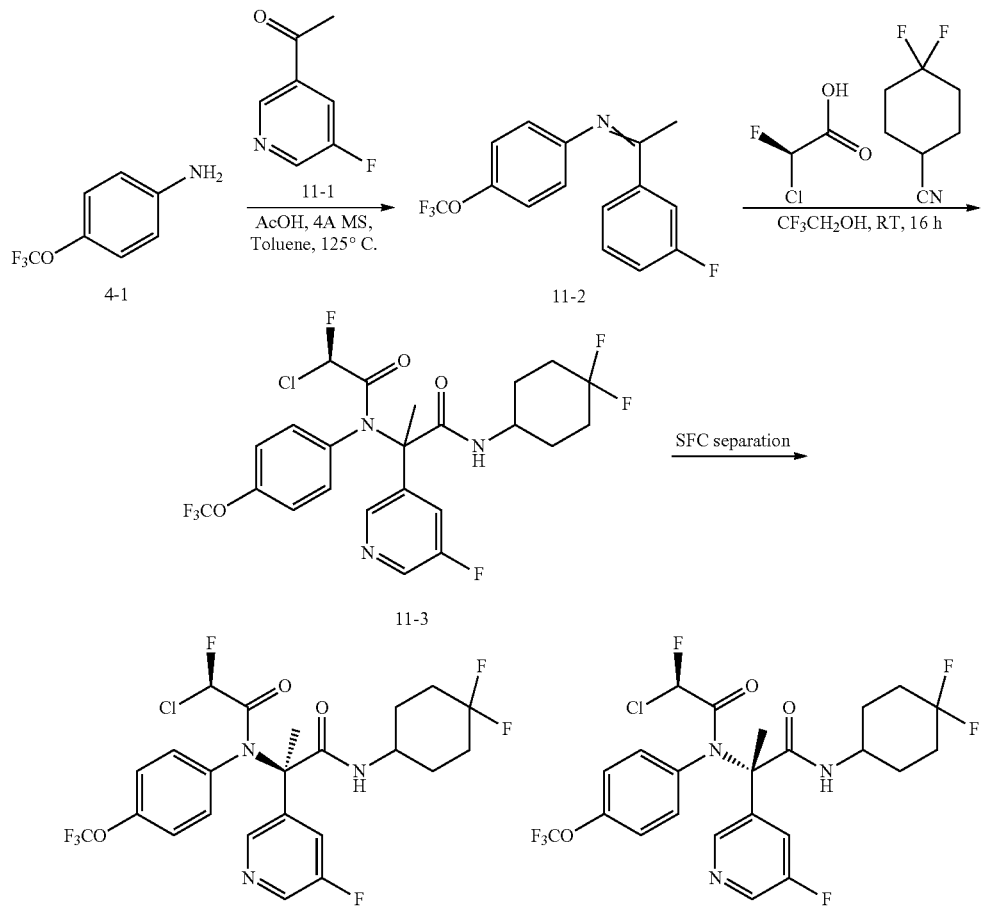

Example 11a and 11b
(Stereochemistry arbitrarily assigned at center between two amides)

The 11-3 (198 mg, 356.20 μmol) was separated by SFC (DAICEL CHIRALCEL OD-H (250 mm*30 mm, 5 m)); Mobile phase: A: Supercritical $CO_2$, B: Neu-ETOH; Isocratic: A:B=90:10; Flow rate: 60 mL/min) to afford two fractions.

Example 11a: (29 mg, 14.65% yield) was obtained. LCMS: (M+H)=556.2. SFC: Retention time: 1.773 min, OD_3_EtOH_DEA_5_40_25ML_7MIN. $^1$H NMR (400 MHz, DMSO-$d_6$): δ8.52-8.41 (m, 2H), 7.82-7.73 (m, 1H), 7.73-7.62 (m, 2H), 7.49-7.39 (m, 1H), 7.39-7.26 (m, 2H), 6.46-6.23 (m, 1H), 3.86 (br s, 1H), 2.01 (br s, 3H), 1.90 (br s, 1H), 1.76 (s, 5H), 1.65-1.50 (m, 2H). $^{19}$F NMR (376 MHz, DMSO-$d_6$): δ −56.90 (s, 3F), −91.84 (br d, J=231.7 Hz, 1F), −99.36 (br d, J=231.7 Hz, 1F), −128.10 (s, 1F), −141.91 (s, 1F).

Example 11b: (61 mg, 29.95% yield) was obtained. LCMS: (M+H)=556.2. SFC: Retention time: 2.257 min, OD_3_EtOH_DEA_5_40_25ML_7MIN. $^1$H NMR (400 MHz, DMSO-$d_6$): δ 8.49-8.40 (m, 2H), 7.75-7.67 (m, 1H), 7.66-7.61 (m, 1H), 7.61-7.54 (m, 1H), 7.52-7.45 (m, 1H), 7.41-7.30 (m, 2H), 6.43-6.20 (m, 1H), 3.85 (br s, 1H), 1.99 (br s, 3H), 1.90 (s, 3H), 1.88-1.68 (m, 3H), 1.67-1.44 (m, 2H). $^{19}$F NMR (376 MHz, DMSO-$d_6$): δ −56.32-−57.54 (m, 3F), −91.99 (br d, J=234.6 Hz, 1F), −99.25 (br d, J=226.0 Hz, 1F), −128.06 (s, 1F), −141.88 (s, 1F).

Examples 13a and 13b

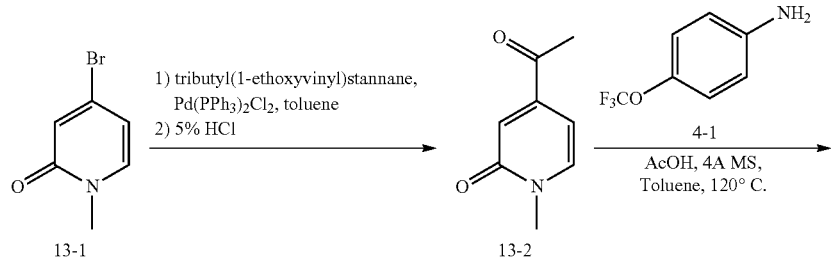

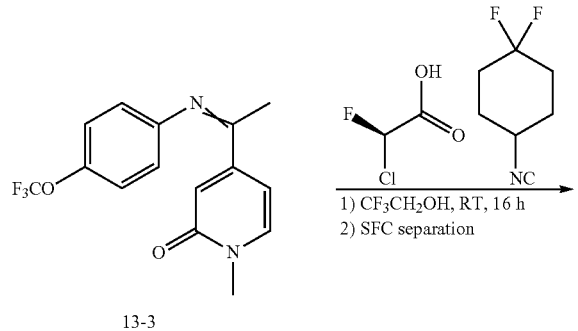

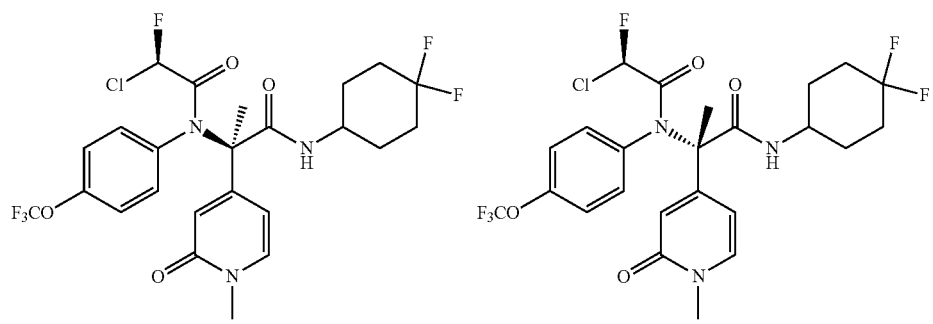

Example 13a and 13b
(Stereochemistry arbitrarily assigned at center between two amides)

To a solution of 4-bromo-1-methyl-pyridin-2-one (4.0 g, 21.27 mmol) in toluene (80 mL) was added tributyl(1-ethoxyvinyl)stannane (9.56 g, 26.47 mmol, 8.93 mL) and Pd(PPh$_3$)$_2$Cl$_2$ (1.49 g, 2.13 mmol). The mixture was heated and stirred at 100° C. for 12 hours under N$_2$. The mixture was quenched with saturated solution of KF (40 mL) before the mixture was cooled to room temperature, then the mixture was treated with 5% hydrochloric acid (40 mL), the reaction was extracted with ethyl acetate (20 mL*3), the organic layers were dried over anhydrous Na$_2$SO$_4$, filtered and concentrated under reduced pressure to give a crude. The crude was purified by column chromatography (SiO$_2$, Petroleum ether/Ethyl acetate=0/1 to 1/0, TLC: petroleum ether:ethyl acetate=0:1, R$_f$=0.2) to give compound 13-2 (2.1 g, 13.89 mmol, 65.30% yield). $^1$H NMR (400 MHz, CDCl$_3$) δ 7.36 (d, J=7.2 Hz, 1H), 7.06 (d, J=1.6 Hz, 1H), 6.60 (dd, J=2.0, 7.2 Hz, 1H), 3.57 (s, 3H), 2.52 (s, 3H).

A mixture of 13-2 (2.1 g, 13.89 mmol), 4-(trifluoromethoxy)aniline (3.69 g, 20.84 mmol, 2.82 mL), 4A MS (500 mg, 13.89 mmol) and acetic acid (5.01 g, 83.35 mmol, 4.77 mL) in toluene (100 mL) was degassed and purged with N$_2$ for 3 times, and then the mixture was stirred at 120° C. for 12 h under N$_2$ atmosphere. The reaction mixture was concentrated under reduced pressure to give a crude product. The residue was purified flash silica gel chromatography (Eluent of 0~100% Ethyl acetate/Petroleum ether gradient @ 20 mL/min) to give 13-3 (1.4 g, 4.51 mmol, 32.48% yield). $^1$H NMR (400 MHz, CDCl$_3$) δ 7.32 (d, J=7.2 Hz, 1H), 7.23 (d, J=8.0 Hz, 2H), 6.99-6.89 (m, 2H), 6.80-6.75 (m, 2H), 3.59 (s, 3H), 2.16 (s, 3H).

To a solution of 13-3 (300.00 mg, 966.90 mol) in CF$_3$CH$_2$OH (4 mL) was added (2R)-2-chloro-2-fluoro-acetic acid (233.07 mg, 1.16 mmol, 56% purity) and 1,1-difluoro-4-isocyano-cyclohexane (154.38 mg, 1.06 mmol). The mixture was stirred at 25° C. for 2 hours. The mixture was concentrated under reduced pressure to give a crude compound 13. The residue was purified by prep-HPLC (column: Boston Green ODS 150*30 mm*5 m; mobile phase: [water (FA)-ACN]; B %: 45%-75%, 6 min) to give desired compound (53 mg, purity 97%).

Compound 13 was further separated by SFC (column: DAICEL CHIRALPAK AD (250 mm*30 mm, 10 μm); mobile phase: [Neu-ETOH]; B %: 15%-15%) to afford two fractions.

Example 13a: (20 mg, 3.55% yield) was obtained. LCMS: (M+H)=568.2. SFC: Retention time: 2.647 min, AD_3_EtOH_DEA_5_40_25ML_7MIN. $^1$HNMR (400 MHz, DMSO-d$_6$): δ7.79-7.63 (m, 1H), 7.54 (s, 1H), 7.51-7.46 (m, 1H), 7.44-7.36 (m, 2H), 6.45-6.28 (m, 2H), 6.27-6.20 (m, 1H), 0.3.90-3.76 (m, 1H), 3.33-3.28 (m, 3H), 2.07-1.93 (m, 3H), 1.92-1.68 (m, 4H), 1.64-1.50 (m, 4H).

Example 13b: (15 mg, 2.61% yield) was obtained. LCMS: (M+H)=568.2. SFC: Retention time: 2.991 min, AD_3_EtOH_DEA_5_40_25ML_7MIN. $^1$HNMR (400 MHz, DMSO-d$_6$): δ7.60-7.52 (m, 2H), 7.49 (d, J=7.2 Hz, 2H), 7.41-7.34 (m, 2H), 6.45-6.27 (m, 2H), 6.22 (dd, J=2.0, 7.2 Hz, 1H), 3.81 (s, 1H), 3.30 (s, 3H), 2.07-1.92 (m, 3H), 1.91-1.65 (m, 7H), 1.63-1.46 (m, 2H).

Examples 14a and 14b

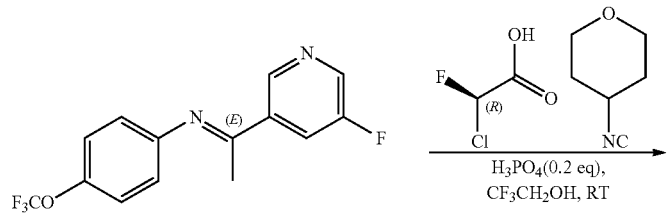

11-2

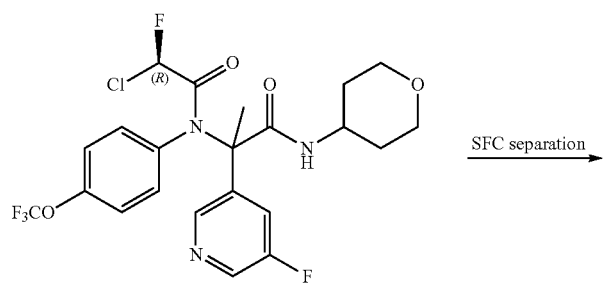

14

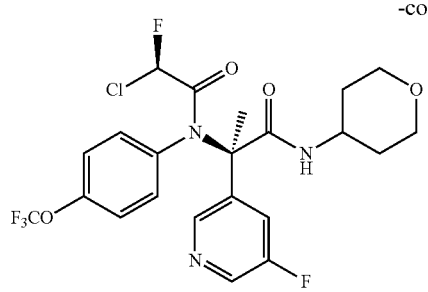 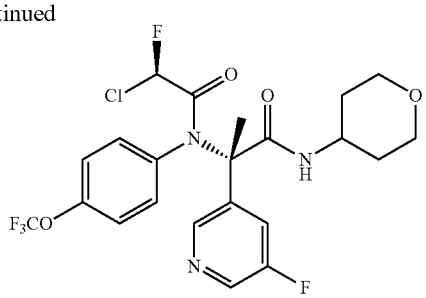

Example 14a and 14b
(Stereochemistry arbitrarily assigned at center between two amides)

To a solution of Compound 11-2 (350 mg, 1.17 mmol) in CF$_3$CH$_2$OH (3 mL) was added H$_3$PO$_4$ (26 mg, 225.52 μmol, 15.48 μL, 85% purity). The mixture was stirred at 25° C. for 30 min. Then the mixture was added 4-isocyanotetrahydropyran (153 mg, 1.17 mmol, 85% purity) and (2R)-2-chloro-2-fluoro-acetic acid (240 mg, 1.41 mmol, 66% purity). The mixture was stirred at 25° C. for 5 hr. The reaction mixture was concentrated under reduced pressure to give a residue. The residue was purified by prep-HPLC (Boston Green ODS 150*30 mm*5 m; Mobile phase: A: water (FA) B: ACN; Gradient condition: from 45% B to 75% B; Flow rate: 35 mL/min). The pure fractions were collected and the volatile solvent was removed by evaporation. The aqueous residue was lyophilized to afford the title compound. Compound 14 (127 mg, 20.80% yield) was obtained. LCMS (M+H) =522.1. $^1$H NMR (400 MHz, DMSO-d$_6$): δ8.53-8.38 (m, 2H), 7.82-7.61 (m, 3H), 7.60-7.49 (m, 1H), 7.47-7.30 (m, 2H), 6.49-6.23 (m, 1H), 4.01-3.77 (m, 3H), 3.36 (br s, 2H), 1.98-1.73 (m, 3H), 1.72-1.58 (m, 2H), 1.57-1.40 (m, 2H). $^{19}$F NMR (376 MHz, DMSO-d$_6$): δ −56.93 (br d, J=20.0 Hz, 3F), −128.12 (br d, J=17.2 Hz, 1F), −141.87 (s, 1F).

The Compound 14 (127 mg, 243.36 μmol) was separated by SFC (DAICEL CHIRALPAK AD (250 mm*30 mm, 10 μm)), Mobile phase: A: Supercritical CO$_2$, B: Neu-ETOH; Isocratic: A:B=85:15; Flow rate: 60 mL/min) to afford two fractions.

Example 14a: (44 mg, 34.65% yield) was obtained. LCMS (M+H)=522.2. SFC: Retention time: 2.272 min, AD_3_EtOH_DEA_5_40_25ML_7MIN. $^1$H NMR (400 MHz, DMSO-d$_6$): δ8.53-8.42 (m, 2H), 7.75 (d, J=8.4 Hz, 1H), 7.72-7.65 (m, 2H), 7.42 (d, J=7.6 Hz, 1H), 7.35 (br s, 2H), 6.47-6.24 (m, 1H), 3.98-3.79 (m, 3H), 3.40-3.34 (m, 2H), 1.78 (s, 3H), 1.72-1.59 (m, 2H), 1.57-1.44 (m, 2H). $^{19}$F NMR (376 MHz, DMSO-d$_6$): δ −56.90 (s, 3F), −128.14 (s, 1F), −141.87 (s, 1F).

Example 14b: (44 mg, 34.65% yield) was obtained. LCMS (M+H)=522.2. SFC: Retention time: 2.762 min, AD_3_EtOH_DEA_5_40_25ML_7MIN. $^1$H NMR (400 MHz, DMSO-d$_6$): δ 8.45 (s, 1H), 8.42 (d, J=2.4 Hz, 1H), 7.75-7.62 (m, 2H), 7.60-7.47 (m, 2H), 7.35 (br s, 2H), 6.47-6.22 (m, 1H), 3.95-3.79 (m, 3H), 3.38-3.33 (m, 2H), 1.91 (s, 3H), 1.73-1.57 (m, 2H), 1.57-1.39 (m, 2H). $^{19}$F NMR (376 MHz, DMSO-d$_6$): δ −56.95 (s, 3F), −128.09 (s, 1F), −141.86 (s, 1F).

Examples 17a and 17b

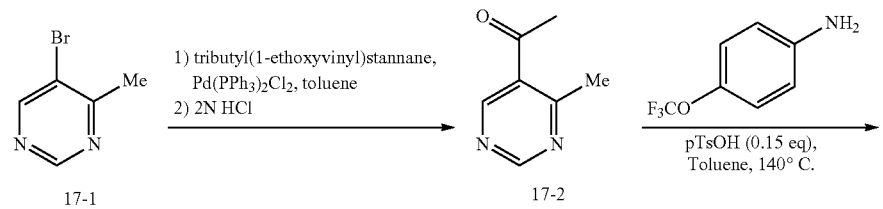

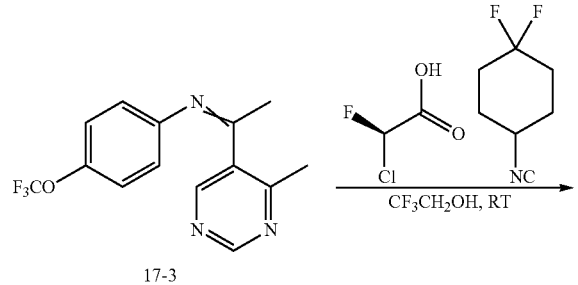

-continued

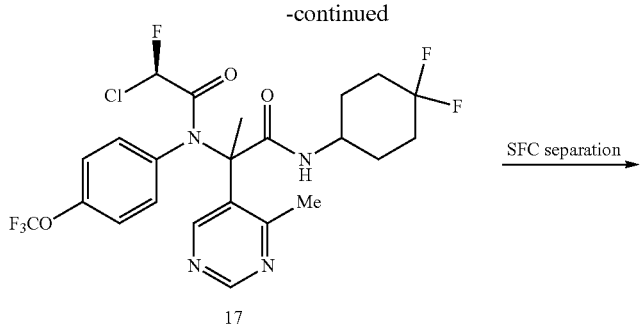

17

SFC separation →

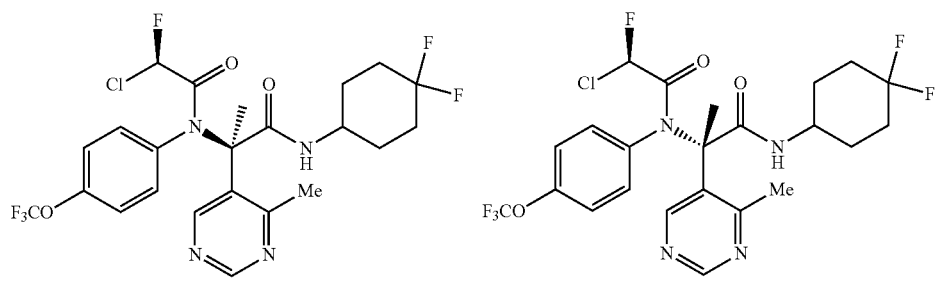

Example 17a and 17b
(Stereochemistry arbitrarily assigned at center between two amides)

To a solution of 17-1 (9 g, 52.02 mmol) and tributyl(1-ethoxyvinyl)stannane (22.37 g, 61.94 mmol, 20.91 mL) in toluene (100 mL) was added Pd(PPh₃)₂Cl₂ (1.83 g, 2.60 mmol). The mixture was stirred at 110° C. for 16 h under N₂. The reaction mixture was filtered and concentrated under reduced pressure to give Compound 5-(1-ethoxyvinyl)-4-methyl-pyrimidine (10 g, crude). To a solution of 5-(1-ethoxyvinyl)-4-methyl-pyrimidine (10 g) was added HCl (2 M, 82.21 mL). The mixture was stirred at 20° C. for 3 h. The reaction was extracted with EtOAc (30 mL×5). The combined organic phase was washed with brine (15 mL), dried over Na₂SO₄, filtered, and concentrated under reduced pressure. Compound 17-2 (5.5 g, crude) was obtained.

A mixture of 17-2 (7.49 g, 42.31 mmol, 5.72 mL), 1-(4-methylpyrimidin-5-yl)ethanone (3 g, 21.15 mmol) and p-TsOH (546.39 mg, 3.17 mmol) in toluene (60 mL) was degassed and purged with N₂ for 3 times, and then the mixture was stirred at 140° C. for 16 h under N₂ atmosphere. The mixture was cooled to room temperature and filtered, and the filtrate was concentrated under reduced pressure. The residue was purified by flash silica gel chromatography (Eluent of 0~50% Ethyl acetate/Dichloromethane @ 40 mL/min). Compound 17-3 (3.74 g) was obtained.

To a solution of 17-3 (600 mg, 2.03 mmol) in CF₃CH₂OH (2 mL) was added (2R)-2-chloro-2-fluoro-acetic acid (464.92 mg, 2.44 mmol) and 1,1-difluoro-4-isocyano-cyclohexane (327.73 mg, 2.03 mmol). The mixture was stirred at 20° C. for 16 h. The reaction mixture was concentrated under reduced pressure. The residue was purified by flash silica gel chromatography (Eluent of 0~20% Ethyl acetate/Petroleum ether gradient @ 20 mL/min). The residue was purified by prep-HPLC (column: Boston Green ODS 150*30 mm*5 m; mobile phase: [water (FA)-ACN]; B %: 50%-80%, 7 min). Compound 17 (51 mg, 89.94 μmol, 4.43% yield, 97.51% purity) was obtained.

The compound 17 (51 mg) was separated by SFC (DAICEL CHIRALPAK AS (250 mm*30 mm, 10 μm)); Mobile phase: A: Supercritical CO₂, B: Neu-ETOH; Isocratic: A:B=90:10; Flow rate: 60 mL/min) to afford two fractions.

Example 17a: (12.85 mg, 24.83% yield) was obtained. LCMS: (M+H)=553.1. SFC: Retention time: 1.174 min, AS_3_EtOH_DEA_5_40_25ML_7MIN. ¹H NMR (400 MHz, DMSO-d₆): δ 8.89 (s, 1H), 8.65 (s, 1H), 7.67 (br t, J=7.0 Hz, 3H), 7.44 (br s, 2H), 6.43-6.25 (m, 1H), 3.80 (br s, 1H), 3.30 (br s, 3H), 2.02-1.81 (m, 4H), 1.75 (s, 3H), 1.66 (br d, J=10.6 Hz, 2H), 1.46 (br d, J=12.5 Hz, 2H). ¹⁹F NMR (376 MHz, DMSO-d₆): δ −56.87 (s, 3F), −92.16 (br d, J=235.8 Hz, 1F), −99.27 (br d, J=242.8 Hz, 1F), −141.49 (br s, 1F)

Example 17b: (12.79 mg, 25.08% yield) was obtained. LCMS (M+H)=553.1. SFC: Retention time: 1.834 min, AS_3_EtOH_DEA_5_40_25ML_7MIN. ¹H NMR (400 MHz, DMSO-d₆): δ 8.92 (s, 1H), 8.74 (s, 1H), 7.83 (br d, J=7.0 Hz, 1H), 7.63 (d, J=7.6 Hz, 1H), 7.54-7.42 (m, 3H), 6.44-6.24 (m, 1H), 3.80 (brs, 1H), 3.31 (br s, 3H), 2.02-1.68 (m, 6H), 1.65 (s, 3H), 1.47 (br d, J=10.8 Hz, 2H). ¹⁹F NMR (376 MHz, DMSO-d₆): δ −56.87 (s, 3F), −91.75--93.12 (m, 1F), −99.13 (br d, J=194.2 Hz, 1F), −141.01 (br s, 1F)

Examples 18a and 18b

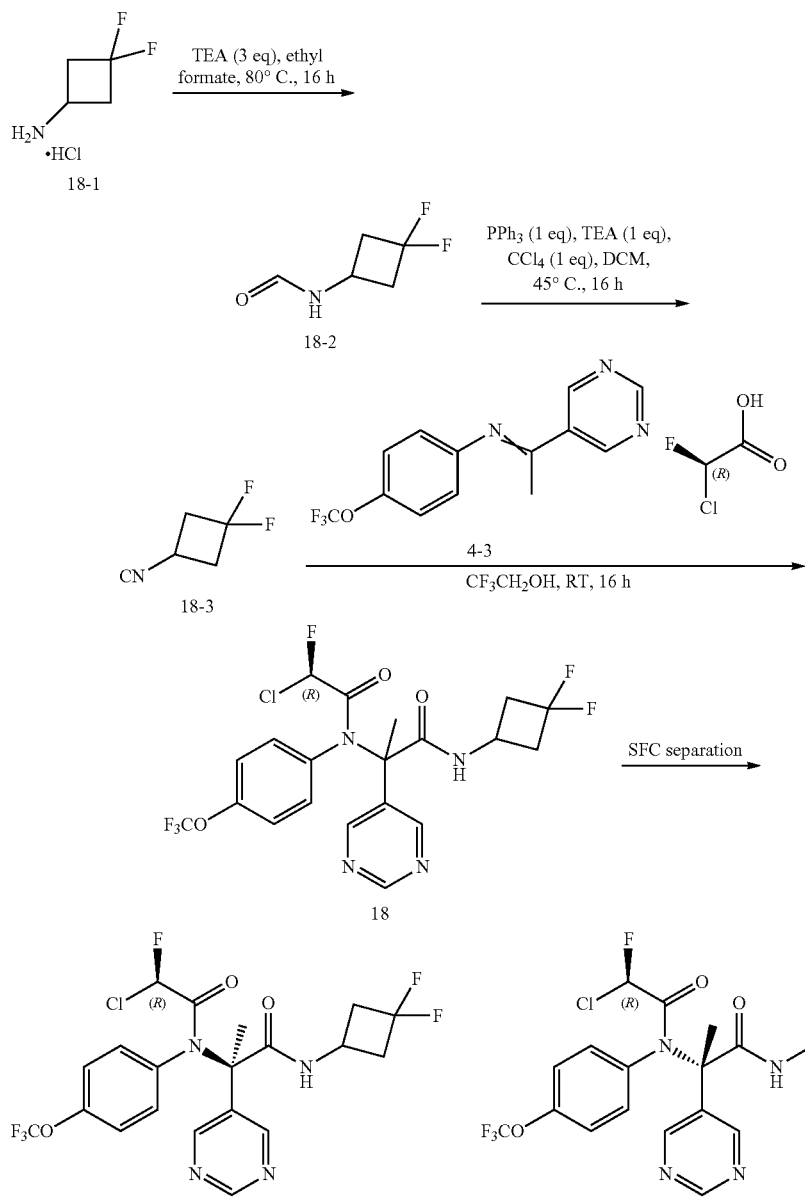

Example 18a and 18b
(Stereochemistry arbitrarily assigned at center between two amides)

To a solution of 18-1 (5 g, 34.83 mmol, HCl salt) in ethyl formate (60 mL) was added TEA (10.57 g, 104.48 mmol, 14.54 mL). The mixture was stirred at 80° C. for 16 hr. The mixture was concentrated under vacuum, diluted with water (30 mL), extracted with DCM (30 mL*2). The organic layer as washed with brine (30 mL), dried over $Na_2SO_4$, filtered, and concentrated under vacuum. 18-2 (4.28 g, crude) was obtained. $^1$H NMR (400 MHz, $CDCl_3$): δ 8.20-8.08 (m, 1H), 6.16 (br s, 1H), 4.43-4.27 (m, 1H), 3.03-2.91 (m, 2H), 2.59-2.44 (m, 2H).

To a solution of 18-2 (4.28 g, 31.68 mmol) in DCM (20 mL) was added $PPh_3$ (8.31 g, 31.68 mmol), TEA (3.21 g, 31.68 mmol, 4.41 mL) and $CCl_4$ (4.87 g, 31.68 mmol, 3.05 mL). The mixture was stirred at 45° C. for 16 hr. The reaction mixture was concentrated under reduced pressure. Then MTBE (30 mL) and PE (30 mL) was added and the mixture was stirred at 20° C. for 2 hours. The reaction was filtered and the filter cake was washed by MTBE (20 mL×3). The combined filtrate was concentrated under reduced pressure. Compound 18-3 (7.35 g, crude) was obtained.

To a solution of Compound 4-1 (2 g, 4.27 mmol) in $CF_3CH_2OH$ (20 mL) was added (2R)-2-chloro-2-fluoro-acetic acid (1.03 g, 5.12 mmol) and 18-3 (999.28 mg, 4.27 mmol). The mixture was stirred at 20° C. for 16 hr. The reaction mixture was concentrated under reduced pressure. The residue was purified by flash silica gel chromatography (Eluent of 0~100% Ethyl acetate/Petroleum ether gradient @ 35 mL/min). The product was further purified by prep- HPLC (column: Boston Green ODS 150*30 mm*5 m; mobile phase: [water (FA)-ACN]; B %: 43%-73%, 6 min). Compound 18 (160 mg, 311.25 μmol, 7.29% yield) was obtained.

The Compound 18 (160 mg) was separated by chiral SFC was separated by SFC (DAICEL CHIRALCEL OD (250 mm*30 mm, 10 μm); Mobile phase: A: Supercritical CO2, B: Neu-ETOH; Isocratic: A:B=85:15; Flow rate: 60 mL/min) concentrated under vacuum to afford two fractions.

Example 18a: (16.52 mg) was obtained. LCMS: (M+H)=511.0. SFC: Retention time: 1.820 min, OD-3_EtOH (DEA)_5_40_25ML. $^1$H NMR (400 MHz, DMSO-d$_6$): δ 9.08 (s, 1H), 8.84 (s, 2H), 8.20 (d, J=6.4 Hz, 1H), 7.87 (dd, J=2.4, 8.5 Hz, 1H), 7.54-7.27 (m, 3H), 6.50-6.32 (m, 1H), 4.17-4.05 (m, 1H), 2.97-2.80 (m, 2H), 2.66-2.52 (m, 2H), 1.64 (s, 3H). $^{19}$F NMR (376 MHz, DMSO-d$_6$): δ −56.82 (br s, 3F), −81.28−−82.71 (m, 1F), −96.15−−97.48 (m, 1F), −142.44 (s, 1F).

Example 18b: (19.34 mg, 32.06% yield) was obtained. LCMS (M+H)=511.0. SFC: Retention time: 2.467 min, OD-3_EtOH (DEA)_5_40_25ML. $^1$H NMR (400 MHz, DMSO-d$_6$): δ 9.04 (s, 1H), 8.83 (s, 2H), 8.16 (d, J=6.4 Hz, 1H), 7.70 (dd, J=2.4, 8.6 Hz, 1H), 7.50-7.35 (m, 3H), 6.43-6.23 (m, 1H), 4.16-4.03 (m, 1H), 2.98-2.77 (m, 2H), 2.60 (br dd, J=5.4, 19.8 Hz, 2H), 1.79 (s, 3H). $^{19}$F NMR (376 MHz, DMSO-d$_6$): δ −56.86 (s, 3F), −81.37−−82.55 (m, 1F), −96.17−−97.35 (m, 1F), −141.95 (s, 1F).

Examples 22a and 22b

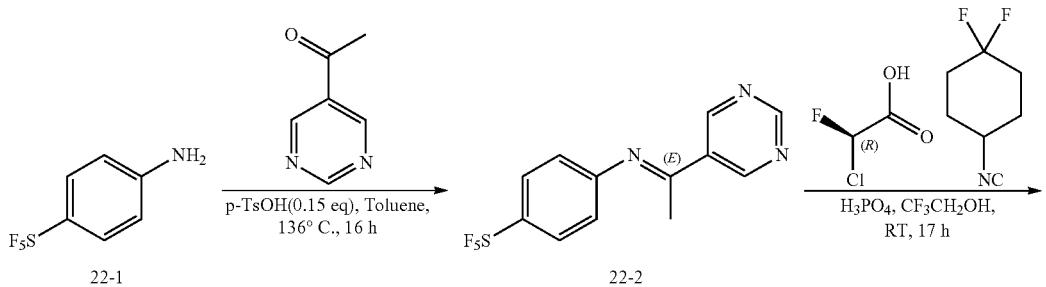

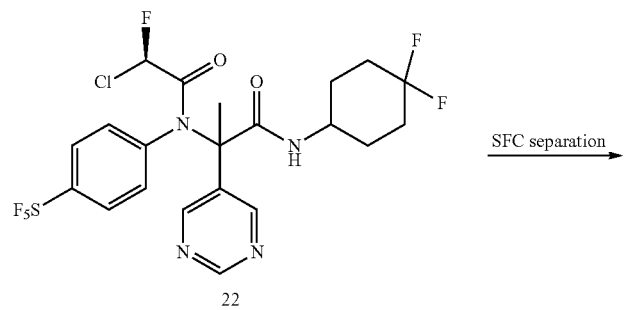

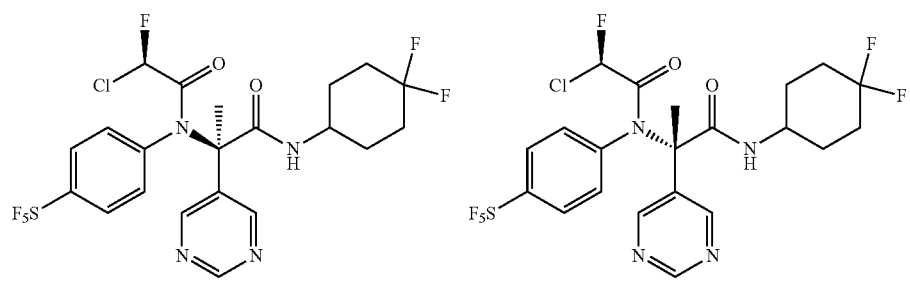

Example 22a and 22b
(Stereochemistry arbitrarily assigned at center between two amides)

To a solution of 22-1 (2.5 g, 11.41 mmol) and 1-pyrimidin-5-ylethanone (1.39 g, 11.41 mmol) in toluene (70 mL) was added p-TsOH (294.63 mg, 1.71 mmol). The mixture was stirred at 136° C. for 16 hr with removal of water by Dean-Stark trap under $N_2$ atmosphere. The reaction was filtered, and the filter cake was washed with toluene (10 mL*2). The filtrate was concentrated under reduced pressure. The residue was purified by flash silica gel chromatography (Eluent of 0~10% DCM/EtOAc @ 20 mL/min). 22-2 (2.02 g, 5.62 mmol, 49.30% yield, 90% purity) was obtained. $^1$HNMR (400 MHz, DMSO-$d_6$) δ 9.38-9.28 (m, 3H), 7.92 (d, J=8.8 Hz, 2H), 7.05 (d, J=8.8 Hz, 2H), 2.28 (s, 3H).

To a solution of 22-2 (1 g, 2.78 mmol) in $CF_3CH_2OH$ (12 mL) was added $H_3PO_4$ (58.72 mg, 509.31 μmol, 34.95 μL). The mixture was stirred at 20° C. for 30 min. Then 1,1-difluoro-4-isocyano-cyclohexane (448.35 mg, 2.78 mmol) and (2R)-2-chloro-2-fluoro-acetic acid (521.19 mg, 2.78 mmol) was added. The mixture was stirred at 20° C. for 17 hr. The reaction was concentrated under reduced pressure to give a residue. The residue was purified by flash silica gel chromatography (Eluent of 0-50% Ethyl acetate/Petroleum ether gradient @ 35 mL/min) and the residue was further purified by prep-HPLC (column: Welch Xtimate C18 150*30 mm*5 m; mobile phase: [water (FA)-ACN]; B %: 52%-82%, 7 min). Example 22 (100 mg, 5.94% yield) was obtained. LCMS: (M+H)=580.7. $^1$HNMR (400 MHz, DMSO-$d_6$) δ 9.07 (d, J=11.4 Hz, 1H), 8.87 (d, J=6.4 Hz, 2H), 8.15-7.80 (m, 3H), 7.80-7.66 (m, 1H), 7.63-7.37 (m, 1H), 6.52-6.26 (m, 1H), 3.86 (s, 1H), 2.10-1.83 (m, 5H), 1.81-1.66 (m, 4H), 1.63-1.40 (m, 2H). $^{19}$F NMR (376 MHz, DMSO-$d_6$) δ 64.03 (d, J=152.6 Hz, 3F), −92.01 (dd, J=64.2, 234.1 Hz, 1F), −99.25 (dd, J=57.2, 234.1 Hz, 1F), −142.27 (d, J=190.7 Hz, 1F).

The compound 22 (100 mg, 172.14 μmol) was separated by SFC (WHELK-01 (250 mm*30 mm, 5 μm)); Mobile phase: A: Supercritical $CO_2$, B: Neu-IPA; Isocratic: A:B=80:20; Flow rate: 60 mL/min) to afford two fractions.

Example 22a: (20 mg, 33.85 μmol, 19.67% yield) was obtained. LCMS: (M+H)=580.9. SFC: Retention time: 4.861 min, SS Whelk O1_IPA_DEA_5_40_25ML. $^1$H NMR (400 MHz, DMSO-$d_6$): δ9.08 (s, 1H), 8.87 (s, 2H), 8.15-7.88 (m, 3H), 7.78 (d, J=8.0 Hz, 1H), 7.47 (s, 1H), 6.53-6.34 (m, 1H), 3.86 (d, J=7.6 Hz, 1H), 2.01 (s, 3H), 1.89-1.69 (m, 3H), 1.65 (s, 3H), 1.62-1.43 (m, 2H). $^{19}$F NMR (376 MHz, DMSO-$d_6$): δ64.02 (d, J=152.6 Hz, 5F), −91.89 (d, J=235.8 Hz, 1F), −99.40 (d, J=232.3 Hz, 1F), −141.21--145.92 (m, 1F).

Example 22b: (30 mg, 29.59% yield) was obtained. LCMS (M+H)=580.9. SFC: Retention time: 5.270 min, SS Whelk O1_IPA_DEA_5_40_25ML. $^1$H NMR (400 MHz, DMSO-$d_6$): δ9.06 (s, 1H), 8.86 (s, 2H), 7.98 (m, 2H), 7.84 (d, J=7.2 Hz, 1H), 7.70 (d, J=8.0 Hz, 1H), 7.61 (d, J=8.2 Hz, 1H), 6.49-6.29 (m, 1H), 3.85 (s, 1H), 2.11-1.82 (m, 5H), 1.78 (s, 3H), 1.66 (m, 1H), 1.61-1.46 (m, 2H). $^{19}$F NMR (376 MHz, DMSO-$d_6$): δ 64.01 (d, J=152.6 Hz, 5F), −92.06 (d, J=232.4 Hz, 1F), −97.67--102.77 (m, 1F), −142.09 (s, 1F).

Examples 23a and 23b

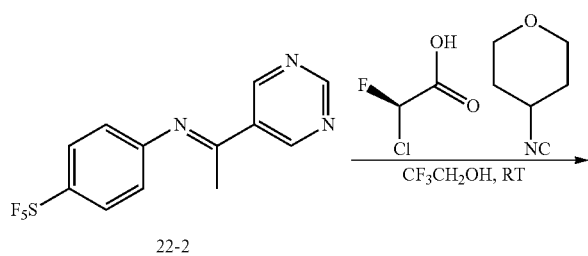

22-2

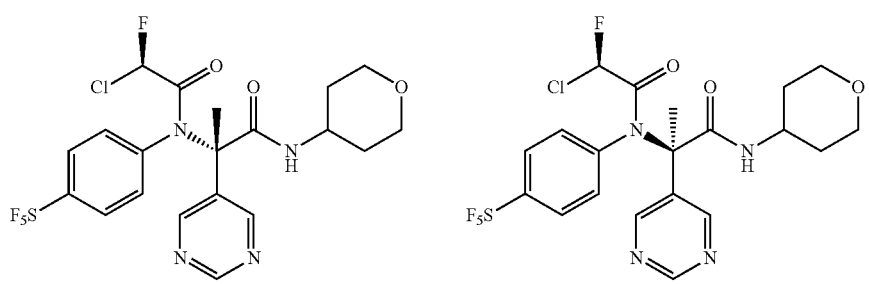

Example 23a and 23b
(Stereochemistry arbitrarily assigned at center between two amides)

To a solution of 22-2 (358.85 mg, 1.11 mmol) in CF$_3$CH$_2$OH (1 mL) was added (2R)-2-chloro-2-fluoro-acetic acid (208.77 mg, 1.11 mmol) and 4-isocyanotetrahydropyran (145.14 mg, 1.11 mmol, 85% purity). The mixture was stirred at 20° C. for 16 h. new added (2R)-2-chloro-2-fluoro-acetic acid (208.77 mg, 1.11 mmol) and 4-isocyanotetrahydropyran (145.14 mg, 1.11 mmol). The mixture was stirred at 20° C. for another 48 h. The reaction mixture was concentrated under reduced pressure to give a residue. The residue was purified by flash silica gel chromatography (Eluent of 0~30% Ethyl acetate/Petroleum ether gradient @ 20 mL/min). The residue was further purified by prep-HPLC (column: Welch Xtimate C18 150*30 mm*5 m; mobile phase: [water (FA)-ACN]; B %: 49%-79%, 7 min), which afford two fractions.

Example 23a: (1.08 mg, 0.2% yield) was obtained. LCMS (M+H)=547.0. SFC: Retention time: 3.536 min, AD_3_IPA_DEA_5_40_25ML_6MIN. $^1$H NMR (400 MHz, DMSO-d$_6$) δ 9.19-8.99 (m, 2H), 8.94-8.79 (m, 2H), 7.61 (d, J=9.4 Hz, 2H), 7.31-7.14 (m, 3H), 3.97-3.60 (m, 4H), 3.26 (br d, J=4.2 Hz, 1H), 2.43 (br dd, J=4.4, 12.6 Hz, 1H), 2.27-2.11 (m, 4H), 1.78 (br d, J=12.3 Hz, 1H), 1.52 (br d, J=11.0 Hz, 1H).

Example 23b: (4.85 mg, 7.98 mol, 7.19e-1% yield) was obtained. LCMS: (M+H)=547.0. HPLC: Retention time: 2.522 min, 10-80AB_4 min. 1 cm. SFC: Retention time: 2.818 min, AD_3_IPA_DEA_5_40_25ML_6MIN. $^1$H NMR (400 MHz, DMSO-d$_6$) δ 9.15 (s, 1H), 9.10 (d, J=3.0 Hz, 1H), 8.94 (s, 2H), 7.65 (d, J=9.5 Hz, 2H), 7.21-7.02 (m, 3H), 4.07-3.80 (m, 4H), 2.93 (br s, 1H), 2.25-2.13 (m, 1H), 2.04 (s, 3H), 1.80 (br d, J=9.0 Hz, 1H), 1.53 (br d, J=13.1 Hz, 1H).

Examples 26a and 26b

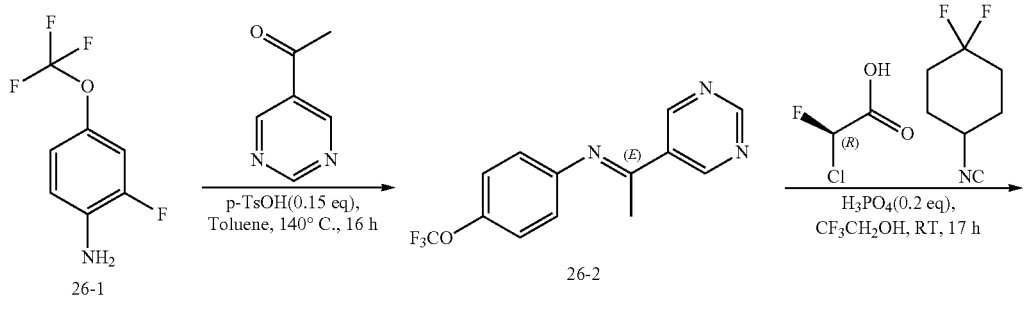

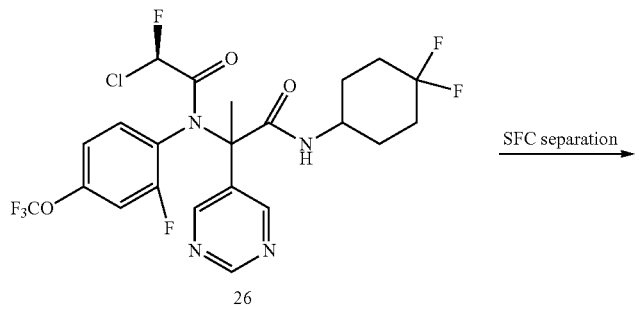

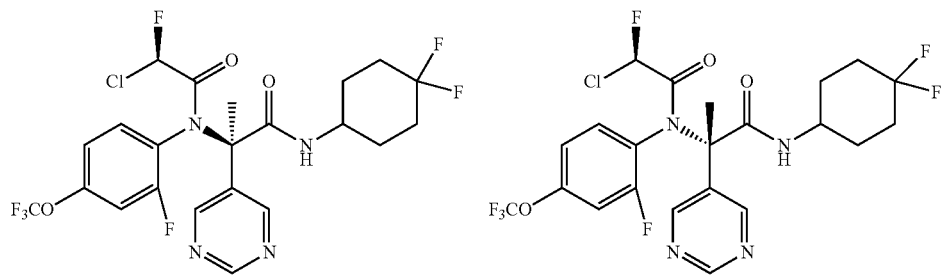

Example 26a and 26b
(Stereochemistry arbitrarily assigned at center between two amides)

A mixture of 26-1 (2 g, 10.25 mmol), 1-pyrimidin-5-ylethanone (1.50 g, 12.30 mmol) and 4-methylbenzenesulfonic acid (264.77 mg, 1.54 mmol) in toluene (50 mL) was heated to reflux (140° C.) for 16 h and remove water by Dean-Stark trap. The reaction mixture was filtered, and the filtrate was concentrated under reduced pressure to give a residue. The residue was purified by flash silica gel chromatography (Eluent of 0~30% Ethyl acetate/Petroleum ether gradient @ 30 mL/min). Compound 26-2 (1.88 g, 5.97 mmol, 58.23% yield, 95% purity) was obtained. $^1$H NMR (400 MHz, DMSO-$d_6$): δ 9.49-9.22 (m, 3H), 7.52 (dd, J=2.0, 10.6 Hz, 1H), 7.29 (td, J=1.2, 8.7 Hz, 1H), 7.13 (t, J=8.9 Hz, 1H), 2.31 (d, J=1.1 Hz, 3H).

To a solution of 26-2 (800 mg, 2.67 mmol) in CF$_3$CH$_2$OH (5 mL) was added H$_3$PO$_4$ (52.33 mg, 534.00 μmol, 31.15 μL). The reaction mixture was stirred at 15° C. for 30 min. Then 1,1-difluoro-4-isocyano-cyclohexane (430.61 mg, 2.67 mmol) and (2R)-2-chloro-2-fluoro-acetic acid (500.57 mg, 2.67 mmol) was added. The reaction mixture was stirred at 15° C. for 17 hr. The reaction mixture was concentrated under reduced pressure to give a residue. The residue was purified by flash silica gel chromatography (Eluent of 0~50% Ethyl acetate/Petroleum ether gradient @ 35 mL/min). The residue was further purified by prep-HPLC (column: Boston Green ODS 150*30 mm*5 m; mobile phase: [water (FA)-ACN]; B %: 53%-83%, 7 min). Compound 26 (87 mg, 5.71% yield) was obtained. LCMS: (M+H)=557.0. HPLC: Retention time: 4.783 min, 10-80AB_8 min. 1 cm. $^1$H NMR (400 MHz, DMSO-$d_6$): δ 9.13-9.01 (m, 1H), 8.90 (d, J=2.1 Hz, 1H), 8.81-8.67 (m, 1H), 8.10-7.21 (m, 4H), 6.69-6.44 (m, 1H), 3.84 (s, 1H), 2.15-1.47 (m, 11H). $^{19}$F NMR (376 MHz, DMSO-$d_6$): δ -54.66--62.10 (m, 3F), -87.95--92.80 (m, 1F), -99.34 (br d, J=231.7 Hz, 1F), -107.02--114.13 (m, 1F), -139.66--144.18 (m, 1F).

The Compound 26 (85 mg, 152.64 μmol) was separated by SFC (DAICEL CHIRALPAK AD (250 mm*30 mm, 10 m); Mobile phase: A: Supercritical CO$_2$, B: Neu-ETOH; Isocratic: A:B=90:10; Flow rate: 60 mL/min) to afford two fractions.

Example 26a: (30 mg, 34.45% yield) was obtained. LCMS: (M+H)=557.2. SFC: Retention time: 1.744 min, AD-3_EtOH (DEA) 5_40_25ML. $^1$H NMR (400 MHz, DMSO-$d_6$): δ 9.11-9.00 (m, 1H), 8.94-8.68 (m, 2H), 8.07-7.18 (m, 4H), 6.67-6.41 (m, 1H), 3.83 (s, 1H), 2.13-1.46 (m, 11H). $^{19}$F NMR (376 MHz, DMSO-$d_6$): δ -52.95--60.01 (m, 3F), -91.95 (d, J=235.8 Hz, 1F), -97.67--101.99 (m, 1F), -108.26--112.58 (m, 1F), -140.03--144.35 (m, 1F).

Example 26b: (32 mg, 37.22% yield) was obtained. LCMS (M+H)=557.2. SFC: Retention time: 2.004 min, AD-3_EtOH (DEA) 5_40_25ML. $^1$H NMR (400 MHz, DMSO-$d_6$): δ 9.11-8.96 (m, 1H), 8.92-8.73 (m, 2H), 7.93-7.74 (m, 1H), 7.73-7.55 (m, 1H), 7.55-7.22 (m, 2H), 6.69-6.42 (m, 1H), 3.83 (s, 1H), 2.13-1.53 (m, 11H). $^{19}$F NMR (376 MHz, DMSO-$d_6$): δ -56.67--57.85 (m, 3F), -92.12 (d, J=228.9 Hz, 1F), -98.91 (s, 1F), -106.68--112.98 (m, 1F), -141.07--143.17 (m, 1F).

Examples 27a and 27b

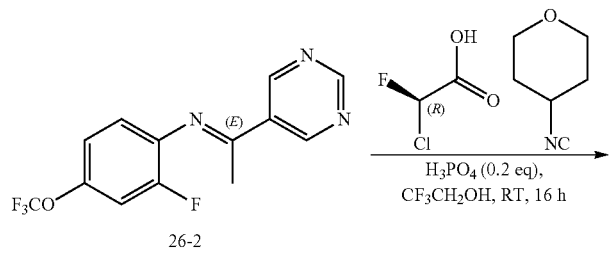
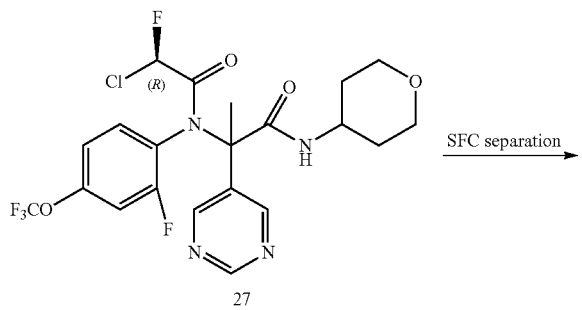

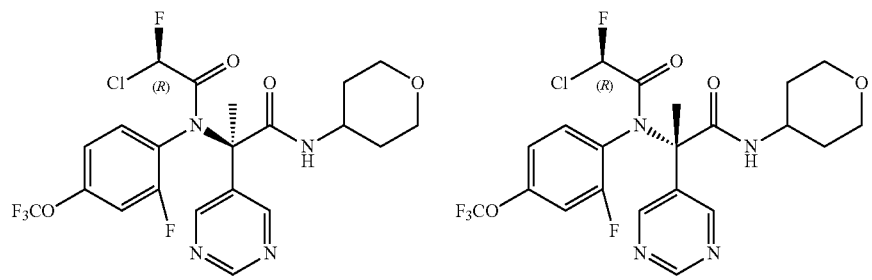

Example 27a and 27b
(Stereochemistry arbitrarily assigned at center between two amides)

To a solution of 26-2 (300 mg, 1.00 mmol) in CF$_3$CH$_2$OH (5 mL) was added dropwise H$_3$PO$_4$ (19.65 mg, 200.52 µmol, 85%). After addition, the mixture was stirred at 25° C. for 0.5 hr, and then 4-isocyanotetrahydropyran (136.19 mg, 1.10 mmol) and (2R)-2-chloro-2-fluoro-acetic acid (225.56 mg, 1.20 mmol) was added. The resulting mixture was stirred at 25° C. for 16 hr. The reaction mixture was concentrated under reduced pressure to give a residue. The residue was purified by flash silica gel chromatography (Eluent of 0~60% Ethyl acetate/Petroleum ether gradient @ 30 mL/min) to give a crude product which was further purified by pre-HPLC (column: Welch Xtimate C18 150*30 mm*5 m; mobile phase: [water (FA)-ACN]; B %: 34%-64%, 7 min) to give compound 27 (75 mg, 13.70% yield). LCMS: (M+H)=523.0.

Compound 27 (75 mg, 143.44 µmol) was separated by SFC DAICEL CHIRALPAK AD (250 mm*30 mm, 10 um), Mobile phase: A: Supercritical CO$_2$, B: Neu-IPA; Isocratic: A:B=85:15) to afford two fractions.

Example 27a: (15 mg, 19.76% yield) was obtained. LCMS: (M+H)=523.2. SFC: Retention time: 1.440 min, OD_ETOH_DEA_5_40_28ML_8MIN. $^1$H NMR (400 MHz, DMSO-d$_6$): δ 9.21-8.97 (m, 1H), 8.93-8.68 (m, 2H), 8.13-7.11 (m, 4H), 6.73-6.43 (m, 1H), 3.92-3.76 (m, 3H), 3.30 (br s, 2H), 2.14 (s, 1H), 1.83-1.31 (m, 6H). $^{19}$F NMR (376 MHz, DMSO-d$_6$): δ −56.40−−58.36 (m, 3F), −107.43−−112.20 (m, 1F), −140.80−−143.60 (m, 1F).

Example 27b: (15 mg, 19.79% yield) was obtained. LCMS (M+H)=533.2. SFC: Retention time: 1.579 min, OD_ETOH_DEA_5_40_28ML_8MIN. $^1$H NMR (400 MHz, DMSO-d$_6$): δ 9.10-8.99 (m, 1H), 8.97-8.73 (m, 2H), 7.94-7.25 (m, 4H), 6.73-6.43 (m, 1H), 3.83 (br s, 3H), 3.31 (br s, 2H), 2.14-1.69 (m, 3H), 1.68-1.30 (m, 4H). $^{19}$F NMR (376 MHz, DMSO-d$_6$): δ −56.40−−58.92 (m, 3F), −108.36−−113.53 (m, 1F), −143.56 (br d, J=313.5 Hz, 1F).

Examples 28a and 28b

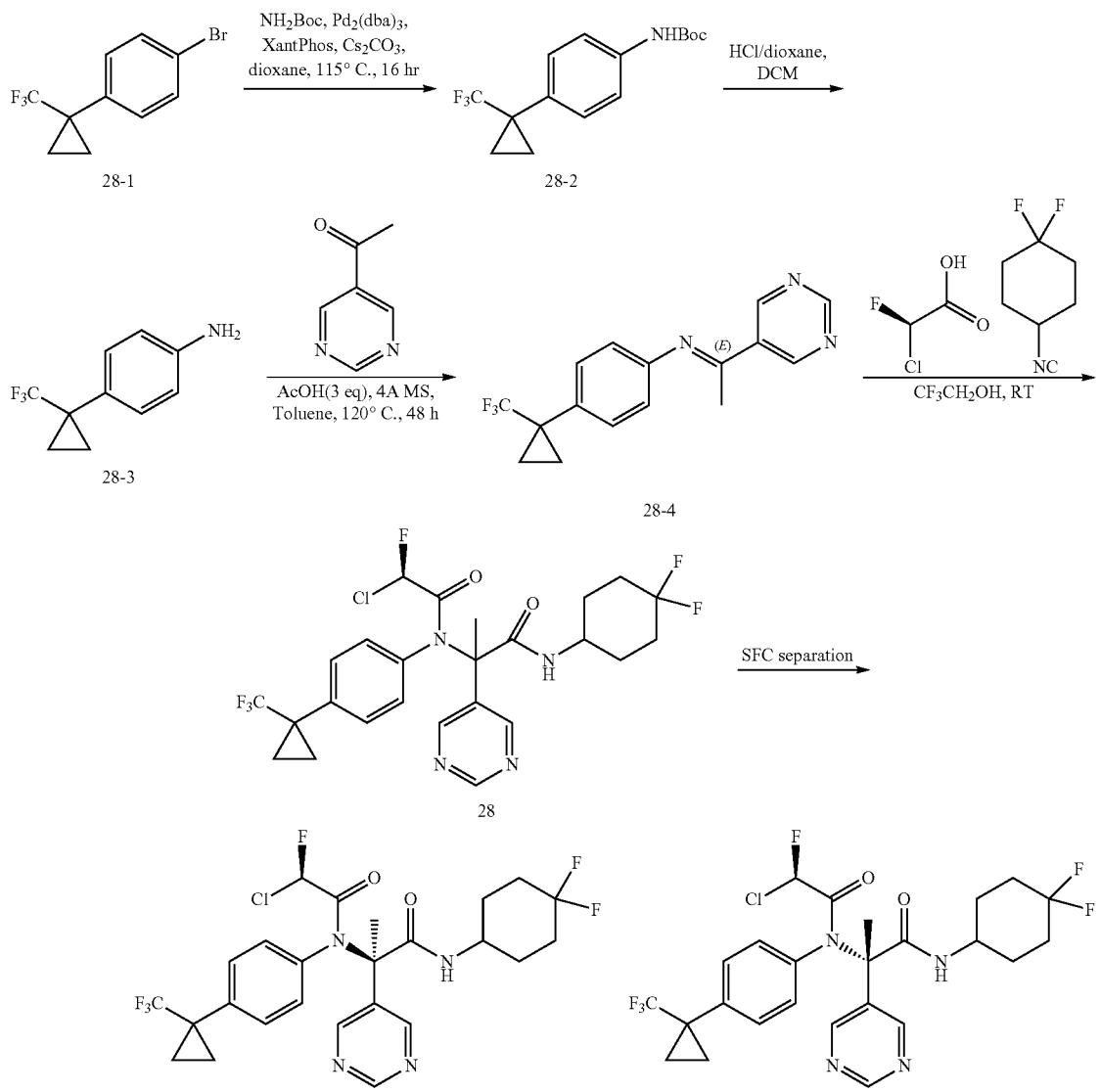

Example 28a and 28b
(Stereochemistry arbitrarily assigned at center between two amides)

A mixture of 28-1 (1 g, 3.77 mmol), tert-butyl carbamate (1.77 g, 15.12 mmol), Xantphos (663 mg, 1.15 mmol) and $Cs_2CO_3$ (7.38 g, 22.64 mmol) in dioxane (20 mL) was degassed and purged with Ar for 3 times, and then $Pd_2(dba)_3$ (363 mg, 396.41 mol) was added. The mixture was stirred at 115° C. for 18 hr under Ar atmosphere. The reaction mixture was filtered, and the filtrate was concentrated under reduced pressure to give a residue. The residue was purified by flash silica gel chromatography (Eluent of 0~10% Ethyl acetate/Petroleum ether gradient @ 35 mL/min). Compound 28-2 (740 mg, 2.46 mmol, 65.10% yield) was obtained. $^1$H NMR (400 MHz, DMSO-$d_6$): δ9.42 (s, 1H), 7.44 (d, J=8.6 Hz, 2H), 7.32 (d, J=8.6 Hz, 2H), 1.47 (s, 9H), 1.30-1.26 (m, 2H), 1.04 (s, 2H).

To a solution of Compound 28-2 (900 mg, 2.99 mmol) in DCM (20 mL) was added HCl/dioxane (4 M, 8.96 mL). The mixture was stirred at 20° C. for 16 hr. The reaction mixture was concentrated under reduced pressure to give a residue. The residue was diluted with 20 mL of DCM. The solution was basified with sat. $Na_2CO_3$ and adjusted to pH=10. The solution was extracted with DCM (30 mL×3). The organic layer was dried over $Na_2SO_4$, filtered, and concentrated under reduced pressure to give a residue. 28-3 (712 mg, crude) was obtained. LCMS: (M+H)=202.8. $^1$H NMR (400 MHz, DMSO-$d_6$): δ 7.06 (d, J=8.3 Hz, 2H), 6.54-6.49 (m, 2H), 5.18 (s, 2H), 1.23-1.18 (m, 2H), 0.95 (s, 2H).

To a solution of Compound 28-3 (771 mg, 3.83 mmol) and 1-(pyrimidin-5-yl)ethan-1-one (468.01 mg, 3.83 mmol) in toluene (30 mL) was added 4A MS (2 g) and AcOH (2.02 g, 33.70 mmol, 1.93 mL, 8.79 eq). The mixture was stirred at 125° C. for 16 hr under $N_2$ atmosphere. The reaction mixture was filtered, and the filtrate was concentrated under reduced pressure to give a residue. Compound 28-4 (1.19 g, crude) was obtained. $^1$H NMR (400 MHz, DMSO-$d_6$): δ 9.33-9.28 (m, 3H), 7.47 (d, J=8.2 Hz, 2H), 6.86 (d, J=8.3 Hz, 2H), 2.30 (s, 3H), 1.37-1.30 (m, 2H), 1.13 (br s, 2H).

To a solution of Compound 28-4 (1.19 g, 3.90 mmol) in $CF_3CH_2OH$ (15 mL) was added (2R)-2-chloro-2-fluoroacetic acid (939.55 mg, 4.68 mmol) and 1,1-difluoro-4-isocyano-cyclohexane (665.61 mg, 3.90 mmol). The mixture was stirred at 20° C. for 16 hr. The reaction mixture was concentrated under reduced pressure. The residue was purified by flash silica gel chromatography (Eluent of 0~100% Ethyl acetate/Petroleum ether gradient @ 35 mL/min). The residue was purified by prep-HPLC (column: Xtimate C18 150*40 mm*10 µm; mobile phase: [water (FA)-ACN]; B %: 45%-75%, 7 min). Compound 28 (340 mg, 603.98 µmol, 15.50% yield) was obtained. LCMS (M+H)=563.1. $^1$H NMR (400 MHz, DMSO-$d_6$): δ 9.03 (d, J=14.4 Hz, 1H), 8.82 (d, J=7.3 Hz, 2H), 7.77-7.65 (m, 1H), 7.62-7.42 (m, 3H), 7.40-7.19 (m, 1H), 6.36-6.10 (m, 1H), 3.82 (br s, 1H), 1.99 (br s, 4H), 1.83-1.73 (m, 3H), 1.70-1.50 (m, 4H), 1.41-1.30 (m, 2H), 1.10 (br d, J=6.6 Hz, 2H).

The Compound 28 (340 mg) was separated by chiral SFC was separated by SFC (DAICEL CHIRALPAK AD (250 mm*30 mm, 10 µm); Mobile phase: A: Supercritical $CO_2$, B: Neu-ETOH; Isocratic: A:B=80:20; Flow rate: 70 mL/min) concentrated under vacuum to afford two fractions.

Example 28a: (130.08 mg, 38.26% yield) was obtained. LCMS (M+H)=563.1. SFC: Retention time: 0.770 min, AD_ETOH_DEA_5_40_4ML_4MIN_5CM. $^1$H NMR (400 MHz, DMSO-$d_6$): δ 9.05 (s, 1H), 8.83 (s, 2H), 7.77-7.67 (m, 2H), 7.59-7.44 (m, 2H), 7.22 (br d, J=8.7 Hz, 1H), 6.35-6.18 (m, 1H), 3.84 (br s, 1H), 2.08-1.87 (m, 4H), 1.85-1.65 (m, 3H), 1.63 (s, 3H), 1.57-1.46 (m, 1H), 1.40-1.33 (m, 2H), 1.12 (br s, 2H). $^{19}$F NMR (376 MHz, DMSO-$d_6$): δ −68.33 (br s, 3F), −91.86 (br d, J=235.8 Hz, 1F), −99.41 (br d, J=235.8 Hz, 1F), −142.19 (br s, 1F).

Example 28b: (131.71 mg, 37.87% yield) was obtained. LCMS (M+H)=563.1. SFC: Retention time: 1.077 min, AD_ETOH_DEA_5_40_4ML_4MIN_5CM. $^1$H NMR (400 MHz, DMSO-$d_6$): δ 9.01 (s, 1H), 8.82 (s, 2H), 7.60 (br t, J=8.6 Hz, 2H), 7.53-7.42 (m, 2H), 7.37 (br d, J=8.0 Hz, 1H), 6.30-6.11 (m, 1H), 3.80 (br d, J=8.1 Hz, 1H), 1.96 (br d, J=8.6 Hz, 4H), 1.78 (s, 4H), 1.69-1.47 (m, 3H), 1.38-1.32 (m, 2H), 1.10 (br s, 2H). $^{19}$F NMR (376 MHz, DMSO-$d_6$): δ −68.39 (s, 3F), −91.35-−92.65 (m, 1F), −98.74-−99.72 (m, 1F), −141.82 (s, 1F).

Examples 29a and 29b

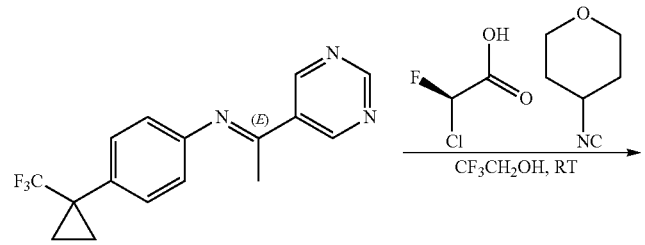

28-4

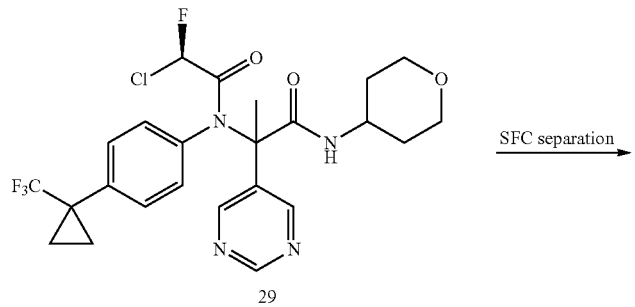

29

SFC separation

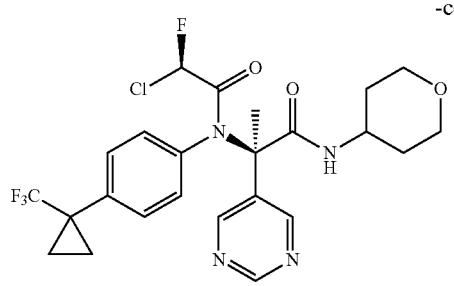 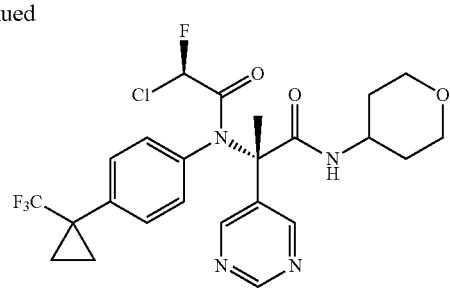

Example 29a and 29b
(Stereochemistry arbitrarily assigned at center between two amides)

To a solution of 28-4 (425 mg, 1.39 mmol) in CF$_3$CH$_2$OH (2 mL) was added (2R)-2-chloro-2-fluoro-acetic acid (318.49 mg, 1.67 mmol) and 4-isocyanotetrahydropyran (182.02 mg, 1.39 mmol). The mixture was stirred at 20° C. for 16 hr. The reaction mixture was concentrated under reduced pressure. The residue was purified by prep-HPLC (column: Boston Green ODS 150*30 mm*5 μm; mobile phase: [water (FA)-ACN]; B %: 55%-85%, 7 min). Compound 29 (120 mg, 209.75 μmol, 15.07% yield) was obtained. LCMS (M+H)=529.1. $^1$H NMR (400 MHz, DMSO-d$_6$): δ 9.03 (d, J=14.5 Hz, 1H), 8.83 (d, J=8.2 Hz, 2H), 7.73 (br d, J=8.1 Hz, 1H), 7.67-7.31 (m, 4H), 6.38-6.09 (m, 1H), 3.83 (br, d, J=8.5 Hz, 3H), 3.30-3.19 (m, 2H), 1.84-1.62 (m, 4H), 1.61-1.41 (m, 3H), 1.40-1.32 (m, 2H), 1.11 (br, d, J=7.9 Hz, 2H).

The Compound 29 (120 mg) was separated by chiral SFC was separated by SFC (DAICEL CHIRALPAK AD (250 mm*30 mm, 10 μm); Mobile phase: A: Supercritical CO$_2$, B: Neu-ETOH; Isocratic: A:B=75:25; Flow rate: 70 mL/min) concentrated under vacuum to afford two fractions.

Example 29a: (36.48 mg, 30.02% yield) was obtained. LCMS (M+H)=529.0. SFC: Retention time: 2.417 min, AD_3_EtOH_DEA_5_40_25ML_6MIN. $^1$H NMR (400 MHz, DMSO-d$_6$): δ 9.04 (s, 1H), 8.84 (s, 2H), 7.72 (br d, J=7.9 Hz, 2H), 7.60-7.44 (m, 2H), 7.26 (br d, J=7.7 Hz, 1H), 6.35-6.16 (m, 1H), 3.92-3.78 (m, 3H), 3.31-3.28 (m, 2H), 1.65 (s, 4H), 1.62-1.41 (m, 3H), 1.40-1.34 (m, 2H), 1.12 (br s, 2H). $^{19}$F NMR (376 MHz, DMSO-d$_6$): δ −68.30 (s, 3F), −142.12 (s, 1F).

Example 29b: (40.19 mg, 33.14% yield) was obtained. LCMS (M+H)=529.1. SFC: Retention time: 3.378 min, AD_3_EtOH_DEA_5_40_25ML_6MIN. $^1$H NMR (400 MHz, DMSO-d$_6$): δ 9.01 (s, 1H), 8.82 (s, 2H), 7.62 (d, J=7.6 Hz, 1H), 7.59-7.54 (m, 1H), 7.52-7.44 (m, 2H), 7.43-7.37 (m, 1H), 6.30-6.12 (m, 1H), 3.82 (br t, J=8.3 Hz, 3H), 3.31-3.27 (m, 2H), 1.80 (s, 3H), 1.67 (br d, J=13.1 Hz, 1H), 1.57-1.40 (m, 3H), 1.39-1.30 (m, 2H), 1.10 (br s, 2H). $^{19}$F NMR (376 MHz, DMSO-d$_6$): δ −68.38 (s, 3F), −141.79 (s, 1F).

Examples 32a and 32b

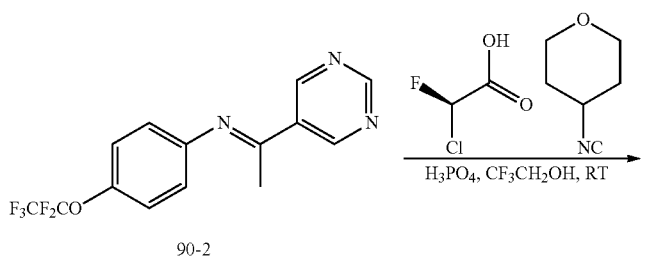

90-2

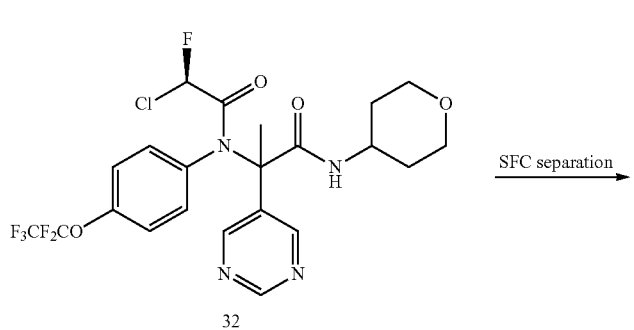

32

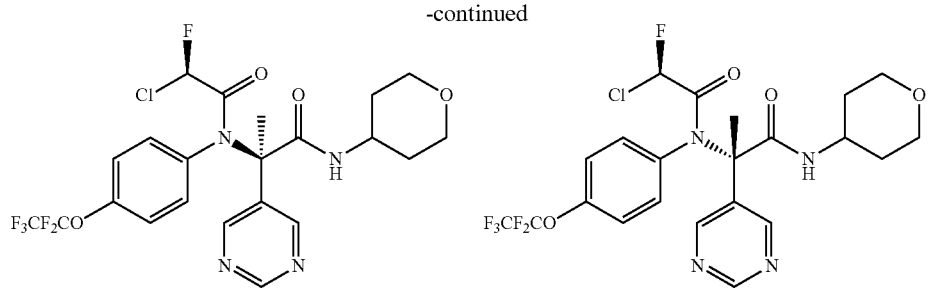

Example 32a and 32b
(Stereochemistry arbitrarily assigned at center between two amides)

To a solution of 90-2 (230 mg, 694.36 mol) in CF₃CH₂OH (2 mL) was added H₃PO₄ (16 mg, 138.78 μmol, 9.52 μL). The mixture was stirred at 25° C. for 30 min. After 30 min, the reaction mixture was added 4-isocyanotetrahydropyran (92 mg, 703.61 μmol) and (2R)-2-chloro-2-fluoro-acetic acid (142 mg, 833.16 μmol). The mixture was stirred at 25° C. for 18 hr. The reaction mixture was concentrated under reduced pressure to give a residue. The residue was purified by flash silica gel chromatography (Eluent of 0~100% Ethyl acetate/Petroleum ether gradient @ 35 mL/min) to get product. The product was purified by prep-HPLC (Welch Xtimate C18 150*30 mm*5 μm; Mobile phase: A: water (FA) B: ACN; Gradient condition: from 46% B to 76% B; Flow rate: 25 mL/min). The pure fractions were collected and the volatile solvent was removed by evaporation. The aqueous residue was lyophilized to afford Compound 32 (28 mg, 7.27% yield).

The Compound 32 (28 mg, 50.46 μmol) was separated by SFC (DAICEL CHIRALPAK AD (250 mm*30 mm, 10 μm)); Mobile phase: A: Supercritical CO₂, B: Neu-MeOH; Isocratic: A:B=85:15; Flow rate: 60 mL/min) to afford two fractions.

Example 32a: (6 mg, 20.89% yield) was obtained. LCMS (M+H)=555.1. SFC: Retention time: 2.107 min, AD-3_EtOH (DEA)_5_40_25ML. ¹H NMR (400 MHz, DMSO-d₆): δ 9.06 (s, 1H), 8.85 (s, 2H), 7.85 (d, J=8.4 Hz, 1H), 7.77 (d, J=8.0 Hz, 1H), 7.49 (d, J=8.8 Hz, 1H), 7.39 (s, 2H), 6.49-6.25 (m, 1H), 4.01-3.73 (m, 3H), 3.41-3.37 (m, 2H), 1.69 (s, 4H), 1.66-1.59 (m, 1H), 1.58-1.41 (m, 2H). ¹⁹F NMR (376 MHz, DMSO-d₆): δ −85.32 (s, 3F), −87.18 (s, 2F), −142.26 (s, 1F).

Example 32b: (5 mg, 17.40% yield) was obtained. LCMS (M+H)=555.1. SFC: Retention time: 2.653 min, AD-3_EtOH (DEA)_5_40_25ML. ¹HNMR (400 MHz, DMSO-d₆): δ9.02 (s, 1H), 8.83 (s, 2H), 7.75-7.62 (m, 2H), 7.59-7.49 (m, 1H), 7.47-7.34 (m, 2H), 6.43-6.17 (m, 1H), 3.97-3.78 (m, 3H), 3.39-3.35 (m, 2H), 1.82 (s, 3H), 1.73-1.64 (m, 1H), 1.64-1.56 (m, 1H), 1.55-1.41 (m, 2H). ¹⁹F NMR (376 MHz, DMSO-d₆): δ −85.30 (s, 3F), −87.17 (br s, 2F), −141.89 (s, 1F).

Examples 33a and 33b

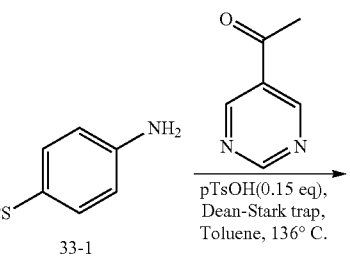

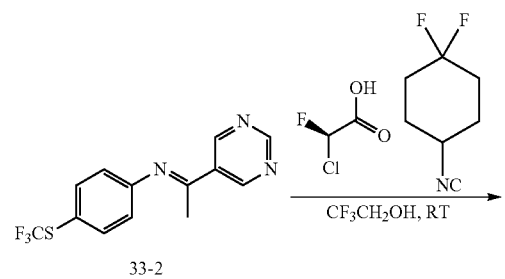

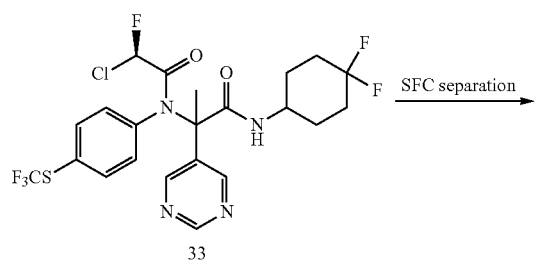

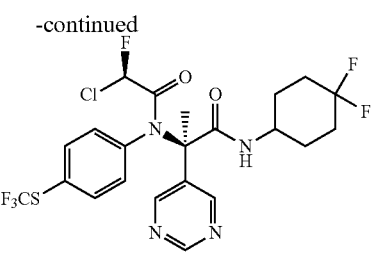

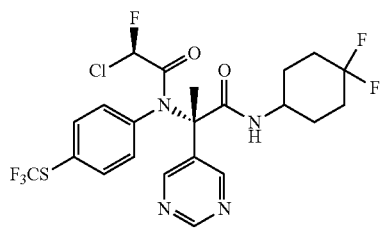

Example 33a and 33b
(Stereochemistry arbitrarily assigned at center between two amides)

To a solution of 33-1 (2 g, 10.35 mmol, 1.48 mL) and 1-pyrimidin-5-ylethanone (1.26 g, 10.35 mmol) in Tol. (30 mL) was added p-TsOH (267.41 mg, 1.55 mmol). The mixture was stirred at 136° C. for 16 hr with removal of water by DeanStark trap under $N_2$ atmosphere. The reaction was filtered, and the filter cake was washed with toluene (10 mL*2). The filtrate was concentrated under reduced pressure. The residue was purified by flash silica gel chromatography (Eluent of 0-16% Ethyl acetate/Petroleum ether gradient @ 30 mL/min). Compound 33-2 (1.85 g, 48.09% yield) was obtained. $^1$H NMR (400 MHz, DMSO-$d_6$): δ 9.36-9.30 (m, 3H), 7.74 (d, J=8.4 Hz, 2H), 7.10-6.96 (m, 2H), 2.34-2.21 (m, 3H).

To a solution of 33-2 (500 mg, 1.35 mmol) in $CF_3CH_2OH$ (5 mL) was added (2R)-2-chloro-2-fluoro-acetic acid (253 mg, 1.35 mmol) and 1,1-difluoro-4-isocyano-cyclohexane (217.73 mg, 1.35 mmol). The mixture was stirred at 20° C. for 16 hr. The reaction mixture was concentrated under reduced pressure to give a residue. The residue was purified by flash silica gel chromatography (Eluent of 0~50% Ethyl acetate/Petroleum ether gradient @ 30 mL/min). Compound 33 (83 mg, 10.95% yield) was obtained. LCMS (M+H)=554.9. $^1$H NMR (400 MHz, DMSO-$d_6$): δ9.03 (d, J=14.4 Hz, 1H), 8.83 (d, J=5.2 Hz, 2H), 7.93-7.62 (m, 4H), 7.58-7.33 (m, 1H), 6.46-6.15 (m, 1H), 3.85 (s, 1H), 2.12-1.91 (m, 3H), 1.90-1.63 (m, 6H), 1.61-1.45 (m, 2H). $^{19}$F NMR (376 MHz, DMSO-$d_6$): δ −41.68 (d, J=27.7 Hz, 3F), −91.36--92.52 (m, 1F), −98.15--99.86 (m, 1F), −142.00 (d, J=114.4 Hz, 1F).

The Compound 33 (80 mg, 144.16 µmol, 1 eq) was separated by SFC (DAICEL CHIRALCEL OD-H (250 mm*30 mm, 5 µm); Mobile phase: A: Supercritical $CO_2$, B: Neu-ETOH; Isocratic: A:B=85:15; Flow rate: 60 mL/min) to afford two fractions.

Example 33a: (27 mg, 32.63% yield) was obtained. LCMS (M+H)=555.1. SFC: Retention time: 0.775 min, AD_ETOH_DEA_5_40_4ML_4MIN_5CM. $^1$H NMR (400 MHz, DMSO-$d_6$): δ 9.05 (s, 1H), 8.83 (s, 2H), 7.89-7.68 (m, 4H), 7.41 (s, 1H), 6.51-6.24 (m, 1H), 3.87 (s, 1H), 2.04-1.57 (m, 11H). $^{19}$F NMR (376 MHz, DMSO-$d_6$): δ −40.01--44.72 (m, 3F), −91.89 (d, J=235.8 Hz, 1F), −99.38 (d, J=232.4 Hz, 1F), −142.16 (s, 1F).

Example 33b: (43 mg, 50.82% yield) was obtained. LCMS (M+H)=555.1. SFC: Retention time: 0.944 min, AD_ETOH_DEA_5_40_4ML_4MIN_5CM. $^1$H NMR (400 MHz, DMSO-$d_6$): δ 9.01 (s, 1H), 8.82 (s, 2H), 7.83-7.63 (m, 4H), 7.55 (br s, 1H), 6.44-6.20 (m, 1H), 3.84 (br d, J=7.2 Hz, 1H), 1.98-1.45 (m, 11H). $^{19}$F NMR (376 MHz, DMSO-$d_6$): δ −39.62--45.89 (m, 3F), −89.04--93.36 (m, 1F), −97.28--102.38 (m, 1F), −141.86 (s, 1F).

Examples 34a and 34b

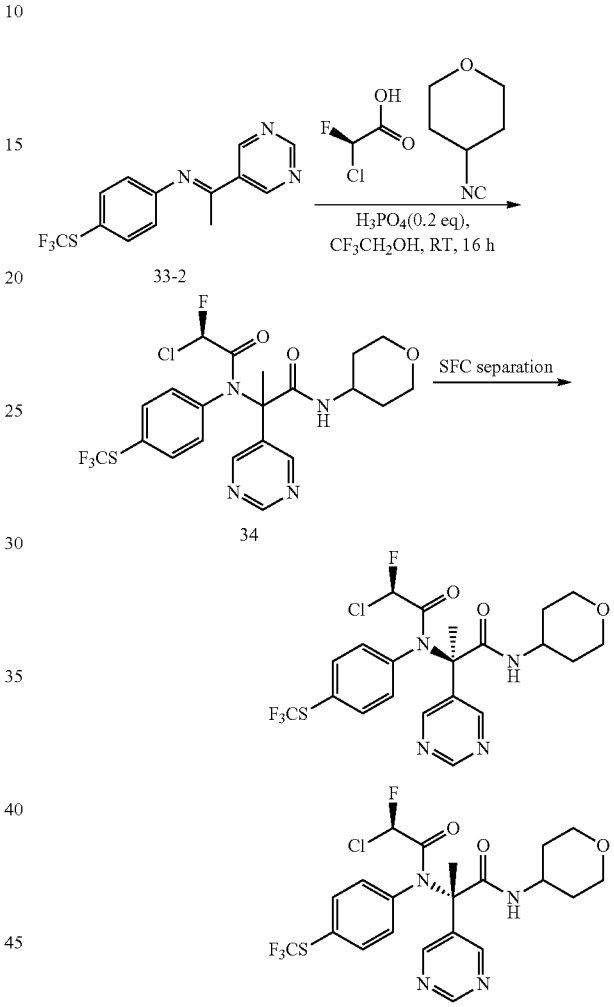

Example 34a and 34b
(Stereochemistry arbitrarily assigned at center between two amides)

To a solution of Compound 33-2 (500 mg, 1.35 mmol) in $CF_3CH_2OH$ (5 mL) was added $H_3PO_4$ (31.13 mg, 270.00 µmol, 18.53 µL). The mixture was stirred at 20° C. for 30 min. Then 4-isocyanotetrahydropyran (214.34 mg, 1.35 mmol) and (2R)-2-chloro-2-fluoro-acetic acid (253 mg, 1.35 mmol) was added. The mixture was stirred at 20° C. for 16 hr. The reaction was concentrated under reduced pressure. The crude was purified by flash silica gel chromatography and further purification by prep-HPLC to give Compound 34 (73 mg, 10.23% yield).

The Compound 34 (98 mg, 188.13 µmol) was separated by SFC (DAICEL CHIRALPAK AD (250 mm*30 mm, 10 µm); Mobile phase: A: Supercritical $CO_2$, B: Neu-ETOH; Isocratic: A:B=75:25; Flow rate: 60 mL/min) to afford two fractions.

Example 34a: (15 mg, 15.17% yield) was obtained. LCNS (M+H)=521.0. SFC: Retention time: 0.930 min, AD_ETOH_DEA_5_40_4ML_4MIN_5CM. $^1$H NMR (400 MHz, DMSO-d$_6$): δ 9.04 (s, 1H), 8.84 (s, 2H), 7.90-7.70 (m, 4H), 7.43 (d, J=6.4 Hz, 1H), 6.46-6.24 (m, 1H), 3.96-3.82 (m, 3H), 3.31-3.18 (m, 2H), 1.73 (s, 3H), 1.69-1.41 (m, 4H). $^{19}$F NMR (376 MHz, DMSO-d$_6$): δ −39.23−−44.32 (m, 3F), −142.12 (s, 1F).

Example 34b: (21 mg, 21.26% yield) was obtained. LCMS (M+H)=521.0. SFC: Retention time: 1.215 min, AD_ETOH_DEA_5_40_4ML_4MIN_5CM. $^1$H NMR (400 MHz, DMSO-d$_6$): δ 9.00 (s, 1H), 8.82 (s, 2H), 7.79-7.65 (m, 4H), 7.58 (d, J=7.6 Hz, 1H), 6.42-6.23 (m, 1H), 3.95-3.78 (m, 3H), 3.22 (m, 2H), 1.86 (s, 3H), 1.68 (d, J=12.4 Hz, 1H), 1.62-1.55 (m, 1H), 1.54-1.41 (m, 2H). $^{19}$F NMR (376 MHz, DMSO-d$_6$): δ −41.72 (s, 3F), −141.85 (s, 1F).

Examples 36a and 36b

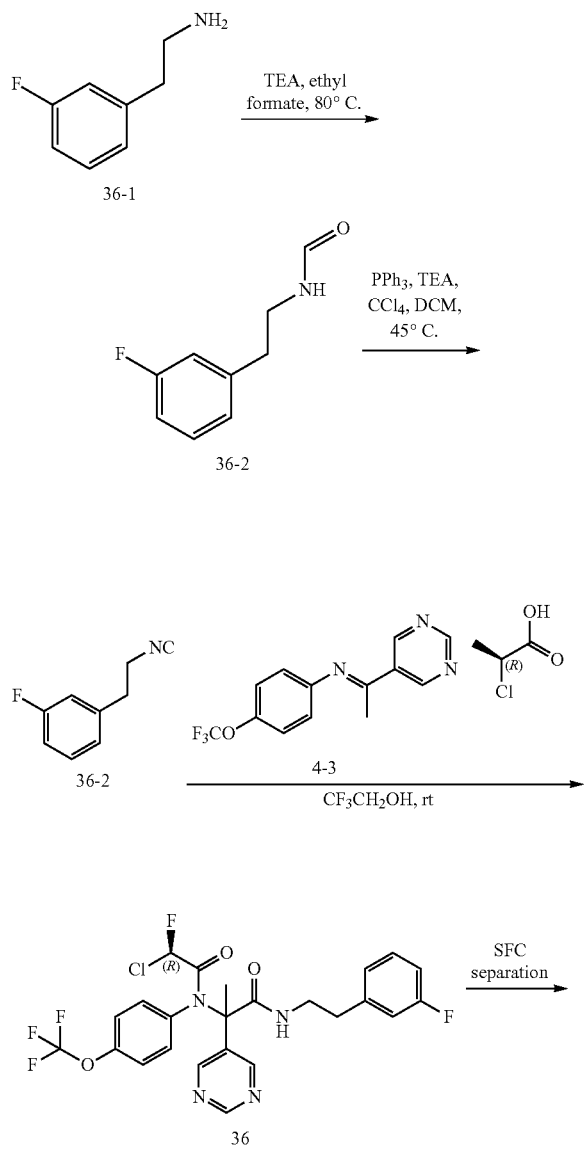

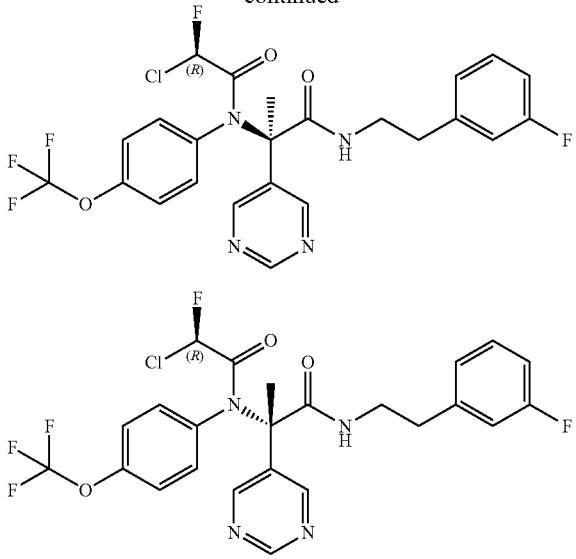

Example 36a and 36b
(Stereochemistry arbitrarily assigned at center between two amides)

To a solution of 36-1 (5 g, 35.93 mmol, 4.67 mL) in ethyl formate (50 mL) was added TEA (7.27 g, 71.85 mmol, 10.00 mL). The mixture was stirred at 80° C. for 16 hr. The mixture was concentrated under vacuum, diluted with water (20 mL), extracted with DCM (20 mL*2). The organic layer as washed with brine (20 mL), dried over Na$_2$SO$_4$, filtered, and concentrated under vacuum. Compound 36-2 (6.46 g, crude) was obtained. LCMS (M+H)=167.8.

To a solution of 36-2 (6.46 g, 30.14 mmol) in DCM (60 mL) was added PPh$_3$ (7.91 g, 30.14 mmol), TEA (3.05 g, 30.14 mmol, 4.20 mL) and CCl$_4$ (4.64 g, 30.14 mmol, 2.90 mL). The mixture was stirred at 45° C. for 16 hr. The reaction mixture was concentrated under reduced pressure. Then MTBE (40 mL) and PE (40 mL) was added and the mixture was stirred at 20° C. for 16 hours. The reaction was filtered and the filter cake was washed by MTBE (20 mL*3). The filtrate was concentrated under reduced pressure. The residue was purified by flash silica gel chromatography (Eluent of 0-10% Ethyl acetate/Petroleum ether gradient @ 35 mL/min). Compound 36-3 (3.8 g, 25.48 mmol, 84.52% yield) was obtained.

To a solution of Compound 4-3 (1.5 g, 5.33 mmol) in CF$_3$CH$_2$OH (20 mL) was added (2R)-2-chloro-2-fluoro-acetic acid (1.29 g, 6.40 mmol) and Compound 36-3 (837.47 mg, 5.33 mmol). The mixture was stirred at 20° C. for 16 hr. The reaction mixture was concentrated under reduced pressure. The residue was purified by flash silica gel chromatography (Eluent of 0-100% Ethyl acetate/Petroleum ether gradient @ 35 mL/min). The residue was purified by prep-HPLC (column: Xtimate C18 150*40 mm*10 m; mobile phase: [water (FA)-ACN]; B %: 45%-75%, 7 min). Compound 36 (530 mg, 976.27 μmol, 18.30% yield) was obtained. LCMS (M+H)=543.1. $^1$HNMR (400 MHz, DMSO-d$_6$) δ 9.09-8.73 (m, 3H), 8.18-7.98 (m, 1H), 7.81-7.57 (m, 1H), 7.56-7.43 (m, 1H), 7.42-7.35 (m, 2H), 7.34-7.27 (m, 1H), 7.08-6.98 (m, 3H), 6.46-6.23 (m, 1H), 3.53-3.38 (m, 2H), 2.84-2.72 (m, 2H), 1.84-1.43 (m, 3H).

The Compound 36 (530 mg, 976.27 μmol) was separated by SFC (Phenomenex-Cellulose-2 (250 mm*30 mm, 5 μm); Mobile phase: A: Supercritical CO$_2$, B: Neu-MeOH; Isocratic: A:B=75:25; Flow rate: 60 mL/min), concentrated under vacuum, which afford two fractions. The residue was further purified by prep-HPLC (column: Boston Green ODS 150*30 mm*5 m; mobile phase: [water (FA)-ACN]; B %: 55%-85%, 7 min).

Example 36a: (84.11 mg, 154.93 mol, 46.73% yield) was obtained. LCMS (M+H)=543.4. SFC: Retention time: 3.656 min, C2_MeOH_DEA_5_40_25ML. $^1$H NMR (400 MHz, DMSO-d$_6$): δ 9.06 (s, 1H), 8.82 (s, 2H), 8.13 (t, J=5.7 Hz, 1H), 7.76 (br d, J=8.7 Hz, 1H), 7.46 (br d, J=9.2 Hz, 1H), 7.40 (s, 2H), 7.36-7.27 (m, 1H), 7.08-6.99 (m, 3H), 6.45-6.26 (m, 1H), 3.53-3.39 (m, 2H), 2.83-2.76 (m, 2H), 1.51 (s, 3H). $^{19}$F NMR (376 MHz, DMSO-d$_6$): δ −56.81 (s, 3F), −113.74 (s, 1F), −142.49 (s, 1F).

Example 36b: (51.98 mg, 95.75 μmol, 31.31% yield) was obtained. LCMS (M+H)=543.4. SFC: Retention time: 4.244 min, C2_MeOH_DEA_5_40_25ML. $^1$H NMR (400 MHz, DMSO-d$_6$): δ9.00 (s, 1H), 8.77 (s, 2H), 8.02 (t, J=5.5 Hz, 1H), 7.61 (br d, J=8.7 Hz, 1H), 7.53 (br d, J=8.6 Hz, 1H), 7.38 (br t, J=7.2 Hz, 2H), 7.33-7.26 (m, 1H), 7.07-6.97 (m, 3H), 6.41-6.25 (m, 1H), 3.48-3.36 (m, 2H), 2.76 (dt, J=3.2, 7.1 Hz, 2H), 1.74 (s, 3H). $^{19}$F NMR (376 MHz, DMSO-d$_6$): δ −56.87 (s, 3F), −113.68 (s, 1F), −141.73 (s, 1F).

Examples 76a, 76b, 76c and 76d

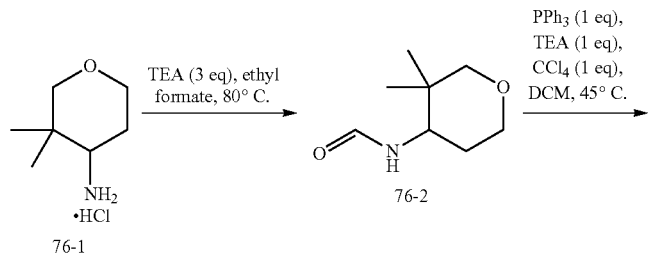

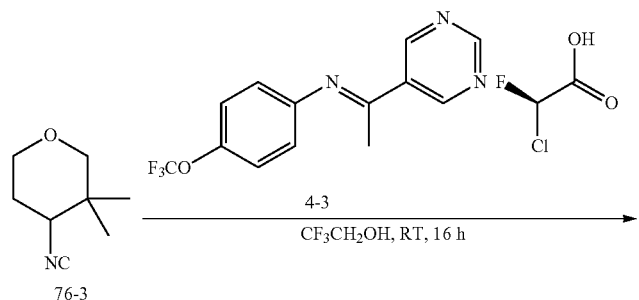

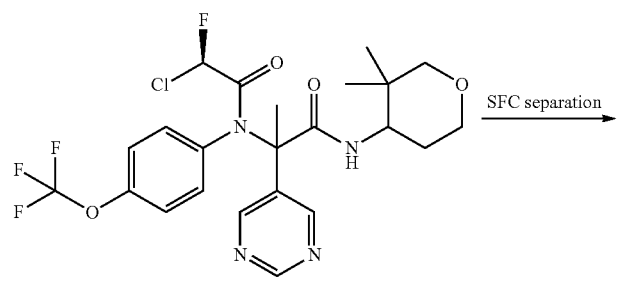

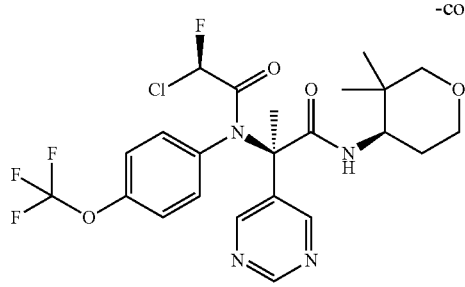
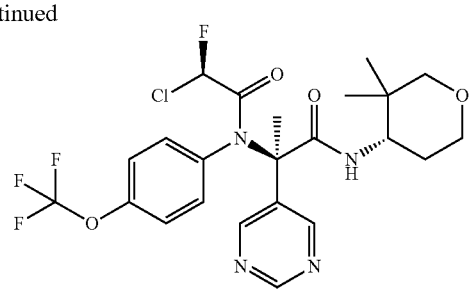
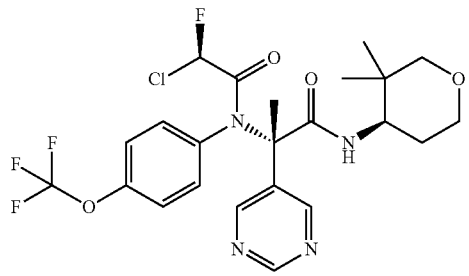
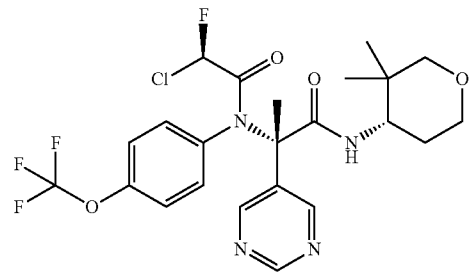

Example 76a, 76b, 76c and 76d
(Stereochemistry arbitrarily assigned at center between two amides and heterocycloalkyl)

To a solution of Compound 76-1 (500 mg, 3.02 mmol HCl) in ethyl formate (20 mL) was added TEA (916 mg, 9.05 mmol, 1.26 mL). The mixture was stirred at 80° C. for 18 hr. The reaction mixture was concentrated under reduced pressure to give a residue. Then the residue was diluted with DCM (10 mL). The organic layer was washed with $H_2O$ (10 mL*2) and brine (10 mL), dried over $Na_2SO_4$, filtered, and concentrated under reduced pressure to give a residue. The crude product was used for next step without further purification. Compound 76-2 (159 mg, 809.11 µmol, 26.81% yield) was obtained. $^1$H NMR (400 MHz, CDCl$_3$): δ 8.23 (s, 1H), 4.12-3.90 (m, 2H), 3.59-3.40 (m, 2H), 3.26-3.09 (m, 1H), 1.72-1.61 (m, 2H), 1.01-0.95 (m, 3H), 0.87 (s, 3H).

A mixture of Compound 76-2 (159 mg, 1.01 mmol), PPh$_3$ (266 mg, 1.01 mmol), TEA (103 mg, 1.02 mmol, 141.68 µL) and CCl$_4$ (156 mg, 1.01 mmol, 97.50 µL) in DCM (1 mL) was stirred at 45° C. for 18 hr under $N_2$ atmosphere. The reaction mixture was filtered, and the filtrate was concentrated under reduced pressure to give a residue. The crude product was used for next step without further purification. Compound 76-3 (140 mg, crude) was obtained.

To a solution of Compound 4-3 (150 mg, 533.37 mol) in CF$_3$CH$_2$OH (2 mL) was added (2R)-2-chloro-2-fluoro-acetic acid (122.03 mg, 640.04 mol) and Compound 76-3 (140 mg, 533.07 µmol). The mixture was stirred at 20° C. for 16 h. The reaction mixture was concentrated under reduced pressure. The residue was purified by flash silica gel chromatography (Eluent of 0-100% Ethyl acetate/Petroleum ether gradient @ 30 mL/min). The residue was purified by prep-HPLC (column: Boston Green ODS 150*30 mm*5 m; mobile phase: [water (FA)-ACN]; B %: 53%-83%, 7 min). Compound 76 (24 mg, 43.45 mol, 8.15% yield) was obtained. LCMS (M+H)=533.1.

Compound 76 (24 µmg) was separated by SFC (DAICEL CHIRALCEL OD-H (250 mm*30 mm, 5 µm)); Mobile phase: A: Supercritical CO$_2$, B: Neu-ETOH; Isocratic: A:B=85:15; Flow rate: 60 mL/min) to afford two fractions. Fraction 1 (17 mg) was separated by SFC (Phenomenex-Cellulose-2 (250 mm*30 mm, 5 µm); Mobile phase: A: Supercritical CO$_2$, B: Neu-ETOH; Isocratic: A:B=60:40; Flow rate: 80 mL/min) to afford two fractions. Fraction 2 (14 mg) was further separated by SFC (DAICEL CHIRALPAK IG (250 mm*30 mm, 10 µm)); Mobile phase: A: Supercritical CO$_2$, B: Neu-IPA; Isocratic: A: B=75:25; Flow rate: 70 mL/min) to afford two fractions.

Example 76a: (2.50 mg, 14.62% yield) was obtained. LCMS (M+H)=533.1. SFC: Retention time: 1.228 min, OD_ETOH_DEA_5_40_28ML_8MIN. $^1$H NMR (400 MHz, DMSO-d$_6$): δ 9.03 (s, 1H), 8.80 (s, 2H), 7.77 (br d, J=8.9 Hz, 1H), 7.50-7.36 (m, 4H), 6.45-6.27 (m, 1H), 3.88 (br d, J=9.7 Hz, 2H), 3.40-3.36 (m, 2H), 3.09 (d, J=11.3 Hz, 1H), 1.76 (s, 4H), 1.40 (br d, J=15.3 Hz, 1H), 0.85 (s, 3H), 0.77 (s, 3H). $^{19}$F NMR (376 MHz, DMSO-d$_6$): δ −56.84 (s, 3F), −141.89 (br s, 1F).

Example 76b: (1.55 mg, 9.00% yield) was obtained. LCMS (M+H)=533.1. SFC: Retention time: 1.315 min, OD_ETOH_DEA_5_40_28ML_8MIN. $^1$H NMR (400 MHz, DMSO-d$_6$): δ 9.09 (s, 1H), 8.96 (s, 2H), 7.87 (br d, J=8.7 Hz, 1H), 7.56-7.33 (m, 4H), 6.43-6.27 (m, 1H), 3.92-3.82 (m, 2H), 3.40 (br d, J=11.2 Hz, 2H), 3.09 (d, J=11.4 Hz, 1H), 1.74 (br dd, J=5.2, 12.9 Hz, 1H), 1.60 (s, 3H), 1.31 (br d, J=11.6 Hz, 1H), 0.91 (s, 3H), 0.77 (s, 3H). $^{19}$F NMR (376 MHz, DMSO-d$_6$): δ −56.78 (s, 3F), −142.45 (s, 1F)

Example 76c: (2.07 mg, 14.79% yield) was obtained. LCMS (M+H)=533.1. SFC: Retention time: 1.528 min, OD_ETOH_DEA_5_40_28ML_8MIN. $^1$H NMR (400 MHz, DMSO-d$_6$): δ 9.06 (s, 1H), 8.93 (s, 2H), 7.69-7.54 (m, 2H), 7.45 (br dd, J=8.8, 13.5 Hz, 2H), 7.33 (d, J=9.1 Hz, 1H), 6.41-6.21 (m, 1H), 3.90-3.80 (m, 2H), 3.39 (br d, J=11.2 Hz, 2H), 3.09 (d, J=11.2 Hz, 1H), 1.69 (s, 4H), 1.33 (br d, J=13.1 Hz, 1H), 0.88 (s, 3H), 0.79 (s, 3H). $^{19}$F NMR (376 MHz, DMSO-d$_6$): δ −56.84 (s, 3F), −141.58 (s, 1F).

Example 76d: (1.18 mg, 8.26% yield) was obtained. LCMS (M+H)=533.1 SFC: Retention time: 1.637 min, OD_ETOH_DEA_5_40_28ML_8MIN. $^1$H NMR (400 MHz, DMSO-d$_6$): δ9.01 (s, 1H), 8.79 (s, 2H), 7.60 (dd, J=4.8, 8.4 Hz, 2H), 7.43-7.36 (m, 2H), 7.32 (d, J=8.9 Hz, 1H), 6.41-6.25 (m, 1H), 3.95-3.83 (m, 2H), 3.41-3.36 (m, 2H), 3.09 (d, J=11.3 Hz, 1H), 1.86 (s, 3H), 1.73 (dt, J=7.3, 12.5 Hz, 1H), 1.37 (br d, J=11.1 Hz, 1H), 0.87 (s, 3H), 0.75 (s, 3H). $^{19}$F NMR (376 MHz, DMSO-d$_6$): δ −56.40−−57.12 (m, 3F), −141.77 (s, 1F)

Examples 77a, 77b, 77c and 77d

To a solution of Compound 77-1 (1 g, 7.74 mmol) in ethyl formate (10 mL) was added TEA (2.35 g, 23.22 mmol, 3.23 mL) The mixture was heated and stirred at 80° C. for 12 hours. The mixture was cooled to room temperature and concentrated under reduced pressure to give Compound 77-2 (1.2 g), which was used directly for the next step.

To a solution of Compound 77-2 (1.2 g, 7.63 mmol) in DCM (14 mL) were added TEA (772.40 mg, 7.63 mmol,

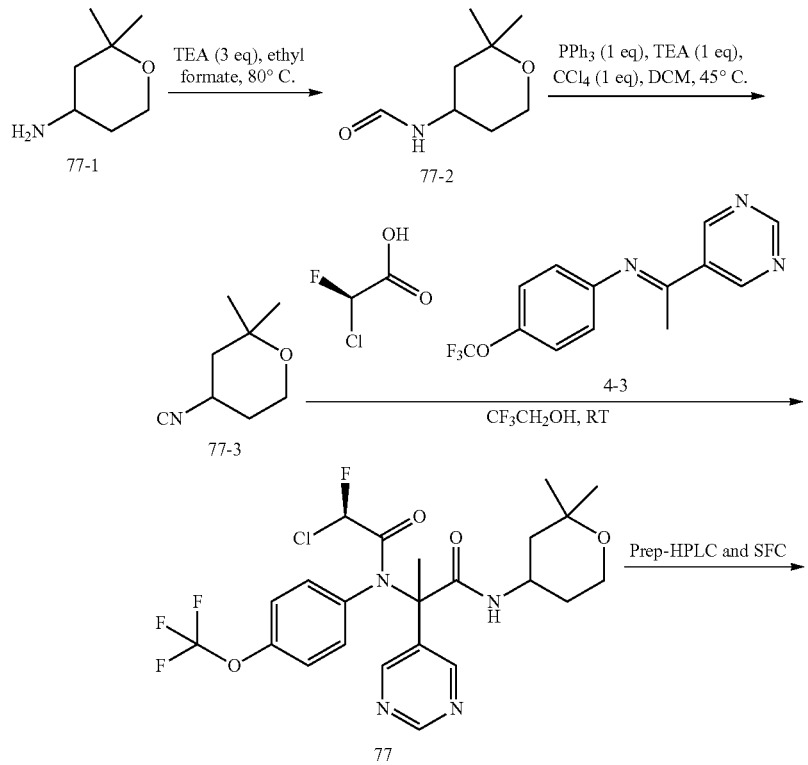

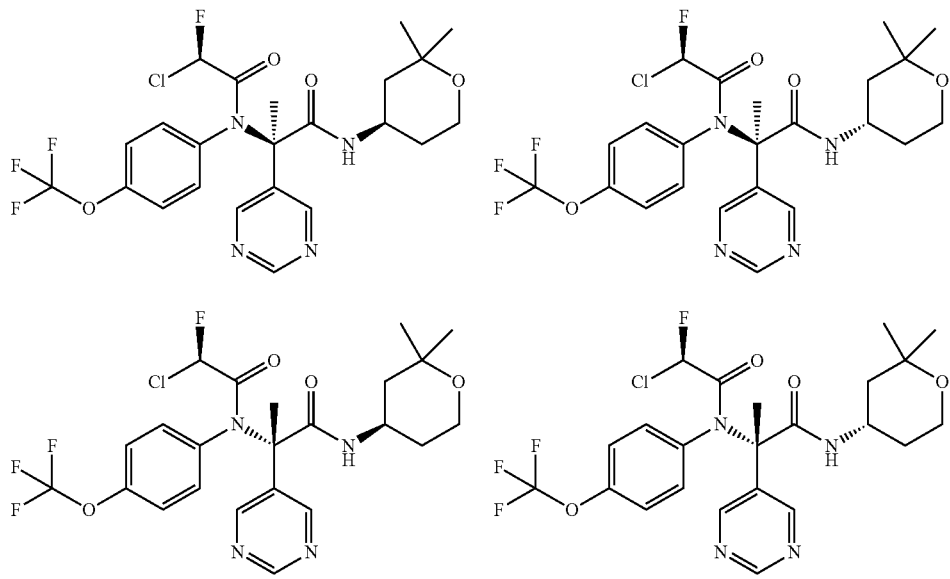

Example 77a, 77b, 77c and 77d
(Stereochemistry arbitrarily assigned at center between two amides and heterocycloalkyl)

1.06 mL), PPh₃ (2.00 g, 7.63 mmol), CCl₄ (1.17 g, 7.63 mmol, 733.83 µL). The mixture was heated and stirred at 45° C. for 12 hours. The mixture was concentrated under reduced pressure to give a crude at 20° C. The mixture was triturated with MTBE (10 mL) to give the product. The residue was purified by flash silica gel chromatography (Eluent of 0~50% dichloromethane/Petroleum ether gradient @100 mL/min). Compound 77-3 (1.0 g, crude) was obtained. 1H NMR (400 MHz, CDCl₃): δ 3.86-3.74 (m, 2H), 3.59 (dt, J=2.4, 12.0 Hz, 1H), 2.06-1.93 (m, 2H), 1.87-1.60 (m, 2H), 1.32-1.25 (m, 3H), 1.18 (s, 3H).

To a solution of Compound 4-1 (1.62 g, 5.75 mmol) in CF₃CH₂OH (10 mL) were added (2R)-2-chloro-2-fluoroacetic acid (775.81 mg, 6.90 mmol), Compound 77-3 (1.0 g, 5.75 mmol), 4A MS (1.0 g, 5.75 mmol). The mixture was stirred at 25° C. for 12 hours. The mixture was concentrated under reduced pressure to give a crude. The crude was purified by flash silica gel chromatography (Eluent of 0~50% Ethyl acetate/Petroleum ether gradient @ 45 mL/min) to give a residue (1.0 g) The residue was purified by HPLC (column: Xtimate C18 150*40 mm*10 m; mobile phase: [water (FA)-ACN]; B %: 35%-65%, 6 min). Compound 77 (500 mg, 938.24 mol, 16.32% yield) was obtained. LCMS (M+H)=533.2.

The Compound 77 (500 mg, 0.948 mmol) was separated by supercritical fluid chromatography (separation condition: DAICEL CHIRALCEL OD-H (250 mm*30 mm, 5 µm)); Mobile phase: A: Supercritical CO₂, B: Neu-IPA, A:B=80:20 at 70 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give two fraction. The pure fraction 1 was collected and the solvent was evaporated under vacuum. The residue was partitioned between acetonitrile (2 mL) and water (10 mL). The solution was lyophilized to dryness to give the title P1 (100 mg), which was separated by supercritical fluid chromatography (separation condition: DAICEL CHIRALPAK IC (250 mm*30 mm, 10 µm)); Mobile phase: A: Supercritical CO₂, B: Neu-IPA, A:B=80:20 at 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give two fraction. The pure fraction 2 was further separated by supercritical fluid chromatography (separation condition: DAICEL CHIRALPAK IG (250 mm*30 mm, 10 µm)); Mobile phase: A: Supercritical CO₂, B: Neu-IPA, A:B=75:25 at 70 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give two fraction.

Example 77a: (8.11 mg) was obtained. LCMS (M+H)=532.8. SFC: Retention time: 1.694 min, IG_3_EtOH_DEA_5_40_28ML_6MIN. ¹H NMR (400 MHz, DMSO-d₆): δ 9.05 (s, 1H), 8.84 (s, 2H), 7.84 (d, J=8.8 Hz, 1H), 7.69 (d, J=8.0 Hz, 1H), 7.48 (d, J=8.8 Hz, 1H), 7.39 (s, 2H), 6.45-6.25 (m, 1H), 4.12-3.96 (m, 1H), 3.71-3.55 (m, 2H), 1.72-1.57 (m, 5H), 1.47-1.34 (m, 1H), 1.26 (t, J=12.4 Hz, 1H), 1.17 (s, 3H), 1.13 (s, 3H). ¹⁹F NMR (376 MHz, DMSO-d₆) δ -56.83 (s, 3F), -142.3 (s, 1F).

Example 77b: (39.92 mg, 7.93% yield) was obtained. LCMS (M+H)=532.8. SFC: Retention time: 1.765 min, IG_3_EtOH_DEA_5_40_28ML_6MIN. ¹H NMR (400 MHz, DMSO-d₆): δ 9.06 (s, 1H), 8.85 (s, 2H), 7.85 (d, J=8.8 Hz, 1H), 7.69 (d, J=8.0 Hz, 1H), 7.48 (d, J=8.8 Hz, 1H), 7.39 (s, 2H), 6.45-6.28 (m, 1H), 4.12-3.99 (m, 1H), 3.66-3.53 (m, 2H), 1.73-1.64 (m, 4H), 1.63-1.55 (m, 1H), 1.40-1.28 (m, 2H), 1.18 (s, 3H), 1.15 (s, 3H). ¹⁹F NMR (376 MHz, DMSO-d₆) δ -56.83 (s, 3F), -142.3 (s, 1F).

Example 77c: (33.26 mg, 6.61% yield) was obtained. LCMS (M+H)=532.9. SFC: Retention time: 1.994 min, IG_3_EtOH_DEA_5_40_28ML_6MIN. ¹H NMR (400 MHz, DMSO-d₆): δ 9.02 (s, 1H), 8.83 (s, 2H), 7.69 (dd, J=2.4, 8.8 Hz, 1H), 7.61 (d, J=8.0 Hz, 1H), 7.54 (dd, J=2.4, 8.4 Hz, 1H), 7.40 (dd, J=8.8, 13.6 Hz, 2H), 6.38-6.22 (m, 1H), 4.10-3.96 (m, 1H), 3.66-3.52 (m, 2H), 1.79 (s, 3H), 1.71-1.65 (m, 1H), 1.59-1.51 (m, 1H), 1.41-1.24 (m, 2H), 1.18 (s, 3H), 1.13 (s, 3H). ¹⁹F NMR (376 MHz, DMSO-d₆) δ -56.87 (s, 3F), -141.87 (s, 1F).

Example 77d: (39.77 mg, 7.81% yield) was obtained. LCMS (M+H)=532.8. SFC: Retention time: 2.738 min, IG_3_EtOH_DEA_5_40_28ML_6MIN. ¹H NMR (400 MHz, DMSO-d₆): δ 9.03 (s, 1H), 8.83 (s, 2H), 7.71-7.51 (m, 3H), 7.46-7.35 (m, 2H), 6.40-6.22 (m, 1H), 4.10-3.98 (m, 1H), 3.67-3.54 (m, 2H), 1.82 (s, 3H), 1.71-1.62 (m, 1H), 1.61-1.53 (m, 1H), 1.43-1.32 (m, 1H), 1.27 (t, J=12.4 Hz, 1H), 1.18 (s, 3H), 1.13 (s, 3H). ¹⁹F NMR (376 MHz, DMSO-d₆) δ -56.87 (s, 3F), -141.89 (s, 1F).

Examples 90a and 90b

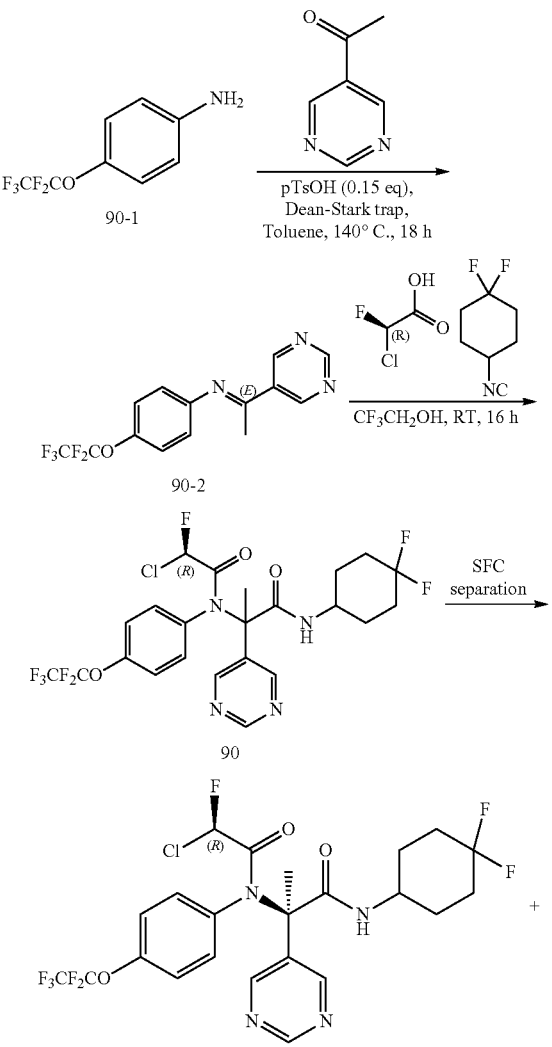

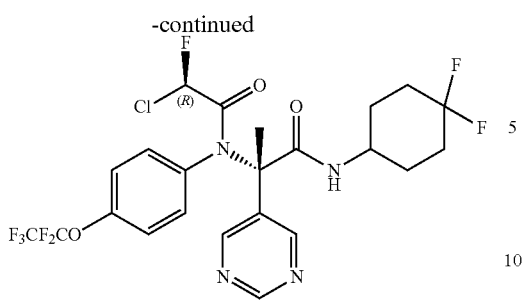

Example of 90a and 90b
(Stereochemistry arbitrarily assigned at center between two amides)

To a solution of 90-1 (400 mg, 1.76 mmol) and 1-(pyrimidin-5-yl)ethan-1-one (322.61 mg, 2.64 mmol) in toluene (20 mL) was added 4-methylbenzenesulfonic acid (60.65 mg, 352.22 μmol). The mixture was stirred at 140° C. for 16 hr. The reaction mixture was filtered and concentrated under reduced pressure to give a residue. The residue was purified by flash silica gel chromatography (Eluent of 0~25% Ethyl acetate/Petroleum ether gradient @ 30 mL/min). The aqueous residue was lyophilized to afford 90-2 (270 mg, 41.66% yield). $^1$H NMR (400 MHz, DMSO-$d_6$): δ 9.32 (s, 3H), 7.39 (d, J=8.8 Hz, 2H), 7.05-6.94 (m, 2H), 2.29 (s, 3H).

To a solution of 90-2 (270 mg, 815.12 μmol) in $CF_3CH_2OH$ (2 mL) was added $H_3PO_4$ (18.79 mg, 163.02 μmol). After addition, the mixture was stirred at 25° C. for 0.5 hr, and then 1,1-difluoro-4-isocyano-cyclohexane (131.46 mg, 815.12 μmol) and (2R)-2-chloro-2-fluoro-acetic acid (183.38 mg, 978.14 μmol) was added. The resulting mixture was stirred at 25° C. for 16 hr. The reaction mixture was concentrated under reduced pressure to give a residue. The residue was purified by flash silica gel chromatography (Eluent of 0~60% Ethyl acetate/Petroleum ether gradient @ 30 mL/min) to give a crude product which was further purified by pre-HPLC (column: Welch Xtimate C18 150*30 mm*5 m; mobile phase: [water (FA)-ACN]; B %: 53%-83%, 7 min) to give compound 90 (80 mg, 16.61% yield). LCMS (M+H)=589.0. $^1$H NMR (400 MHz, DMSO-$d_6$): δ 9.05 (d, J=12.8 Hz, 1H), 8.84 (d, J=5.6 Hz, 2H), 7.98-7.63 (m, 2H), 7.57-7.31 (m, 3H), 6.50-6.12 (m, 1H), 3.86 (br s, 1H), 2.11-1.46 (m, 11H).
The Compound 90 (70.0 mg, 118.8 μmol) was separated by SFC (WHELK-01 (250 mm*30 mm, 5 μm)), Mobile phase: A: Supercritical $CO_2$, B: Neu-EtOH; Isocratic: A:B=80:20) to afford two fractions.

Example 90a: (12 mg, 16.59% yield) was obtained. LCMS (M+H)=589.0. SFC: Retention time: 2.367 min, (SS) Whelk-01_EtOH (DEA)_5_4. $^1$H NMR (400 MHz, DMSO-$d_6$): δ9.12-9.04 (m, 1H), 8.94-8.81 (m, 2H), 7.96-7.69 (m, 2H), 7.62-7.32 (m, 3H), 6.50-6.28 (m, 1H), 3.98-3.79 (m, 1H), 2.20-1.96 (m, 2H), 1.94-1.47 (m, 9H). $^{19}$F NMR (376 MHz, DMSO-$d_6$): δ −85.31 (s, 3F), −87.18 (s, 2F), −90.50-−92.79 (m, 1F), −98.64-−101.39 (m, 1F), −142.09-−142.89 (m, 1F).

Example 90b: (12 mg, 16.18% yield) was obtained. LCMS (M+H)=589.1. SFC: Retention time: 2.594 min, (SS) Whelk-01_EtOH (DEA)_5_4. $^1$H NMR (400 MHz, DMSO-$d_6$): δ 9.12-9.04 (m, 1H), 8.94-8.81 (m, 2H), 7.96-7.69 (m, 2H), 7.62-7.32 (m, 3H), 6.50-6.28 (m, 1H), 3.98-3.79 (m, 1H), 2.20-1.96 (m, 2H), 1.94-1.47 (m, 9H). $^{19}$F NMR (376 MHz, DMSO-$d_6$): δ −85.04-−85.42 (m, 3F), −86.87-−87.35 (m, 2 F), −92.04 (br d, J=233.0 Hz, 1F), −97.87-−101.44 (m, 1F), −141.92 (br s, 1F).

Examples 92a and 92b

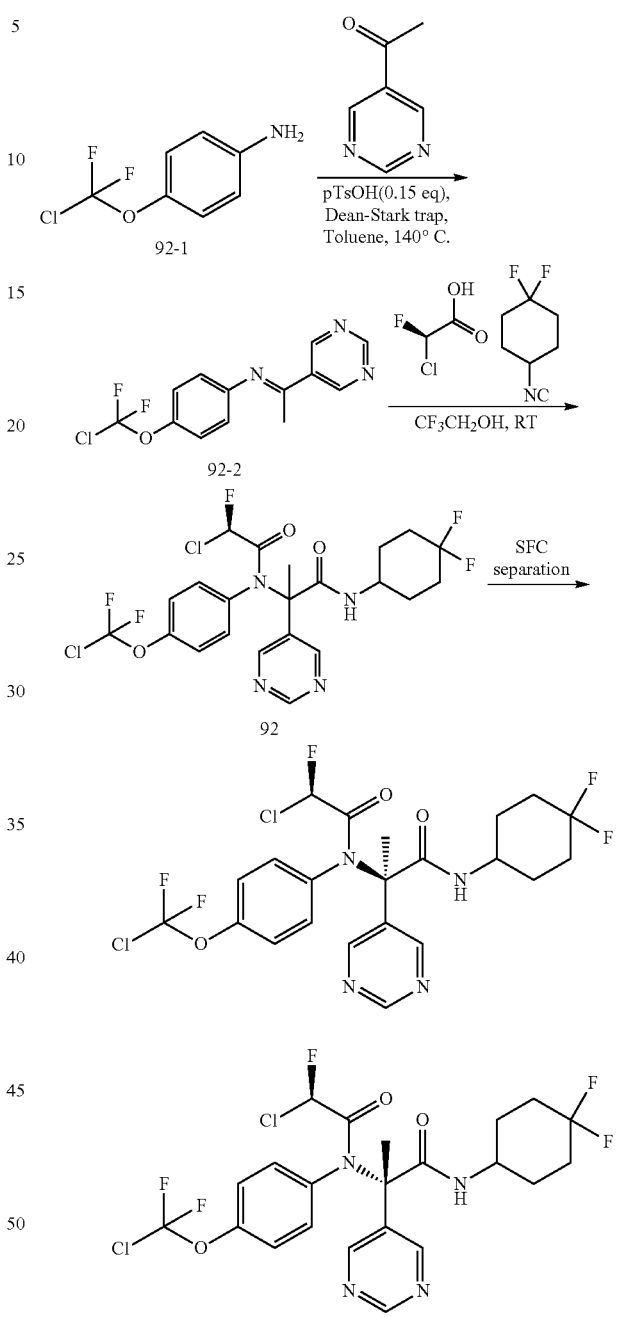

Example 92a and 92b
(Stereochemistry arbitrarily assigned at center between two amides)

To a solution of Compound 92-1 (2.0 g, 10.33 mmol) in toluene (60 mL) was added p-TsOH (210.26 mg, 1.22 mmol) and 1-pyrimidin-5-ylethanone (1.15 g, 9.39 mmol) at Dean-Stark trap, The mixture was heated and stirred at 140° C. for 12 hours. The mixture was filtered, and the filtered cake was wash with toluene (20 mL*3), the organic layer was concentrated under reduced pressure to give a crude. The crude was purified by flash silica gel chromatography (Eluent of 0~30% Ethyl acetate/Petroleum ether gradient @ 45 mL/min, TLC: Petroleum ether:Ethyl acetate=3:1, Rf=0.4) to give Compound 92-2 (1.7 g, 5.71 mmol, 60.80% yield).

To a solution of Compound 92-2 (1.35 g, 4.53 mmol) in CF$_3$CH$_2$OH (2 mL) were added H$_3$PO$_4$ (104.57 mg, 906.99 μmol, 62.24 μL), the mixture was stirred at 25° C. for 1 hour, then (2R)-2-chloro-2-fluoro-acetic acid (927.50 mg, 5.44 mmol, 66% purity) and 1,1-difluoro-4-isocyano-cyclohexane (658.25 mg, 4.53 mmol). The mixture was stirred at 25° C. for 12 hours. The mixture was concentrated under reduced pressure to give a crude. The crude was purified by flash silica gel chromatography (Eluent of 0~100% Ethyl acetate/Petroleum ether gradient @ 40 mL/min, TLC (petroleum ether:ethyl acetate=0:1, Rf=0.4)) to give a crude (300 mg). The crude was prep-HPLC (column: Boston Green ODS 150*30 mm*5 m; mobile phase: [water (FA)-ACN]; B %: 60%-90%, 7 min) to give Compound 92 (57 mg, 15.20% yield). LCMS (M+H)=554.6.

The compound 92 (50 mg, 90.04 μmol) was separated by chiral SFC column: DAICEL CHIRALCEL OD-H (250 mm*30 mm, 5 um); mobile phase: [Neu-ETOH]; B %: 15%-15%; Mobile phase: A: Supercritical CO$_2$, B: Neu-ETOH; Isocratic: A:B=85:15; Flow rate: 60 mL/min), concentrated under vacuum to afford two fractions.

Example 92a: (10.97 mg) was obtained. LCMS (M+H)=555.1. SFC: Retention time: 1.555 min, OD_ETOH_DEA_5_40_28ML_8MIN. $^1$H NMR (400 MHz, METHANOL-d$_4$): δ9.04 (s, 1H), 8.92 (s, 2H), 7.70 (d, J=7.2 Hz, 1H), 7.42 (d, J=8.8 Hz, 2H), 7.38-7.32 (m, 1H), 6.30-6.12 (m, 1H), 3.95 (t, J=10.8 Hz, 1H), 2.07 (d, J=8.0 Hz, 2H), 2.01-1.86 (m, 4H), 1.82 (s, 3H), 1.74-1.58 (m, 2H). $^{19}$F NMR (376 MHz, METHANOL-d$_4$) δ −27.36 (s, 2F), −94.53--105.14 (m, 2F), −145.33 (s, 1F).

Example 92b: (6.51 mg) was obtained. LCMS (M+H)=555.1. SFC: Retention time: 1.972 min, OD_ETOH_DEA_5_40_28ML_8MIN. $^1$H NMR (400 MHz, CD$_3$OD): δ 9.01 (s, 1H), 8.90 (s, 2H), 7.68 (dd, J=2.4, 8.4 Hz, 1H), 7.43-7.39 (m, 1H), 7.39-7.31 (m, 2H), 6.27-6.11 (m, 1H), 3.92 (t, J=11.2 Hz, 1H), 2.06 (dd, J=4.0, 7.2 Hz, 2H), 1.97-1.89 (m, 6H), 1.88-1.81 (m, 1H), 1.72-1.58 (m, 2H). $^{19}$F NMR (376 MHz, CD$_3$OD): δ −25.83--29.74 (m, 2F), −93.88--104.98 (m, 2F), −145.27 (s, 1F).

Examples 94a and 94b

Example 94a and 94b
(Stereochemistry arbitrarily assigned at center between two amides)

To a solution of Compound 92-2 (1.35 g, 4.53 mmol) in CF$_3$CH$_2$OH (2 mL) were added H$_3$PO$_4$ (104.57 mg, 906.99 μmol, 62.24 μL), the mixture was stirred at 25° C. for 1 hour, then (2R)-2-chloro-2-fluoro-acetic acid (927.50 mg, 5.44 mmol, 66% purity) and 4-isocyanotetrahydropyran (504.02 mg, 4.53 mmol). The mixture was stirred at 25° C. for 12 hours. The mixture was concentrated under reduced pressure to give a crude. The crude was purified by flash silica gel chromatography (Eluent of 0~100% Ethyl acetate/Petroleum ether gradient @ 40 mL/min, TLC (petroleum ether: ethyl acetate=0:1, Rf=0.4)) to give a crude (300 mg). The crude was prep-HPLC (column: Boston Green ODS 150*30 mm*5 m; mobile phase: [water (FA)-ACN]; B %: 48%-78%, 7 min) to give Compound 94 (57 mg, 2.11% yield). LCMS (M+H)=520.7.

The compound 94 (46 mg, 88,24 μmol) was separated by chiral SFC column: DAICEL CHIRALCEL OD-H (250 mm*30 mm, 5 μm); mobile phase: [Neu-ETOH]; B %: 20%-20%, min; Mobile phase: A: Supercritical CO$_2$, B: Neu-ETOH; Isocratic: A:B=80:20; Flow rate: 60 mL/min), concentrated under vacuum to afford two fractions.

Example 94a: (7.38 mg) was obtained. LCMS (M+H)=521.1. SFC: Retention time: 1.797 min, OD_ETOH_DEA_5_40_28ML_8MIN. $^1$H NMR (400 MHz, CD$_3$OD): δ 9.07 (s, 1H), 8.97-8.87 (m, 2H), 7.73 (d, J=8.4 Hz, 1H), 7.48-7.29 (m, 3H), 6.32-6.15 (m, 1H), 4.11-3.91 (m, 3H), 3.56-3.45 (m, 2H), 1.91-1.74 (m, 5H), 1.71-1.55 (m, 2H). $^{19}$F NMR (376 MHz, CD$_3$OD): δ −27.34 (s, 2F), −145.3 (s, 1F).

Example 94b: (10.02 mg) was obtained. LCMS (M+H)=521.1. SFC: Retention time: 2.189 min, OD_ETOH_DEA_5_40_28ML_8MIN. $^1$H NMR (400 MHz, CD$_3$OD): δ 9.05 (s, 1H), 8.97-8.87 (m, 2H), 7.71 (d, J=8.4 Hz, 1H), 7.47-7.30 (m, 3H), 6.30-6.12 (m, 1H), 4.08-3.91 (m, 3H), 3.55-3.44 (m, 2H), 1.83-1.74 (m, 5H), 1.71-1.54 (m, 2H). $^{19}$F NMR (376 MHz, CD$_3$OD) δ −27.34 (s, 2F), −145.3 (s, 1F).

Examples 95a and 95b

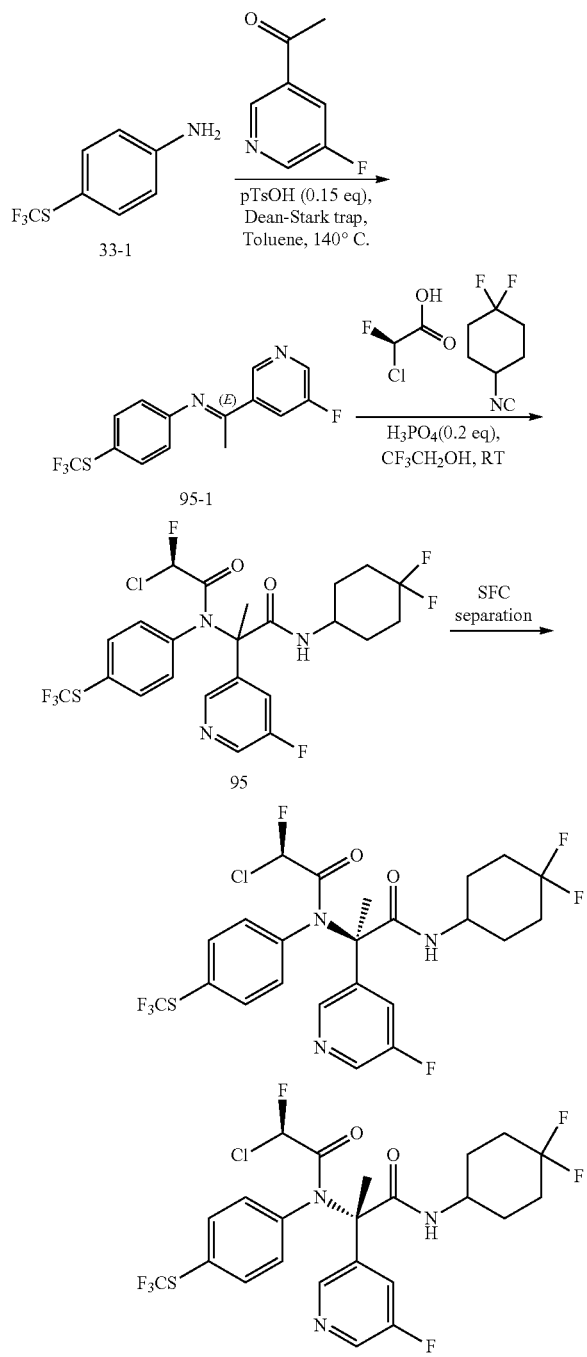

Example of 95a and 95b
(Stereochemistry arbitrarily assigned at center between two amides)

To a 33-1 (1.2 g, 6.21 mmol, 888.89 μL) and 1-(5-fluoropyridin-3-yl)ethan-1-one (576.13 mg, 4.14 mmol) in toluene (25 mL) was added p-TsOH (106.96 mg, 621.15 μmol). The mixture was stirred at 140° C. for 16 hr. The reaction mixture was filtered, and the filtrate was concentrated under reduced pressure to give a residue. The residue was purified by flash silica gel chromatography twice (Eluent of 0~20% Ethyl acetate/Petroleum ether gradient @ 35 mL/min). Compound 95-1 (620 mg, 1.78 mmol, 42.87% yield) was obtained.

To a solution of Compound 95-1 (310.00 mg, 986.32 μmol) in $CF_3CH_2OH$ (2 mL) was added $H_3PO_4$ (19.33 mg, 197.26 μmol, 11.51 μL), (2R)-2-chloro-2-fluoro-acetic acid (188.05 mg, 986.32 μmol) and 1,1-difluoro-4-isocyano-cyclohexane (159.07 mg, 986.32 μmol). The mixture was stirred at 20° C. for 16 hr. The reaction mixture was concentrated under reduced pressure. The residue was purified by flash silica gel chromatography (Eluent of 0~30% Ethyl acetate/Petroleum ether gradient @ 30 mL/min). The residue was purified by prep-HPLC (column: Welch Xtimate C18 150*30 mm*5 m; mobile phase: [water (FA)-ACN]; B %: 57%-87%, 7 min). Compound 95 (55 mg, 94.84 μmol, 9.62% yield, 98.62% purity) was obtained.

The Compound 95 (55 mg) was separated by chiral SFC was separated by SFC (DAICEL CHIRALPAK AD (250 mm*30 mm, 10 μm); Mobile phase: A: Supercritical $CO_2$, B: Neu-IPA; Isocratic: A:B=90:10; Flow rate: 80 mL/min) concentrated under vacuum to afford two fractions.

Example 95a: (19.34 mg, 34.22% yield) was obtained. LCMS (M+H)=572.1. SFC: Retention time: 2.471 min, AD-3_IPA(DEA)_5_40_25ML. $^1$H NMR (400 MHz, DMSO-$d_6$): δ 8.46 (s, 1H), 8.43 (d, J=2.7 Hz, 1H), 7.76 (brs, 2H), 7.67 (br d, J=8.1 Hz, 3H), 7.37 (br s, 1H), 6.45-6.24 (m, 1H), 3.87 (br d, J=8.0 Hz, 1H), 2.07-1.87 (m, 4H), 1.84 (s, 3H), 1.78 (br s, 2H), 1.63-1.50 (m, 2H). $^{19}$F NMR (376 MHz, DMSO-$d_6$): δ −41.83 (s, 3F), −91.86 (br d, J=232.4 Hz, 1F), −99.37 (br d, J=232.4 Hz, 1F), −128.08 (br s, 1F), −141.75 (s, 1F).

Example 95b: (18.37 mg, 31.42% yield) was obtained. LCMS (M+H)=572.1. SFC: Retention time: 2.630 min, AD-3_IPA(DEA)_5_40_25ML. $^1$H NMR (400 MHz, DMSO-$d_6$): δ 8.44 (s, 1H), 8.38 (d, J=2.6 Hz, 1H), 7.71-7.62 (m, 4H), 7.55 (br d, J=8.2 Hz, 2H), 6.44-6.22 (m, 1H), 3.86 (br s, 1H), 2.07-1.81 (m, 7H), 1.75 (br t, J=15.1 Hz, 2H), 1.65-1.45 (m, 2H). $^{19}$F NMR (376 MHz, DMSO-$d_6$): δ −40.85-−44.01 (m, 3F), −91.97 (br d, J=232.4 Hz, 1F), −99.29 (br d, J=235.8 Hz, 1F), −128.06 (s, 1F), −141.86 (s, 1F).

Examples 96a and 96b

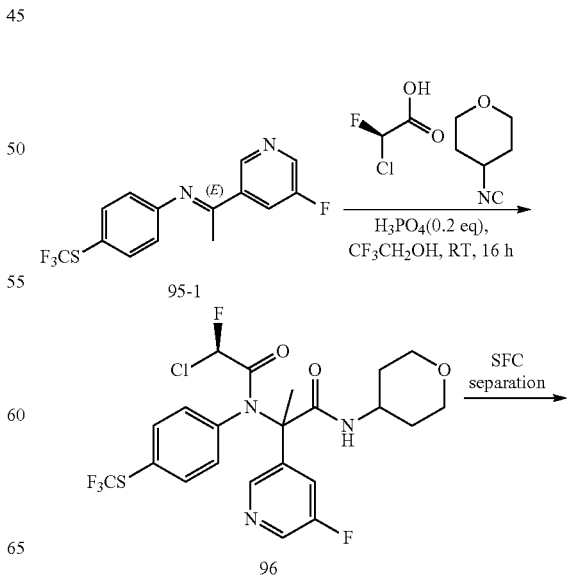

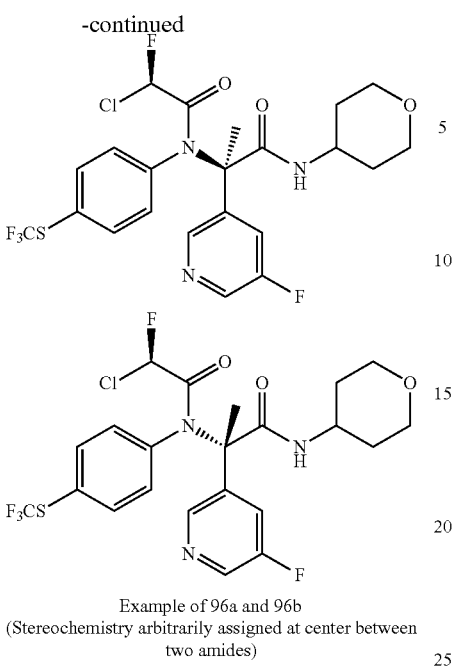

Example of 96a and 96b
(Stereochemistry arbitrarily assigned at center between two amides)

To a solution of Compound 95-1 (310.00 mg, 986.32 mol) in CF$_3$CH$_2$OH (2 mL) was added 85% H$_3$PO$_4$ (19.33 mg, 197.26 μmol, 11.51 μL), 4-isocyanotetrahydropyran (128.97 mg, 986.32 μmol) and (2R)-2-chloro-2-fluoro-acetic acid (188.05 mg, 986.32 μmol). The mixture was stirred at 20° C. for 16 hr. The reaction mixture was concentrated under reduced pressure. The residue was purified by flash silica gel chromatography (Eluent of 0~70% Ethyl acetate/Petroleum ether gradient @ 20 mL/min). The residue was purified by prep-HPLC (column: Welch Xtimate C18 150*30 mm*5 m; mobile phase: [water (FA)-ACN]; B %: 50%-80%, 7 min). Compound 96 (75 mg, 139.42 mol, 14.14% yield, 100% purity) was obtained. LCMS (M+H)=538.0. $^1$H NMR (400 MHz, DMSO-d$_6$): δ 8.48-8.43 (m, 1H), 8.40 (dd, J=2.6, 15.1 Hz, 1H), 7.74 (br s, 1H), 7.71-7.64 (m, 3H), 7.55 (d, J=8.0 Hz, 1H), 7.35 (br d, J=8.6 Hz, 1H), 6.43-6.24 (m, 1H), 4.01-3.79 (m, 3H), 3.31-3.24 (m, 2H), 2.01-1.82 (m, 3H), 1.69-1.58 (m, 2H), 1.55-1.43 (m, 2H).

The Compound 96 (75 mg) was separated by chiral SFC was separated by SFC (DAICEL CHIRALCEL OD (250 mm*30 mm, 10 μm); Mobile phase: A: Supercritical CO$_2$, B: Neu-ETOH; Isocratic: A:B=80:20; Flow rate: 80 mL/min) concentrated under vacuum to afford two fractions.

Example 96a: (16.65 mg, 22.20% yield) was obtained. LCMS (M+H)=549.1. SFC: Retention time: 2.228 min, OD_3_EtOH_DEA_5_40_25ML_6MIN. $^1$H NMR (400 MHz, DMSO-d$_6$): δ 8.46 (s, 1H), 8.42 (d, J=2.6 Hz, 1H), 7.74 (br s, 2H), 7.70-7.63 (m, 3H), 7.40 (br s, 1H), 6.44-6.24 (m, 1H), 3.95-3.80 (m, 3H), 3.29 (br s, 2H), 1.85 (s, 3H), 1.71-1.60 (m, 2H), 1.56-1.45 (m, 2H). $^{19}$F NMR (376 MHz, DMSO-d$_6$): δ −41.13−−43.31 (m, 3F), −128.11 (s, 1F), −141.68 (s, 1F).

Example 96b: (13.02 mg, 25.89% yield) was obtained. LCMS (M+H)=537.9. SFC: Retention time: 2.909 min, OD_3_EtOH_DEA_5_40_25ML_6MIN. $^1$H NMR (400 MHz, DMSO-d$_6$): δ 8.45 (s, 1H), 8.38 (d, J=2.5 Hz, 1H), 7.70-7.63 (m, 4H), 7.55 (d, J=8.0 Hz, 2H), 6.42-6.23 (m, 1H), 3.93-3.80 (m, 3H), 3.29 (br s, 2H), 1.98 (s, 3H), 1.70-1.59 (m, 2H), 1.57-1.43 (m, 2H). $^{19}$F NMR (376 MHz, DMSO-d$_6$): δ −39.70−−46.27 (m, 3F), −128.10 (s, 1F), −141.82 (s, 1F).

Examples 97a and 97b

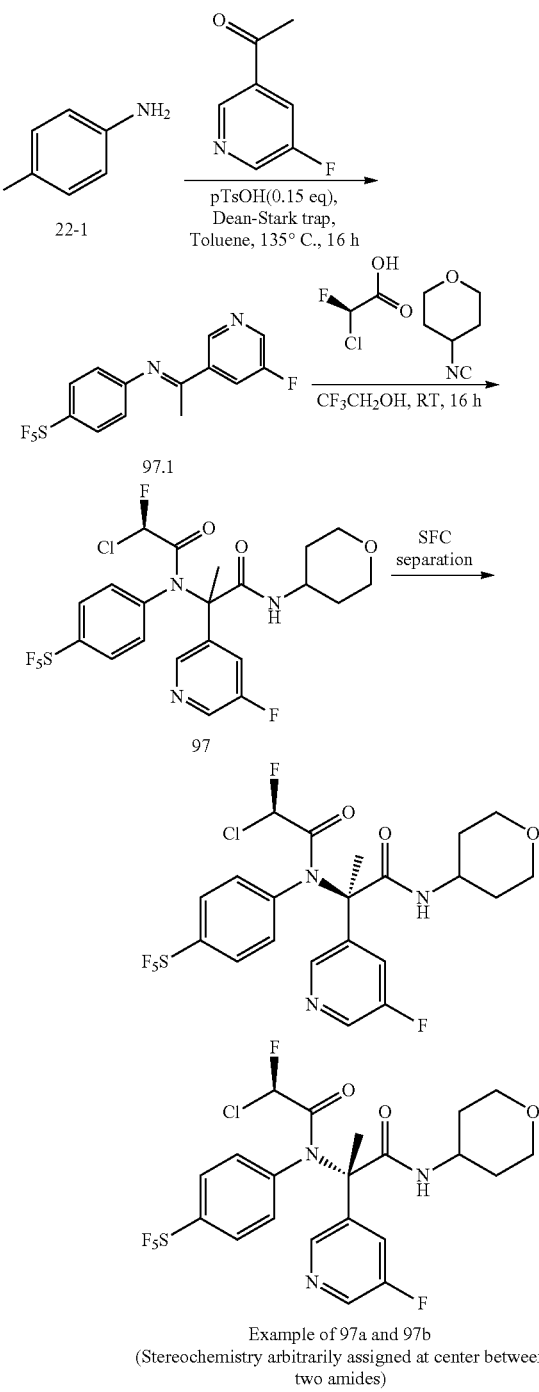

Example of 97a and 97b
(Stereochemistry arbitrarily assigned at center between two amides)

To a solution of Compound 22-1 (1.4 g, 6.39 mmol) and 1-(5-fluoro-3-pyridyl) ethanone (600 mg, 4.31 mmol) in toluene (70 mL) was added p-TsOH (109.99 mg, 638.76 μmol). The mixture was stirred at 135° C. for 16 hr with removal of water by Dean-Stark trap under N$_2$ atmosphere. The reaction was filtered, and the filter cake was washed with toluene (10 mL×2). The filtrate was concentrated under reduced pressure. The residue was purified by flash silica gel chromatography (Eluent of 0~100% DCM/Petroleum ether gradient@ 20 mL/min). Compound 97-1 (357 mg, 23.40% yield). $^1$H NMR (400 MHz, DMSO-d$_6$): δ 9.03 (s, 1H), 8.75 (d, J=2.8 Hz, 1H), 8.22 (d, J=9.8 Hz, 1H), 7.91 (d, J=8.8 Hz, 2H), 7.03 (d, J=8.2 Hz, 2H), 2.27 (s, 3H).

To a solution of Compound 97-1 (357 mg, 1.05 mmol) in CF$_3$CH$_2$OH (2 mL) was added (2R)-2-chloro-2-fluoro-acetic acid (211 mg, 1.05 mmol). Then 4-isocyanotetrahydropyran (167 mg, 1.05 mmol) was added and the mixture was stirred at 15° C. for 16 hr. The reaction was concentrated under reduced pressure. The residue was purified by flash silica gel chromatography (Eluent of 0~100% Ethyl acetate/Petroleum ether gradient @ 25 mL/min). Compound 97 (100 mg, 16.71% yield). LCMS (M+H)=563.9. $^1$H NMR (400 MHz, DMSO-d$_6$): 8.54-8.40 (m, 2H), 8.04-7.40 (m, 6H), 6.52-6.27 (m, 1H), 3.97-3.76 (m, 3H), 3.30-3.10 (m, 2H), 1.93-1.71 (m, 3H), 1.71-1.38 (m, 4H).

Compound 97 (100 mg, 177.33 μmol) was separated by SFC (DAICEL CHIRALPAK AD (250 mm*30 mm, 10 μm); Mobile phase: A: Supercritical CO$_2$, B: Neu-IPA; Isocratic: A:B=85:15; Flow rate: 80 mL/min) to afford two fractions. The two fractions were further purified by prep-HPLC (column: Boston Green ODS 150*30 mm*5 m; mobile phase: [water (FA)-ACN]; B %: 53%-83%, 7 min).

Example 97a: (15 mg, 14.83% yield) was obtained. LCMS (M+H)=564.2. SFC: Retention time: 2.389 min, AD_3_IPA_DEA_5_40_25ML_6MIN. $^1$H NMR (400 MHz, DMSO-d$_6$): δ 8.59-8.45 (m, 2H), 8.11-7.81 (m, 3H), 7.80-7.67 (m, 2H), 7.47 (s, 1H), 6.58-6.26 (m, 1H), 3.98-3.75 (m, 3H), 3.31-3.18 (m, 2H), 1.76 (s, 3H), 1.71-1.59 (m, 2H), 1.59-1.42 (m, 2H). $^{19}$F NMR (376 MHz, DMSO-d$_6$): δ 63.99 (br d, J=151.6 Hz, 5F), −128.02 (s, 1F), −142.20 (s, 1F).

Example 97b: (20 mg, 19.75% yield) was obtained. LCMS (M+H)=564.2. SFC: Retention time: 2.701 min, AD_3_IPA_DEA_5_40_25ML_6MIN. $^1$H NMR (400 MHz, DMSO-d$_6$): δ 8.56-8.41 (m, 2H), 7.92 (d, J=8.4 Hz, 2H), 7.82-7.57 (m, 4H), 6.49-6.27 (m, 1H), 3.84 (d, J=11.2 Hz, 3H), 3.30 (s, 2H), 1.90 (s, 3H), 1.67 (d, J=12.4 Hz, 1H), 1.62-1.55 (m, 1H), 1.55-1.40 (m, 2H). $^{19}$F NMR (376 MHz, DMSO-d$_6$): δ 63.96 (br d, J=148.8 Hz, 5F), −127.95 (s, 1F), −142.05 (s, 1F).

Examples 98a and 98b

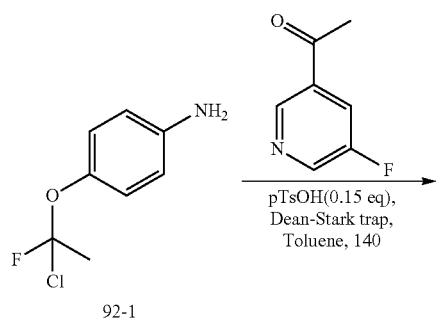

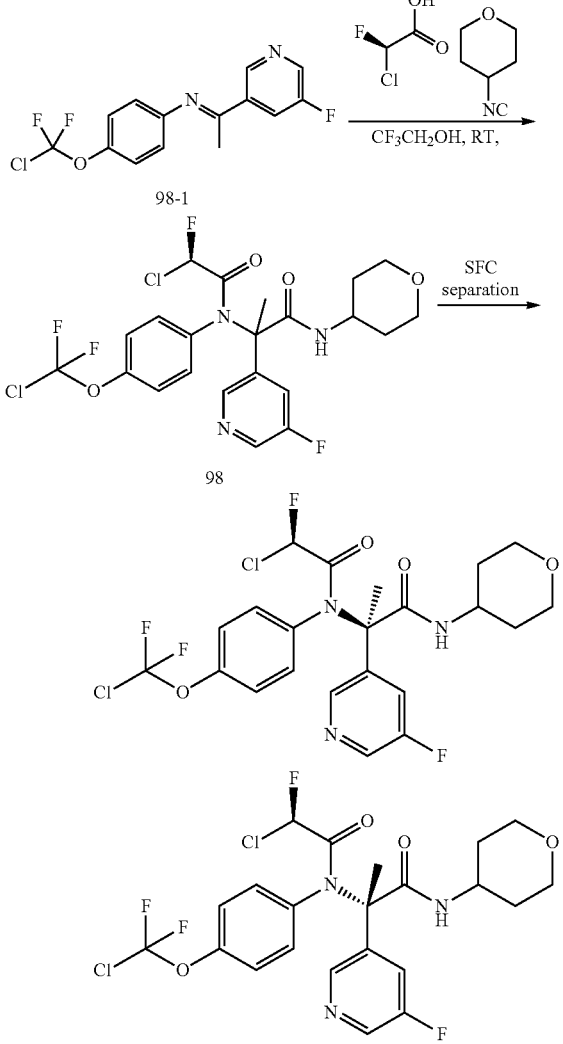

Example of 98a and 98b
(Stereochemistry arbitrarily assigned at center between two amides)

To a solution of compound 92-1 (2.0 g, 10.33 mmol) in toluene (60 mL) were added p-TsOH (192.71 mg, 1.12 mmol) and 1-(5-fluoropyridin-3-yl)ethan-1-one (1.20 g, 8.61 mmol) at Dean-Stark trap, The mixture was heated and stirred at 140° C. for 12 hours. The mixture was filtered and the filtered cake was washed with toluene (30 mL*3), the organic layers were concentrated under reduced pressure to give a crude. The crude was purified by flash silica gel chromatography (Eluent of 0~25% Ethyl acetate/Petroleum ether gradient @ 45 mL/min TLC: petroleum ether; ethyl acetate=3:1 Rf=0.5) to give compound 98-1 (1.3 g, 4.13 mmol, 47.99% yield). $^1$H NMR (400 MHz, CDCl$_3$) δ 8.87 (t, J=1.6 Hz, 1H), 8.51 (d, J=2.8 Hz, 1H), 8.02-7.96 (m, 1H), 7.22-7.15 (m, 2H), 6.76-6.71 (m, 2H), 2.22 (s, 3H).

To a solution of compound 98-1 (230 mg, 730.88 μmol) in CF$_3$CH$_2$OH (2 mL) were added (2R)-2-chloro-2-fluoro-acetic acid (167.22 mg, 877.05 mol, 59% purity), 4-isocyanotetrahydropyran (81.23 mg, 730.88 μmol) and 4A MS (200 mg, 730.88 μmol). The mixture was stirred at 25° C. for 2 hours. The mixture was filtered, and the organic layers was concentrated under reduced pressure to give a crude. The crude was purified by flash silica gel chromatography (Eluent of 0-100% Ethyl acetate/Petroleum ether gradient @30 mL/min, TLC: petroleum ether:ethyl acetate=1:1, Rf=0.2) and purified by prep-HPLC (column: Boston Green ODS 150*30 mm*5 m; mobile phase: [water (FA)-ACN]; B %: 55%-85%, 7 min) to give compound 98 (60 mg, 111.46 mol, 15.25% yield). LCMS (M+H)=539.8.

The residue compound 98 (60 mg, 111.4 μmol) was separated by supercritical fluid chromatography (separation condition: DAICEL CHIRALPAK AD (250 mm*30 mm, 10 μm)); Mobile phase: A: Supercritical CO2, B: Neu-ETOH, A:B=80:20 at 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm), which afford two fractions. The pure fraction was collected and the solvent was evaporated under vacuum. The residue was partitioned between acetonitrile (2 mL) and water (10 mL). The solution was lyophilized to dryness to give the title compound.

Example 98a: (16.05 mg, 24.16% yield) was obtained. LCMS (M+H)=538.0 SFC: Retention time: 2.425 min, AD_3_EtOH_DEA_5_40_25ML_6MIN. $^1$H NMR (400 MHz, CD$_3$OD): δ 8.54 (s, 1H), 8.39 (d, J=2.4 Hz, 1H), 7.77 (td, J=2.4, 10.2 Hz, 1H), 7.67-7.59 (m, 1H), 7.46-7.36 (m, 2H), 7.31 (d, J=8.8 Hz, 1H), 6.32-6.15 (m, 1H), 4.13-4.02 (m, 1H), 4.00-3.93 (m, 2H), 3.58-3.46 (m, 2H), 1.94 (s, 3H), 1.91-1.82 (m, 2H), 1.70-1.54 (m, 2H), 1.70-1.54 (m, 1H), 1.70-1.54 (m, 2H). $^{19}$F NMR (376 MHz, CD$_3$OD) δ −27.29 (s, 2F), −128.11 (s, 1F), −141.97−−146.50 (m, 1F).

Example 98b: (20.35 mg, 31.70% yield) was obtained. LCMS (M+H)=538.4. SFC: Retention time: 2.866 min, AD_3_EtOH_DEA_5_40_25ML_7MIN. $^1$H NMR (400 MHz, CD$_3$OD): δ 8.49 (s, 1H), 8.32 (d, J=2.4 Hz, 1H), 7.76-7.73 (m, 1H), 7.58-7.52 (m, 1H), 7.46-7.40 (m, 1H), 7.28 (d, J=8.8 Hz, 2H), 6.28-6.13 (m, 1H), 4.07-4.00 (m, 1H), 3.95 (t, J=9.2 Hz, 2H), 3.53-3.45 (m, 2H), 2.06 (s, 3H), 1.89-1.76 (m, 2H), 1.68-1.50 (m, 2H). $^{19}$F NMR (376 MHz, CD$_3$OD): δ −26.51−−28.09 (m, 2F), −128.20 (s, 1F), −143.35−−147.88 (m, 1F).

Examples 99a and 99b

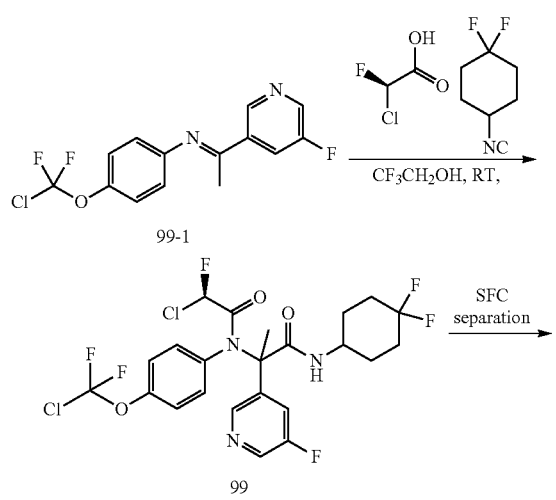

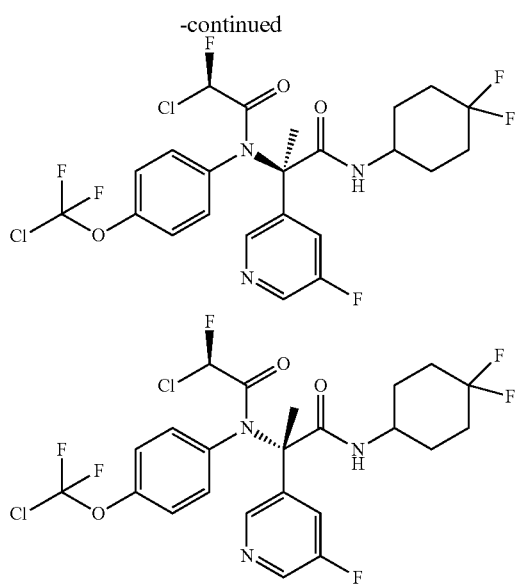

Example of 99a and 99b
(Stereochemistry arbitrarily assigned at center between two amides)

To a solution of compound 98-1 (230 mg, 730.88 μmol) in CF$_3$CH$_2$OH (2 mL) were added (2R)-2-chloro-2-fluoroacetic acid (167.22 mg, 877.05 μmol), 1,1-difluoro-4-isocyano-cyclohexane (106.09 mg, 730.88 μmol) and 4A MS (200 mg, 730.88 μmol). The mixture was stirred at 25° C. for 2 hours. The mixture was filtered and the organic layers was concentrated under reduced pressure to give a crude. The crude was purified by flash silica gel chromatography (Eluent of 0-100% Ethyl acetate/Petroleum ether gradient @30 mL/min, TLC: petroleum ether:ethyl acetate=1:1, Rf=0.5) and purified by prep. HPLC (column: Boston Green ODS 150*30 mm*5 m; mobile phase: [water (FA)-ACN]; B %: 62%-92%, 7 min) to give compound 99 (60 mg, 104.84 mol, 14.34% yield). LCMS (M+H)=572.2.

The residue compound 99 (60 mg, 104.8 μmol) was separated by supercritical fluid chromatography (separation condition: DAICEL CHIRALPAK AD (250 mm*30 mm, 10 μm)); Mobile phase: A: Supercritical CO$_2$, B: Neu-ETOH, A:B=90:10 at 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm), which afford two fractions. The pure fraction was collected, and the solvent was evaporated under vacuum. The residue was partitioned between acetonitrile (2 mL) and water (10 mL). The solution was lyophilized to dryness to give title compound.

Example 99a: (14.88 mg, 24.80% yield) was obtained. LCMS (M+H)=573.8. SFC: Retention time: 1.935 min, OD_3_EtOH_DEA_5_40_25ML_6MIN. $^1$H NMR (400 MHz, CD$_3$OD): δ 8.41 (s, 1H), 8.26 (d, J=2.4 Hz, 1H), 7.65 (td, J=2.4, 10.4 Hz, 1H), 7.56-7.47 (m, 1H), 7.34-7.23 (m, 2H), 7.22-7.14 (m, 1H), 6.21-6.04 (m, 1H), 3.86 (t, J=11.2 Hz, 1H), 2.04-1.84 (m, 5H), 1.81 (s, 3H), 1.79-1.71 (m, 1H), 1.65-1.48 (m, 2H). $^{19}$F NMR (376 MHz, CD$_3$OD) δ −24.74−−30.45 (m, 2F), −93.89−−107.68 (m, 2F), −125.61−−131.72 (m, 1F), −145.01 (br. s, 1F).

Example 99b: (6.19 mg, 10.27% yield) was obtained. LCMS (M+H)=573.9. SFC: Retention time: 2.400 min, OD_3_EtOH_DEA_5_40_25ML_6MIN. $^1$H NMR (400 MHz, CD$_3$OD): δ 8.48 (s, 1H), 8.32 (d, J=2.4 Hz, 1H), 7.74

(td, J=2.4, 10.4 Hz, 1H), 7.58-7.52 (m, 1H), 7.46-7.38 (m, 1H), 7.28 (d, J=8.8 Hz, 2H), 6.29-6.11 (m, 1H), 3.94 (t, J=10.8 Hz, 1H), 2.05 (s, 5H), 1.99-1.82 (m, 4H), 1.74-1.57 (m, 2H). $^{19}$F NMR (376 MHz, CD$_3$OD) δ −27.05-−27.53 (m, 2F), −91.31-−107.89 (m, 2F), −128.18 (s, 1F), −145.24 (s, 1F).

Examples 100a and 100b

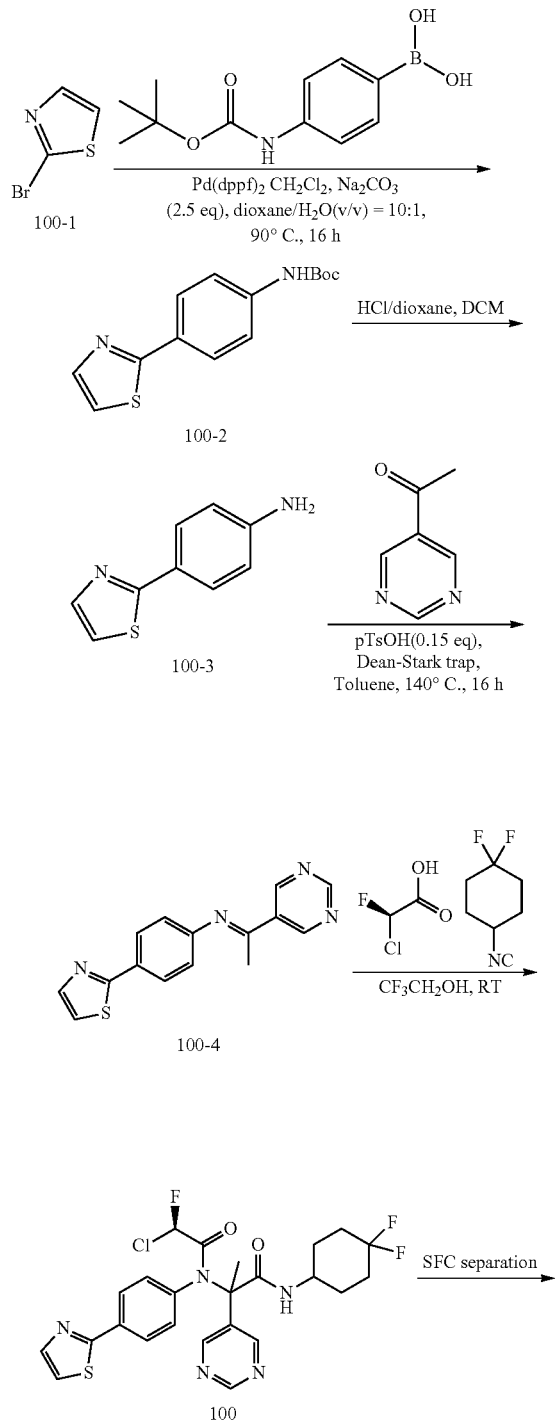

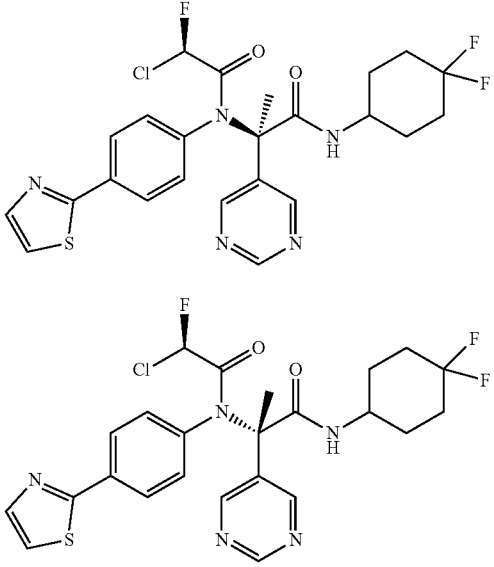

Example 100a and 100b
(Stereochemistry arbitrarily assigned at center between two amides)

To a solution of Compound 100-1 (10 g, 60.97 mmol) and [4-(tert-butoxycarbonylamino) phenyl]boronic acid (14.60 g, 61.58 mmol) in dioxane (100 mL) and Water (10 mL) was added Na$_2$CO$_3$ (16.15 g, 152.42 mmol) and Pd(dppf)Cl$_2$—CH$_2$Cl$_2$ (2.49 g, 3.05 mmol). The mixture was stirred at 90° C. for 16 h under N$_2$. The mixture was filtered and concentrated under reduced pressure to give a crude, the crude was diluted with ethyl acetate (150 mL) and water (150 mL). The water layer was extracted with ethyl acetate (150 mL×5), the organic layers were dried over anhydrous Na$_2$SO$_4$, filtered and concentrated under reduced pressure to give a crude. The residue was purified by flash silica gel chromatography (Eluent of 0~30% Ethyl acetate/Petroleum ether gradient @85 mL/min) to give Compound 100-2 (7.18 g, 16.38% yield). LCMS (M+H)=276.9. $^1$H NMR (400 MHz, DMSO-d$_6$): δ 1.47-1.49 (m, 9H) 7.44 (br d, J=8.34 Hz, 2H) 7.73 (d, J=8.34 Hz, 2H) 7.83 (s, 1H) 9.19-9.51 (m, 1H).

To a solution of 100-2 (7.18 g, 25.97 mmol) in DCM (70 mL) was added HCl/dioxane (4 M, 50 mL, 7.70 eq). The reaction was concentrated, the residue was added water (50 mL). The mixture was adjusted with sat. Na$_2$CO$_3$ to pH=8 and then extracted with DCM (100 mL×3), The organic layers were washed with brine (50 mL), dried over anhydrous Na$_2$SO$_4$, filtered and concentrated under reduced pressure to give a crude. Compound 100-3 (1.0 g, crude), which was used for next step without further purification.

To a solution of Compound 100-3 (1 g, 4.54 mmol) and 1-pyrimidin-5-ylethanone (550 mg, 4.50 mmol) in Tol. (70 mL) was added p-TsOH (117.25 mg, 680.90 μmol). The mixture was stirred at 140° C. for 16 h with removal of water by Dean-Stark trap under N$_2$ atmosphere. The reaction mixture was filtered, and the filtrate was concentrated under reduced pressure. The residue was purified by flash silica gel chromatography (Eluent of 0-10% Ethyl acetate/Petroleum ether gradient @ 25 mL/min). Compound 100-4 (688 mg, 51.36% yield). $^1$H NMR (400 MHz, DMSO-d$_6$): δ 9.38-9.30 (m, 3H), 8.05-7.94 (m, 2H), 7.92 (d, J=3.2 Hz, 1H), 7.76 (d, J=3.2 Hz, 1H), 6.99 (d, J=8.4 Hz, 2H), 2.33 (s, 3H).

To a solution of Compound 100-4 (344 mg, 1.23 mmol) in CF$_3$CH$_2$OH (1.5 mL) was added (2R)-2-chloro-2-fluoroacetic acid (230.05 mg, 1.23 mmol). Then 1, 1-difluoro-4-isocyano-cyclohexane (197.90 mg, 1.23 mmol) was added and the mixture was stirred at 15° C. for 16 hr. The reaction mixture was concentrated under reduced pressure to give a residue. The residue was purified by flash silica gel chromatography (Eluent of 0-50% Ethyl acetate/Petroleum ether gradient @ 20 mL/min). Compound 100 (234 mg, 33.47% yield) was obtained. LCMS (M+H)=537.9. $^1$H NMR (400 MHz, DMSO-$d_6$): δ 9.03 (d, J=18.4 Hz, 1H), 8.85 (d, J=7.6 Hz, 2H), 7.99-7.90 (m, 3H), 7.85 (t, J=3.6 Hz, 1H), 7.77-7.62 (m, 2H), 7.50-7.27 (m, 1H), 6.49-6.25 (m, 1H), 3.87 (s, 1H), 1.97-1.82 (m, 5H), 1.79-1.65 (m, 3H), 1.64-1.38 (m, 3H).

The Compound 100 (120 mg, 223.05 mol) was separated by SFC (DAICEL CHIRALPAK AD (250 mm*30 mm, 10 m); Mobile phase: A: Supercritical $CO_2$, B: Neu-MeOH; Isocratic: A:B=60:40; Flow rate: 80 mL/min) to afford two fractions.

Example 100a: (45 mg, 37.10% yield) was obtained. LCMS (M+H)=538.0. SFC: Retention time: 1.556 min, AD_3_EtOH_DEA_40_25ML. $^1$H NMR (400 MHz, DMSO-$d_6$): δ 9.07 (s, 1H), 8.87 (s, 2H), 8.07 (d, J=9.6 Hz, 1H), 8.01-7.94 (m, 2H), 7.92-7.82 (m, 2H), 7.75 (d, J=8.4 Hz, 1H), 7.31 (d, J=6.8 Hz, 1H), 6.52-6.31 (m, 1H), 3.91 (s, 1H), 2.02 (m, 4H), 1.81 (m, 2H), 1.66 (s, 3H), 1.63-1.47 (m, 2H). $^{19}$F NMR (376 MHz, DMSO-$d_6$): δ -91.81 (d, J=231.7 Hz, 1F), -99.38 (d, J=234.6 Hz, 1F), -142.24 (s, 1F).

Example 100b: (43 mg, 34.60% yield) was obtained. LCMS (M+H)=538.0. SFC: Retention time: 2.085 min, AD_3_EtOH_DEA_40_25ML. $^1$H NMR (400 MHz, DMSO-$d_6$): δ 9.03 (s, 1H), 8.86 (s, 2H), 8.05-7.91 (m, 3H), 7.86 (d, J=3.2 Hz, 1H), 7.74-7.64 (m, 2H), 7.46 (d, J=7.2 Hz, 1H), 6.48-6.22 (m, 1H), 3.88 (br s, 1H), 2.10-1.90 (m, 4H), 1.85-1.73 (m, 5H), 1.60 (m, 2H). $^{19}$F NMR (376 MHz, DMSO-$d_6$): δ -92.04 (d, J=234.6 Hz, 1F), -99.16 (d, J 231.7 Hz, 1F), -141.73 (s, 1F).

Examples 101a and 101b

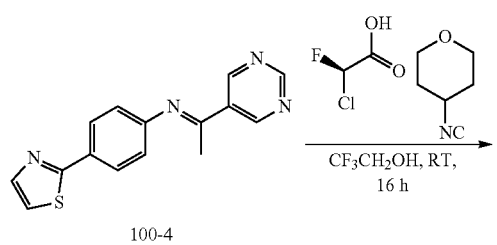

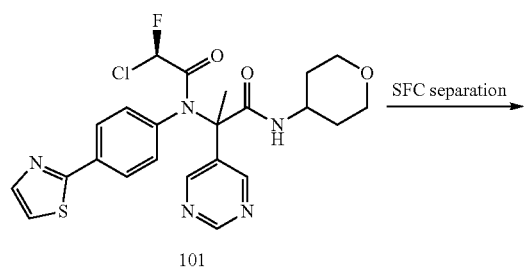

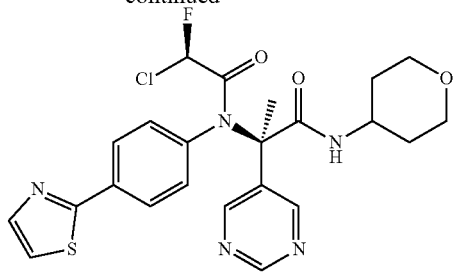

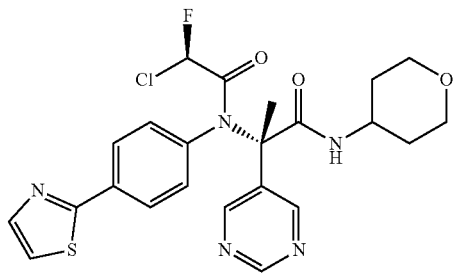

Example of 101a and 101b
(Stereochemistry arbitrarily assigned at center between two amides)

To a solution of Compound 100-4 (4 mg, 1.23 mmol) in $CF_3CH_2OH$ (1.5 mL) was added (2R)-2-chloro-2-fluoro-acetic acid (230.60 mg, 1.23 mmol). Then 4-isocyanotetra-hydropyran (195.29 mg, 1.23 mmol) was added and the mixture was stirred at 15° C. for 16 hr. The reaction mixture was concentrated under reduced pressure. The residue was purified by flash silica gel chromatography (Eluent of 0~100% Ethyl acetate/Petroleum ether gradient @ 20 mL/min). Compound 101 (200 mg, 31.56% yield). LCMS (M+H)=503.9. $^1$H NMR (400 MHz, DMSO-$d_6$): δ 9.04 (d, J=18.0 Hz, 1H), 8.87 (d, J=8.0 Hz, 2H), 8.02-7.92 (m, 4H), 7.85-7.76 (m, 1H), 7.68 (d, J=7.6 Hz, 1H), 7.55-7.28 (m, 1H), 6.51-6.26 (m, 1H), 3.81 (s, 3H), 3.51-3.39 (m, 2H), 1.83 (s, 3H), 1.55-1.37 (m, 4H).

The compound 101 (100 mg) was separated by chiral SFC was separated by SFC (DAICEL CHIRALPAK AD (250 mm*30 mm, 10 m); Mobile phase: A: Supercritical $CO_2$, B: Neu-ETOH; Isocratic: A:B=60:40; Flow rate: 80 mL/min) concentrated under vacuum to afford two fractions.

Example 101a: (37 mg, 35.22% yield) was obtained. LCMS (M+H)=503.7. SFC: Retention time: 1.801 min, AD_ETOH_DEA_5_40_4ML_4MIN_5CM. $^1$H NMR (400 MHz, DMSO-$d_6$): δ 9.07 (s, 1H), 8.88 (s, 2H), 8.06 (d, J=8.8 Hz, 1H), 8.02-7.93 (m, 2H), 7.90-7.83 (m, 2H), 7.79 (d, J=8.0 Hz, 1H), 7.34 (d, J=8.4 Hz, 1H), 6.49-6.30 (m, 1H), 4.00-3.81 (m, 3H), 3.43-3.34 (m, 2H), 1.77-1.63 (m, 5H), 1.61-1.42 (m, 2H). $^{19}$F NMR (376 MHz, DMSO-$d_6$): δ -140.82--145.53 (m, 1F).

Example 101b: (20 mg, 18.65% yield) was obtained. LCMS (M+H)=504.2. SFC: Retention time: 2.178 min, AD_ETOH_DEA_5_40_4ML_4MIN_5CM. $^1$H NMR (400 MHz, DMSO-$d_6$): δ 9.02 (s, 1H), 8.86 (s, 2H), 8.04-7.90 (m, 3H), 7.86 (d, J=3.2 Hz, 1H), 7.75-7.60 (m, 2H), 7.49 (d, J=8.2 Hz, 1H), 6.48-6.24 (m, 1H), 4.00-3.80 (m, 3H), 3.47-3.37 (m, 2H), 1.83 (s, 3H), 1.74-1.61 (m, 2H), 1.58-1.44 (m, 2H). $^{19}$F NMR (376 MHz, DMSO-$d_6$): δ -141.73 (s, 1F).

Examples 102a and 102b

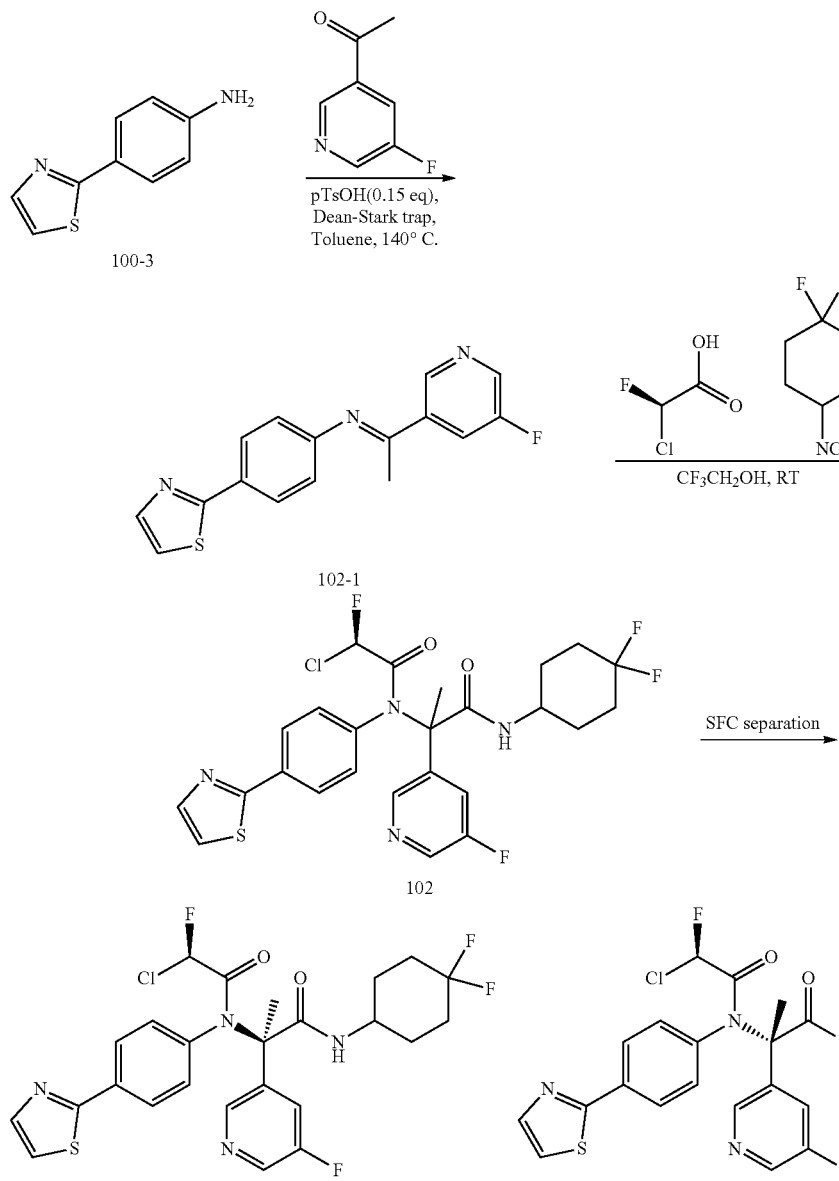

Example 102a and 102b
(Stereochemistry arbitrarily assigned at center between two amides)

To a solution of 100-3 (1.4 g, 7.94 mmol) in toluene (30 mL) was added p-TsOH (227.99 mg, 1.32 mmol) and 1-(5-fluoro-3-pyridyl)ethanone (921.00 mg, 6.62 mmol). The mixture was stirred at 140° C. for 16 h with Dean-Stark trap. The reaction mixture was filtered, the filtrate was concentrated in vacuo. The residue was purified by flash silica gel chromatography (Eluent of 0~20% Ethyl acetate/ Petroleum ether gradient @ 20 mL/min). Compound 102-1 (814 mg, 2.19 mmol, 33.08% yield, 80% purity) was obtained. To a solution of 102-1 (400.00 mg, 1.08 mmol) in $CF_3CH_2OH$ (1 mL) was added (2R)-2-chloro-2-fluoro-acetic acid (302.64 mg, 1.61 mmol) and 1,1-difluoro-4-iso-cyano-cyclohexane (234.31 mg, 1.29 mmol). The mixture was stirred at 20° C. for 16 hr. The reaction mixture was concentrated under reduced pressure. The residue was purified by flash silica gel chromatography (Eluent of 0~50% Ethyl acetate/Petroleum ether gradient @ 20 mL/min) and further purified by prep-HPLC (column: Welch Xtimate C18 150*30 mm*5 m; mobile phase: [water (FA)-ACN]; B %: 50%-80%, 7 min). Compound 102 (34 mg, 61.26 mol, 5.69% yield) was obtained. Compound 102 (34 mg, 61.26 µmol) was further separated by SFC (column: DAICEL CHIRALPAK AD (250 mm*30 mm, 10 µm); mobile phase: [Neu-ETOH]; B %: 35%-35%, min), which afford two fractions.

Example 102a: (9.56 mg, 28.12% yield) was obtained. LCMS (M+H)=555.0. SFC: Retention time: 1.280 min, AD_3_EtOH_DEA_40_25ML. $^1$H NMR (400 MHz, DMSO-$d_6$) δ 8.52 (s, 1H), 8.48 (d, J=2.6 Hz, 1H), 8.03 (br d, J=7.4 Hz, 1H), 7.97 (d, J=3.2 Hz, 1H), 7.93 (br d, J=8.6

Hz, 1H), 7.87 (d, J=3.2 Hz, 1H), 7.82-7.73 (m, 2H), 7.68 (d, J=8.0 Hz, 1H), 7.29 (br d, J=8.0 Hz, 1H), 6.51-6.31 (m, 1H), 3.90 (br d, J=7.5 Hz, 1H), 2.15-1.79 (m, 6H), 1.74 (s, 3H), 1.66-1.54 (m, 2H). $^{19}$F NMR (376 MHz, DMSO-d$_6$): δ −91.81 (br d, J=232.4 Hz, 1F), −99.34 (br d, J=235.8 Hz, 1F), −127.99 (s, 1F), −141.87 (br s, 1F).

Example 102b: (10.77 mg, 31.68% yield) was obtained. LCMS (M+H)=555.0. SFC: Retention time: 1.600 min, AD_3_EtOH_DEA_40_25ML. $^1$H NMR (400 MHz, DMSO-d$_6$) δ 8.49 (s, 1H), 8.42 (d, J=2.6 Hz, 1H), 7.97-7.89 (m, 3H), 7.85 (d, J=3.2 Hz, 1H), 7.76 (br d, J=10.7 Hz, 1H), 7.64 (d, J=7.9 Hz, 1H), 7.58 (br d, J=7.7 Hz, 1H), 7.47 (br d, J=7.9 Hz, 1H), 6.47-6.26 (m, 1H), 3.87 (br s, 1H), 2.08-1.76 (m, 9H), 1.69-1.49 (m, 2H). $^{19}$F NMR (376 MHz, DMSO-d$_6$): δ −91.99 (br d, J=228.9 Hz, 1F), −99.17 (br d, J=221.9 Hz, 1F), −127.86 (s, 1F), −141.67 (s, 1F).

Examples 103a and 103b

150*30 mm*5 μm; mobile phase: [water (FA)-ACN]; B %: 42%-72%, 7 min). Compound 103 (65 mg, 113.54 μmol, 8.44% yield, 91% purity) was obtained.

Compound 103 (67 mg, 128.60 μmol) was further separated by SFC (column: DAICEL CHIRALPAK AD (250 mm*30 mm, 10 μm); mobile phase: [Neu-ETOH]; B %: 40%-40%, min), which afford two fractions.

Example 103a: (15.77 mg, 23.54% yield) was obtained. LCMS (M+H)=521.1. SFC: Retention time: 1.727 min, AD_3_EtOH_DEA_40_25ML. $^1$H NMR (400 MHz, DMSO-d$_6$) δ 8.59-8.44 (m, 2H), 8.02 (br d, J=8.0 Hz, 1H), 7.98 (d, J=2.9 Hz, 1H), 7.94 (br d, J=8.1 Hz, 1H), 7.87 (d, J=3.1 Hz, 1H), 7.76 (br d, J=10.7 Hz, 2H), 7.71 (d, J=7.7 Hz, 1H), 7.33 (br d, J=7.3 Hz, 1H), 6.50-6.27 (m, 1H), 4.02-3.81 (m, 3H), 3.39 (br s, 2H), 1.91-1.49 (m, 7H). $^{19}$F NMR (376 MHz, DMSO-d$_6$): δ −128.00 (br s, 1F), −141.83 (br s, 1F).

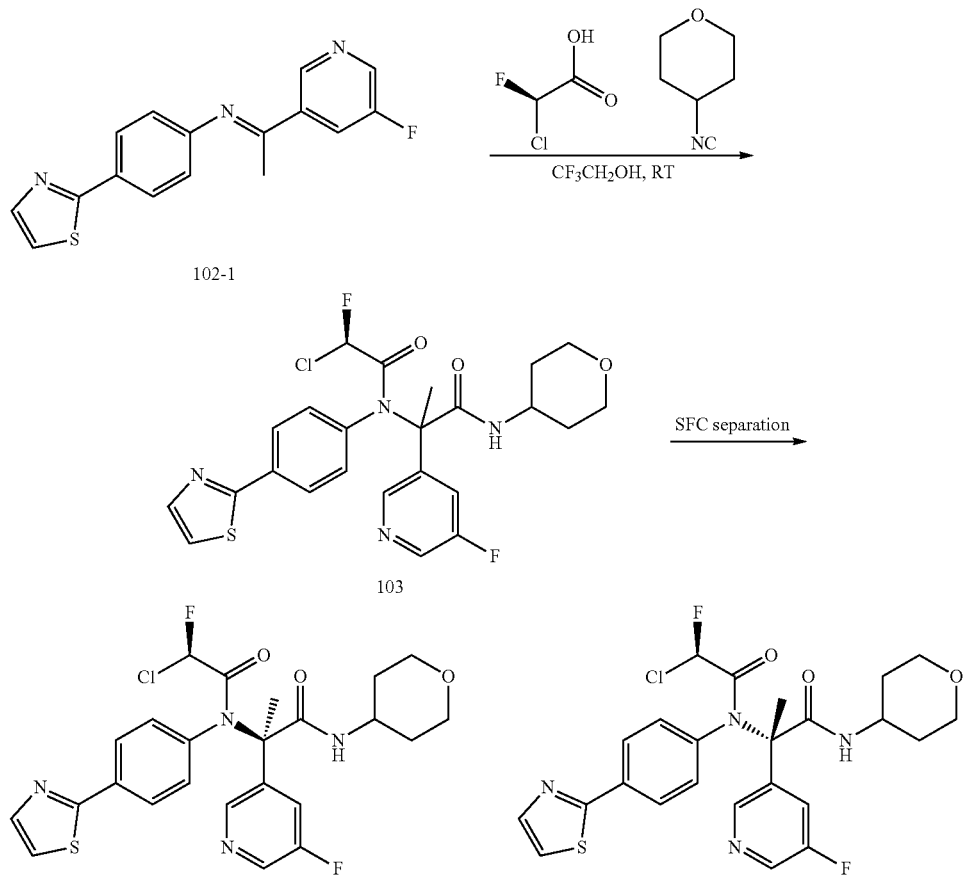

Example 103a and 103b
(Stereochemistry arbitrarily assigned at center between two amides)

To compound 102-1 (400 mg, 1.35 mmol) in CF$_3$CH$_2$OH (1 mL) was added (2R)-2-chloro-2-fluoro-acetic acid (378.30 mg, 2.02 mmol) and 4-isocyanotetrahydropyran (224.26 mg, 1.61 mmol). The mixture was stirred at 20° C. for 16 h. The reaction mixture was concentrated under reduced pressure to give a residue. The residue was purified by flash silica gel chromatography (Eluent of 0~50% Ethyl acetate/Petroleum ether gradient @ 20 mL/min) and further purified by prep-HPLC (column: Welch Xtimate C18

Example 103b: (26.96 mg, 40.24% yield) was obtained. LCMS (M+H)=521.0. SFC: Retention time: 2.471 min, AD_3_EtOH_DEA_40_25ML. $^1$H NMR (400 MHz, DMSO-d$_6$) δ 8.50 (s, 1H), 8.42 (d, J=2.6 Hz, 1H), 7.96 (d, J=3.2 Hz, 1H), 7.93 (br d, J=8.0 Hz, 2H), 7.86 (d, J=3.2 Hz, 1H), 7.77 (dd, J=2.1, 10.6 Hz, 1H), 7.66 (d, J=7.7 Hz, 1H), 7.57 (br d, J=7.4 Hz, 1H), 7.51 (br d, J=7.7 Hz, 1H), 6.52-6.23 (m, 1H), 3.96-3.80 (m, 3H), 3.38 (s, 2H), 1.92 (s, 3H), 1.79-1.63 (m, 2H), 1.60-1.40 (m, 2H). $^{19}$F NMR (376 MHz, DMSO-d$_6$): δ −127.87 (s, 1F), −141.67 (s, 1F).

Examples 104a and 104b

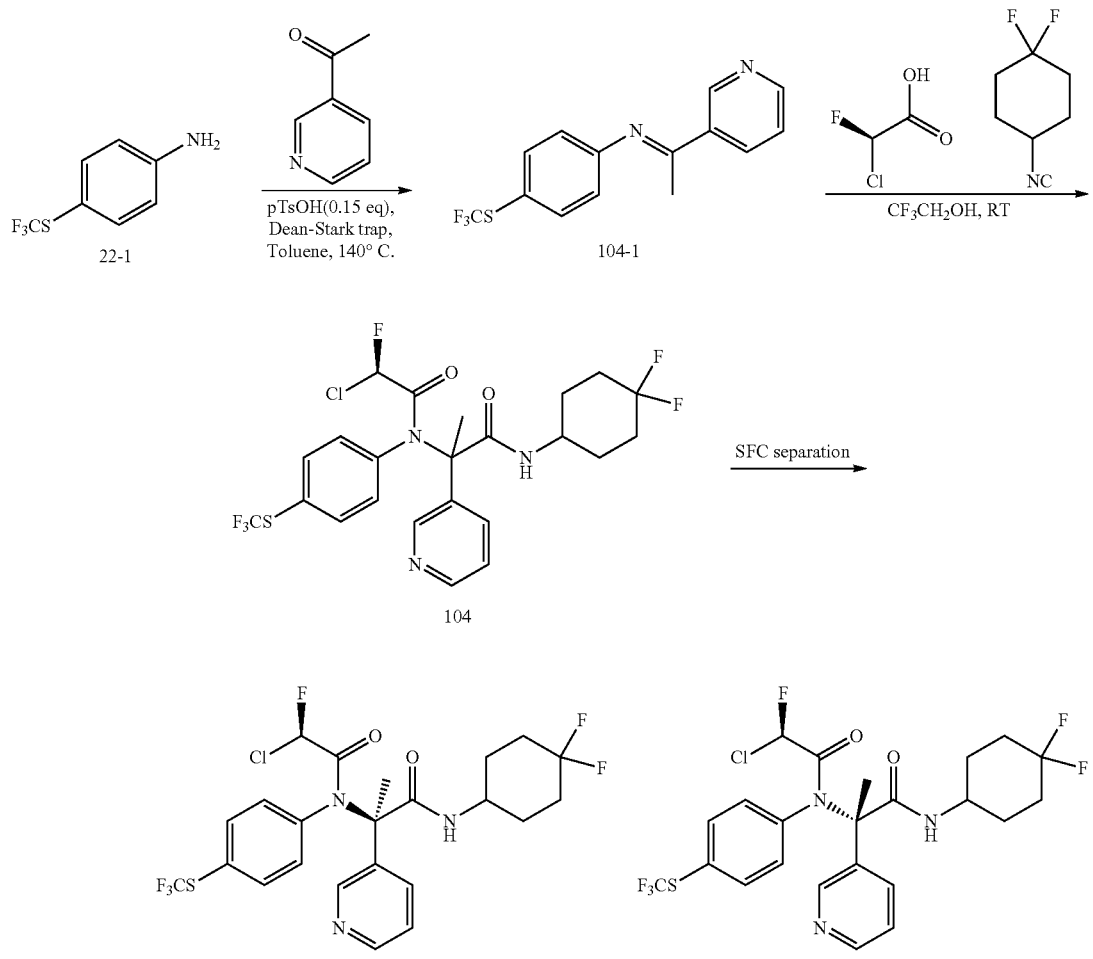

Example 104a and 104b
(Stereochemistry arbitrarily assigned at center between two amides)

To a solution of Compound 22-1 (2 g, 10.35 mmol, 1.48 mL) and 1-(pyrimidin-5-yl)ethan-1-one (836.05 mg, 6.90 mmol, 760.04 µL) in toluene (30 mL) was added pTsOH (178.27 mg, 1.04 mmol). The mixture was stirred at 140° C. for 16 hr. The reaction mixture was filtered, and the filtrate was concentrated under reduced pressure to give a residue. The residue was purified by flash silica gel chromatography (Eluent of 0~100% DCM/Petroleum ether gradient @ 35 mL/min). Compound 104-1 (590 mg, 1.69 mmol, 24.52% yield) was obtained.

To a solution of Compound 104-1 (295 mg, 995.58 mol) in $CF_3CH_2OH$ (2 mL) was added (2R)-2-chloro-2-fluoroacetic acid (227.78 mg, 1.19 mmol) and 1,1-difluoro-4-isocyano-cyclohexane (160.56 mg, 995.58 µmol). The mixture was stirred at 20° C. for 16 hr. The reaction mixture was concentrated under reduced pressure. The residue was purified by flash silica gel chromatography (Eluent of 0~100% Ethyl acetate/Petroleum ether gradient @ 20 mL/min). The residue was purified by prep-HPLC (column: Boston Green ODS 150*30 mm*5 µm; mobile phase: [water (FA)-ACN]; B %: 50%-80%, 7 min). Compound 104 (125 mg, 224.95 µmol, 22.60% yield) was obtained. LCMS (M+H)=554.0.

The Compound 104 (125 mg) was separated by chiral SFC was separated by SFC (DAICEL CHIRALCEL OD (250 mm*30 mm, 10 µm)); Mobile phase: A: Supercritical $CO_2$, B: Neu-ETOH; Isocratic: A:B=80:20; Flow rate: 70 mL/min) concentrated under vacuum to afford two fractions.

Example 104a: (15.02 mg, 12.02% yield) was obtained. LCMS (M+H)=554.0. SFC: Retention time: 2.578 min, OD-3_EtOH (DEA)_5_40_25ML. $^1$H NMR (400 MHz, DMSO-$d_6$): δ 8.52 (d, J=2.3 Hz, 1H), 8.32 (dd, J=1.3, 4.6 Hz, 1H), 7.73-7.55 (m, 5H), 7.33 (br s, 1H), 7.19 (dd, J=4.8, 8.2 Hz, 1H), 6.39-6.20 (m, 1H), 3.88 (br d, J=7.7 Hz, 1H), 1.99 (br s, 3H), 1.89 (s, 4H), 1.77 (br s, 2H), 1.64-1.47 (m, 2H). $^{19}$F NMR (376 MHz, DMSO-$d_6$): δ −41.80 (s, 3F), −91.88 (br d, J=232.3 Hz, 1F), −99.30 (br d, J=232.4 Hz, 1F), −141.40 (s, 1F).

Example 104b: (16.79 mg, 13.43% yield) was obtained. LCMS (M+H)=554.0. SFC: Retention time: 2.872 min, OD-3_EtOH (DEA)_5_40_25ML. $^1$H NMR (400 MHz, DMSO-$d_6$): δ 8.52 (d, J=2.1 Hz, 1H), 8.28 (dd, J=1.4, 4.7 Hz, 1H), 7.70-7.56 (m, 4H), 7.54-7.41 (m, 2H), 7.15 (dd, J=4.6, 8.0 Hz, 1H), 6.43-6.17 (m, 1H), 3.84 (br d, J=7.3 Hz, 1H), 2.08-1.82 (m, 7H), 1.75 (br s, 2H), 1.67-1.42 (m, 2H). $^{19}$F NMR (376 MHz, DMSO-$d_6$): δ −41.86 (s, 3F), −91.95 (br d, J=232.3 Hz, 1F), −99.26 (br d, J=235.8 Hz, 1F), −141.74 (br s, 1F).

Examples 105a and 105b

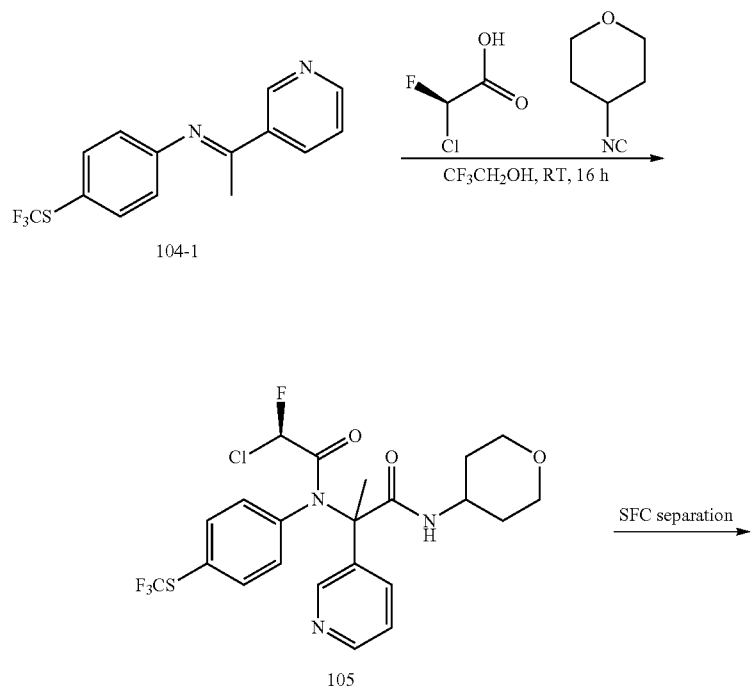

Example 105a and 105b
(Stereochemistry arbitrarily assigned at center between two amides)

To a solution of Compound 104-1 (295 mg, 995.58 mol) in CF₃CH₂OH (2 mL) was added (2R)-2-chloro-2-fluoroacetic acid (227.78 mg, 1.19 mmol) and 4-isocyanotetrahydropyran (130.18 mg, 995.58 mol). The mixture was stirred at 20° C. for 16 hr. The reaction mixture was concentrated under reduced pressure. The residue was purified by flash silica gel chromatography (Eluent of 0~100% Ethyl acetate/Petroleum ether gradient @ 20 mL/min). The residue was purified by prep-HPLC (column: Boston Green ODS 150*30 mm*5 μm; mobile phase: [water (FA)-ACN]; B %: 47%-77%, 7 min). Compound 105 (112 mg, 215.41 mol, 21.64% yield) was obtained. LCMS (M+H)=520.0.

The Compound 105 (112 mg) was separated by chiral SFC was separated by SFC (DAICEL CHIRALPAK AD (250 mm*30 mm, 10 μm)); Mobile phase: A: Supercritical CO₂, B: Neu-MeOH; Isocratic: A:B=75:25; Flow rate: 60 mL/min) concentrated under vacuum to afford two fractions.

Example 105a: (15.48 mg, 13.70% yield) was obtained. LCMS (M+H)=519.9. SFC: Retention time: 3.301 min, AD-3_EtOH (DEA)_5_40_25ML. $^1$H NMR (400 MHz, DMSO-$d_6$): δ 8.54 (d, J=2.0 Hz, 1H), 8.34 (d, J=4.9 Hz, 1H), 7.77-7.54 (m, 5H), 7.37 (br s, 1H), 7.21 (dd, J=4.6, 8.0 Hz, 1H), 6.44-6.18 (m, 1H), 3.98-3.81 (m, 3H), 3.16 (br s, 2H), 1.93 (s, 3H), 1.68 (br s, 2H), 1.59-1.43 (m, 2H). $^{19}$F NMR (376 MHz, DMSO-$d_6$): δ −41.80 (s, 3F), −141.37 (s, 1F).

Example 105b: (15.96 mg, 14.18% yield) was obtained. LCMS (M+H)=520.0. SFC: Retention time: 3.803 min, AD-3_EtOH (DEA)_5_40_25ML. $^1$H NMR (400 MHz, DMSO-$d_6$): δ 8.55 (d, J=2.0 Hz, 1H), 8.30 (d, J=3.5 Hz, 1H), 7.71-7.58 (m, 4H), 7.57-7.42 (m, 2H), 7.16 (dd, J=4.8, 8.0 Hz, 1H), 6.42-6.19 (m, 1H), 3.95-3.79 (m, 3H), 3.31-3.27 (m, 2H), 2.05 (s, 3H), 1.71-1.60 (m, 2H), 1.60-1.38 (m, 2H). $^{19}$F NMR (376 MHz, DMSO-$d_6$): δ −41.87 (s, 3F), −141.72 (br s, 1F).

Examples 106a and 106b

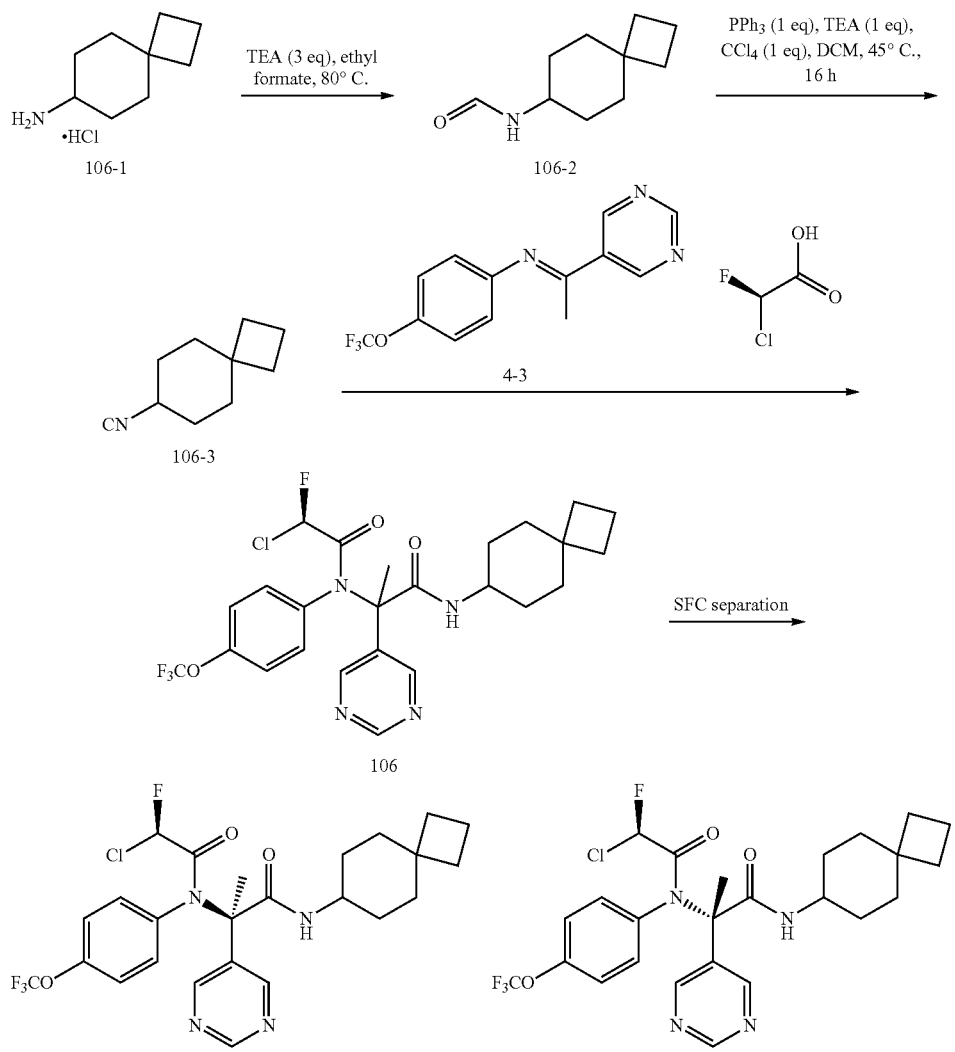

Example 106a and 106b
(Stereochemistry arbitrarily assigned at center between two amides)

To a solution of Compound 106-1 (200 mg, 1.14 mmol HCl) in ethyl formate (20 mL) was added TEA (345.55 mg, 3.41 mmol, 475.32 µL). The mixture was stirred at 80° C. for 16 h. The mixture was concentrated under vacuum, diluted with water (30 mL), extracted with DCM (10 mL*3). The organic layer as washed with brine (10 mL), dried over $Na_2SO_4$, filtered, and concentrated under vacuum. Compound 106-2 (185 mg, crude) was obtained. LCMS (M+H)=167.8.

To a solution of Compound 106-2 (185 mg, 1.11 mmol in DCM (10 mL) was added $CCl_4$ (170.15 mg, 1.11 mmol, 106.34 µL), $PPh_3$ (290.13 mg, 1.11 mmol) and TEA (111.93 mg, 1.11 mmol, 153.96 µL). The mixture was stirred at 45° C. for 16 hr. The mixture was diluted with DCM (10 mL), filtered, and concentrated under vacuum. The crude product was triturated with PE (10 mL) and MTBE (10 mL) at 20° C. for 60 min. The mixture was filtered and the filter cake was washed by MTBE (10 mL*3). The filtrate was concentrated under reduced pressure. Compound 106-3 (384 mg, crude) was obtained.

To a solution of Compound 4-3 (150 mg, 533.37 mol) in $CF_3CH_2OH$ (2 mL) was added (2R)-2-chloro-2-fluoro-acetic acid (119.99 mg, 640.04 µmol) and Compound 106-3 (159.19 mg, 533.37 µmol). The mixture was stirred at 20° C. for 16 hr. The reaction mixture was concentrated under reduced pressure. The residue was purified by flash silica gel chromatography (Eluent of 0~100% Ethyl acetate/Petroleum ether gradient @ 20 mL/min). The residue was purified by prep-HPLC (column: Boston Green ODS 150*30 mm*5 µm; mobile phase: [water (FA)-ACN]; B %: 63%-93%, 7 min). Compound 106 (19 mg, 34.60 mol, 6.49% yield) was obtained. LCMS (M+H)=543.0.

The Compound 106 (19 mg) was separated by chiral SFC (DAICEL CHIRALCEL OD (250 mm*30 mm, 10 µm)); Mobile phase: A: Supercritical $CO_2$, B: Neu-ETOH; Isocratic: A:B=85:15; Flow rate: 80 mL/min) concentrated under vacuum to afford two fractions.

Example 106a: (3.68 mg, 19.37% yield) was obtained. LCMS (M+H)=543.1. SFC: Retention time: 2.168 min, OD_3_EtOH_DEA_5_40_25ML_6MIN. $^1$H NMR (400 MHz, DMSO-d$_6$): δ 9.05 (s, 1H), 8.84 (s, 2H), 7.83 (br d, J=8.9 Hz, 1H), 7.63 (d, J=8.1 Hz, 1H), 7.47 (br d, J=8.8 Hz, 1H), 7.39 (br s, 2H), 6.44-6.27 (m, 1H), 3.57 (br d, J=3.8 Hz, 1H), 1.85-1.78 (m, 2H), 1.77-1.70 (m, 4H), 1.69-1.64 (m, 5H), 1.62-1.50 (m, 2H), 1.33-1.20 (m, 4H). $^{19}$F NMR (376 MHz, DMSO-d$_6$): δ −56.85 (s, 3F), −142.13 (br s, 1F).

Example 106b: (5.80 mg, 30.53% yield) was obtained. LCMS (M+H)=543.1. SFC: Retention time: 2.858 min, OD_3_EtOH_DEA_5_40_25ML_6MIN. $^1$H NMR (400 MHz, DMSO-d$_6$): δ9.02 (s, 1H), 8.82 (s, 2H), 7.66 (br d, J=8.6 Hz, 1H), 7.58-7.49 (m, 2H), 7.46-7.35 (m, 2H), 6.39-6.21 (m, 1H), 3.55 (br s, 1H), 1.85-1.76 (m, 5H), 1.75-1.63 (m, 6H), 1.61-1.44 (m, 2H), 1.31-1.20 (m, 4H). $^{19}$F NMR (376 MHz, DMSO-d$_6$): δ −56.88 (s, 3F), −141.87 (s, 1F).

Examples 107a and 107b

To a solution of Compound 107-1 (100 mg, 708.16 mol) in ethyl formate (10 mL). The mixture was stirred at 80° C. for 16 hr. The mixture was concentrated under vacuum, diluted with water (20 mL), extracted with DCM (10 mL*3). The organic layer as washed with brine (10 mL), dried over Na$_2$SO$_4$, filtered, and concentrated under vacuum. Compound 107-2 (130 mg, crude) was obtained. LCMS (M+H)=169.8.

To a solution of Compound 107-2 (130 mg, 768.23 μmol) in DCM (10 mL) was added TEA (77.74 mg, 768.23 μmol, 106.93 μL) PPh$_3$ (201.50 mg, 768.23 μmol) and CCl$_4$ (118.17 mg, 768.23 μmol, 73.86 μL). The mixture was stirred at 45° C. for 16 hr. The mixture was diluted with DCM (10 mL), filtered, and concentrated under vacuum. The crude product was triturated with PE (10 mL) and MTBE (10 mL) at 2° C. for 60 min. The mixture was filtered and the filter cake was washed by MTBE (10 mL*3). The filtrate was concentrated under reduced pressure. Compound 107-3 (116 mg, crude) was obtained.

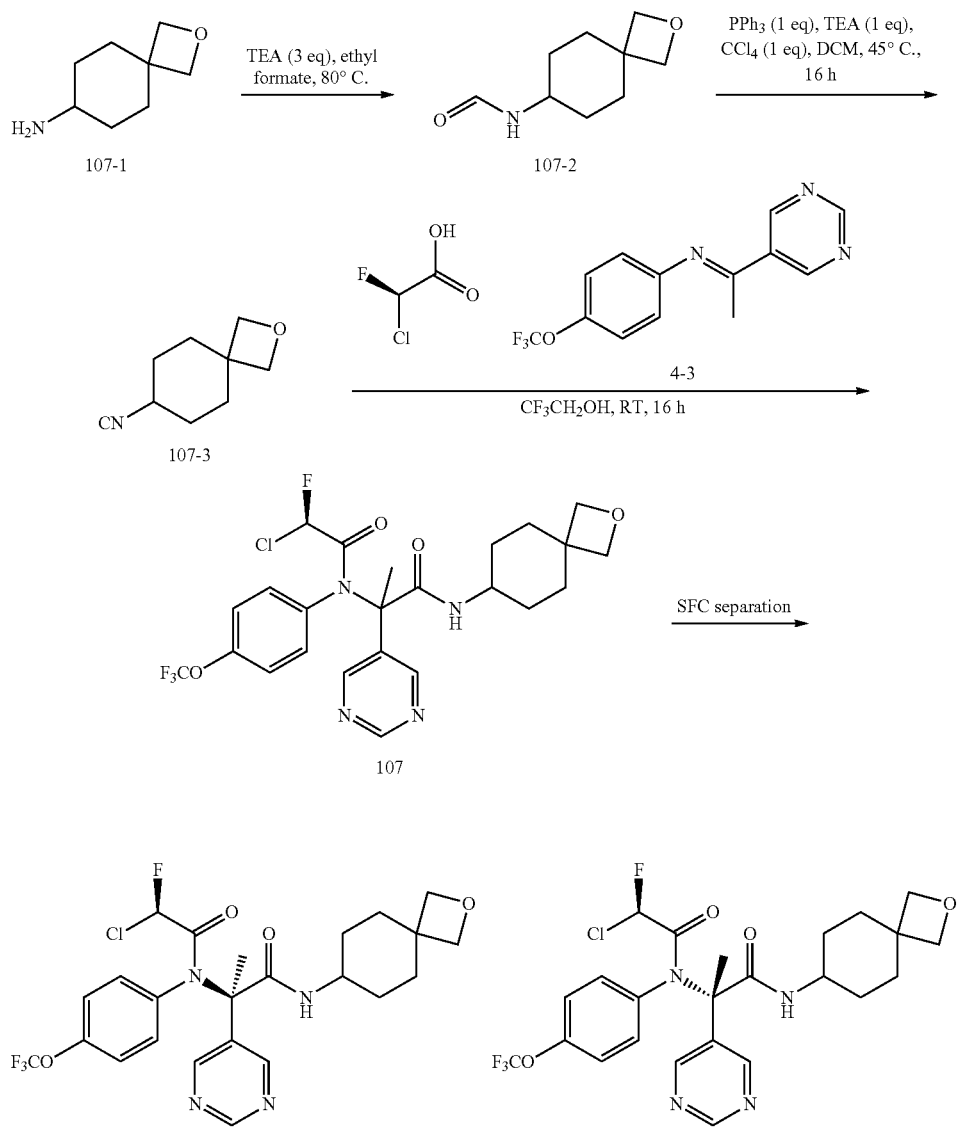

Example 107a and 107b
(Stereochemistry arbitrarily assigned at center between two amides)

To a solution of Compound 4-3 (200 mg, 711.15 mol in CF₃CH₂OH (2 mL) was added (2R)-2-chloro-2-fluoro-acetic acid (159.99 mg, 853.39 µmol) and Compound 107-3 (107.53 mg, 711.15 µmol). The mixture was stirred at 20° C. for 16 hr. The reaction mixture was concentrated under reduced pressure. The crude product was purified with reverse phase silica gel column (Cis, 40 g) using water and acetonitrile as eluents (Mobile phase A water (0% FA), Mobile phase B acetonitrile, Mobile phase B from 30% to 60%). The residue was purified by prep-HPLC (column: Boston Green ODS 150*30 mm*5 m; mobile phase: [water (FA)-ACN]; B %: 40%-70%, 6 min). Compound 107 (28 mg, 49.84 mol, 7.01% yield) was obtained. LCMS (M+H)=545.1.

The Compound 107 (28 mg) was separated by chiral SFC was separated by SFC (column: DAICEL CHIRALCEL OD-H (250 mm*30 mm, 5 µm); Mobile phase: A: Supercritical CO₂, B: Neu-IPA; Isocratic: A:B=75:25; Flow rate: 70 mL/min) concentrated under vacuum to afford two fractions.

Example 107a: (3.30 mg, 11.43% yield) was obtained. LCMS (M+H)=545.1. SFC: Retention time: 2.832 min, OD_3_IPA_DEA_5_40_25ML_6MIN. ¹H NMR (400 MHz, DMSO-d₆): δ 9.05 (s, 1H), 8.83 (s, 2H), 7.83 (br d, J=9.2 Hz, 1H), 7.62 (d, J=8.1 Hz, 1H), 7.48 (br d, J=9.3 Hz, 1H), 7.39 (s, 2H), 6.47-6.26 (m, 1H), 4.31 (s, 2H), 4.21 (s, 2H), 3.60 (br d, J=8.1 Hz, 1H), 2.06 (br d, J=13.6 Hz, 2H), 1.66 (s, 5H), 1.46 (br dd, J=3.5, 7.6 Hz, 2H), 1.29-1.20 (m, 2H). ¹⁹F NMR (376 MHz, DMSO-d₆): δ −56.84 (s, 3F), −142.20 (br s, 1F).

Example 107b: (5.85 mg, 19.78% yield) was obtained. LCMS (M+H)=545.1. SFC: Retention time: 3.516 min, OD_3_EtOH_DEA_5_40_25ML_6MIN. ¹H NMR (400 MHz, DMSO-d₆): δ 9.02 (s, 1H), 8.81 (s, 2H), 7.69-7.62 (m, 1H), 7.56-7.49 (m, 2H), 7.40 (br dd, J=8.8, 12.9 Hz, 2H), 6.38-6.22 (m, 1H), 4.31-4.26 (m, 2H), 4.20 (s, 2H), 3.63-3.52 (m, 1H), 2.01 (br d, J=6.1 Hz, 2H), 1.78 (s, 3H), 1.70-1.53 (m, 2H), 1.51-1.40 (m, 2H), 1.26-1.17 (m, 2H). ¹⁹F NMR (376 MHz, DMSO-d₆): δ −56.81−−57.11 (m, 3F), −141.91 (s, 1F).

Examples 108a and 108b

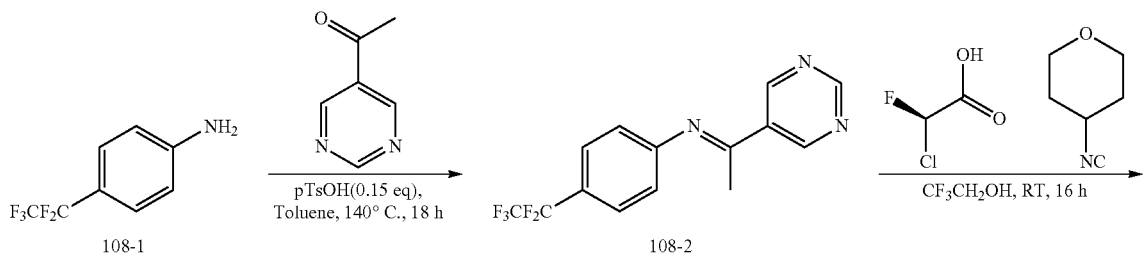

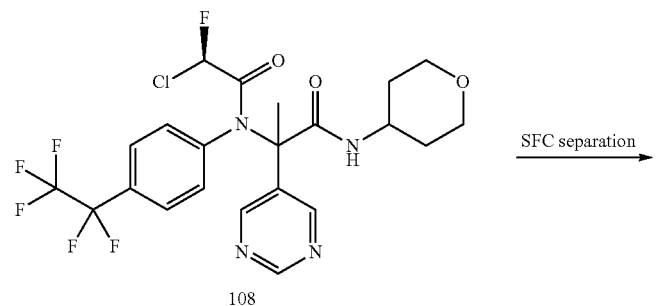

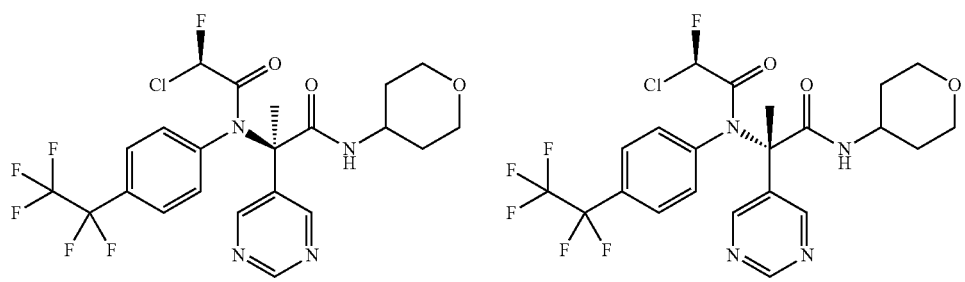

Example 108a and 108b
(Stereochemistry arbitrarily assigned at center between two amides)

To a solution of Compound 108-1 (500 ing, 2.368 minol) in toluene (30 mL) was added 1-(pyrimidin-5-yl)ethan-1-one (289.22 mg, 0.237 mmol) and 4-methylbenzenesulfonic acid (40.78 g, 2.046 mmol). The mixture was stirred at 140° C. for 18 h under $N_2$ atmosphere. The mixture was concentrated under reduced pressure to give a residue. The residue was purified by flash silica gel chromatography (Eluent of 20% acetone/Petroleum ether gradient @ 20 mL/min) to give compound 108-2 (400 mg, crude).

To a solution of Compound 108-2 (500 mg, 0.952 mmol) in $CF_3CH_2OH$ (3 mL) was added (2R)-2-chloro-2-fluoroacetic acid (214.07 mg, 0.952 mmol) and 4-isocyanotetrahydropyran (88.14 mg, 0.793 mmol). The mixture was stirred at 25° C. for 16 hr. The reaction mixture was concentrated under reduced pressure to give a residue. The residue was purified by prep-HPLC (Phenomenex Gemini-NX C18 75*30 mm*3 μm; Mobile phase: A: water (FA) B: ACN; Gradient condition: from 37% B to 67% B; Flow rate: 25 mL/min). The pure fractions were collected and the volatile solvent was removed by evaporation. The aqueous residue was lyophilized to afford Compound 108 (90 mg, 20.43% yield). LCMS (M+H)=539.1.

The Compound 108 (90 mg, 0.167 mmol) was separated by SFC (Chiralcel OD-3 100×4.6 mm I.D., 3 m Mobile phase: A: $CO_2$ B: ethanol (0.05% DEA) Gradient: from 5% to 40% of B in 4 min and hold 40% for 2.5 min, then 5% of B for 1.5 min Flow rate: 2.8 mL/min), which afford two fractions.

Example 108a: (1.80 mg, 2.00% yield) was obtained. LCMS (M+H)=539.0. SFC: Retention time: 1.542 min, OD_ETOH_DEA_5_40_28ML_8MIN. $^1$H NMR (400 MHz, DMSO-$d_6$): δ 1.39-1.77 (m, 7H), 3.29 (s, 2H), 3.78-3.93 (m, 3H), 6.32-6.46 (m, 1H), 7.48-7.58 (m, 1H), 7.79 (d, 3H), 7.95 (s, 1H), 8.85 (s, 2H), 9.04 (s, 1H). $^{19}$F NMR (376 MHz, DMSO-$d_6$): δ −142.32 (s, 1F), −113.59 (br s, 2F), −84.02 (s, 3F).

Example 108b: (3.45 mg, 3.78% yield) was obtained. LCMS (M+H)=539.2. SFC: Retention time: 1.879 min, OD_ETOH_DEA_5_40_28ML_8MIN. $^1$H NMR (400 MHz, DMSO-$d_6$): δ 1.46 (s, 2H), 1.51-1.60 (m, 1H), 1.64-1.74 (m, 1H), 1.85 (s, 3H), 3.29 (s, 2H), 3.74-3.94 (m, 3H), 6.25-6.41 (m, 1H), 7.64-7.69 (m, 1H), 7.72 (s, 3H), 7.77-7.82 (m, 1H), 8.82 (s, 2H), 9.00 (s, 1H). $^{19}$F NMR (376 MHz, DMSO-$d_6$): δ −142.01 (s, 1 F), −113.68 (s, 2 F), −84.07 (s, 3 F).

Examples 109a and 109b

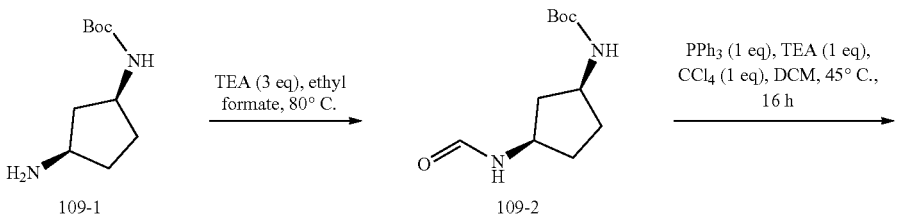

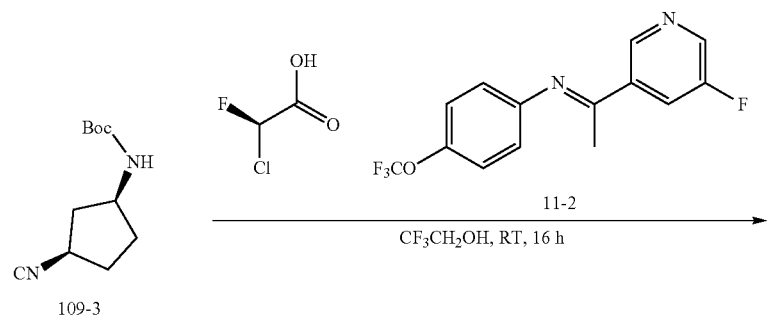

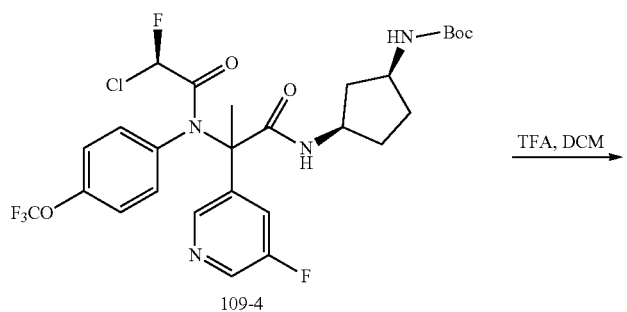

-continued

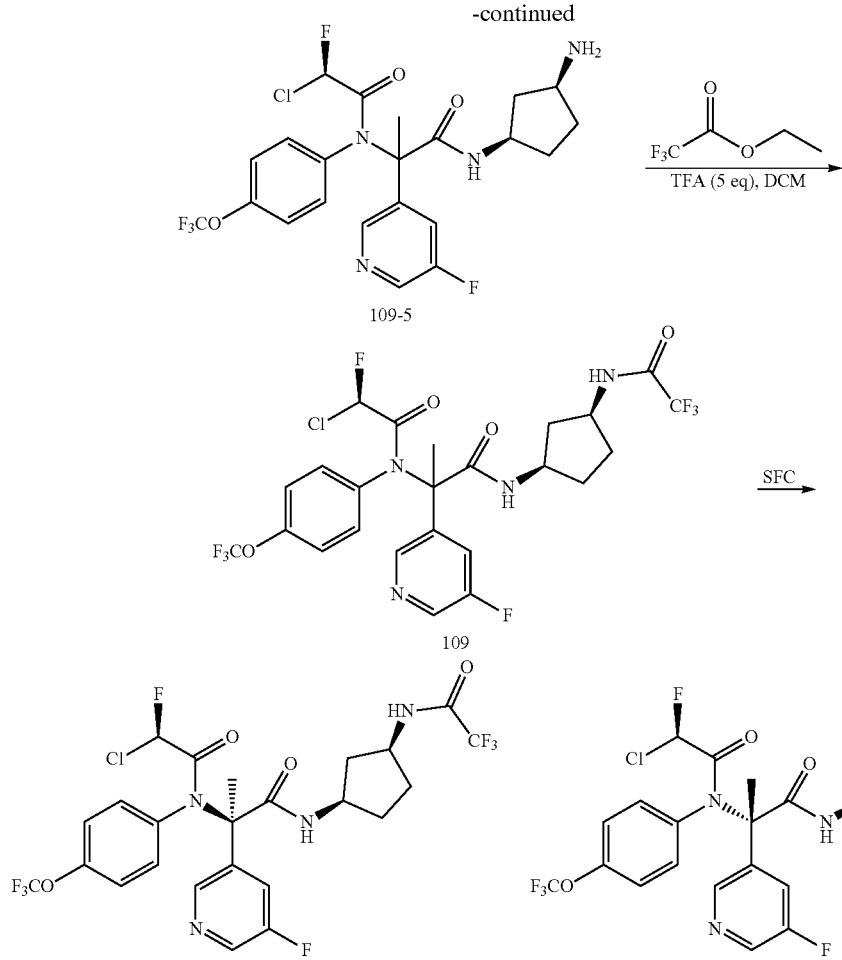

Example 109a and 109b
(Stereochemistry arbitrarily assigned at center between two amides)

To a solution of Compound 109-1 (1.3 g, 6.49 mmol) in ethyl formate (10 mL) was added TEA (1.97 g, 19.47 mmol, 2.71 mL) The mixture was heated and stirred at 80° C. for 12 hours. The mixture was cooled to room temperature and concentrated under reduced pressure to give a crude Compound 109-2 (1.5 g, crude).

To a solution of Compound 109-2 (1.5 g, 6.57 mmol) in DCM (8 mL) were added $PPh_3$ (1.72 g, 6.57 mmol), TEA (664.88 mg, 6.57 mmol, 914.55 µL, 1 eq), $CCl_4$ (1.01 g, 6.57 mmol, 631.70 µL). The mixture was heated and stirred at 45° C. for 12 hours. The mixture was cooled to room temperature and concentrated under reduced pressure to give a crude at 20° C. which was purified by flash silica gel chromatography (Eluent of 0-100% dichloromethane/Petroleum ether gradient @ 35 mL/min). TLC (petroleum ether:dichloromethane=0:1, Rf=0.4)). Compound 109-3 (500 mg, 2.38 mmol, 36.19% yield) was obtained. $^1H$ NMR (400 MHz, $CDCl_3$): δ 4.65 (m, 1H), 4.03-3.82 (m, 2H), 2.42-2.28 (m, 1H), 2.09-1.82 (m, 3H), 1.80-1.59 (m, 2H), 1.38 (s, 9H).

To a solution of Compound 11-2 in $CF_3CH_2OH$ (2 mL) were added (2R)-2-chloro-2-fluoro-acetic acid (560 mg, 2.94 mmol), Compound 109-3 (500 mg, 2.38 mmol) and 4A MS (200 mg, 2.38 mmol). The mixture was stirred at 25° C. for 12 hours. The mixture was concentrated under reduced pressure to give a crude and purified by flash silica gel chromatography (Eluent of 0~100% Ethyl acetate/Petroleum ether gradient @ 30 mL/min) to give a residue Compound 109-4 (500 mg, 791.07 mol, 33.27% yield). LCMS (M+H)=620.8.

To a solution of Compound 109-4 (500 mg, 0.805 mmol) in DCM (5 mL) was added TFA (0.308 mL, 4.026 mmol), the mixture was stirred at 25° C. for 1 hour. The mixture was diluted with dichloromethane (40 mL) and adjusted to pH=12 by the solution of sodium hydroxide (3 M, 8 mL) and extracted with dichloromethane (10 mL*2). The combined organic layers were dried over anhydrous $Na_2SO_4$, filtered and concentrated under reduced pressure to give Compound 109-5 (300 mg, crude) as. The crude was used to the next step directly without further purification.

To a solution of Compound 109-5 (300 mg, 0.576 mmol) in DCM (10 mL) was added DMAP (35.18 mg, 0.288 mmol) and ethyl 2,2,2-trifluoroacetate (245.49 mg, 1.728 mmol), the mixture was stirred at 25° C. for 12 hour, The mixture was concentrated under reduced pressure to give a crude which was purified by prep-HPLC (Column: Boston Green ODS 150*30 mm*5 m, Mobile Phase A: water (FA), Mobile Phase B: acetonitrile, Flow rate: 25 mL/min, gradient condition from 55% B to 85%) to give Compound 109 (60 mg, 16.89% yield). LCMS (M+H)=616.8.

The residue Compound 109 (60 mg, 0.097 mmol) was separated by supercritical fluid chromatography (separation condition: DAICEL CHIRALCEL OD-H (250 mm*30 mm, 5 μm)); Mobile phase: A: Supercritical CO2, B: Neu-IPA, A:B=85:15 at 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm), which afford two fractions.

Example 109a: (12.77 mg) was obtained. LCMS (M+H)=617.1. SFC: Retention time: 2.590 min, OD_3_IPA_DEA_5_40_25ML_6MIN. $^1$H NMR (400 MHz, CD$_3$OD): δ 9.49 (d, J 6.8 Hz, 1H), 8.47-8.41 (m, 2H), 7.83 (d, J 7.2 Hz, 1H), 7.75-7.64 (m, 2H), 7.45-7.31 (m, 3H), 6.43-6.29 (m, 1H), 4.18-3.96 (m, 2H), 2.35-2.22 (m, 1H), 1.95-1.85 (m, 2H), 1.80 (s, 3H), 1.73-1.64 (m, 2H), 1.60-1.49 (m, 1H). $^{19}$F NMR (376 MHz, CD$_3$OD) δ −56.92 (s, 3F), −74.19 (s, 3F), −128.04 (s, 1F), −141.92 (s, 1F).

Example 109b: (20.53 mg) was obtained. LCMS (M+H)=617.1. SFC: Retention time: 2.849 min, OD_3_IPA_DEA_5_40_25ML_6MIN. $^1$H NMR (400 MHz, CD$_3$OD): δ 9.47 (d, J 6.8 Hz, 1H), 8.49-8.41 (m, 2H), 7.80-7.64 (m, 2H), 7.54 (dd, J 4.8, 8.4 Hz, 2H), 7.40-7.30 (m, 2H), 6.45-6.23 (m, 1H), 4.13-3.99 (m, 2H), 2.26-2.16 (m, 1H), 1.92 (s, 3H), 1.89-1.78 (m, 2H), 1.72-1.49 (m, 3H). $^{19}$F NMR (376 MHz, CD$_3$OD) δ −55.25−−58.93 (m, 3F), −73.81−−74.92 (m, 3F), −126.74−−128.76 (m, 1F), −140.33−−142.54 (m, 1F).

Examples 110a and 110b

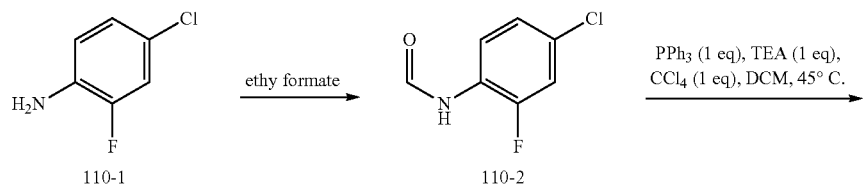

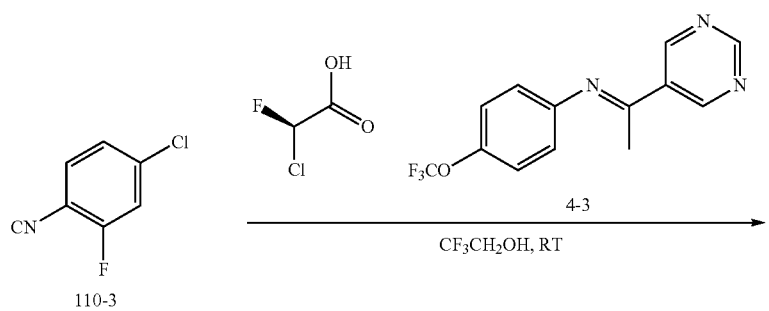

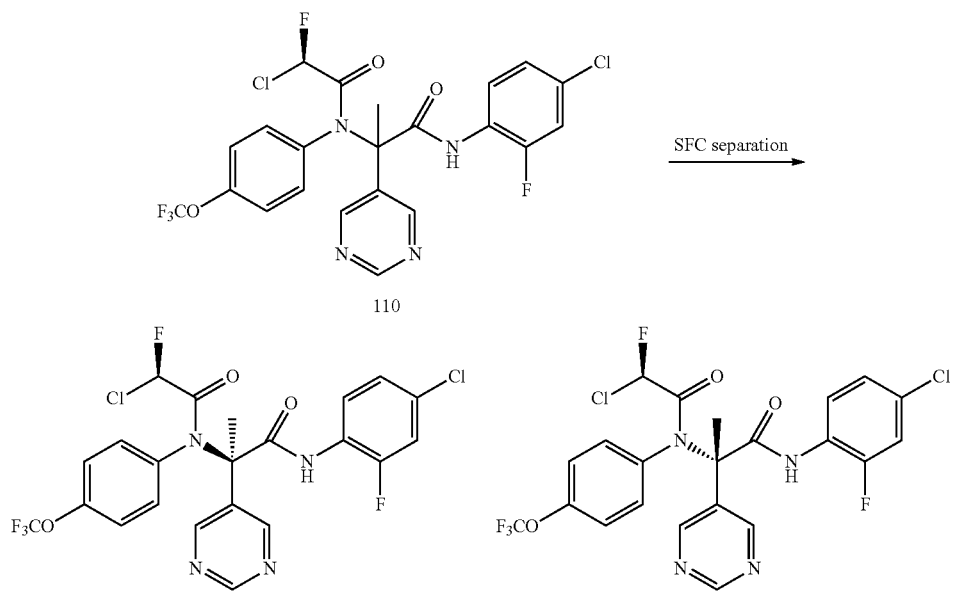

Example 110a and 110b
(Stereochemistry arbitrarily assigned at center between two amides)

To a solution of 110-1 (2 g, 13.74 mmol, 1.53 mL) in ethyl formate (20 mL). The mixture was stirred at 20° C. for 4 hr. The reaction mixture was concentrated under reduced pressure to give a residue. The residue was purified by flash silica gel chromatography (Eluent of 0~5% Ethyl acetate/ Petroleum ether gradient @ 20 mL/min). Compound 110-2 (921 mg, 5.15 mmol, 37.46% yield) was obtained.

To a solution of 110-2 (921 mg, 5.31 mmol) in DCM (10 mL) was added TEA (536.92 mg, 5.31 mmol, 738.55 μL) and $PPh_3$ (1.39 g, 5.31 mmol), $CCl_4$ (816.21 mg, 5.31 mmol, 510.13 μL). The mixture was stirred at 45° C. for 16 h. The reaction mixture was concentrated under reduced pressure to give a residue. The residue was purified by flash silica gel chromatography (Eluent of 0~5% Ethyl acetate/Petroleum ether gradient @ 20 mL/min).
Compound 110-3 (4.2 g, crude) was obtained.

To a solution of 4-3 (400 mg, 1.42 mmol) in $CF_3CH_2OH$ (1 mL) was added (2R)-2-chloro-2-fluoro-acetic acid (319.98 mg, 1.71 mmol) and 110-3 (442.50 mg, 1.42 mmol). The mixture was stirred at 20° C. for 16 h. The reaction mixture was filtered, the filtrate was concentrated in vacuo. The residue was purified by flash silica gel chromatography (Eluent of 0~50% Ethyl acetate/Petroleum ether gradient @ 20 mL/min) and further purified by prep-HPLC (column: Welch Xtimate C18 150*30 mm*5 m; mobile phase: [water (FA)-ACN]; B %: 56%-86%, 7 min). Compound 110 (35 mg, 62.45 mol, 4.39% yield) was obtained.

Compound 110 (35 mg, 63.72 mol) was further separated by SFC (column: (S,S) WHELK-01 (250 mm*30 mm, 5 μm); mobile phase: [Neu-IPA]; B %: 35%-35%, min), which afford two fractions.

Example 110a: (8.13 mg, 23.23% yield) was obtained. LCMS (M+H)=549.0. SFC: Retention time: 3.470 min, (SS)Whelk-01_IPA(DEA)_5_40. $^1$H NMR (400 MHz, DMSO-$d_6$) δ 9.76 (s, 1H), 9.13 (s, 1H), 8.99-8.87 (m, 2H), 7.99 (dd, J=2.8, 8.8 Hz, 1H), 7.60-7.41 (m, 4H), 7.37-7.22 (m, 2H), 6.56-6.34 (m, 1H), 1.72 (s, 3H).

Example 110b: (9.89 mg, 28.26% yield) was obtained. LCMS (M+H)=549.1. SFC: Retention time: 3.951 min, (SS)Whelk-01_IPA(DEA)_5_40. $^1$H NMR (400 MHz, DMSO-$d_6$) δ 9.70 (s, 1H), 9.07 (s, 1H), 8.92 (s, 2H), 7.76 (dd, J=2.4, 8.7 Hz, 1H), 7.58-7.40 (m, 5H), 7.34 (br d, J=8.5 Hz, 1H), 6.49-6.28 (m, 1H), 1.91 (s, 3H).

Examples 111a and 111b

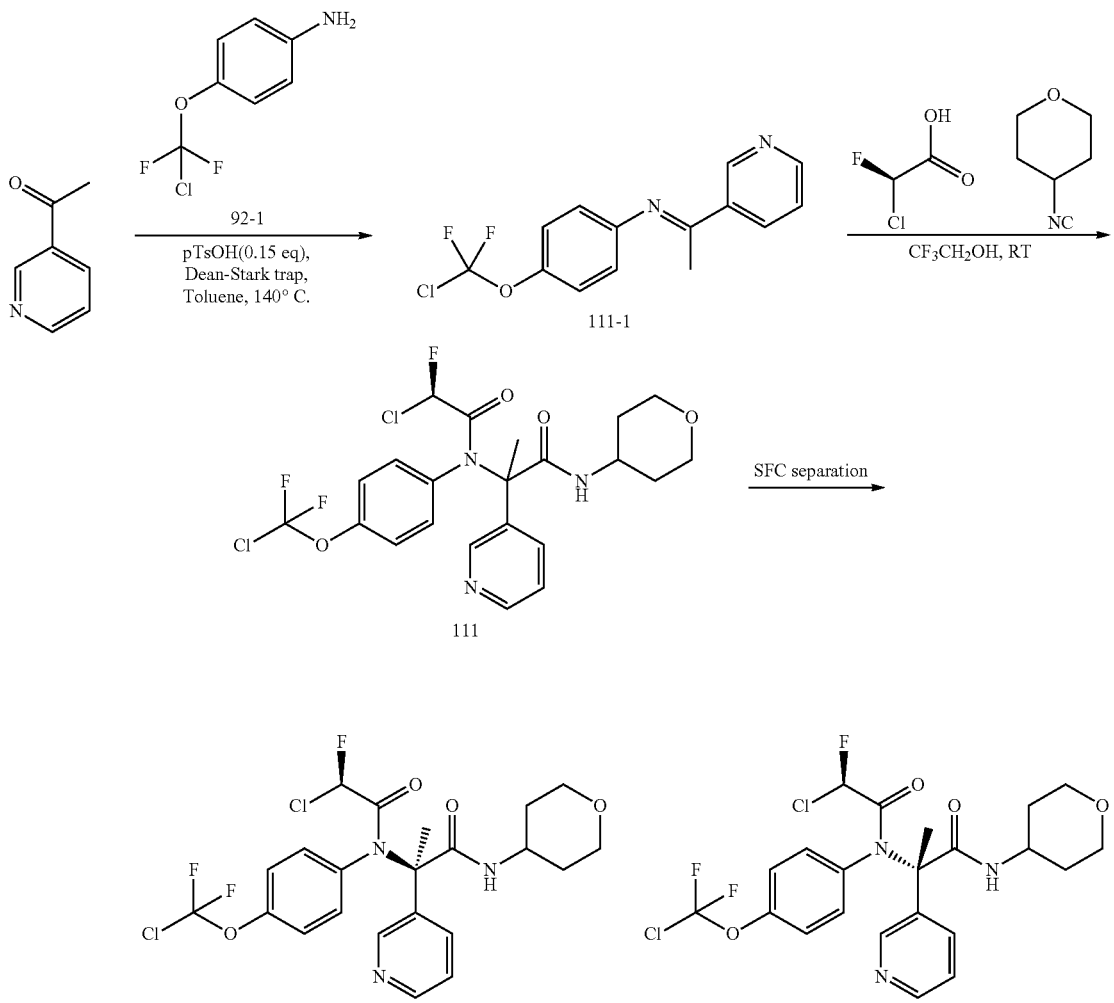

Example 111a and 111b
(Stereochemistry arbitrarily assigned at center between two amides)

To a solution of 1-(pyridin-3-yl)ethan-1-one (1 g, 8.26 mmol, 909.09 µL) and Compound 92-1 (1.60 g, 8.26 mmol) in toluene (30 mL) was added p-TsOH (213.23 mg, 1.24 mmol). The mixture was stirred at 140° C. for 16 h. The reaction mixture was concentrated under reduced pressure. The residue was purified by flash silica gel chromatography (Eluent of 0~20% Ethyl acetate/Petroleum ether gradient @ 35 mL/min). Compound 111-1 (673 mg, 1.70 mmol, 20.61% yield) was obtained.

To a solution of Compound 111-1 (673 mg, 2.27 mmol) in CF$_3$CH$_2$OH (10 mL) was added (2R)-2-chloro-2-fluoroacetic acid (510.31 mg, 2.72 mmol) and 4-isocyanotetrahydropyran (296.59 mg, 2.27 mmol). The mixture was stirred at 20° C. for 16 hr. The reaction mixture was concentrated under reduced pressure. The residue was purified by flash silica gel chromatography (Eluent of 0~100% Ethyl acetate/Petroleum ether gradient @ 30 mL/min). The residue was purified by prep-HPLC (column: Boston Green ODS 150*30 mm*5 m; mobile phase: [water (FA)-ACN]; B %: 45%-75%, 7 min). The residue was purified by prep-HPLC (column: Boston Green ODS 150*30 mm*5 m; mobile phase: [water (FA)-ACN]; B %: 40%-70%, 7 min). Compound 111 (110 mg, 204.45 µmol, 53.19% yield) was obtained. LCMS (M+H)=520.0.

The Compound 111 (110 mg, 211 mol) was separated by SFC (column: DAICEL CHIRALCEL OD-H (250 mm*30 mm, 5 µm); Mobile phase: A: Supercritical CO$_2$, B: Neu-ETOH; Isocratic: A:B=75:25; Flow rate: 70 mL/min), concentrated under vacuum to afford two fractions.

Example 111a: (20.99 mg, 19.08% yield) was obtained. LCMS (M+H)=520.0. SFC: Retention time: 2.646 min, OD_3_EtOH_DEA_5_40_25ML_6MIN. $^1$H NMR (400 MHz, DMSO-d$_6$): δ 8.54 (d, J=2.3 Hz, 1H), 8.35 (d, J=4.8 Hz, 1H), 7.73-7.58 (m, 3H), 7.40-7.20 (m, 4H), 6.43-6.22 (m, 1H), 3.98-3.79 (m, 3H), 3.32-3.25 (m, 2H), 1.91 (s, 3H), 1.67 (br s, 2H), 1.59-1.42 (m, 2H). $^{19}$F NMR (376 MHz, DMSO-d$_6$): δ −24.97 (s, 2F), −141.43 (s, 1F).

Example 111b: (36.34 mg, 32.19% yield) was obtained. LCMS (M+H)=520.0. SFC: Retention time: 3.482 min, OD_3_EtOH_DEA_5_40_25ML_6MIN. $^1$H NMR (400 MHz, DMSO-d$_6$): δ 8.54 (s, 1H), 8.31 (d, J=4.6 Hz, 1H), 7.67 (brdd, J=7.9, 16.6 Hz, 2H), 7.56-7.42 (m, 2H), 7.30-7.15 (m, 3H), 6.44-6.22 (m, 1H), 3.85 (br d, J=4.9 Hz, 3H), 3.31-3.21 (m, 2H), 2.03 (s, 3H), 1.66 (br s, 2H), 1.58-1.39 (m, 2H). $^{19}$F NMR (376 MHz, DMSO-d$_6$): δ −24.95 (s, 2F), −141.76 (br s, 1F).

Examples 112a and 112b

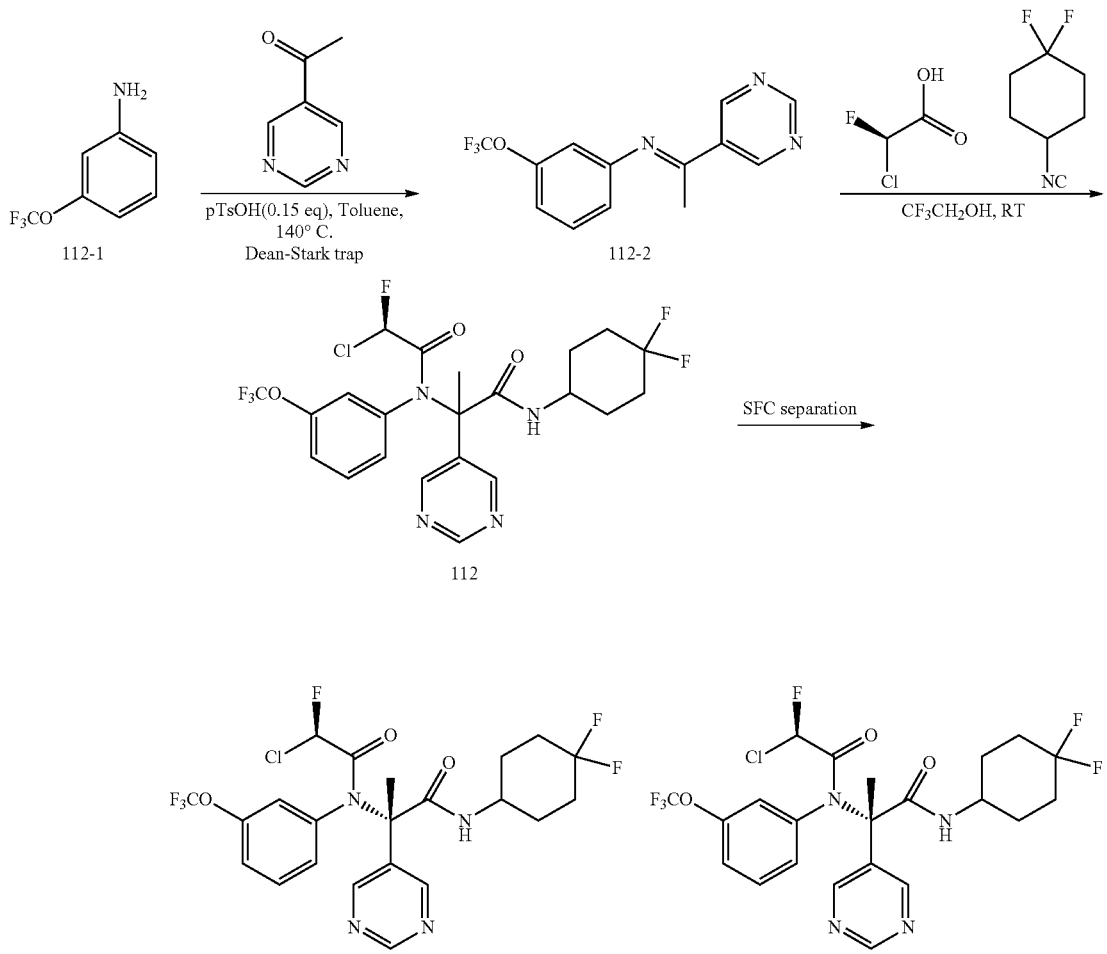

Example 112a and 112b
(Stereochemistry arbitrarily assigned at center between two amides)

To a solution of Compound 112-1 (1.00 g, 5.646 mmol) in toluene (30 mL) was added 1-(pyrimidin-5-yl)ethan-1-one (830 mg, 6.796 mmol) and 4-methylbenzenesulfonic acid (146 mg, 0.848 mmol). The reaction was stirred at 140° C. for 18 hr. The combined reaction mixture was filtered and the filtrate was concentrated under reduced pressure to give a residue. The residue was purified by flash silica gel chromatography (Eluent of 0~60% EA/PE ether gradient @ 40 mL/min) to give compound 112-2 (2.5 g, crude) was obtained.

To a solution of Compound 112-2 (2.52 g, 8.960 mmol) in $CF_3CH_2OH$ (18 mL) was added (2R)-2-chloro-2-fluoroacetic acid (2.42 g, 10.752 mmol) and 1,1-difluoro-4-isocyanocyclohexane (1.30 g, 8.960 mmol). The mixture was stirred at 20° C. for 18 h under $N_2$ atmosphere. The reaction mixture was concentrated under reduced pressure. The residue was purified by flash silica gel chromatography (Eluent of 0~60% EA/PE ether gradient @ 40 mL/min) to get product. The residue was purified by prep-HPLC (Xtimate C18 150*40 mm*10 m; Mobile phase: A: water (FA) B: ACN; Gradient condition: from 45% B to 75% B; Flow rate: 60 mL/min) to afford compound 112 (1.3 g, 26.92% yield) was obtained. LCMS (M+H)=539.1. $^1$H NMR (400 MHz, DMSO-$d_6$): δ 9.10-8.97 (m, 1H), 8.89-8.71 (m, 2H), 7.87-7.63 (m, 2H), 7.62-7.21 (m, 3H), 6.52-6.13 (m, 1H), 3.89 (br s, 1H), 2.12-1.43 (m, 11H).

The Compound 112 (143.5 mg, 0.27 mmol) was separated by SFC (DAICEL CHIRALCEL OD (250 mm*30 mm, 10 μm)), Mobile phase: A: Supercritical $CO_2$, B: Neu-IPA; Isocratic: A:B=90:10; Flow rate: 100 mL/min) to afford two fractions.

Example 112a: (43 mg, 38.23% yield) was obtained. LCMS (M+H)=539.1. SFC: Retention time: 2.182 min, OD_3_IPA_DEA_5_40_25ML_6MIN. $^1$H NMR (400 MHz, DMSO-$d_6$): δ9.11-8.96 (m, 1H), 8.88-8.73 (m, 2H), 7.88-7.66 (m, 2H), 7.64-7.39 (m, 2H), 7.34-7.20 (m, 1H), 6.58-6.20 (m, 1H), 3.89 (br s, 1H), 2.11-1.88 (m, 4H), 1.82 (br s, 4H), 1.68 (br s, 1H), 1.65-1.47 (m, 2H). $^{19}$F NMR (376 MHz, DMSO-$d_6$): δ −56.95 (br d, J=80.5 Hz, 3F), −91.87 (br dd, J=16.6, 233.0 Hz, 1F), −99.38 (br d, J=237.2 Hz, 1F), −142.12 (br s, 1F).

Example 112b: (48 mg, 41.43% yield) was obtained. LCMS (M+H)=539.1. SFC: Retention time: 2.498 min, OD_3_IPA_DEA_5_40_25ML_6MIN. $^1$H NMR (400 MHz, DMSO-$d_6$): δ9.07-8.96 (m, 1H), 8.89-8.74 (m, 2H), 7.78-7.49 (m, 3H), 7.48-7.36 (m, 2H), 6.46-6.14 (m, 1H), 3.87 (br s, 1H), 2.11-1.95 (m, 3H), 1.89 (s, 2H), 1.86-1.71 (m, 4H), 1.68-1.45 (m, 2H). $^{19}$F NMR (376 MHz, DMSO-$d_6$): δ −56.98 (d, J=25.0 Hz, 3F), −89.39--93.15 (m, 1F), −97.38--101.99 (m, 1F), −141.94 (d, J=49.9 Hz, 1F).

Examples 113a and 113b

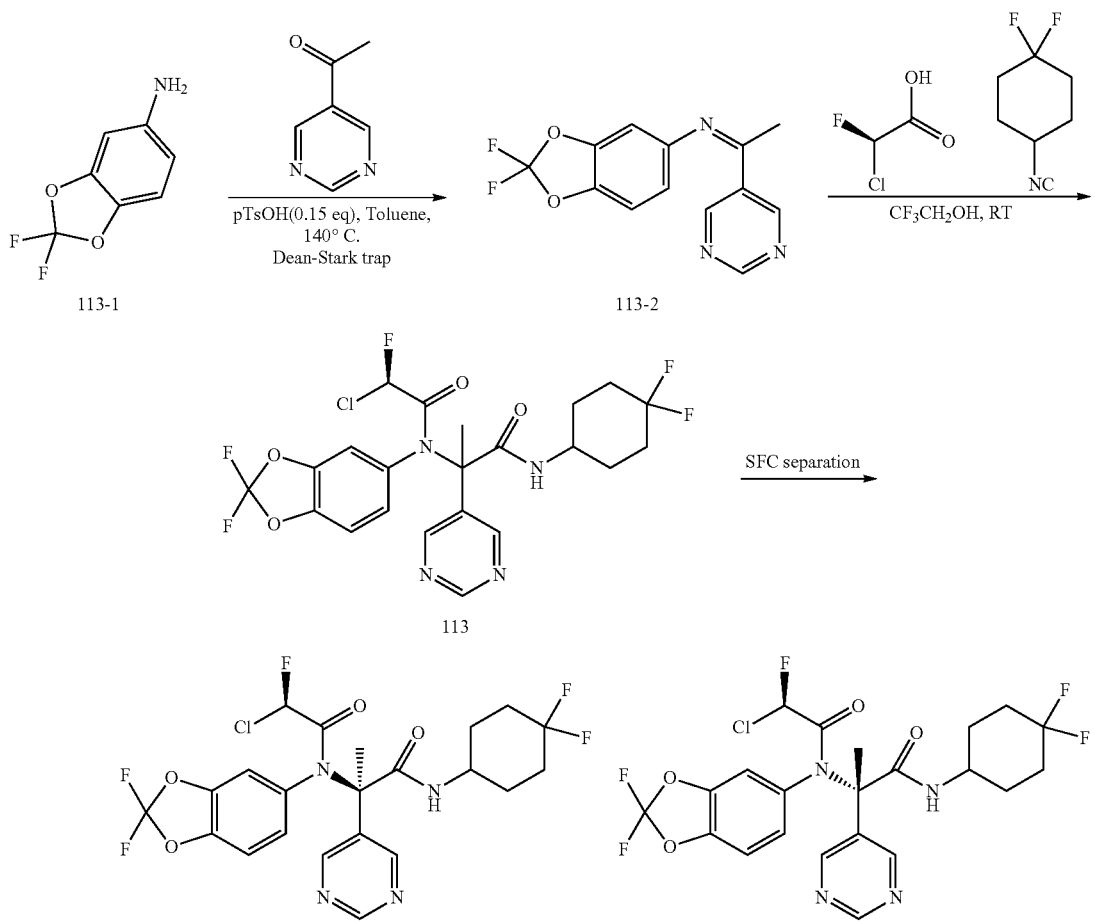

Example 113a and 113b
(Stereochemistry arbitrarily assigned at center between two amides)

To a solution of 113-1 (1 g, 5.776 mmol) in toluene (30 mL) was added 1-(pyrimidin-5-yl)ethan-1-one (776.01 mg, 6.354 mmol) and p-TsOH (149.19 mg, 0.866 mmol). The mixture was heated and stirred at 140° C. for 12 hours with Dean-Stark trap. The mixture was filtered, and the filtrate was concentrated under reduced pressure to give compound 113-2 (0.9 g, 56.2% yield).

To a solution of compound 113-2 (200 mg, 0.721 mmol) in 2,2,2-trifluoroethanol (3 mL) was added (2R)-2-chloro-2-fluoroacetic acid (162.29 mg, 0.866 mmol) and 1,1-difluoro-4-isocyanocyclohexane (104.71 mg, 0.721 mmol). The mixture was stirred at 25° C. for 12 hours. The reaction mixture was concentrated under reduced pressure. The residue was purified by flash silica gel chromatography and further purified by prep-HPLC (Xtimate C18 150*40 mm*10 m; Mobile phase: A: water (FA) B: ACN; Gradient condition: from 45% B to 75% B; Flow rate: 60 mL/min) to give compound 113 (100 mg).

Compound 113 (100 mg, 0.187 mmol) was separated by supercritical fluid chromatography (separation condition: DAICEL CHIRALCEL OD (250 mm*30 mm, 10 μm)); Mobile phase: A: Supercritical $CO_2$, B: Neu-IPA, A:B=85:15 at 100 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm), which afford two fractions. The pure fraction was collected and further purified by prep-HPLC to give title compound.

Example 113a: (7.24 mg, 7.24%) was obtained. LCMS (M+H)=535.1. SFC: Retention time: 2.322 min, OD_3_IPA_DEA_5_40_25ML_6MIN. $^1$H NMR (400 MHz, DMSO-$d_6$) δ 9.20 (d, J=2.0 Hz, 1H), 8.82 (s, 1H), 8.79 (s, 1H), 7.24-7.14 (m, 2H), 7.09-7.04 (m, 1H), 6.13-5.95 (m, 1H), 4.06-3.85 (m, 1H), 2.14-2.04 (m, 4H), 1.97-1.80 (m, 2H), 1.59-1.50 (m, 5H).

Example 113b: (5.80 mg, 0.011 mmol, 5.80%) was obtained. LCMS (M+H)=534.9. SFC: Retention time: 2.765 min, OD_3_IPA_DEA_5_40_25ML_6MIN. $^1$H NMR (400 MHz, DMSO-$d_6$) δ 9.05 (s, 1H), 8.88-8.82 (m, 2H), 7.64-7.57 (m, 1H), 7.48-7.40 (m, 2H), 6.48-6.29 (m, 1H), 3.89-3.81 (m, 1H), 2.06-1.89 (m, 6H), 1.78-1.74 (m, 3H), 1.63-1.52 (m, 2H).

Examples 114a and 114b

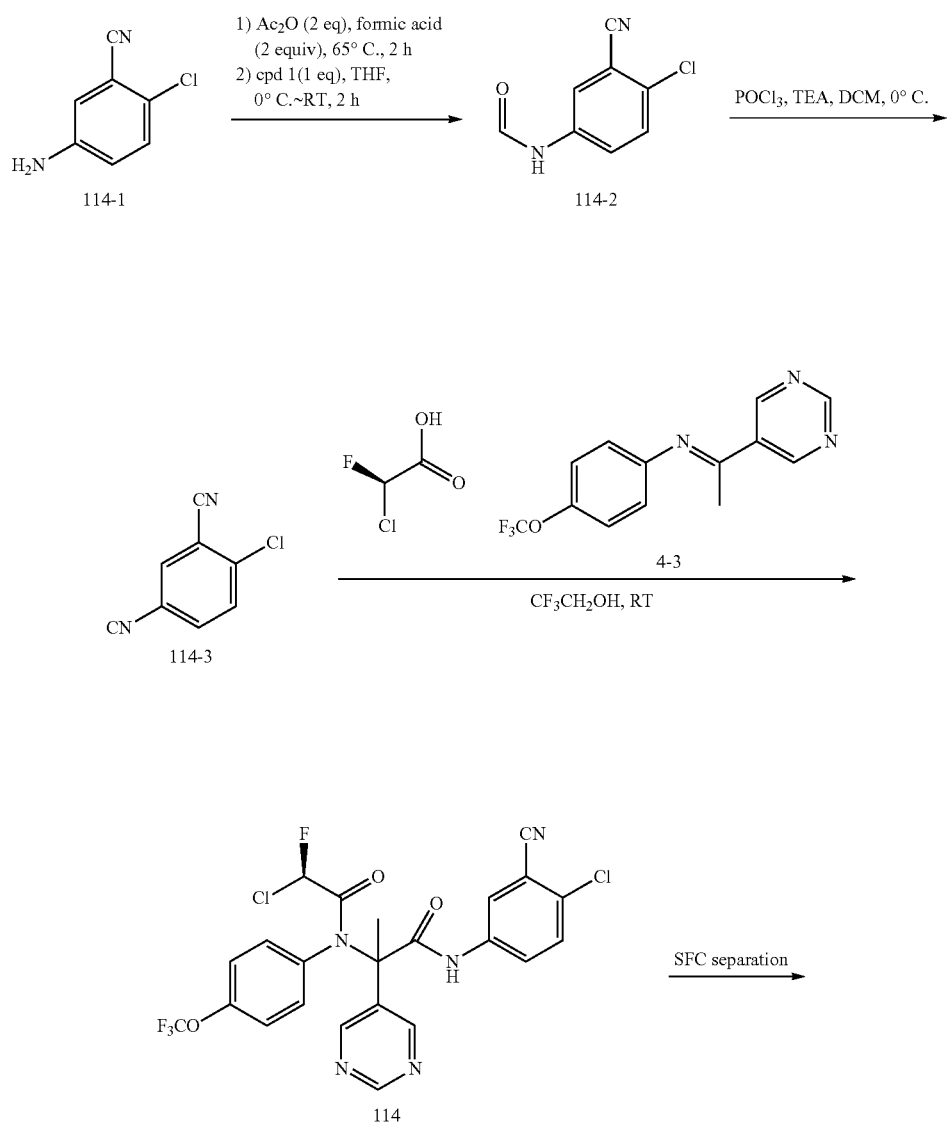

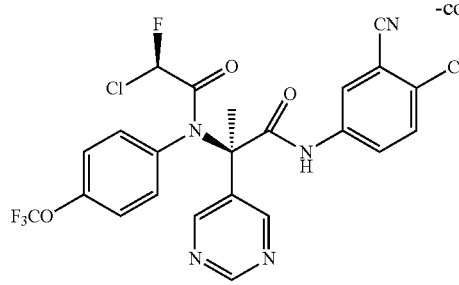
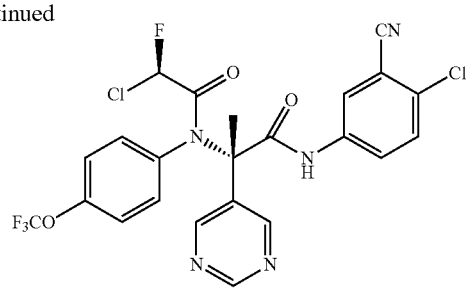

Example 114a and 114b
(Stereochemistry arbitrarily assigned at center between two amides)

A mixture of formic acid (8.3 mL, 217.297 mmol) and acetic anhydride (18.9 mL, 201.237 mmol) were stirred at 55° C. for 2 h. acetic formic anhydride (17.20 g, 78.129 mmol) was obtained as a colorless liquid. The mixture was used for next step without further purification. To a solution of 114-1 (2 g, 13.108 mmol) in THF (20 mL) was added the above acetic formic anhydride (11.54 g, 131.079 mmol), and the reaction was stirred at 20° C. for 20 h. The reaction mixture was concentrated under reduced pressure to give a residue. The residue was purified by flash silica gel chromatography to give compound 114-2 (608 mg, 1.683 mmol, 12.84% yield).

To a solution of 114-2 (600 mg, 3.322 mmol) in DCM (10 mL) was added TEA (2.8 mL, 20.144 mmol). The mixture was degassed and purged with $N_2$ for 3 times. $POCl_3$ (0.4 mL, 4.305 mmol) was added dropwise at 0° C. The mixture was stirred at 0° C. for 2 hr. The reaction mixture was concentrated under reduced pressure. The residue was purified by flash silica gel chromatography (Eluent of 0~50% Ethyl acetate/Petroleum ether gradient @ 30 mL/min). Compound 114-3 (311 mg, 1.913 mmol, 57.58% yield) was obtained.

To a solution of 4-1 (370 mg, 1.32 mmol) and 114-3 (214 mg, 1.32 mmol) in $CF_3CH_2OH$ (3 mL) was added (2R)-2-chloro-2-fluoroacetic acid (296 mg, 1.58 mmol). The mixture was stirred at 20° C. for 18 h under $N_2$ atmosphere. The reaction mixture was concentrated under reduced pressure. The residue was purified by flash silica gel chromatography and further purified by prep-HPLC to give compound 114 (38 mg, 4.3% yield).

Compound 114 (38 mg, 0.068 mmol) was separated by chiral SFC (Phenomenex-Cellulose-2 (250 mm*30 mm, 10 μm); Mobile phase: A: Supercritical CO2, B: Neu-ETOH; Isocratic: A:B=70:30; Flow rate: 150 mL/min) and concentrated under vacuum and lyophilized to afford two fractions.

Example 114a: (14 mg, 0.024 mmol, 33.84%) was obtained. LCMS (M+H)=556.1. SFC: Retention time: 3.470 min, C2_EtOH_DEA_5_40_25ML. $^1$H NMR (400 MHz, DMSO-$d_6$) δ 9.94 (s, 1H), 9.16 (s, 1H), 8.89 (s, 2H), 8.18 (s, 1H), 8.03-7.65 (m, 3H), 7.61-7.21 (m, 3H), 6.60-6.19 (m, 1H), 1.87 (s, 3H). $^{19}$F NMR (376 MHz, DMSO-$d_6$): δ -56.92 (br d, J=27.7 Hz, 3F), -142.12 (br s, 1F).

Example 114b: (15 mg, 0.027 mmol, 36.88%) was obtained. LCMS (M+H)=556.1. SFC: Retention time: 4.984 min, C2_EtOH_DEA_5_40_25ML. $^1$H NMR (400 MHz, DMSO-$d_6$) δ 9.98 (s, 1H), 9.18 (s, 1H), 8.91 (s, 2H), 8.20 (s, 1H), 8.07-7.86 (m, 2H), 7.82-7.70 (m, 1H), 7.62-7.49 (m, 1H), 7.48-7.37 (m, 1H), 7.36-7.23 (m, 1H), 6.62-6.37 (m, 1H), 1.77 (s, 3H). $^{19}$F NMR (376 MHz, DMSO-$d_6$): δ -52.61--58.57 (m, 3F), -139.36--144.28 (m, 1F).

Examples 115a and 115b

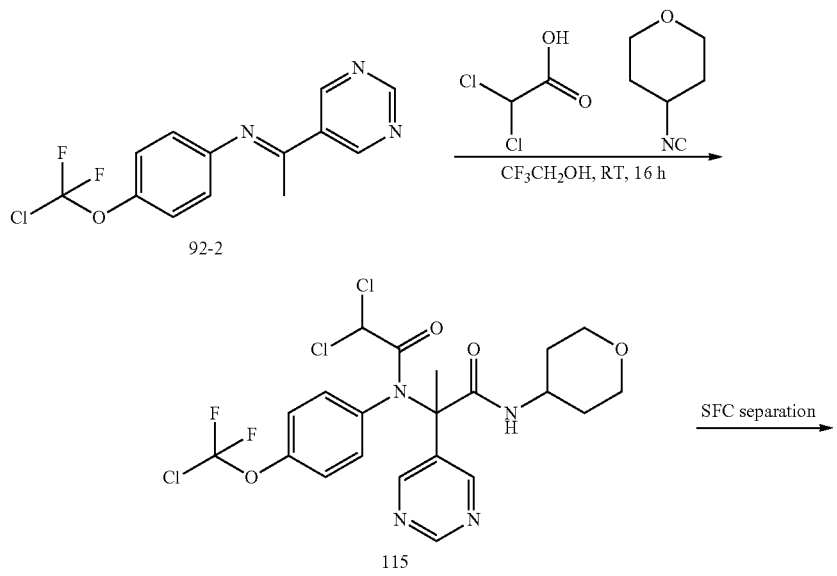

-continued

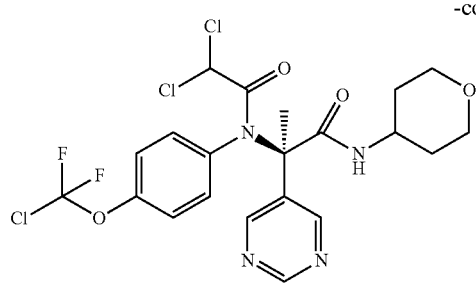
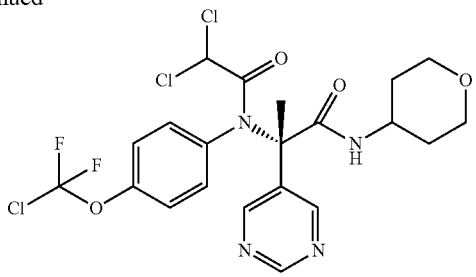

Example 115a and 115b
(Stereochemistry arbitrarily assigned at center between two amides)

The following compounds were prepared according to similar procedure as described for Example 94a and 94b.

Example 115a: (112.20 mg, 43% yield) was obtained. LCMS (M+H)=537.1. SFC: Retention time: 2.600 min, OD_3_EtOH_DEA_5_40_25ML_6MIN. $^1$HNMR (400 MHz, DMSO-d$_6$): δ 9.03 (s, 1H), 8.81 (s, 2H), 7.84-7.65 (m, 2H), 7.53-7.31 (m, 3H), 6.10 (s, 1H), 3.85 (d, J=1.2 Hz, 3H), 3.32-3.31 (m, 1H), 3.31-3.26 (m, 1H), 1.85-1.38 (m, 7H). $^{19}$F NMR (376 MHz, DMSO-d$_6$): δ −25.05 (s, 2F).

Example 115b: (110.28 mg, 42.29% yield) was obtained. LCMS (M+H)=537.1. SFC: Retention time: 3.000 min, OD_3_EtOH_DEA_5_40_25ML_6MIN. $^1$HNMR (400 MHz, DMSO-d$_6$): δ 9.03 (s, 1H), 8.81 (s, 2H), 7.80-7.70 (m, 2H), 7.44 (d, J=8.2 Hz, 2H), 7.40-7.33 (m, 1H), 6.10 (s, 1H), 3.94-3.78 (m, 3H), 3.33-3.32 (m, 1H), 3.30 (s, 1H), 1.79 (s, 3H), 1.75-1.41 (m, 4H). $^{19}$F NMR (376 MHz, DMSO-d$_6$): δ −25.05 (s, 2F).

Example A: In Vitro Assay (SARS-CoV-2 M$^{pro}$ Enzymatic Assay

The C-His6-tagged SARS-CoV-2 MPRO (NC_045512) was cloned, expressed in *E. coli*, and purified by WuXi. The substrate of Dabcyl-KTSAVLQIISGFRKME-(Edans) was synthesized by Genscript. The assay buffer contained 20 mM of Tris-HCl (pH=7.3), 100 mM of NaCl, 1 mM of EDTA, 5 mM of TCEP and 0.1% BSA. The final concentrations of the Mpro protein and substrate were 25 nM and M, respectively, in the MPRO enzymatic assay. Reference compound GC376 was provided by WuXi AppTec and was included in each plate to ensure assay robustness. Test compounds were tested at single dose or 10 doses titration, in duplicate. Compounds were added to an assay plate (384w format) using ECHO, in duplicate wells. The final concentration is 10 μM for the single dose experiment. As for the full dose response experiment, samples were 3-fold serially diluted starting from 25 μM for 10 doses and added to an assay plate, in duplicate wells. The final concentrations (M) of each compound was 25, 8.33, 2.778, 0.926, 0.309, 0.103, 0.034, 0.011, 0.0038, and 0.0013. MPRO protein (25 μL, 30 nM) was added to an assay plate containing test compounds using a Multidrop. The test compound and MPRO protein were pre-incubated at RT for 30 min. Then, substrate (5 μL, 150 μM) was added to an assay plate. For 100% inhibition controls (HPE, high percent effect), 1 μM of GC376 was added. For no inhibition controls (ZPE, zero percent effect), the same volume of DMSO was added. The final DMSO concentration was 1%. Each activity testing point had a relevant background control without the enzyme to remove the fluorescence interference of the compound. After 60 min incubation at 30° C., the fluorescence signal (RFU) was detected using a microplate reader M2e (SpectraMax) at Ex/Em=340 nm/490 nm.

The inhibition activity was calculated using the formula below, IC50 values were calculated using the Inhibition % data.

Inhibition %=((CPD−BGHPE)−(ZPE−BGZPE))/
((HPE−BGHPE)−(ZPE−BGZPE))×100 where, HPE is high percent effect controls (1 μM of GC376+enzyme+substrate); ZPE is zero percent effective controls (enzyme+substrate, no compound); CPD is compound activity testing wells (compound+enzyme+substrate; and BG is background control wells (no enzyme).

IC50 values of compounds were calculated with the GraphPad Prism software using the nonlinear regression model of log(inhibitor) vs. response–variable slope (four parameters). Representative biochemical data is presented in Table 2.

TABLE 2

| Example | M pro IC$_{50}$ |
|---------|-----------------|
| 1a | A |
| 1b | C |
| 2a | A |
| 2b | C |
| 3a | A |
| 3b | D |
| 4a | A |
| 4b | C |
| 5a | A |
| 5b | C |
| 6a | A |
| 6b | A |
| 6c | C |
| 6d | D |
| 8 | A |
| 11a | A |
| 11b | C |
| 13a | D |
| 13b | D |
| 14a | A |
| 14b | D |
| 18a | A |
| 18b | C |
| 22a | A |
| 22b | C |
| 23a | C |
| 23b | A |
| 26a | B |
| 26b | C |
| 27a | B |
| 27b | C |
| 28a | A |
| 28b | D |
| 29a | B |
| 29b | D |

TABLE 2-continued

| Example | M pro IC$_{50}$ |
|---|---|
| 32a | A |
| 32b | C |
| 33a | A |
| 33b | B |
| 34a | A |
| 34b | D |
| 36a | A |
| 36b | D |
| 76a | A |
| 76b | B |
| 76c | D |
| 76d | D |
| 77a | A |
| 77b | A |
| 77c | C |
| 77d | D |
| 90a | A |
| 90b | B |
| 92a | A |
| 92b | B |
| 94a | A |
| 94b | C |
| 95a | A |
| 95b | C |
| 96a | A |
| 96b | NT |
| 97a | A |
| 97b | D |
| 98a | A |
| 98b | C |
| 99a | A |
| 99b | C |
| 100a | A |
| 100b | B |
| 101a | A |
| 101b | NT |
| 102a | A |
| 102b | B |
| 103a | A |
| 103b | D |
| 104a | A |
| 104b | C |
| 105a | A |
| 105b | D |
| 106a | A |
| 106b | D |
| 107a | A |
| 107b | D |
| 108a | B |
| 108b | D |
| 109a | A |
| 109b | C |
| 110a | A |
| 110b | C |
| 111a | A |
| 111b | D |
| 112a | B |
| 112b | D |
| 113a | A |
| 113b | D |
| 114a | NT |
| 114b | NT |
| 115a | A |
| 115b | C |

IC50 (nM): 0 < A ≤ 100; 100 < B ≤ 1,000; 1,000 < C ≤ 10,000; 10,000 < D

Example B: In Vitro Antiviral Cell-Based Assay (Live SARS-CoV-2

CellTiter-Glo® Luminescent Assay for Determination of CC50 of Each Compound in Cell Cultures:

Multiple cell lines can be used depending on customer's request. For each cell line, 4×10$^4$ cells/well in a 96-well plate are incubated with 7 concentrations (depending on its water solubility and using 2-fold dilution) in triplicate of the individual compound for 24 h, 48 h, 72 h, respectively. After that, addition of substrate for cell viability will be performed, followed by luminance detection 10 min later. The 50% cytotoxic concentrations (CC50) of the antiviral agents will be calculated by SigmaPlot (Systat Software Inc., San Jose, Calif., USA) in an Excel add-in ED50V10.

SARS-CoV-2 Viral Load Reduction Assay:

Multiple cell lines can be used depending on customer's request. Also, different variants of concern (e.g. alpha, gamma, kappa, and delta etc.) can be included according to the customer's request. For each cell line, cells will be infected by 0.1 MOI SARS-CoV-2 for 1 h. After that, the infectious inoculum will be replaced with drug-containing medium which is serial-diluted (7 concentrations). The culture supernatants of the SARS-CoV-2-infected cells are harvested at 48 h post-inoculation (hpi) for qRT-PCR analysis of viral RNA load. A total of 140 µL of culture supernatant will be lysed with 560 µL of AVL buffer, which is subsequently extracted for total RNA with the QIAamp viral RNA mini kit (Qiagen, Hilden, Germany). qRT-PCR will be used for quantitation of SARS-CoV-2 replication using the QuantiNova Probe RT-PCR kit (Qiagen) with a LightCycler 480 Real-Time PCR System (Roche). Each 20 µL reaction mixture is 10 µL of 2× QuantiNova Probe RT-PCR Master Mix, 1.2 µL of RNase-free water, 0.2 µL of QuantiNova Probe RT-Mix, 1.6 µL each of 10 M forward and reverse primer, 0.4 µL of M probe, and 5 µL of extracted RNA as the template. Reactions will be incubated at 45° C. for 10 min for reverse transcription, 95° C. for 5 min for denaturation, follow by 45 cycles of 95° C. for 5 s and 55° C. for 30 s. Signal detection and measurement are taken in each cycle after the annealing step. The cycling profile end with a cooling step at 40° C. for 30 s. The primers and probe sequences are against the RNA-dependent RNA polymerase/helicase (RdRP/Hel) gene region of SARS-CoV-2: Forward primer: 5'-CGCATACAGTCTTRCAGGCT-3'; Reverse primer: 5'-GTGTGATGTTGAWATGACATGGTC-3'; specific probe: 5'-FAM TTAAGATGTGGTGCTTGCAT-ACGTAGAC-IABkFQ-3'.

Plaque Reduction Assay

Different variants of concern of SARS-CoV-2 (e.g. alpha, gamma, delta, and kappa etc.) can be included according to the customer's request. VeroE6 cells will be seeded at 2×10$^5$ cells/well in 24-well tissue culture plates on the day before carrying out the assay. After 24 h of incubation, 50 plaque-forming units (PFU) of SARS-CoV-2 will be added to the cell monolayer and the plates are further incubated for 1 h at 37° C. in 5% CO2 before removal of unbound viral particles by aspiration of the media and washing once with DMEM. Monolayers are then overlaid with media containing 1.5% low melting agarose (Cambrex Corporation, East Rutherford, N.J., USA) in DMEM and appropriate concentrations of individual compound (5 concentrations), inverted and incubated as above for another 72 h. The wells are then fixed with 10% formaldehyde (BDH, Merck, Darmstadt, Germany) overnight. After removal of the agarose plugs, the monolayers are stained with 0.7% crystal violet (BDH, Merck) and the plaques counted. The percentage of plaque inhibition relative to the control (i.e., without the addition of compound) wells will be determined for each antiviral agent concentration. EC50 was calculated using a sigma plot (SPSS) in an Excel add-in ED50V10. The plaque reduction assay experiments are performed in triplicate.

TABLE 3

| Example | Vero EC$_{50}$ (μM) |
|---------|---------------------|
| 1a | B |

IC50 (nM): 0 < A ≤ 100; 100 < B ≤ 1,000; 1,000 < C ≤ 10,000; 10,000 < D

What is claimed is:

1. A compound of Formula (Ia), or a pharmaceutically acceptable salt or stereoisomer thereof:

Formula (Ia)

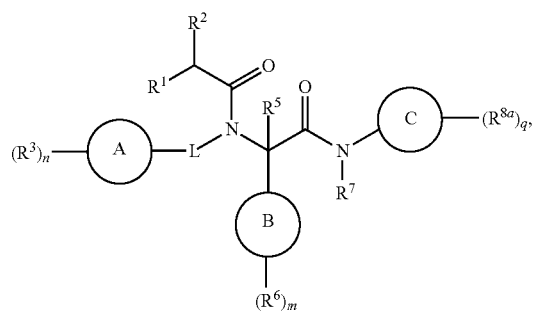

wherein:
R$^1$ is fluoro and R$^2$ is chloro;

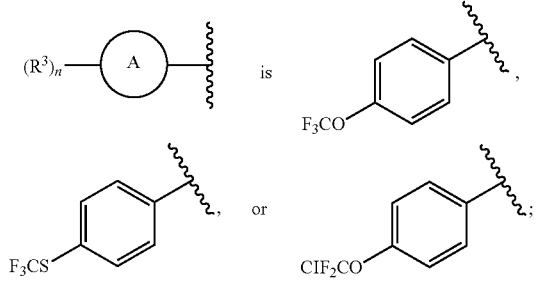

L is —(CR$^4$R$^4$)$_p$—;
each R$^4$ is independently hydrogen, halogen, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;
p is 0;
R$^5$ is C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl;

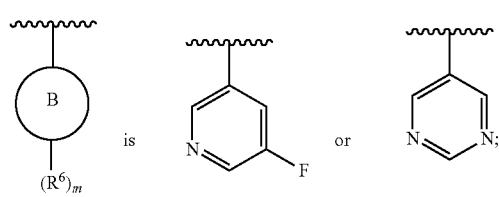

R$^7$ is hydrogen, C$_1$-C$_6$alkyl, C$_1$-C$_6$haloalkyl, C$_1$-C$_6$hydroxyalkyl, C$_1$-C$_6$aminoalkyl, or C$_1$-C$_6$heteroalkyl; and

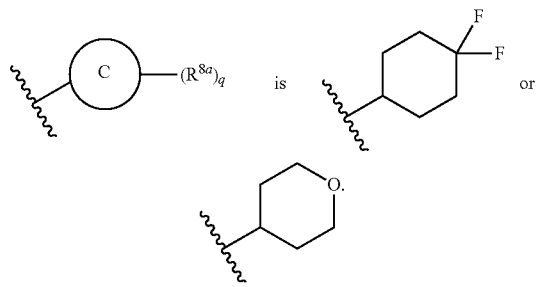

2. The compound of claim 1, or a pharmaceutically acceptable salt or stereoisomer thereof, wherein R$^5$ is C$_1$-C$_6$alkyl.

3. The compound of claim 1, or a pharmaceutically acceptable salt or stereoisomer thereof, wherein R$^5$ is methyl.

4. The compound of claim 1, or a pharmaceutically acceptable salt or stereoisomer thereof, wherein R$^7$ is hydrogen.

5. The compound of claim 1 selected from the group consisting of:

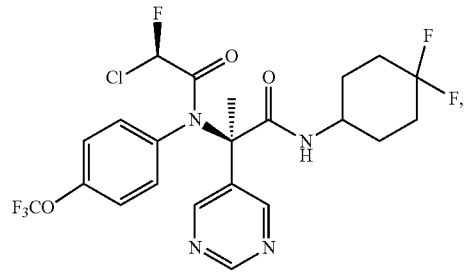

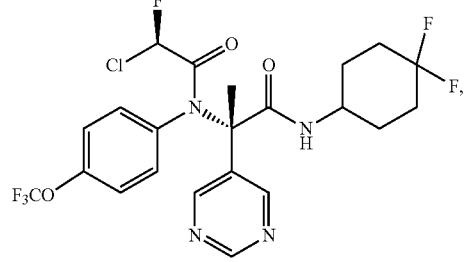

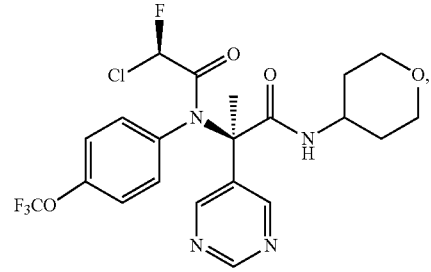

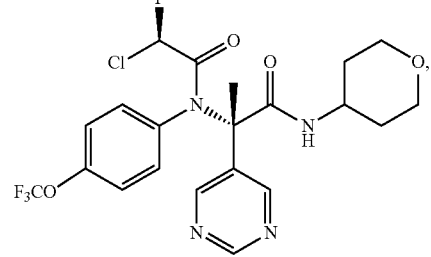

-continued
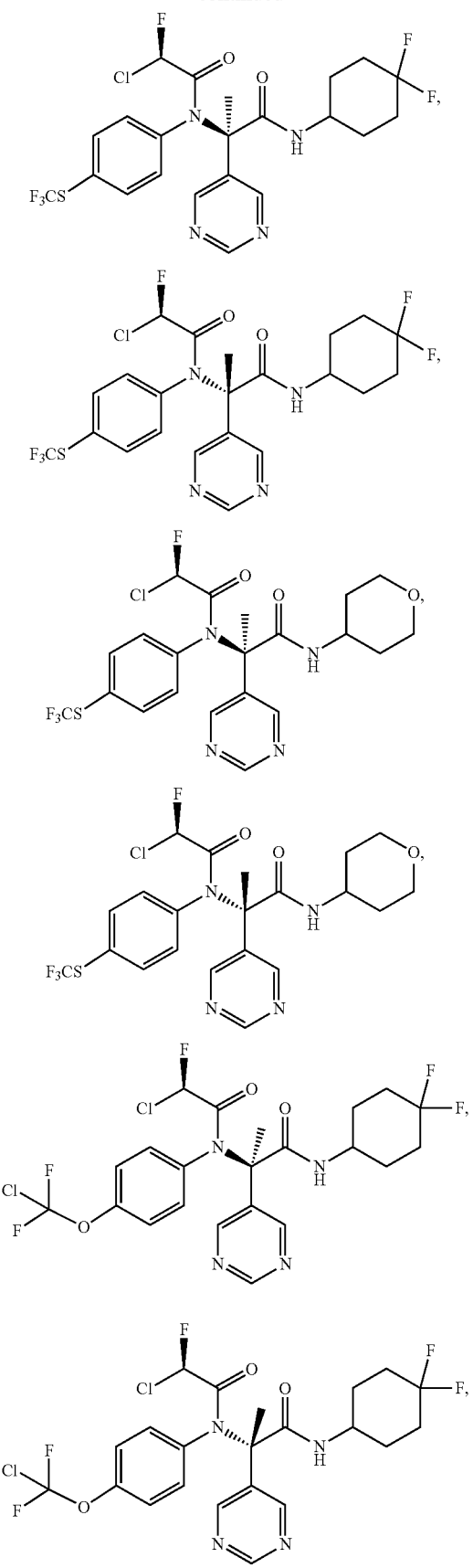
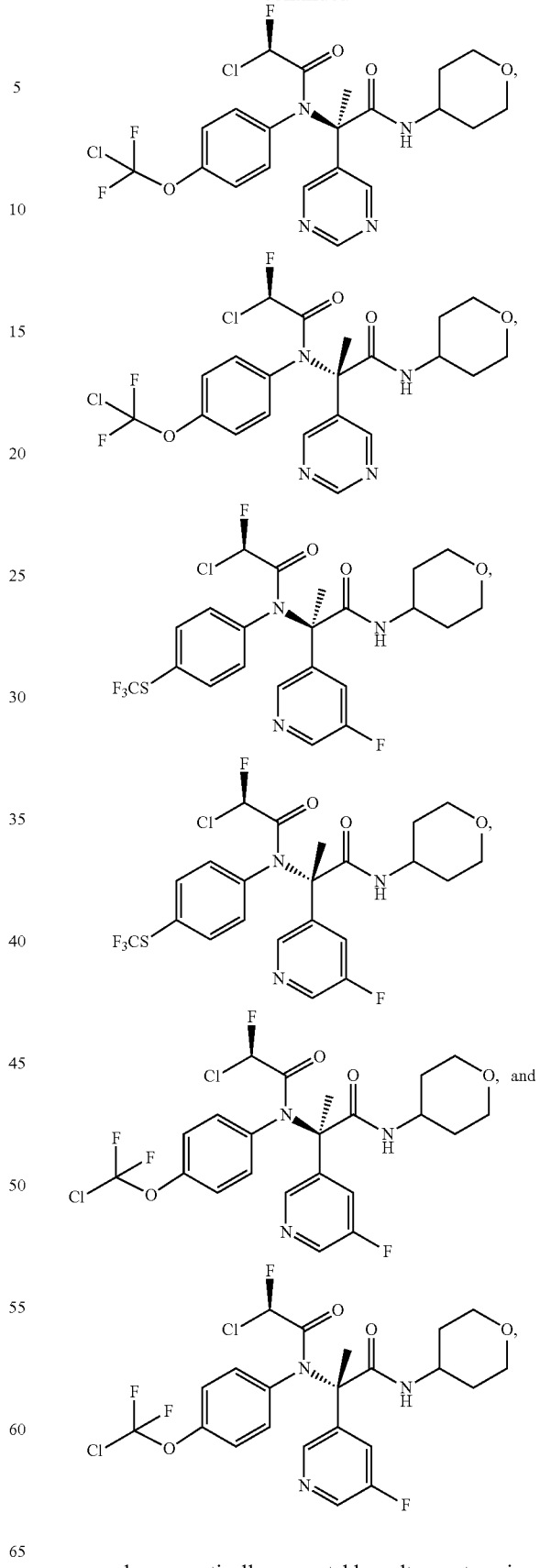
or a pharmaceutically acceptable salt or stereoisomer thereof.

6. The compound of claim 1, or a pharmaceutically acceptable salt or stereoisomer thereof, selected from the group consisting of:

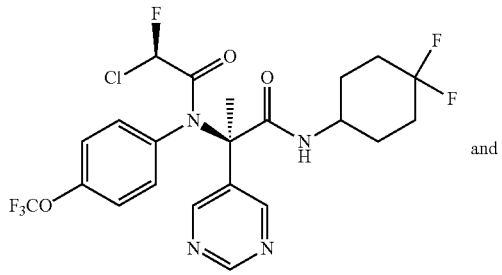

and

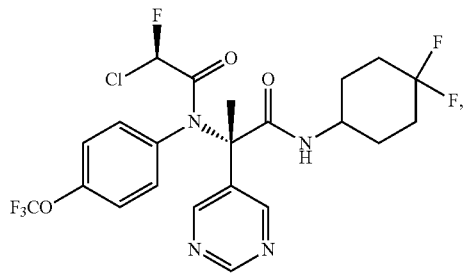

or a pharmaceutically acceptable salt thereof.

7. The compound of claim 1, or a pharmaceutically acceptable salt or stereoisomer thereof, selected from the group consisting of:

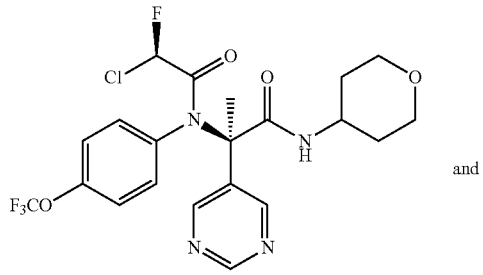

and

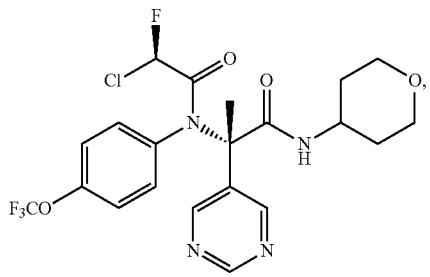

or a pharmaceutically acceptable salt thereof.

8. The compound of claim 1, or a pharmaceutically acceptable salt or stereoisomer thereof, selected from the group consisting of:

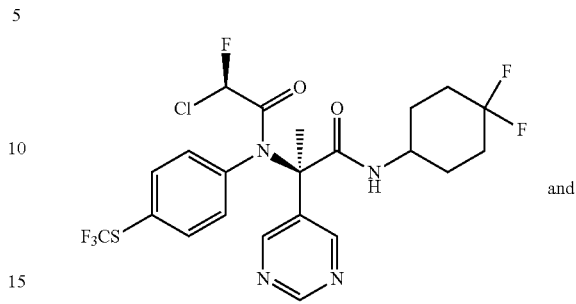

and

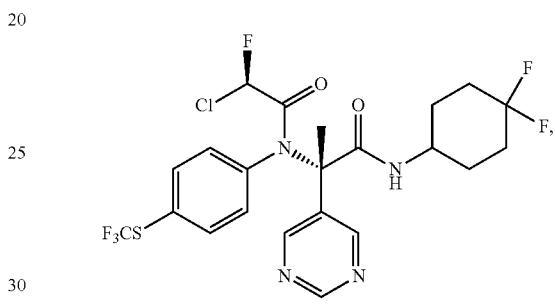

or a pharmaceutically acceptable salt thereof.

9. The compound of claim 1, or a pharmaceutically acceptable salt or stereoisomer thereof, selected from the group consisting of:

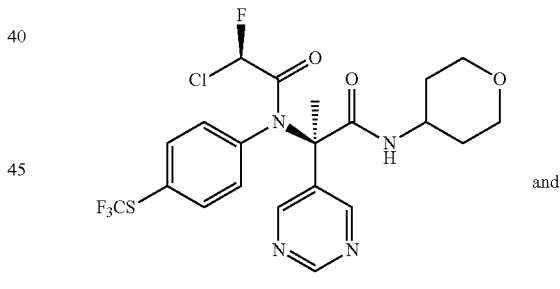

and

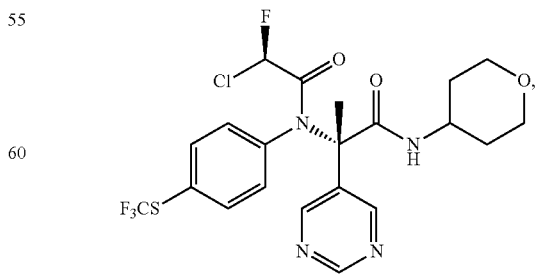

or a pharmaceutically acceptable salt thereof.

10. The compound of claim 1, or a pharmaceutically acceptable salt or stereoisomer thereof, selected from the group consisting of:

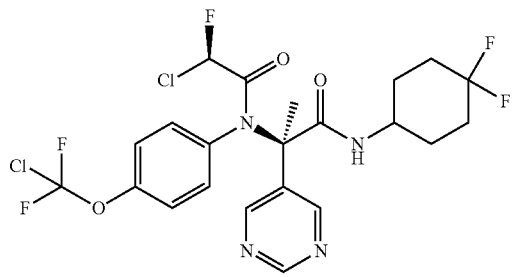

and

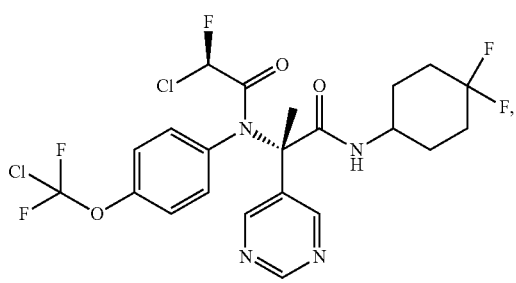

or a pharmaceutically acceptable salt thereof.

11. The compound of claim 1, or a pharmaceutically acceptable salt or stereoisomer thereof, selected from the group consisting of:

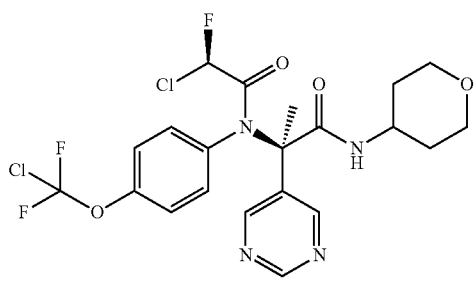

and

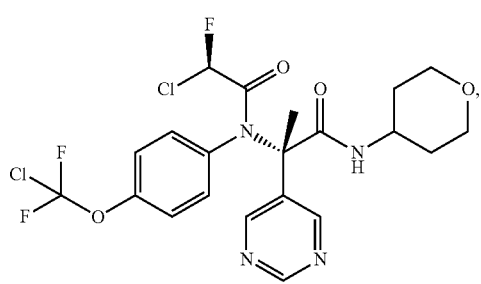

or a pharmaceutically acceptable salt thereof.

12. The compound of claim 1, or a pharmaceutically acceptable salt or stereoisomer thereof, selected from the group consisting of:

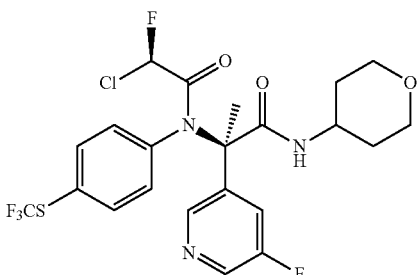

and

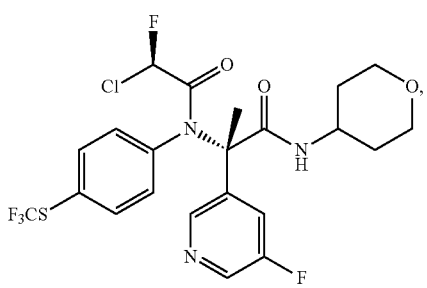

or a pharmaceutically acceptable salt thereof.

13. The compound of claim 1, or a pharmaceutically acceptable salt or stereoisomer thereof, selected from the group consisting of:

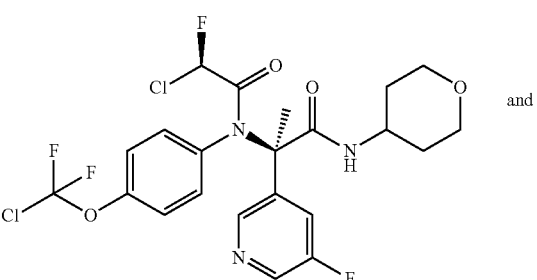

and

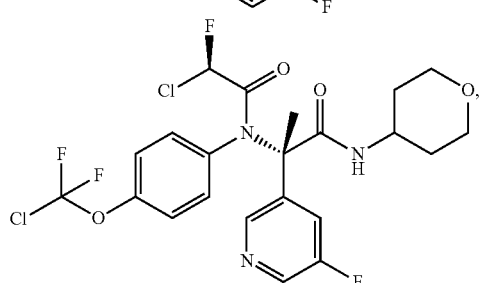

or a pharmaceutically acceptable salt thereof.

14. A method of treating a coronavirus infection in a patient in need thereof, comprising administering to the patient a compound of claim 1, or a pharmaceutically acceptable salt or stereoisomer thereof.

15. A pharmaceutical composition comprising (i) a compound of Formula (Ia), or a pharmaceutically acceptable salt or stereoisomer thereof:

Formula (Ia)

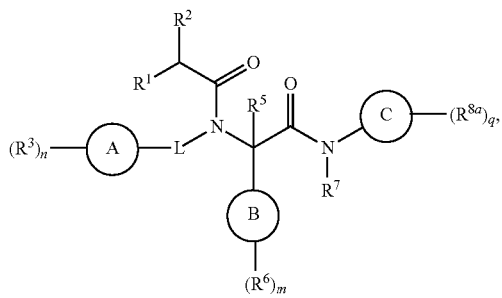

wherein:

$R^1$ is fluoro and $R^2$ is chloro;

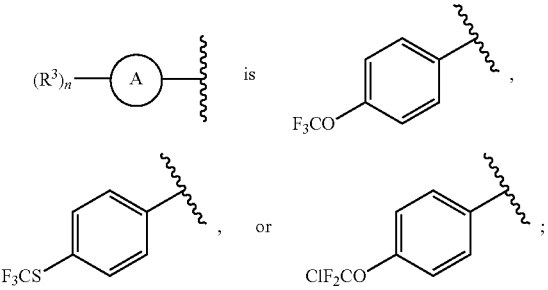

L is —$(CR^4R_4)_p$—;

each $R^4$ is independently hydrogen, halogen, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;

p is 0;

$R^5$ is $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl;

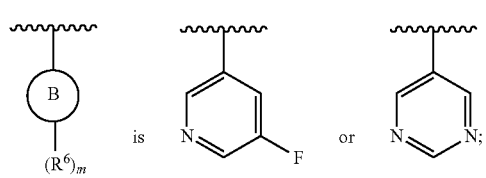

$R^7$ is hydrogen, $C_1$-$C_6$alkyl, $C_1$-$C_6$haloalkyl, $C_1$-$C_6$hydroxyalkyl, $C_1$-$C_6$aminoalkyl, or $C_1$-$C_6$heteroalkyl; and

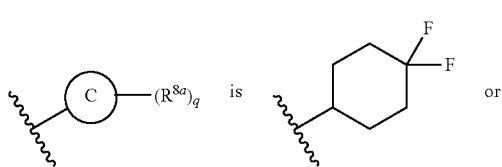

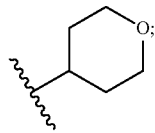

and (ii) a pharmaceutically acceptable excipient.

16. The pharmaceutical composition of claim 15, wherein $R^5$ is $C_1$-$C_6$alkyl.

17. The pharmaceutical composition of claim 15, wherein $R^5$ is methyl.

18. The pharmaceutical composition of claim 15, wherein $R^7$ is hydrogen.

19. The pharmaceutical composition of claim 15, wherein the compound of Formula (Ia) is selected from the group consisting of:

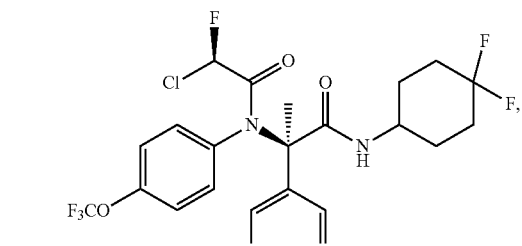

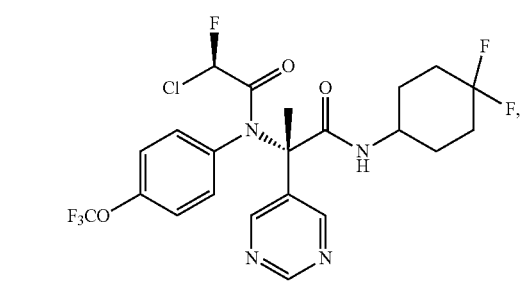

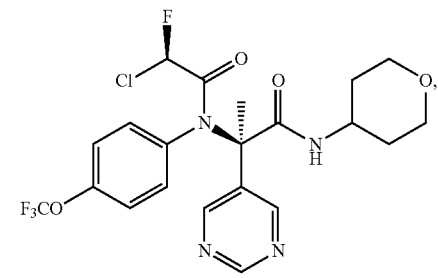

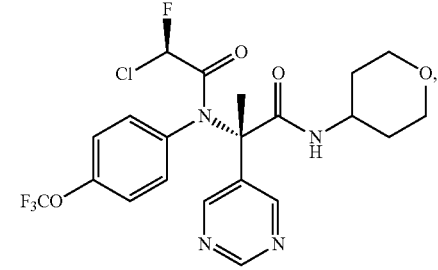

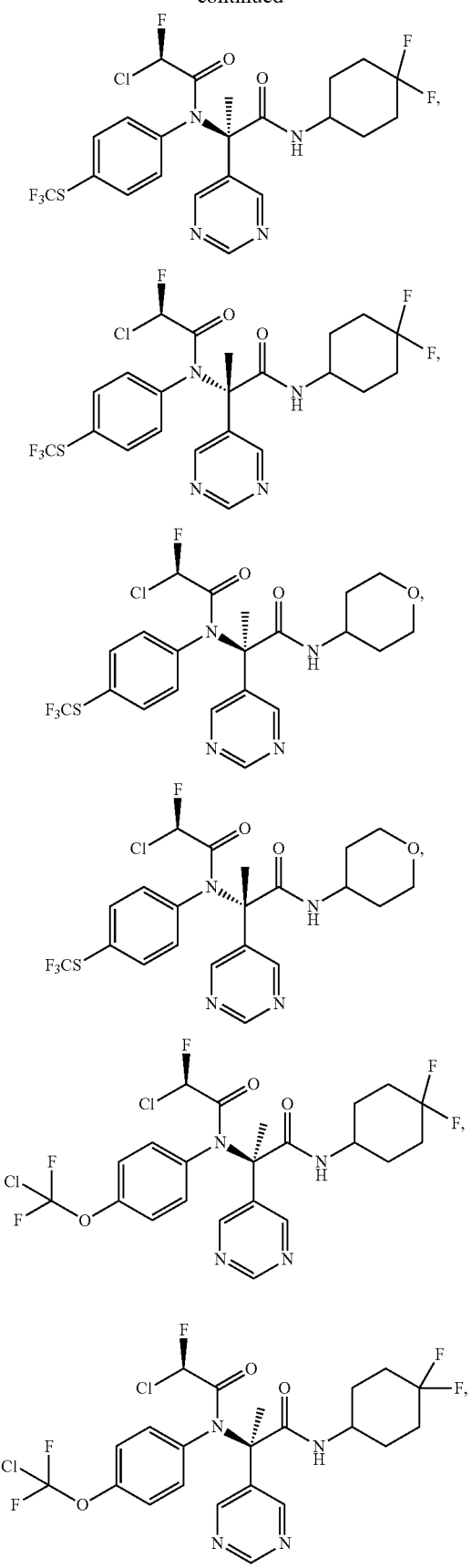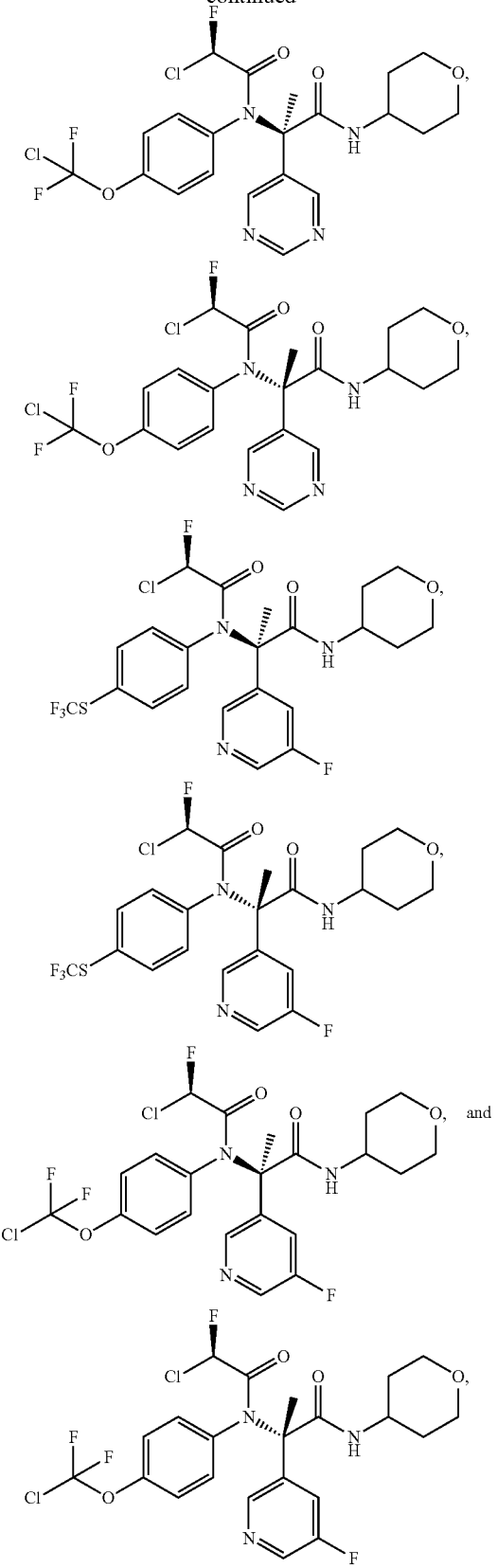
or a pharmaceutically acceptable salt or stereoisomer thereof.

20. The pharmaceutical composition of claim 15, wherein the compound of Formula (Ia) is selected from the group consisting of:

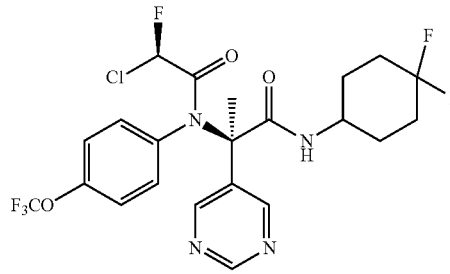

and

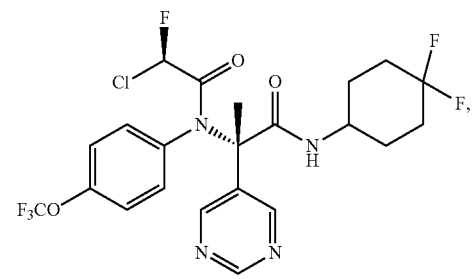

or a pharmaceutically acceptable salt thereof.

21. The pharmaceutical composition of claim 15, wherein the compound of Formula (Ia) is selected from the group consisting of:

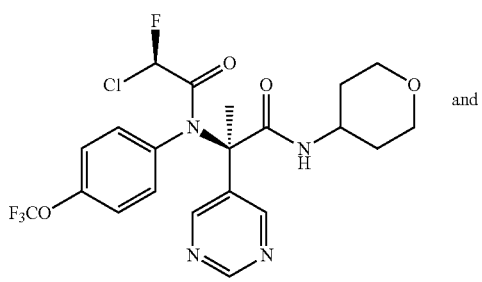

and

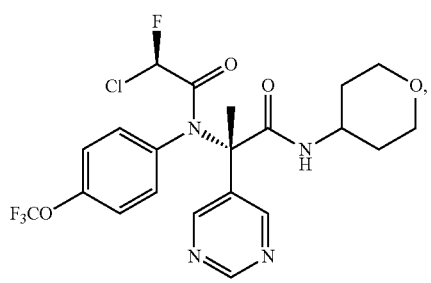

or a pharmaceutically acceptable salt thereof.

22. The pharmaceutical composition of claim 15, wherein the compound of Formula (Ia) is selected from the group consisting of:

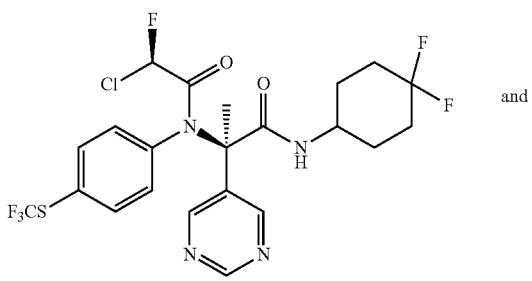

and

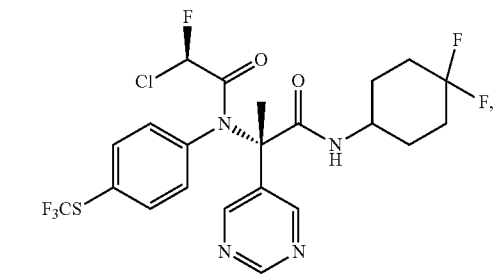

or a pharmaceutically acceptable salt thereof.

23. The pharmaceutical composition of claim 15, wherein the compound of Formula (Ia) is selected from the group consisting of:

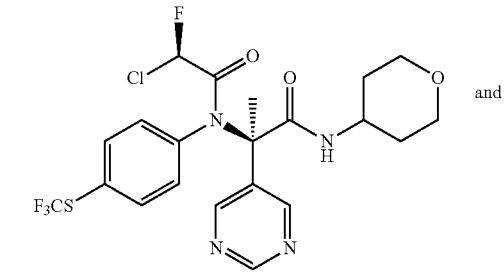

and

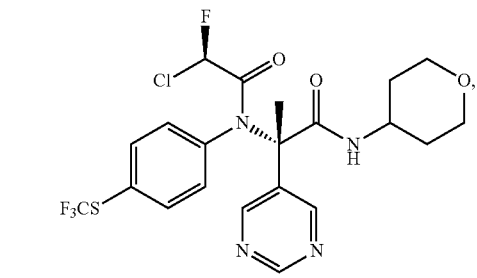

or a pharmaceutically acceptable salt thereof.

24. The pharmaceutical composition of claim 15, wherein the compound of Formula (Ia) is selected from the group consisting of:

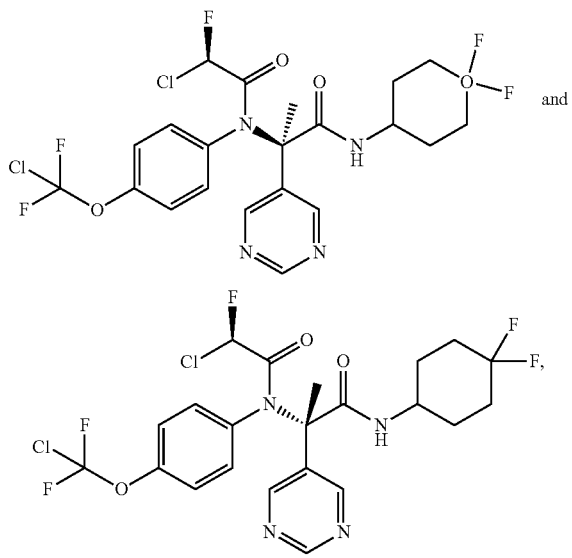

or a pharmaceutically acceptable salt thereof.

25. The pharmaceutical composition of claim 15, wherein the compound of Formula (Ia) is selected from the group consisting of:

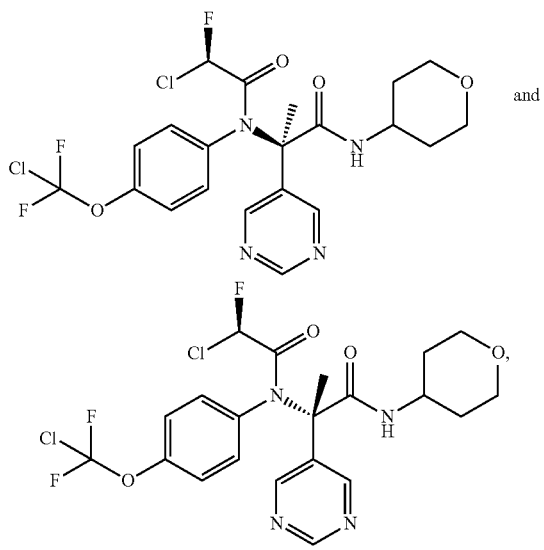

or a pharmaceutically acceptable salt thereof.

26. The pharmaceutical composition of claim 15, wherein the compound of Formula (Ia) is selected from the group consisting of:

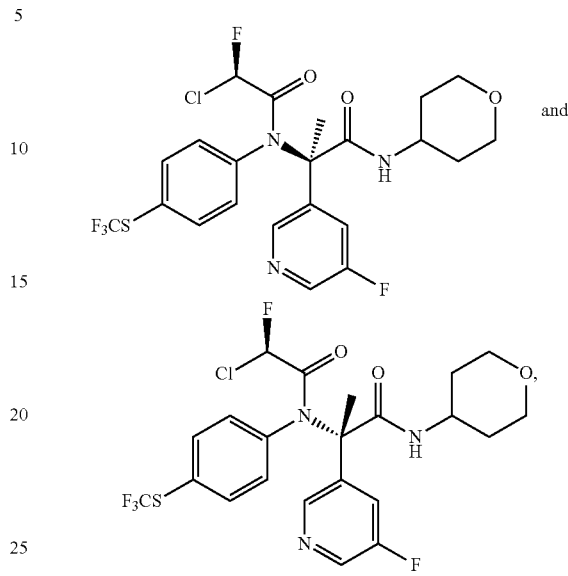

or a pharmaceutically acceptable salt thereof.

27. The pharmaceutical composition of claim 15, wherein the compound of Formula (Ia) is selected from the group consisting of:

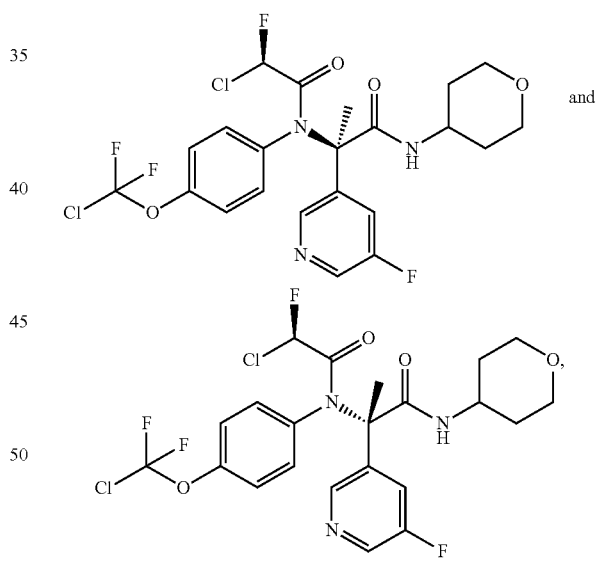

or a pharmaceutically acceptable salt thereof.

* * * * *

UNITED STATES PATENT AND TRADEMARK OFFICE
CERTIFICATE OF CORRECTION

PATENT NO. : 11,731,944 B2
APPLICATION NO. : 18/107127
DATED : August 22, 2023
INVENTOR(S) : Xiao Ding et al.

Page 1 of 1

It is certified that error appears in the above-identified patent and that said Letters Patent is hereby corrected as shown below:

In the Claims

Column 201, Line 38:
In Claim 15, replace: "L is – $(CR^4R_4)_p$–;" with -- L is –$(CR^4R^4)_p$–; --

Column 203, Lines 55-65 (the last structure in Column):

In Claim 19, replace: " 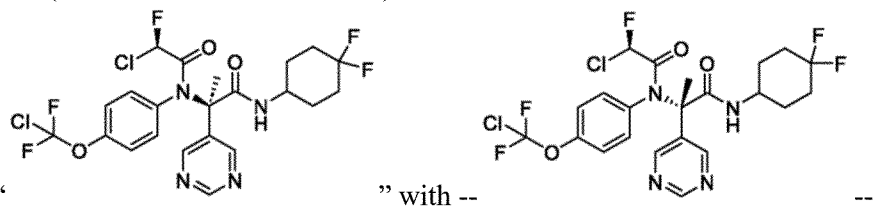 " with -- --

Column 207, Lines 5-15 (the first structure in Column):

In Claim 24, replace: " 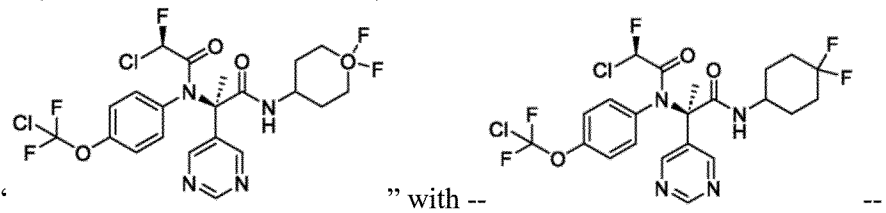 " with -- --

Signed and Sealed this
Thirty-first Day of October, 2023

Katherine Kelly Vidal
*Director of the United States Patent and Trademark Office*